US012807971B2

(12) United States Patent
Semsey et al.

(10) Patent No.: US 12,807,971 B2
(45) Date of Patent: Nov. 24, 2026

(54) TYPE OF CRISPR/CAS SYSTEM

(71) Applicant: SNIPR BIOME APS, Copenhagen (DK)

(72) Inventors: Szabolcs Semsey, Copenhagen (DK); Ioannis Mougiakos, Copenhagen (DK); Emilie Søndberg, Copenhagen (DK); Jasper Clube, Copenhagen (DK)

(73) Assignee: SNIPR BIOME APS, Copenhagen (DK)

( * ) Notice: Subject to any disclaimer, the term of this patent is extended or adjusted under 35 U.S.C. 154(b) by 0 days.

(21) Appl. No.: 18/753,324

(22) Filed: Jun. 25, 2024

(65) Prior Publication Data

US 2025/0002942 A1 Jan. 2, 2025

Related U.S. Application Data

(63) Continuation of application No. PCT/EP2023/073881, filed on Aug. 31, 2023.

(30) Foreign Application Priority Data

Aug. 31, 2022 (GB) ..................................... 2212688

(51) Int. Cl.
*C12N 15/90* (2006.01)
*C12N 9/22* (2006.01)
*C12N 9/88* (2006.01)
*C12N 15/11* (2006.01)

(52) U.S. Cl.
CPC ............. *C12N 15/902* (2013.01); *C12N 9/22* (2013.01); *C12N 9/88* (2013.01); *C12N 15/11* (2013.01); *C07K 2319/00* (2013.01); *C12N 2310/20* (2017.05)

(58) Field of Classification Search
CPC .......... C12N 15/902; C12N 9/22; C12N 9/88; C12N 15/11; C12N 2310/20; C12N 9/78; C12N 15/62; C12N 15/113; C07K 2319/00; C07K 14/26
See application file for complete search history.

(56) References Cited

U.S. PATENT DOCUMENTS 9,701,964 B2 7/2017 Clube et al.
10,195,273 B2 2/2019 Clube
10,300,043 B2 5/2019 Kashyap et al.
10,300,138 B2 5/2019 Clube
10,300,139 B2 5/2019 Clube
10,363,308 B2 7/2019 Clube et al.
10,463,049 B2 11/2019 Clube et al.
10,506,812 B2 12/2019 Clube
10,524,477 B2 1/2020 Clube et al.
10,561,148 B2 2/2020 Clube
10,582,712 B2 3/2020 Clube et al.
10,596,255 B2 3/2020 Clube
10,603,379 B2 3/2020 Clube et al.
10,624,349 B2 4/2020 Clube
10,738,289 B2 8/2020 Silva et al.
10,751,427 B2 8/2020 Clube
10,760,075 B2 9/2020 Sommer et al.
10,765,740 B2 9/2020 Clube
10,920,222 B2 2/2021 Sommer et al.
10,953,090 B2 3/2021 Clube et al.
10,993,930 B2 5/2021 Kashyap et al.
11,141,481 B2 10/2021 Clube
11,147,830 B2 10/2021 Clube
11,291,723 B2 4/2022 Clube
11,351,252 B2 6/2022 Clube
11,400,110 B2 8/2022 Clube
11,421,227 B2 8/2022 Sommer et al.
11,471,530 B2 10/2022 Clube
11,471,531 B2 10/2022 Clube et al.
11,485,973 B2 11/2022 Sommer et al.
11,517,582 B2 12/2022 Clube et al.
11,547,716 B2 1/2023 Clube
11,578,333 B2 2/2023 Martinez et al.
11,612,617 B2 3/2023 Clube
11,629,350 B2 4/2023 Martinez et al.
11,642,363 B2 5/2023 Clube et al.
11,643,653 B2 5/2023 Sommer et al.
11,788,085 B2 10/2023 Sommer et al.
11,844,760 B2 12/2023 Clube et al.
11,851,663 B2 12/2023 Martinez et al.
(Continued)

FOREIGN PATENT DOCUMENTS

CA 3009194 A1 * 7/2017 ......... A61K 39/0011
EP 2951295 B1 8/2018
(Continued)

OTHER PUBLICATIONS

UniProt A0A2J4R842 (Year: 2018).*
Unitprot A0A024HVG4 (Year: 2019).*
UniProt A0A218N5E7 (Year: 2019).*
UniProt A0A483H222 (Year: 2018).*
Kleinstiver (Nature biotechnology 33.12 (2015): 1293-1298) (Year: 2015).*
Becker (Genome Announcements 3.4 (2015): 10-1128) (Year: 2015).*
Ma (Molecular plant 8.8 (2015): 1274-1284) (Year: 2015).*
(Continued)

*Primary Examiner* — Neil P Hammell
*Assistant Examiner* — Kyle T Rega
(74) *Attorney, Agent, or Firm* — MORRISON & FOERSTER LLP

(57) ABSTRACT

The technology described herein relates to new CRISPR/Cas systems and components thereof, vectors, proteins, fusion proteins, ribonucleoprotein complexes and methods of using the new system and components. The new system can be used in CRISPRi applications and can be fused to any number of effector domain modalities, such as nucleases, base editors, prime editors and the like to perform various DNA modifications.

31 Claims, 30 Drawing Sheets

Specification includes a Sequence Listing.

(56) References Cited

U.S. PATENT DOCUMENTS

| | | | |
|---|---|---|---|
| 11,878,002 | B2 | 1/2024 | Kashyap et al. |
| 11,891,629 | B2 | 2/2024 | Clube |
| 11,931,426 | B2 | 3/2024 | Clube |
| 12,076,375 | B2 | 9/2024 | Haaber et al. |
| 12,178,884 | B2 | 12/2024 | Clube |
| 12,318,445 | B2 | 6/2025 | Clube |
| 2015/0376585 | A1 | 12/2015 | Silva et al. |
| 2016/0333348 | A1 | 11/2016 | Clube et al. |
| 2017/0196225 | A1 | 7/2017 | Clube et al. |
| 2017/0246221 | A1 | 8/2017 | Clube et al. |
| 2017/0260513 | A1 | 9/2017 | Silva et al. |
| 2018/0064114 | A1 | 3/2018 | Clube |
| 2018/0064115 | A1 | 3/2018 | Clube et al. |
| 2018/0070594 | A1 | 3/2018 | Clube et al. |
| 2018/0084785 | A1 | 3/2018 | Clube |
| 2018/0084786 | A1 | 3/2018 | Clube |
| 2018/0140698 | A1 | 5/2018 | Clube et al. |
| 2018/0146681 | A1 | 5/2018 | Clube |
| 2018/0273940 | A1 | 9/2018 | Sommer et al. |
| 2018/0303934 | A1 | 10/2018 | Clube et al. |
| 2018/0326057 | A1 | 11/2018 | Clube et al. |
| 2018/0326093 | A1 | 11/2018 | Clube |
| 2019/0133135 | A1 | 5/2019 | Clube |
| 2019/0134194 | A1 | 5/2019 | Clube et al. |
| 2019/0160120 | A1 | 5/2019 | Haaber |
| 2019/0230936 | A1 | 8/2019 | Clube |
| 2019/0240325 | A1 | 8/2019 | Clube |
| 2019/0240326 | A1 | 8/2019 | Clube |
| 2019/0321468 | A1 | 10/2019 | Clube |
| 2019/0321469 | A1 | 10/2019 | Clube et al. |
| 2019/0321470 | A1 | 10/2019 | Clube |
| 2020/0030444 | A1 | 1/2020 | Clube |
| 2020/0068901 | A1 | 3/2020 | Clube et al. |
| 2020/0077663 | A1 | 3/2020 | Clube et al. |
| 2020/0085066 | A1 | 3/2020 | Clube |
| 2020/0087660 | A1 | 3/2020 | Sommer et al. |
| 2020/0115716 | A1 | 4/2020 | Martinez et al. |
| 2020/0121787 | A1 | 4/2020 | Clube |
| 2020/0128832 | A1 | 4/2020 | Clube et al. |
| 2020/0164070 | A1 | 5/2020 | Clube |
| 2020/0205416 | A1 | 7/2020 | Clube |
| 2020/0254035 | A1 | 8/2020 | Haaber |
| 2020/0267992 | A1 | 8/2020 | Clube |
| 2020/0337313 | A1 | 10/2020 | Clube et al. |
| 2020/0390886 | A1 | 12/2020 | Clube |
| 2021/0009996 | A1 | 1/2021 | Sommer et al. |
| 2021/0060180 | A1 | 3/2021 | Clube |
| 2021/0113689 | A1 | 4/2021 | Clube |
| 2021/0147827 | A1 | 5/2021 | Clube |
| 2021/0147857 | A1 | 5/2021 | Clube |
| 2021/0163960 | A1 | 6/2021 | Martinez et al. |
| 2021/0189406 | A1 | 6/2021 | Martinez et al. |
| 2021/0198665 | A1 | 7/2021 | Sommer et al. |
| 2021/0230559 | A1 | 7/2021 | Clube |
| 2021/0283167 | A1 | 9/2021 | Clube |
| 2021/0290654 | A1 | 9/2021 | Clube |
| 2021/0386773 | A1 | 12/2021 | Clube |
| 2022/0162270 | A1 | 5/2022 | Szabolcs |
| 2022/0170013 | A1 | 6/2022 | Liu et al. |
| 2022/0233575 | A1 | 7/2022 | Clube et al. |
| 2022/0241318 | A1 | 8/2022 | Clube et al. |
| 2022/0259588 | A1 | 8/2022 | Sommer et al. |
| 2022/0273696 | A1 | 9/2022 | Clube |
| 2022/0275380 | A1 | 9/2022 | Porse |
| 2022/0282245 | A1 | 9/2022 | Sommer et al. |
| 2022/0290133 | A1 | 9/2022 | Sommer et al. |
| 2022/0362280 | A1 | 11/2022 | Clube |
| 2022/0387559 | A1 | 12/2022 | Haaber et al. |
| 2023/0193241 | A1 | 6/2023 | Clube et al. |
| 2023/0248822 | A1 | 8/2023 | Clube |
| 2023/0330167 | A1 | 10/2023 | Haaber |
| 2023/0364268 | A1 | 11/2023 | Clube |
| 2024/0082289 | A1 | 3/2024 | Clube et al. |
| 2024/0117323 | A1 | 4/2024 | Clube |
| 2024/0141365 | A1 | 5/2024 | Martinez et al. |
| 2024/0384279 | A1 | 11/2024 | Munck et al. |
| 2025/0043291 | A1 | 2/2025 | Le Miere et al. |
| 2025/0049895 | A1 | 2/2025 | Haaber et al. |
| 2025/0161345 | A1 | 5/2025 | Clube et al. |
| 2025/0186479 | A1 | 6/2025 | Clube et al. |
| 2025/0186625 | A1 | 6/2025 | Clube |

FOREIGN PATENT DOCUMENTS

| | | | |
|---|---|---|---|
| EP | 4428233 | A1 | 9/2024 |
| WO | 2014/118719 | A1 | 8/2014 |
| WO | 2014/121222 | A1 | 8/2014 |
| WO | 2015/136541 | A2 | 9/2015 |
| WO | 2016/141108 | A1 | 9/2016 |
| WO | 2016/177682 | A1 | 11/2016 |
| WO | 2016/201380 | A1 | 12/2016 |
| WO | 2017/074566 | A1 | 5/2017 |
| WO | 2017/123418 | A1 | 7/2017 |
| WO | 2017/123559 | A2 | 7/2017 |
| WO | 2017/136792 | A2 | 8/2017 |
| WO | 2018/213771 | A1 | 11/2018 |
| WO | 2019/014391 | A1 | 1/2019 |
| WO | 2019/168953 | A1 | 9/2019 |
| WO | 2019/232415 | A1 | 12/2019 |
| WO | 2020/097424 | A1 | 5/2020 |
| WO | 2020/123483 | A1 | 6/2020 |
| WO | 2020/181178 | A1 | 9/2020 |
| WO | 2020/181180 | A1 | 9/2020 |
| WO | 2020/181193 | A1 | 9/2020 |
| WO | 2020/181195 | A1 | 9/2020 |
| WO | 2020/181202 | A1 | 9/2020 |
| WO | 2020/229372 | A1 | 11/2020 |
| WO | 2020/232063 | A1 | 11/2020 |
| WO | 2020/252370 | A1 | 12/2020 |
| WO | 2020/257610 | A1 | 12/2020 |
| WO | 2020/257707 | A1 | 12/2020 |
| WO | 2021/146394 | A1 | 7/2021 |
| WO | 2021/146397 | A1 | 7/2021 |
| WO | 2021/163421 | A1 | 8/2021 |
| WO | 2021/173808 | A1 | 9/2021 |
| WO | 2021/188618 | A1 | 9/2021 |
| WO | 2021/188819 | A1 | 9/2021 |
| WO | 2021/242897 | A1 | 12/2021 |
| WO | 2022/063986 | A2 | 3/2022 |
| WO | 2022/072636 | A1 | 4/2022 |
| WO | 2022/097070 | A1 | 5/2022 |
| WO | 2022/146718 | A1 | 7/2022 |
| WO | 2022/150779 | A1 | 7/2022 |
| WO | 2022/169909 | A2 | 8/2022 |
| WO | 2022/204406 | A1 | 9/2022 |
| WO | 2022/221273 | A1 | 10/2022 |
| WO | 2023/098482 | A1 | 6/2023 |
| WO | 2023/098485 | A1 | 6/2023 |
| WO | 2023/225667 | A2 | 11/2023 |
| WO | 2024/184403 | A2 | 9/2024 |

OTHER PUBLICATIONS

Hua (Molecular plant 12.7 (2019): 1003-1014) (Year: 2019).*

Kummari (Journal of biosciences 45.1 (2020): 119) (Year: 2020).*

Guzman (Journal of bacteriology 177.14 (1995): 4121-4130) (Year: 1995).*

Electrocompetent *E. coli*, "Making Electrocompetent *E. coli* Cells (small batch)", available online at:: <https://barricklab.org/twiki/bin/view/Lab/ProtocolsElectrocompetentCells>, Dec. 10, 2024, 2 pages.

Gawin, A. et al. (Mar. 9, 2017). "The XylS/Pm Regulator/Promoter System and its Use in Fundamental Studies of Bacterial Gene Expression, Recombinant Protein Production and Metabolic Engineering," Microb. Biotechnol. 10 (4):702-718.

Hamilton, T.A. et al. (2019). "Efficient Inter-Species Conjugative Transfer of a CRISPR Nuclease for Targeted Bacterial Killing," Nature Comms. 10:4544, 9 pages.

International Search Report and Written Opinion, mailed Dec. 19, 2024, for PCT Application No. PCT/EP2024/074264, filed Aug. 31, 2023, 19 pages.

(56) References Cited

OTHER PUBLICATIONS

Kelly, C.L. et al. (Mar. 15, 2016). "A Rhamnose-Inducible System for Precise and Temporal Control of Gene Expression in Cyanobacteria," ACS Synth. Biol. 7(4):1056-1066.
Mimee, M. et al. (Jul. 29, 2015). "Programming a Human Commensal Bacterium, Bacteroides thetaiotaomicron, to Sense and Respond to Stimuli in the Murine Gut Microbiota," Cell Syst. 1(1):62-71.62-71.
Rincón, A.F.C. et al. (2023). "Unlocking the Strength of Inducible Promoters in Gram-Negative Bacteria," Microb. Biotechnol. 16(5):961-976.
Rodriguez-Garcia, A. et al. (Jan. 1, 2005). "Natural and Synthetic Tetracycline-Inducible Promoters for use in the Antibiotic-Producing Bacteria Streptomyces," Nucleic Acids Research 33(9):e87, 9 pages. Supplementary Information.
Ruiz, L. et al. (2012). "Controlled Gene Expression in Bifidobacteria by Use of a Bile-Responsive Element," Appl. Environ. Microbiol. 78(2):581-585.
Villaverde, A. et al. (Oct. 1993). "Fine Regulation of cl857-Controlled Gene Expression in Continuous Culture of Recombinant *Escherichia coli* by Temperature," Appl. Environ. Microbiol. 59(10):3485-3487.
Wegerer, A. et al. (Jan. 14, 2008). "Optimization of an *E. coli* L-rhamnose-Inducible Expression Vector: Test of Various Genetic Module Combinations," BMC Biotechnology 8(2):1-12.
Villa, L. et al. (2012, e-pub. Apr. 17, 2012). "Completed Sequencing of an IncH Plasmid Carrying the blaNDM-1, blaCTX-M-15 and qnrB1 Genes," Journal of Antimicrobial Chemotherapy 67:1645-1650.
Wang, H. et al. (Aug. 20, 2018). "Delivery of the Cas9 or TevCas9 Systems into Phaeodactylum tricornutum via Conjugation of Plasmids from a Bacterial Donor," Bio-protocol 8(16):1-14.
Wolfs, J.M. et al. (Dec. 27, 2016). "Biasing Genome-Editing Events Toward Precise Length Deletions with an RNA-Guided TevCas9 Dual Nuclease," Proc. Natl. Acad. Sci. USA 113(52):14988-14993.
Young et al., "The repurposing of type I-E CRISPR-Cascade for gene activation in plants—supplementary tables", Communications Biology, Oct. 18, 2019, XP093106642.
Young, J. et al. (Oct. 18, 2019). "The Repurposing of Type I-E CRISPR-Cascade for Gene Activation in Plants," Communications Biology 2(383):1-7.
Zhao, D. et al. (Jan. 2020). "Glycosylase Base Editors Enable C-to-A and C-to-G Base Changes," Nature Biotechnology 39(1):35-40.
Zheng, Y et al. (Mar. 4, 2020). "Endogenous Type I CRISPR-Cas: From Foreign DNA Defense to Prokaryotic Engineering," Frontiers in Bioengineering and Biotechnology 8(62):1-17.
Anonymous et al. (Jun. 27, 2023). "Conference Program," CRISPER 2023, TOC, 14 pages.
Becker, L. et al. (Jul. 9, 2015). "Complete Genome Sequence of a CTX-M-15-Producing Klebsiella pneumoniae Outbreak Strain from Multilocus Sequence Type 514," Genome Announcements 3(4):e00742-15, 2 pages.
Benz, F. (Jun. 2023). "In Trans Adaptation and RNA-Guided Silencing by a Klebsiella Plasmid-Encoded Type IV-A3 CRISPR-Cas," Institut Pasteur, Abstract Only, 1 page.
Benz, F. et al. (Jun. 23, 2023). "Type IV-A3 CRISPR-Cas Systems Drive Inter-Plasmid Conflicts by Acquiring Spacers in trans," bioRxiv, 45 pages.
Cepatie, R. et al. (Jun. 2023). "Structural Basis of Type IV-A Mediated CRISPR Interference," LSC-EMBL Partnership Institute for Genome Editing Technologies, Abstract Only, 1 page.
Cepatie, R. et al. (Jun. 2023). "Structural Basis of Type IV-A Mediated CRISPR Interference," LSC-EMBL Partnership Institute for Genome Editing Technologies, Poster, 1 page.
Chen, L. et al. (2020). "Precise and Programmable C:G to G:C Base Editing in Genomic DNA,", Biorxiv, 19 pages.
Cui, L. et al. (2018). "A CRISPRi Screen in *E. coli* Reveals Sequence-Specific Toxicity of dCas9," Nature Comm. 9:1912, 10 pages.
Database (Jul. 14, 2015). "CP011314.1—*Klebsiella pneumoniae* Subsp. *pneumoniae* Strain 234-12 Plasmid pKpn23412-362, Complete Sequence," 159 pages.
Database (Jul. 26, 2016). "HG918041—Klebsiella Pneumoniae Kp15 Plasmid pENVA Complete Sequence," 116 pages.
Database (Jul. 26, 2022). "ON256214—*Zea mays* Cultivar Jing724 bHLH Transcription Factor ZmR1 (ZmR1) Gene," 4 pages.
Edgell, D.R. et al. (Jul. 3, 2001). "Related homing Endonucleases I-Bmol and I-Tevl Use Different Strategies to Cleave Homologous Recognition Sites," Proc. Natl. Acad. Sci. USA 98(14):7898-7903.
Gaudelli, N.M. et al. (Nov. 23, 2017). "Programmable Base Editing of A•T to G•C in Genomic DNA Without DNA Cleavage," Nature 551(7681):464-471, 37 pages.
GB2212688.2 (Feb. 21, 2023). Patents Act 1977: Search Report under Section 17, 2 pages.
Guo, X. et al. (Nov. 2022, e-pub. Sep. 29, 2022). "Characterization of the Self-Targeting Type IV CRISPR Interference System in Pseudomonas oleovorans," Nature Microbiology 7:1870-1878.
Guzman, L.-M. et al. (Jul. 1995). "Tight Regulation, Modulation, and High-Level Expression by Vectors Containing the Arabinose PBAD Promoter," J. Bacteriol. 77(14):4121-4130.
Hancks, D.C. et al. (Jun. 2012). "Active Human Retrotransposons: Variation and Disease," Curr. Opin. Genet. Dev. 22(3):191-203, 20 pages.
International Search Report and Written Opinion, mailed Dec. 19, 2023, for PCT Application No. PCT/EP2023/073881, filed Aug. 31, 2023, 14 pages.
Jackson, R. (Jun. 2023). "Structure and Function of Type IV CRISPR Systems and Their Anti-CRISPRS," Utah State University, Abstract Only, 1 page.
Jia, N. (Jun. 2023). "Type IV-A CRISPR-Csf Complex: Assembly, dsDNA Targeting and CasDinG Recruitment," Southern University of Science and Technology, Abstract Only, 1 page.
Jinek, M. et a. (Aug. 17, 2012). "A Programmable Dual RNA-Guided DNA Endonuclease in Adaptive Bacterial Immunity," Science 337(6096):816-821.
Kalderon, D. et al. (Dec. 1984). "A Short Amino Acid Sequence Able to Specify Nuclear Location," Cell 39(3):499-509.
Kleinstiver, B.P. et al. (Jun. 2014). "The I-Tevl Nuclease and Linker Domains Contribute to the Specificity of Monomeric TALENs," G3—Genes Genomes Genetics 4:1155-1165.
Kleinstiver, B.P. et al. (May 22, 2012). "Monomeric Site-Specific Nucleases for Genome Editing," Proc. Natl. Acad. Sci. USA 109(21):8061-8066.
Komor, A.C. et al. (Oct. 20, 2016). "Programmable Editing of a Target Base in Genomic DNA Without Double-Stranded DNA Cleavage," Nature 533(7603):420-424.
Kurt, I.C. et al. (Jan. 2021). "CRISPR C-to-G Base Editors for Inducing Targeted DNA Transversions in Human Cells," Nature Biotechnology 39(1):41-46, 24 pages.
Leenay, R.T. et al. (Apr. 7, 2016). "Identifying and Visualizing Functional PAM Diversity Across CRISPR-Cas Systems," Technology 62(1):137-147.
Luo, M.L. et al. (2015, e-pub. Oct. 17, 2014). "Repurposing Endogenous Type I CRISPR-Cas Systems for Programmable Gene Repression," Nucleic Acids Research 43(1):674-681.
Luo, M.L. et al. (Oct. 17, 2014). Supplementary-Information—"Repurposing Endogenous Type I CRISPR-Cas Systems for Programmable Gene Repression," Nucleic Acids Research, pp. 15.
Makarova, K.S. et al. (Nov. 2015). "An Updated Evolutionary Classification fCRISPR-Cas Systems," Nat. Rev. Microbiol. 13(11):722-736, 31 pages.
Medina-Aparicio, L. et al. (2018, e-pub. Jan. 9, 2018). "The CRISPR-Cas System in Enterobacteriaceae," Pathogens and Disease 76(1):1-15.
Mol, C.D. et al. (Sep. 8, 1995). "Crystal Structure of Human Uracil-DNA Glycosylase in Complex with a Protein Inhibitor: Protein Mimicry of DNA," Cell, 82(5):701-708.
Newire, E. et al. (Aug. 12, 2020). "Identification of a Type IV-A CRISPR-Cas System Located Exclusively on IncHI1B/IncFIB Plasmids in Enterobacteriaceae," Frontiers in Microbiology 11(1937):1-11.

(56) References Cited

OTHER PUBLICATIONS

Nishida, K. et al. (Sep. 16, 2016). "Targeted Nucleotide Editing Using Hybrid Prokaryotic and Vertebrate Adaptive Immune Systems," Science 353(6305).aaf8729-1-aaf8729-8, 9 pages.
Office Action received for European Patent Application No. 23765455.3, mailed on May 28, 2024, 5 pages.
Özcan, A. et al. (2018). "Type IV CRISPR RNA Processing and Effector Complex Formation in Aromatoleum aromaticum," Nature Microbiology, 10 pages.
Pinilla-Redondo, R. et al. (2020, e-pub. Dec. 27, 2019). "Type IV CRISPR-Case Systems are Highly Diverse and Involved in Competition Between Plasmids," Nucleic Acids Research 48(4):2000-2012.
Qi, L. S. et al. (Feb. 28, 2013). "Repurposing CRISPR as an RNA-Guided Platform for Sequence-Specific Control of Gene Expression," Cell 152(5):1173-1183.
Randau, L. (Jun. 2023). "Functional and Structural Characterization of Type IV-A CRISPR-Cas Mediated CRIPR Interference," Philipps Universität Marburg, Abstract Only, 1 page.
Rath, D. et al. (2015, e-pub. Nov. 30, 2014). "Efficient Programmable Gene Silencing by Cascade," Nucleic Acids Research 43(1):237-246.
Response to Written opinion, dated Mar. 16, 2022, for European Patent Application No. 20702442.3, 14 pages.
Roey, P.V. et al. (2005). "Homing Endonuclease I-Tevl: An Atypical Zinc Finger with a Novel Function," Molecular Biology Intelligence Unit, pp. 35-38.
Roy, A.C. (Sep. 18, 2015). "Isolation and Characterisation of Relaxed Specificity I-Tevl Nuclease Domain Mutants," Western University, London, Ontario, 131 pages.
Sanchez-Londono, M. et al. (Jun. 2023). "Type IV-A CRISPR-Cas Activity of Pseudomonas oleovorans: Autoimmunity and Natural CRISPRi Regulation," Phillips-Universität Marburg, Abstract Only, 1 page.
Schellenberger, V. et al. (2009, e-pub Nov. 15, 2009). "A Recombinant Polypeptide Extends the in vivo Half-Life of Peptides and Proteins in a Tunable Manner," Nat. Biotechnol. 27(12):1186-1190.
Schlüter, A. et al. (Jul. 2014). "IncH-Type Plasmid Harboring blaCTX¬M-15, bla DHA-1 , and qnrB4 Genes Recovered from Animal Isolates," Antimicrobial Agents and Chemotherapy 58(7):3768-3773.
Semenova, E. et al. (Jun. 21, 2011). "Interference by Clustered Regularly Interspaced Short Palindromic Repeat (CRISPR) RNA is Governed by a Seed Sequence," Proc. Natl. Acad. Sci. USA 108(25):10098-10103.
Summons to Attend Oral Proceedings Pursuant to Rule 115(1) EPC, for European Patent Application No. 16719873.8, 40 pages.
Taylor, H.N. et al. (May 21, 2021). "Positioning Diverse Type IV Structures and Functions Within Class 1 CRISPR-Cas Systems," Frontiers in Microbiology 12(671522):1-10.
Updated Claim Letter for European Patent Application No. 23765455.3, dated Apr. 9, 2024, 18 pages.
International Preliminary Report on Patentability, issued Mar. 1, 2025 for PCT Application No. PCT/EP2023/073881, filed Aug. 31, 2023, 9 pages.
Uniprot "A0A345WXC7—CRISPR Type AFERR-Associated Protein Csf2," 3 pages.

* cited by examiner

*Constructs showing full activity

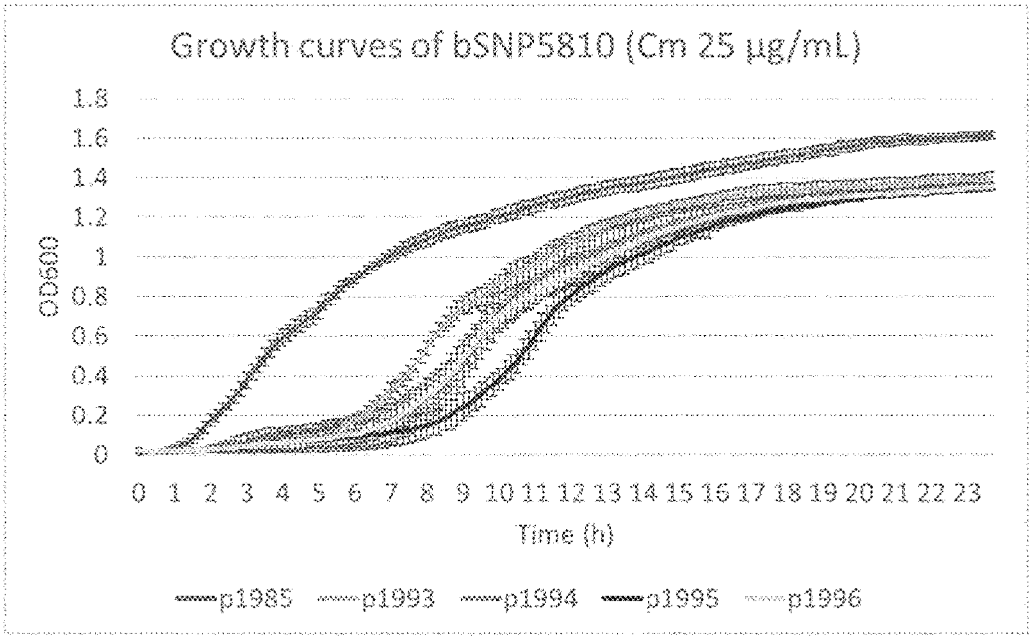
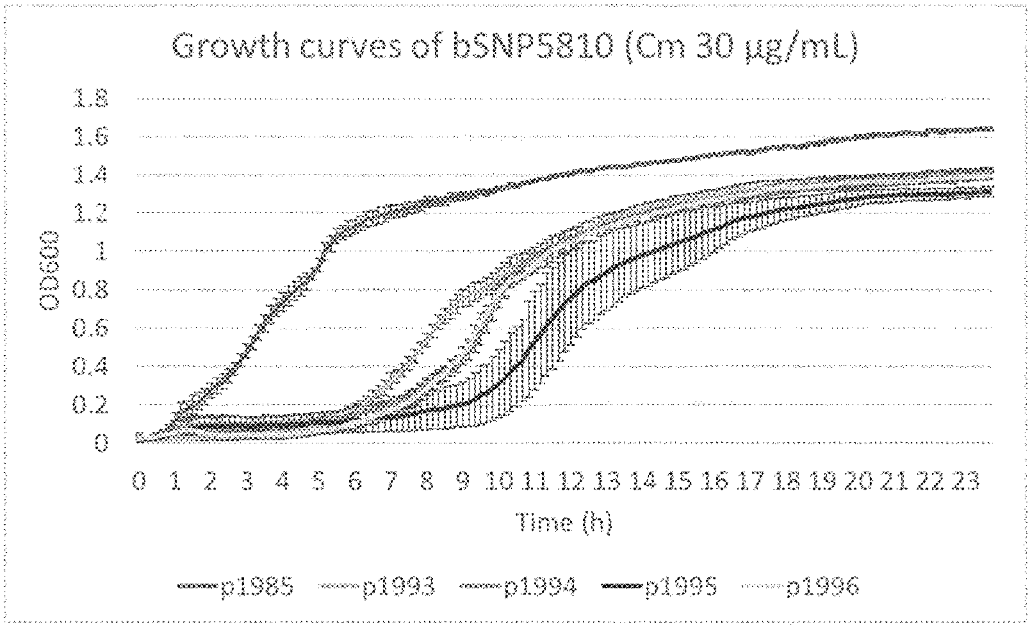
FIG. 10B

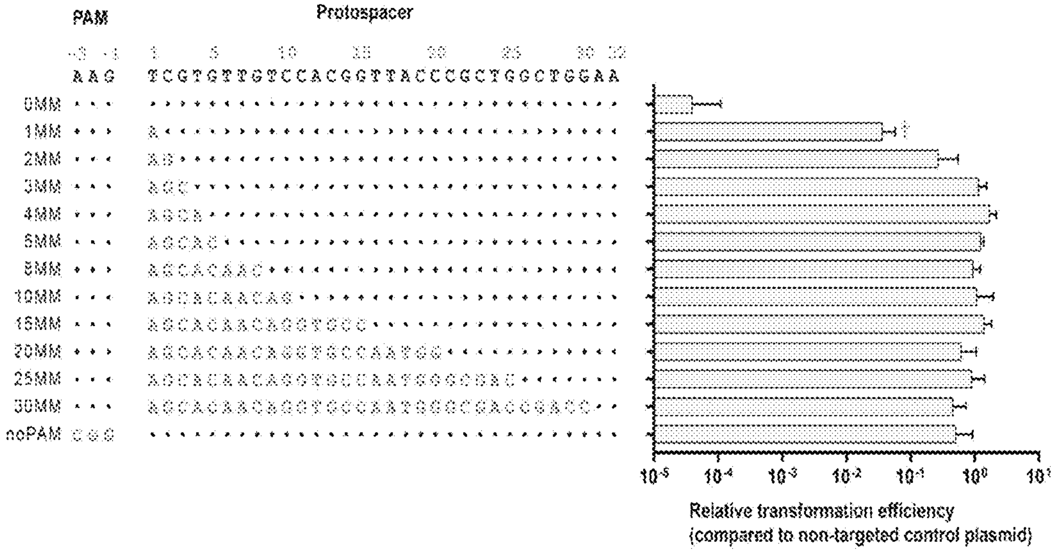
FIG. 13A: PAM proximal mismatches (stretches)
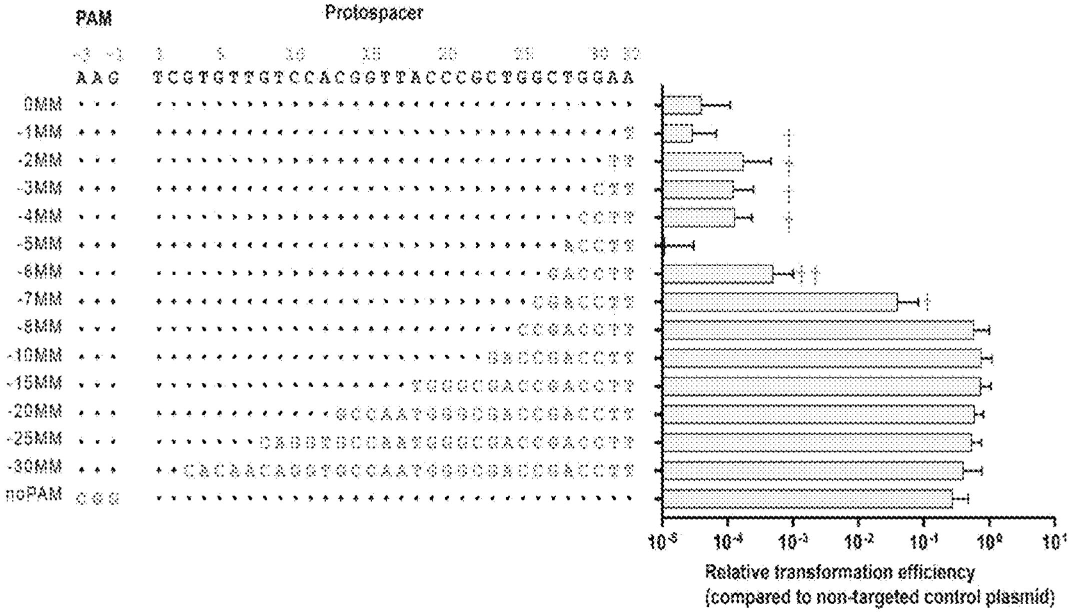
FIG. 13B: PAM distal mismatches (stretches)

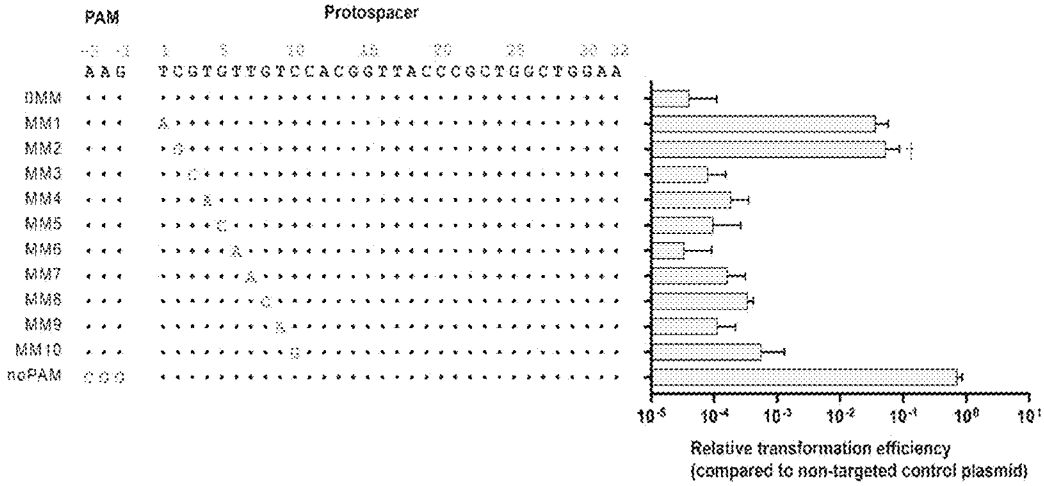
FIG. 13C: PAM proximal single mismatches
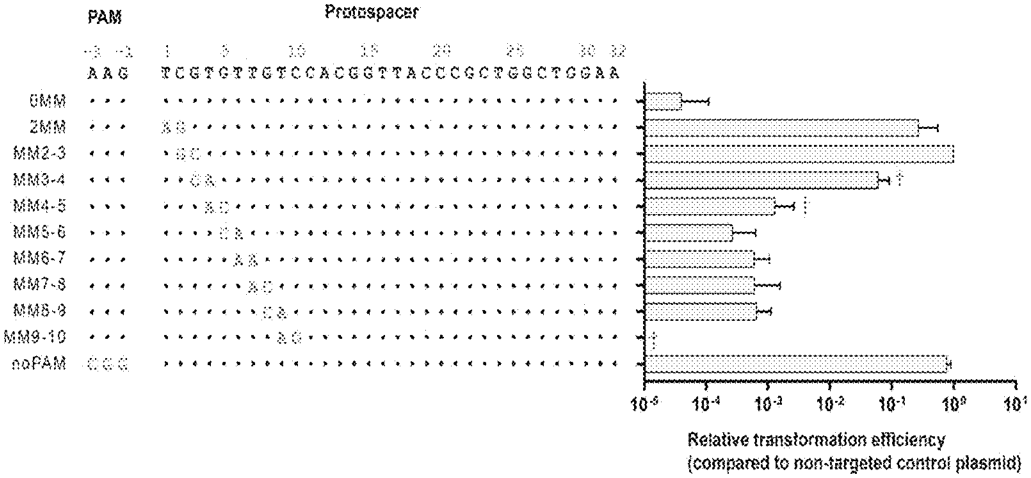
FIG. 13D: PAM proximal double mismatches
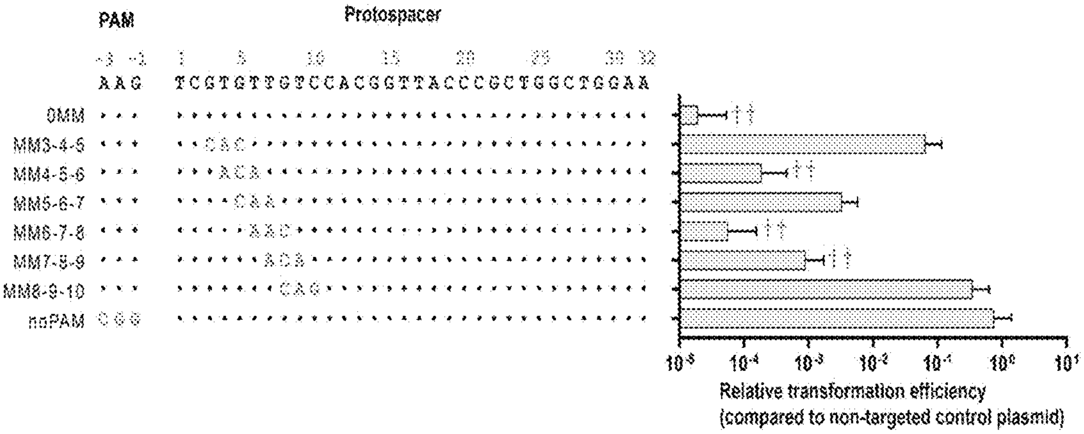
FIG. 13E: PAM proximal triple mismatches:

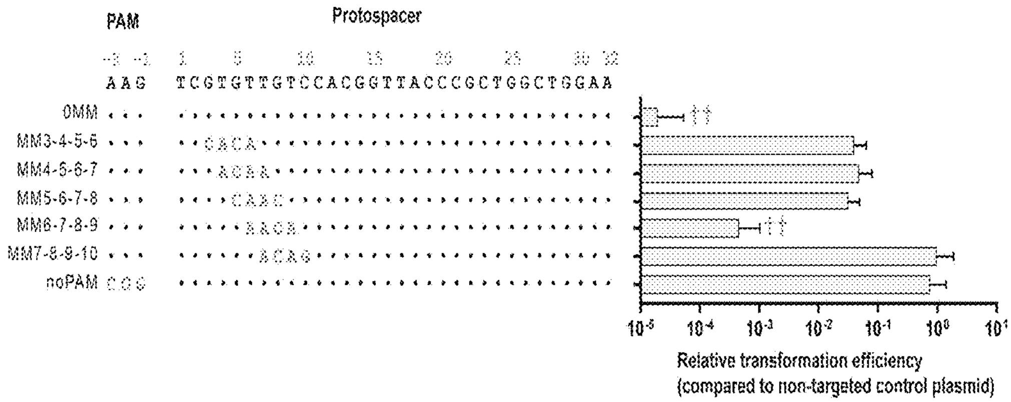
FIG. 13F: PAM proximal quadruple mismatches

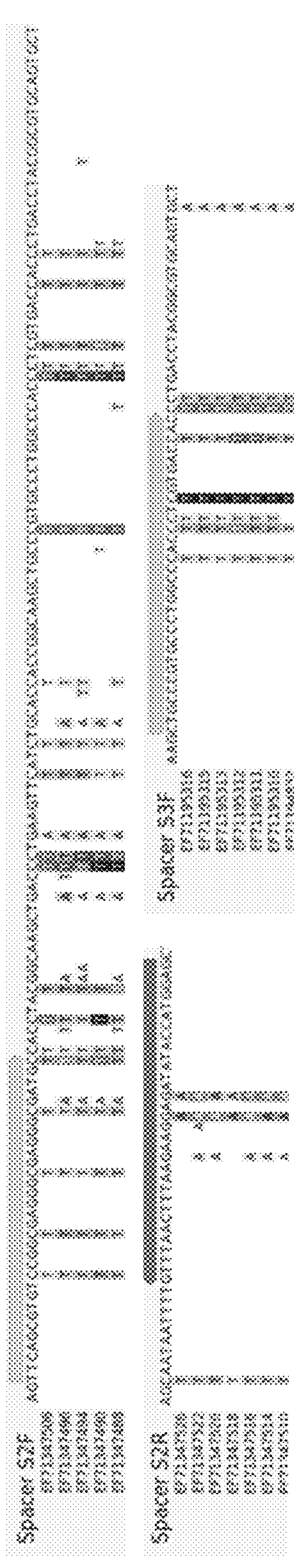
FIG. 21A: PmCDA1-Cas-S1
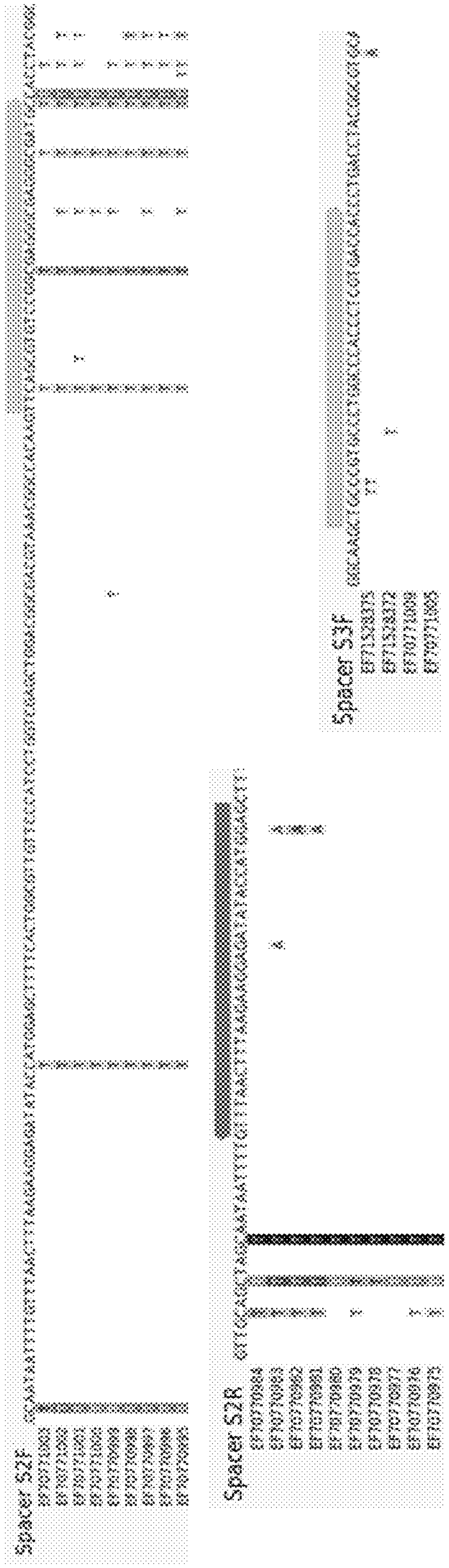
FIG. 21B: PmCDA1-Cas-S1 (Δcas-S3)

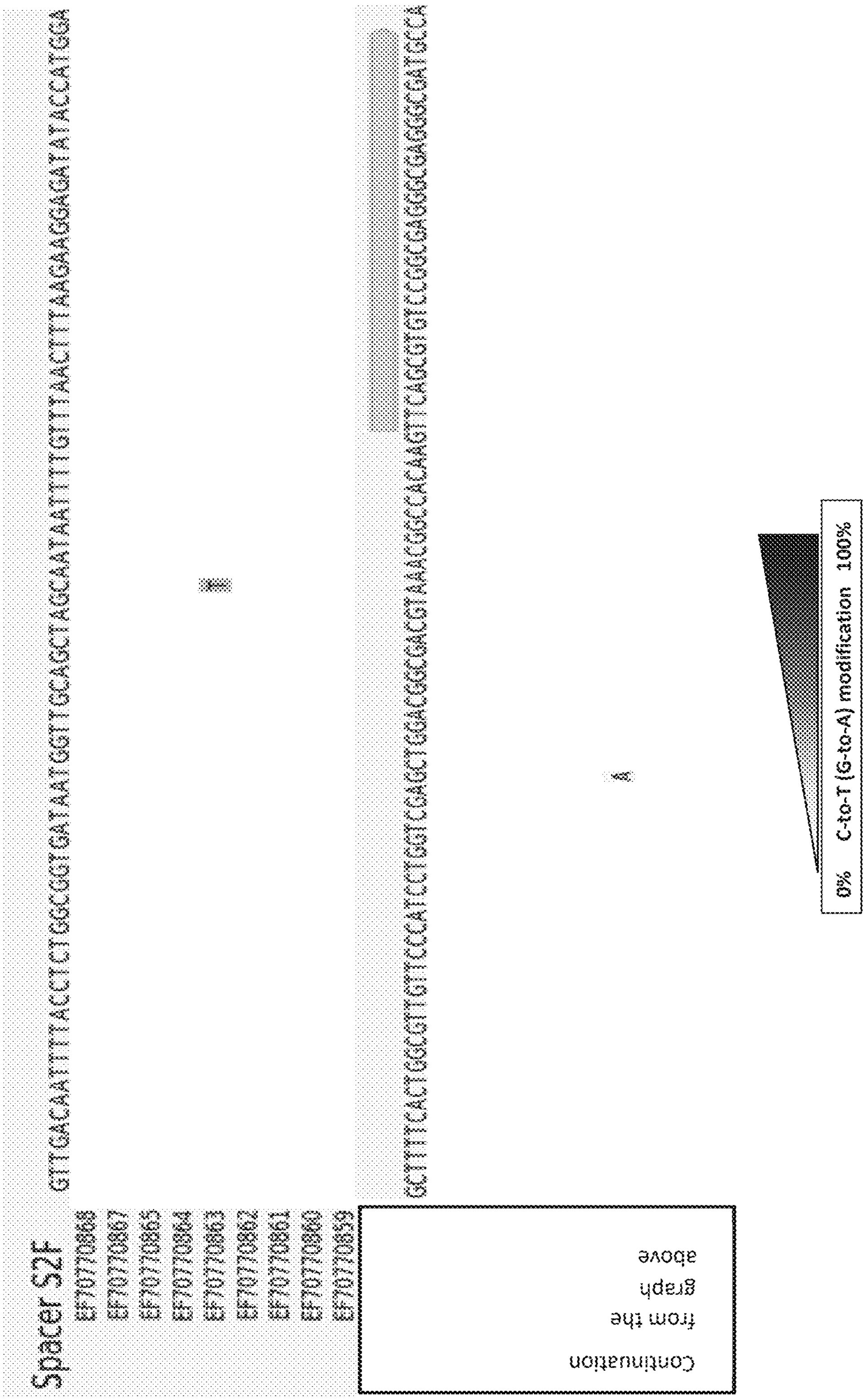
FIG. 21C: PmCDA1-Cas-S3

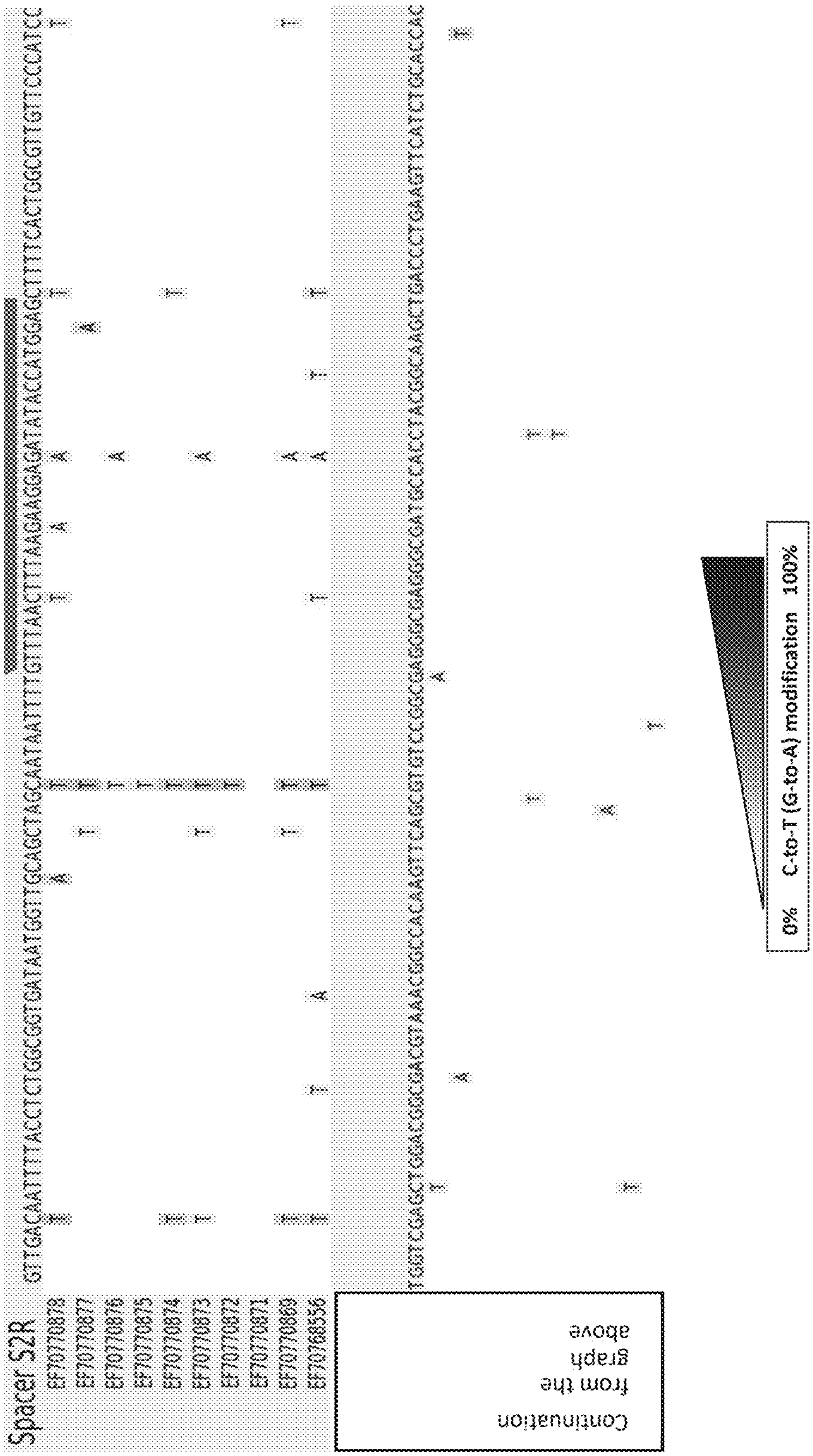
FIG. 21D : PmCDA1-Cas-S3

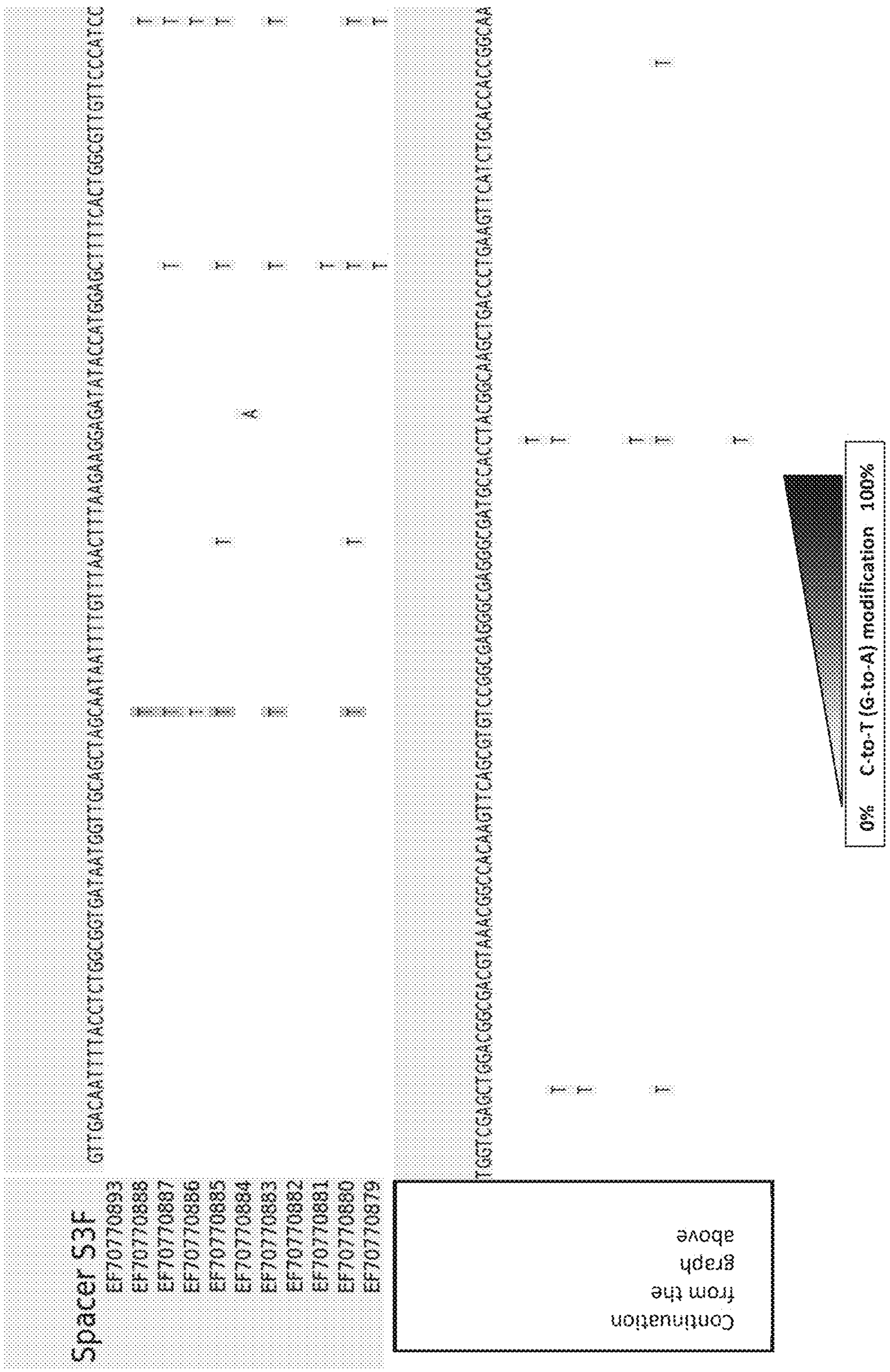
FIG. 21E : PmCDA1-Cas-S3

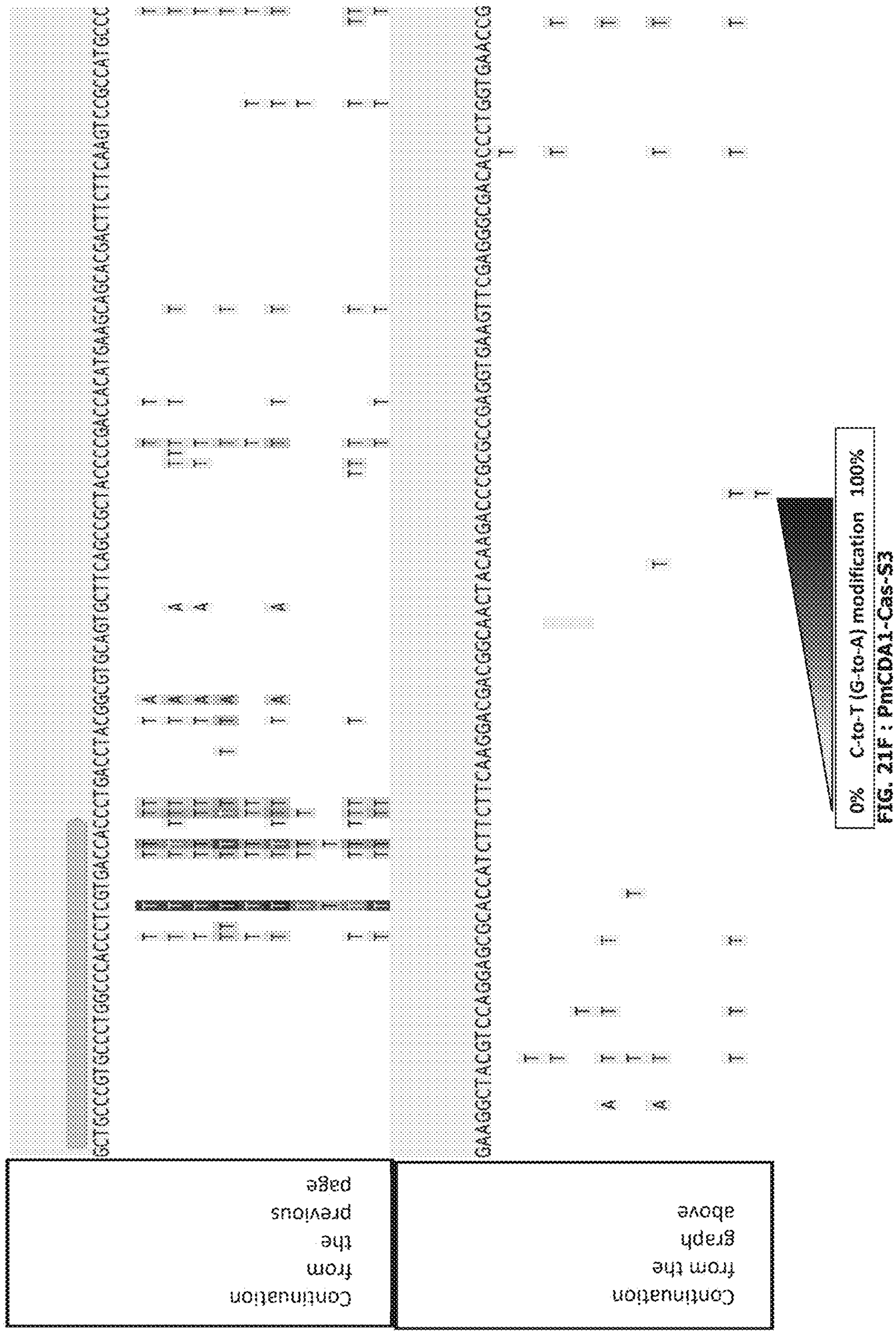
FIG. 21F : PmCDA1-Cas-S3

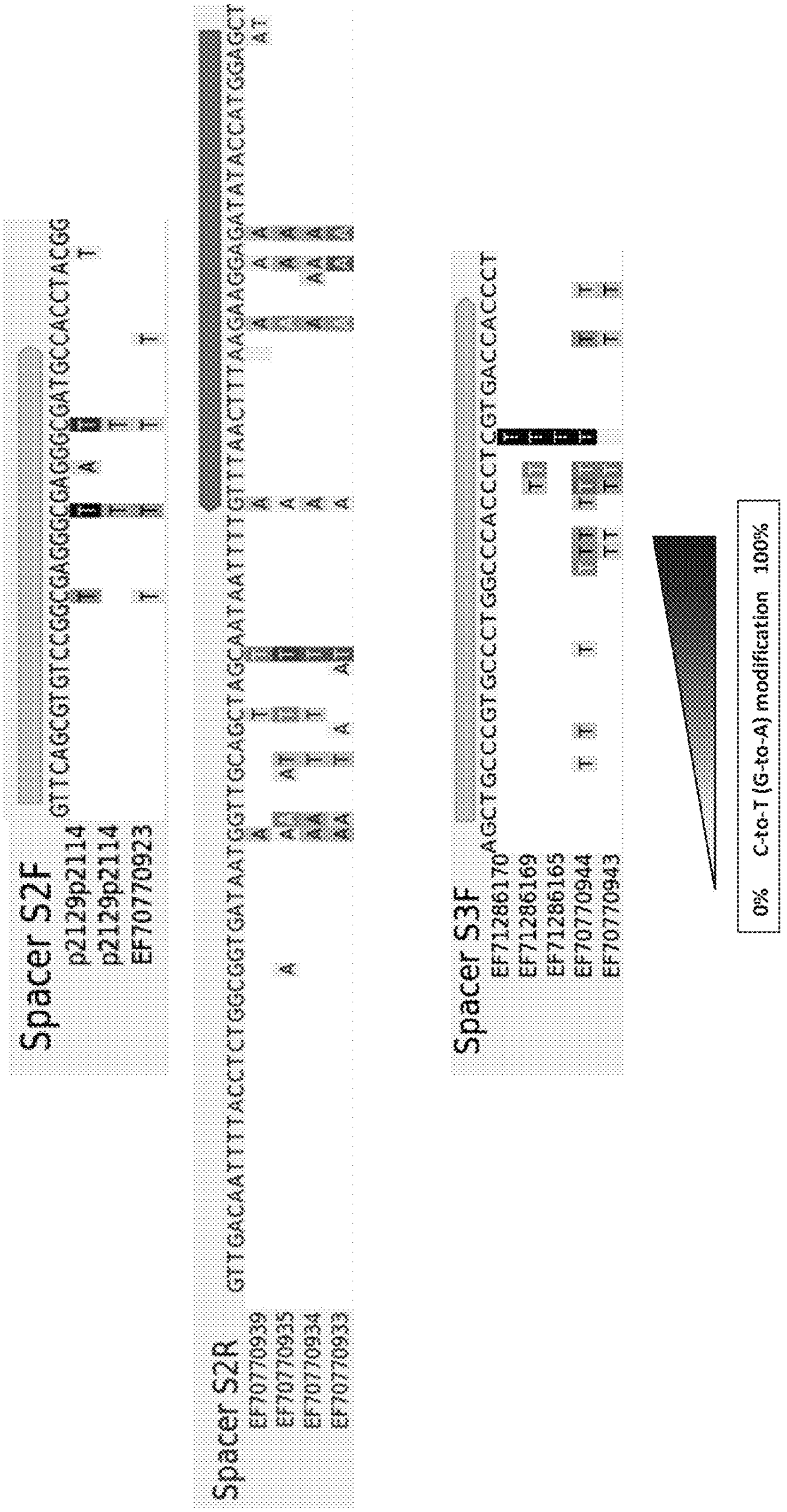
FIG. 21G: PmCDA1-Cas-S4

SEQUENCE LISTING

```
Sequence total quantity: 70
SEQ ID NO: 1            moltype = AA  length = 263
FEATURE                 Location/Qualifiers
source                  1..263
                        mol_type = protein
                        organism = synthetic construct
SEQUENCE: 1
LNHPVESVYS ALTSILLPYM GEPVPVQRNC SCCGRAPSEF DGVGFELVNA YRERVVHCRP  60
CQTFFVSAPE LMGVENPKKP TTGQKFGMWS GVGAVINVED NSSVLLAPQG VVNKLPEHFF  120
DHVEVITATS GQHLEYLFNT ELKFPLIYIQ NFGVKTYELV RSLRVSLSAD AIYTCADQLL  180
TRQNEVLYML DLTKAKELHQ EIKNYSKKEI DIFIRTVTLL AYSRITPEAA SNEFKKNNLI  240
PLLLLLPTDP HQRLSILHLL KKV                                           263

SEQ ID NO: 2            moltype = AA  length = 188
FEATURE                 Location/Qualifiers
source                  1..188
                        mol_type = protein
                        organism = synthetic construct
SEQUENCE: 2
MIYYDNAFRL RIRHTSVYQI HQHLDFFMQE RKGEKLPYSF KIFPGTGDDS LLLVRTATAL  60
ELPGEKKREL ILSEGHEIKF ITSMAIFHKG TKSEGRGRRQ FAPSEEASYQ LALTKLAKAG  120
FKPGQIVVSG PKFVHIVKGN AGRGFTLPVF TVQGTAIISN QQEAEVGIVY GVGPKRVFGC  180
GFMHLAGQ                                                            188

SEQ ID NO: 3            moltype = AA  length = 624
FEATURE                 Location/Qualifiers
source                  1..624
                        mol_type = protein
                        organism = synthetic construct
SEQUENCE: 3
MNTSAVFESA GLSLRKVQQD YIEAAAGALT QDHKVALISA ETGVGKTLGY LVPALLILLK  60
NPEAKFVIAT NSHALMHQIF RSDRPLLEQI AEQCGIKVTF SRLMGKANYV SLEKVRGLLL  120
MDEFTDLDTV KVLEKLANWS KPLVEFEEEY GELPAQITPE MVTYSIWDDI QDIDDIRLNA  180
LSANFIVTTH AMVMVDCMCN HRILGDKENM YLIIDEADIF VDMLEVWKQR RFNLRELTSA  240
FNEHIPRNGV HVIDQLMNDV TSIAGDLHFC STPAAVALFD NSFNALSKVG REIKNEAARK  300
AFFDCIYSWE MLGLSGGQKG VGVSNKRREP ALIAVNPFIG MNVGRYCTQW RSALLTSATL  360
SITSTPETGM EWLCKALGLT SDTISIRKIF SPDVYGSMKL TIAGADFPKV FNDPKEQIFS  420
GQWLKAVVEQ LSCIQGPALV LTASHYETRM IANQLGEVSQ PVYIQKAGQA LSEIIKQYQE  480
IPGILISAGA SVGVSPRGEN GEQIFQDLII TRIPFLPPDR MKAESLYGYL KERGYSRTFE  540
AVNRNIYLDN LRKVIRKAKQ SIGRGIRSEN DTVRIIILDP RFPEPTDLSS KHRSLEHIIP  600
VRFRRAYRSC EILSPAYCEE DIQC                                          624

SEQ ID NO: 4            moltype = AA  length = 235
FEATURE                 Location/Qualifiers
source                  1..235
                        mol_type = protein
                        organism = synthetic construct
```

```
SEQUENCE: 4
VLNFKPYRVI MSSLTPVVIS GIAPSLDGIL YEALSQAIPS NEPGVVLARL KEILLFNDEL  60
GVFHASSLRF GITPEQGIGA TTSVRCDYLS PEKLSTAMFS PRIHRGVFTR VLLTGGPTKR  120
RMTTRPAYSA PYLTFDFVGS SEAVEILLNH AHVGVGYDFF SAANGEFNNV TILPLDIDTS  180
ISNEGMALRP VPVNSGLNGI KGVSPLIPPY FVGEKLNIVH PAPVRTQLIS SLLRG       235

SEQ ID NO: 5           moltype = AA  length = 343
FEATURE                Location/Qualifiers
source                 1..343
                       mol_type = protein
                       organism = synthetic construct
SEQUENCE: 5
MRTLNFNGKI STLEPLTVTV KNAVSTSGHR LPRNGGFNAA PYFPGTSIRG TLRHAAHKVI  60
VDRVGLNADG KSSFDLAEHF MLAQGVDING EAETFAPGEI NAGAELRSKN PLISLFGRWG  120
LSGKVGIGNA IPDGDNQWGM FGGGARSIMF QRDESLMEFL ETDQVDRLER LLEEQAEASV  180
DISQIKTEQD ALKKAMKSAD KDTKAELQIK VRELDEKIQA RKDQKQESRE SIRRPIDPYE  240
AFITGAELSH RMSIKNATDE EAGLFISALI RFAAEPRFGG HANHNCGLVE AHWTVTTWKP  300
GELVPVTLGE IVITPNGVEI TGDELFAMVK AFNENQSFDF TAR                    343

SEQ ID NO: 6           moltype = DNA  length = 29
FEATURE                Location/Qualifiers
source                 1..29
                       mol_type = other DNA
                       organism = synthetic construct
SEQUENCE: 6
gtattccccc cgtgtgcggg ggttatcgg                                   29

SEQ ID NO: 7           moltype = DNA  length = 748
FEATURE                Location/Qualifiers
source                 1..748
                       mol_type = other DNA
                       organism = synthetic construct
SEQUENCE: 7
ttgaatcatc ctgtagagtc agtatatagc gctctgacga gtattttatt gccctatatg  60
ggtgagcctg tgcctgtgca acgaaattgc tcatgctgcg gcagagcgcc ctcagagttc  120
gacggggtag gcttcgagct ggtcaacgcc tacagggaac gtgttgtgca ttgccgtcct  180
tgccagacat tttttgtttc tgctccagaa ctgatgggcg tggagaaccc caaaaaacca  240
acaaccggcc agaaatttgg catgtggtct ggtgttgggg ctgttattaa cgttgaagac  300
aattcttcgg ttcttttagc ccctcaggga gtggtcaata aactacctga gcatttttc  360
gatcacgtag aagtcatcac ggccaccagc ggtcagcacc tggaatacct gtttaacacc  420
gaacttaaat tcccgctgat ttatattcaa aacttcggcg tgaaaaccta cgagcttgtt  480
cgctcactgc gggtcagtct gagtgccgac gcaatttata cctgtgccga tcaactactg  540
acccggcaga acgaagtcct ttacatgctg gatttaacaa aggctaaaga actccatcag  600
gaaataaaaa actactccaa aaaagagata gacatcttta tcagaacagt aaccctgctg  660
gcctattcgc ggataactcc tgaagctgcc tcgaatgagt ttaagaaaaa caacctcatt  720
ccgttactgc tgcttctgcc gactgatc                                    748

SEQ ID NO: 8           moltype = DNA  length = 567
FEATURE                Location/Qualifiers
source                 1..567
                       mol_type = other DNA
                       organism = synthetic construct
SEQUENCE: 8
atgatttact acgataatgc gtttcggttg cgtatccgtc acacaagtgt ttaccagatc  60
caccagcacc tggatttttt catgcaggaa cgtaagggag agaagctgcc gtactctttt  120
aaaatttttc ccggtaccgg ggatgattcg ttactcctgg tccgcacagc cacagctctg  180
gagttgccag gggagaaaaa aagagagctt attctctctg agggccatga aatcaagttc  240
attacgtcaa tggccatctt tcataaagga acaaagtcag aaggccgtgg ccgacgccag  300
tttgctccat ccgaagaggc tagttatcag ttggccctca ccaaattagc gaaggctggt  360
tttaaacccg gtcaaatcgt cgtcagtggc ccgaaattcg tccatatcgt caaaggaaat  420
gctggacgcg gttttacgct acccgtattc acggtacagg gtaccgccat aatcagcaat  480
caacaggaag ctgaagttgg aatcgtttat ggcgtaggcc ctaaacgcgt atttggttgc  540
ggtttcatgc atctggcggg gcagtag                                     567

SEQ ID NO: 9           moltype = DNA  length = 1871
FEATURE                Location/Qualifiers
source                 1..1871
                       mol_type = other DNA
                       organism = synthetic construct
SEQUENCE: 9
atgaatacat cagcggtatt tgagtctgcc ggattgtcgt tacgtaaggt ccaacaggat  60
tatatcgagg ctgcagctgg tgcgctgact caggatcata aagttgcact gattagtgct  120
gaaacaggtg taggaaaaac gctgggctat ctggtaccgg cgcttctgat tctgctgaaa  180
aacccagagg caaaatttgt gatagccacg aattctcatg ccctgatgca ccagatattc  240
agaagcgatc gtcctctcct tgaacagata gctgaacaat gcggcataaa agttactttt  300
tcccggctta tggggaaagc aaattacgta tccctggaga aagtacgtgg actgttactc  360
atggacgaat ttaccgatct ggatacggtt aaggtccttg aaaaactcgc taactggtca  420
aaacctctgg ttgagtttga agaagagtat ggtgaactgc cagcgcagat cacgccagag  480
atggtcacct actccatctg ggatgatata caggacattg atgatattcg cctgaatgct  540
```

```
ctcagtgcta actttatagt tacgacccat gcgatggtaa tggtcgactg tatgtgtaat  600
caccgcatcc tcggtgacaa agaaaatatg tacctcatta ttgatgaggc agacattttt  660
gtagatatgc ttgaggtctg gaaacagcgg cgcttcaacc tcagagagtt gaccagtgcg  720
ttcaatgaac atattccacg taatggcgtg catgtcatcg accagttaat gaacgacgtg  780
acttcgatag cgggcgatct gcatttttgt agtacgcctg cagcggttgc cttgtttgac  840
aatagcttta acgccttatc aaaggtaggg cgggaaataa aaaatgaagc ggcccggaaa  900
gctttctttg actgtatcta cagctgggaa atgctcggat tgtccggggg gcaaaagggt  960
gtaggcgttt ccaataaacg tcgtgaacca gccctgatcg ctgtaaaccc gtttatcggg  1020
atgaatgtgg gcagatactg cactcaatgg cgtagtgcgt tactgacgtc ggctacgctc  1080
tcaattacca gtaccccaga gaccggaatg gagtggttat gtaaagctct ggggttaacc  1140
agcgatacga tttcaatcag gaaaatattc tccccagacg tctatggctc aatgaagctg  1200
accatcgccg gtgctgattt tccaaaggtg ttcaatgacc cgaaagaaca gatattttca  1260
ggtcaatggt taaaggcagt agttgaacaa ttgtcctgta ttcaggggcc agctctggta  1320
ttaactgcca gccattatga aaccaggatg attgccaatc agctgggtga ggtctcgcaa  1380
ccagtttata ttcagaaagc aggtcaggcc ctgtccgaaa ttattaaaca gtatcaggag  1440
ataccaggga ttcttatttc tgccggtgct tctgttggtg tgagcccacg aggcgagaat  1500
ggggaacaga ttttccagga tttaatcatt acccggatac ctttcttacc tccggacaga  1560
atgaaggctg aaagccttta tgggtatctg aaggaacgag gctatagtcg tacctttgag  1620
gcagttaacc gtaacatcta cctggataat ttgcggaaag ttattcgtaa agcaaagcag  1680
tctatagggc gggggattcg tagtgaaaat gataccgtca ggataattat cctcgatccg  1740
cgtttcccgg aacctactga cctttcgtct aaacatcggt cgcttgaaca cattattccc  1800
gttcgatttc gtcgtgcata tcgttcgtgt gaaattttat ctccggcgta ttgtgaagag  1860
gatatccagt g                                                       1871
```

```
SEQ ID NO: 10          moltype = DNA  length = 708
FEATURE                Location/Qualifiers
source                 1..708
                       mol_type = other DNA
                       organism = synthetic construct
SEQUENCE: 10
gtgttaaatt ttaaaccgta tcgggtcatc atgtcttctc tgacaccggt ggtcatcagt  60
gggatagccc catcgctgga cggcattctg tatgaagcac tgtctcaggc gatacccagt  120
aacgagccag gagtcgtatt ggctcgtctt aaggaaatac ttctattcaa cgatgaactg  180
ggtgttttcc atgcttcatc tctacgtttt ggcataacgc ccgaacaggg gattggggcg  240
acaacaagcg tacgttgcga ttatctcagt cccgaaaaac tgagcactgc aatgttctct  300
cctcgtatcc acaggggggt gtttacgcgt gtcctcctga ccgggggccc cacgaagaga  360
aggatgacaa cccgtccagc ttattctgca ccctatttaa cgtttgattt tgtcggctct  420
tctgaggctg tagaaatact gcttaaccat gcccatgttg gcgttggtta tgactttttc  480
tctgcagcta atggagagtt taacaatgtg acaattcttc ctctcgatat cgacacgagt  540
atatccaacg agggtatggc attgcgtccg gtacctgtta attcgggtct gaatggtatc  600
aaaggagtat caccacttat tcctccctat ttcgttggtg aaaagctaaa cattgtccac  660
ccagcaccag ttcgtactca attgatttct tctttattgc gaggctaa                708
```

```
SEQ ID NO: 11          moltype = DNA  length = 1032
FEATURE                Location/Qualifiers
source                 1..1032
                       mol_type = other DNA
                       organism = synthetic construct
SEQUENCE: 11
atgagaactt taaacttcaa cggtaaaatt tcgactctgg aaccactgac tgtaacagta  60
aaaaatgcgg tctcaacttc cggccatcgc ttgcctcgta acggtggatt caatgcagcc  120
ccgtactttc caggtaccag cattcgggga actcttcgtc atgctgcgca taaggtcatt  180
gtcgatcgtg tgggccttaa tgcagacgga aaatcatcct tcgacctggc agaacatttc  240
atgctggccc agggggtgga tatcaatggt gaagccgaaa ccttcgcgcc aggtgaaatc  300
aatgctggtg ctgaactacg tagcaaaaac ccgttaatca gcttgtttgg tcgttgggga  360
ttaagcggca aagttggtat agggaatgct atcccggatg gtgataacca gtgggggatg  420
tttggtggtg gtgcccgctc aattatgttt cagcgtgacg aaagtctgat ggagtttctt  480
gagacagacc aggttgatcg tcttgaacgc ctgctcgagg aacaggctga ggcaagtgtg  540
gatatctctc agatcaaaac agagcaagat gcactcaaaa aggcgatgaa gtcggctgat  600
aaagacacca aagctgagct tcaaatcaaa gtacgggagc tcgatgaaaa aattcaggcc  660
cgcaaagatc agaagcagga atctcgcgag tcaattcgcc gcccgattga cccgtatgaa  720
gcgtttatca ccggcgcaga actcagccat cgcatgagta ttaaaaatgc gactgatgag  780
gaagcagggc ttttcatttc tgcattaatc cgctttgcag ccgaaccacg ttttggcggt  840
catgcgaatc ataactgcgg tctggtggag gctcactgga cagttacgac ctggaagccg  900
ggtgaactgg taccagttac acttggagaa atcgtcatca caccgaatgg tgttgagatt  960
accggggacg agttgtttgc tatggtaaag gcattcaatg aaaatcaatc ttttgatttc  1020
actgcccgct aa                                                      1032
```

```
SEQ ID NO: 12          moltype = DNA  length = 5636
FEATURE                Location/Qualifiers
source                 1..5636
                       mol_type = other DNA
                       organism = synthetic construct
SEQUENCE: 12
ttgaatcatc ctgtagagtc agtatatagc gctctgacga gtattttatt gccctatatg  60
ggtgagcctg tgcctgtgca acgaaattgc tcatgctgcg gcagagcgcc ctcagagttc  120
gacggggtag gcttcgagct ggtcaacgcc tacagggaac gtgttgtgca ttgccgtcct  180
tgccagacat tttttgtttc tgctccagaa ctgatgggcg tggagaaccc caaaaaacca  240
acaaccggcc agaaatttgg catgtggtct ggtgttgggg ctgttattaa cgttgaagac  300
```

-continued

```
aattcttcgg ttcttttagc ccctcaggga gtggtcaata aactacctga gcattttttc  360
gatcacgtag aagtcatcac ggccaccagc ggtcagcacc tggaatacct gtttaacacc  420
gaacttaaat tcccgctgat ttatattcaa aacttcggcg tgaaaaccta cgagcttgtt  480
cgctcactgc gggtcagtct gagtgccgac gcaatttata cctgtgccga tcaactactg  540
acccggcaga acgaagtcct ttacatgctg gatttaacaa aggctaaaga actccatcag  600
gaaataaaaa actactccaa aaaagagata gacatcttta tcagaacagt aaccctgctg  660
gcctattcgc ggataactcc tgaagctgcc tcgaatgagt ttaagaaaaa caacctcatt  720
ccgttactgc tgcttctgcc gactgatccc catcaacgcc tgagcatttt gcacctcttg  780
aaaaaggtat aaccatgatt tactacgata atgcgtttcg gttgcgtatc cgtcacacaa  840
gtgtttacca gatccaccag cacctggatt ttttcatgca ggaacgtaag ggagagaagc  900
tgccgtactc ttttaaaatt tttcccggta ccggggatga ttcgttactc ctggtccgca  960
cagccacagc tctggagttg ccaggggaga aaaaaagaga gcttattctc tctgagggcc  1020
atgaaatcaa gttcattacg tcaatggcca tctttcataa aggaacaaag tcagaaggcc  1080
gtggccgacg ccagtttgct ccatccgaag aggctagtta tcagttggcc ctcaccaaat  1140
tagcgaaggc tggttttaaa cccggtcaaa tcgtcgtcag tggcccgaaa ttcgtccata  1200
tcgtcaaagg aaatgctgga cgcggtttta cgctacccgt attcacggta cagggtaccg  1260
ccataatcag caatcaacag gaagctgaag ttggaatcgt ttatggcgta ggccctaaac  1320
gcgtatttgg ttgcggtttc atgcatctgg cggggcagta gtcatgaata catcagcggt  1380
atttgagtct gccggattgt cgttacgtaa ggtccaacag gattatatcg aggctgcagc  1440
tggtgcgctg actcaggatc ataaagttgc actgattagt gctgaaacag gtgtaggaaa  1500
aacgctgggc tatctggtac cggcgcttct gattctgctg aaaaacccag aggcaaaatt  1560
tgtgatagcc acgaattctc atgccctgat gcaccagata ttcagaagcg atcgtcctct  1620
ccttgaacag atagctgaac aatgcggcat aaaagttact ttttcccggc ttatggggaa  1680
agcaaattac gtatccctgg agaaagtacg tggactgtta ctcatggacg aatttaccga  1740
tctggatacg gttaaggtcc ttgaaaaact cgctaactgg tcaaaacctc tggttgagtt  1800
tgaagaagag tatggtgaac tgccagcgca gatcacgcca gagatggtca cctactccat  1860
ctgggatgat atacaggaca ttgatgatat tcgcctgaat gctctcagtg ctaactttat  1920
agttacgacc catgcgatgg taatggtcga ctgtatgtgt aatcaccgca tcctcggtga  1980
caaagaaaat atgtacctca ttattgatga ggcagacatt tttgtagata tgcttgaggt  2040
ctggaaacag cggcgcttca acctcagaga gttgaccagt gcgttcaatg aacatattcc  2100
acgtaatggc gtgcatgtca tcgaccagtt aatgaacgac gtgacttcga tagcgggcga  2160
tctgcatttt tgtagtacgc ctgcagcggt tgccttgttt gacaatagct ttaacgcctt  2220
atcaaaggta gggcgggaaa taaaaaatga agcggcccgg aaagctttct ttgactgtat  2280
ctacagctgg gaaatgctcg gattgtccgg ggggcaaaag ggtgtaggcg tttccaataa  2340
acgtcgtgaa ccagccctga tcgctgtaaa cccgtttatc gggatgaatg tgggcagata  2400
ctgcactcaa tggcgtagtg cgttactgac gtcggctacg ctctcaatta ccagtacccc  2460
agagaccgga atggagtggt tatgtaaagc tctggggtta accagcgata cgatttcaat  2520
caggaaaata ttctccccag acgtctatgg ctcaatgaag ctgaccatcg ccggtgctga  2580
ttttccaaag gtgttcaatg acccgaaaga acagatattt tcaggtcaat ggttaaaggc  2640
agtagttgaa caattgtcct gtattcaggg gccagctctg gtattaactg ccagccatta  2700
tgaaaccagg atgattgcca atcagctggg tgaggtctcg caaccagttt atattcagaa  2760
agcaggtcag gccctgtccg aaattattaa acagtatcag gagataccag ggattcttat  2820
ttctgccggt gcttctgttg gtgtgagccc acgaggcgag aatggggaac agattttcca  2880
ggatttaatc attacccgga tacctttctt acctccggac agaatgaagg ctgaaagcct  2940
ttatgggtat ctgaaggaac gaggctatag tcgtaccttt gaggcagtta accgtaacat  3000
ctacctggat aatttgcgga aagttattcg taaagcaaag cagtctatag ggcgggggat  3060
tcgtagtgaa aatgataccg tcaggataat tatcctcgat ccgcgtttcc cggaacctac  3120
tgacctttcg tctaaacatc ggtcgcttga acacattatt cccgttcgat ttcgtcgtgc  3180
atatcgttcg tgtgaaattt tatctccggc gtattgtgaa gaggatatcc agtgttaaat  3240
tttaaaccgt atcgggtcat catgtcttct ctgacaccgg tggtcatcag tgggatagcc  3300
ccatcgctgg acggcattct gtatgaagca ctgtctcagg cgatacccag taacgagcca  3360
ggagtcgtat tggctcgtct taaggaaata cttctattca acgatgaact gggtgttttc  3420
catgcttcat ctctacgttt tggcataacg cccgaacagg ggattggggc gacaacaagc  3480
gtacgttgcg attatctcag tcccgaaaaa ctgagcactg caatgttctc tcctcgtatc  3540
cacaggggggg tgtttacgcg tgtcctcctg accgggggcc ccacgaagag aaggatgaca  3600
acccgtccag cttattctgc accctattta acgtttgatt ttgtcggctc ttctgaggct  3660
gtagaaatac tgcttaacca tgcccatgtt ggcgttggtt atgacttttt ctctgcagct  3720
aatggagagt ttaacaatgt gacaattctt cctctcgata tcgacacgag tatatccaac  3780
gagggtatgg cattgcgtcc ggtacctgtt aattcgggtc tgaatggtat caaaggagta  3840
tcaccactta ttcctcccta tttcgttggt gaaaagctaa acattgtcca cccagcacca  3900
gttcgtactc aattgatttc ttctttattg cgaggctaat ttcatgagaa ctttaaactt  3960
caacggtaaa atttcgactc tggaaccact gactgtaaca gtaaaaaatg cggtctcaac  4020
ttccggccat cgcttgcctc gtaacggtgg attcaatgca gccccgtact ttccaggtac  4080
cagcattcgg ggaactcttc gtcatgctgc gcataaggtc attgtcgatc gtgtgggcct  4140
taatgcagac ggaaaatcat ccttcgacct ggcagaacat ttcatgctgg cccagggggt  4200
ggatatcaat ggtgaagccg aaaccttcgc gccaggtgaa atcaatgctg gtgctgaact  4260
acgtagcaaa aacccgttaa tcagcttgtt tggtcgttgg ggattaagcg gcaaagttgg  4320
tatagggaat gctatcccgg atggtgataa ccagtggggg atgtttggtg gtggtgcccg  4380
ctcaattatg tttcagcgtg acgaaagtct gatggagttt cttgagacag accaggttga  4440
tcgtcttgaa cgcctgctcg aggaacaggc tgaggcaagt gtggatatct ctcagatcaa  4500
aacagagcaa gatgcactca aaaaggcgat gaagtcggct gataaagaca ccaaagctga  4560
gcttcaaatc aaagtacggg agctcgatga aaaaattcag gcccgcaaag atcagaagca  4620
ggaatctcgc gagtcaattc gccgcccgat tgacccgtat gaagcgttta tcaccggcgc  4680
agaactcagc catcgcatga gtattaaaaa tgcgactgat gaggaagcag ggcttttcat  4740
ttctgcatta atccgctttg cagccgaacc acgttttggc ggtcatgcga atcataactg  4800
cggtctggtg gaggctcact ggacagttac gacctggaag ccgggtgaac tggtaccagt  4860
tacacttgga gaaatcgtca tcacaccgaa tggtgttgag attaccgggg acgagttgtt  4920
tgctatggta aaggcattca atgaaaatca atcttttgat ttcactgccc gctaactcca  4980
aaagctggtg gattttagtg gcgctattta atattttata atcaaccggt tatttttaga  5040
```

```
gtattccccc cgtgtgcggg ggttatcggt ggggcgttgt tgaataaata gatattatgc  5100
tgcgggccta ccaaaacgtc ggtctttccc aacgcaaaat cagtaggtta aggttaaagt  5160
cgggagctac tcacaatagt gacaagcatc tttgactaaa gcaggcgcgc caaaacagca  5220
tgattcccta ttattcaaca aagcctatcg gtggtgctct caaccgtcac ccgctggctg  5280
gaagtattcc ccccgtgtgc gggggttatc ggtcgtgttg tccacggtta cccgctggct  5340
ggaagtattc cccccgcatg cgggggttat cggttaccaa tggggaaaaa tcttcatttg  5400
taaatgtatt ccccccgcat gcgggggtta tcggaacatc agtggaaatc cactgcggcg  5460
tattctcccc gcatgcgggg gttatcggcg aaaacggcaa ccttcataaa aacgtctttt  5520
gtattccccc cgtgtgcggg ggttatcggc cgagattgag taaagcaaag taacggcggt  5580
ggtattcccc ccgcatgcgg gggttatcgg caggttatac tggcaaaacg tcgatg      5636

SEQ ID NO: 13          moltype =   length =
SEQUENCE: 13
000

SEQ ID NO: 14          moltype = DNA  length = 85
FEATURE                Location/Qualifiers
source                 1..85
                       mol_type = genomic DNA
                       organism = Escherichia coli
SEQUENCE: 14
aacctaaata tttgttgtta agctgcaatg gaaacggtaa aagcggctag tatttaaagg  60
gatggatgac atctcagcgt tgtcg                                         85

SEQ ID NO: 15          moltype = DNA  length = 160
FEATURE                Location/Qualifiers
source                 1..160
                       mol_type = other DNA
                       organism = synthetic construct
SEQUENCE: 15
cctgatgcgt gaacgtgacg gacgtaacca ccgcgacatg tgtgtgctgt tccgctgggc  60
atgctgagct aacaccgtgc gtgttgacaa ttttacctct ggcggtgata atggttgcag  120
ctagcaataa ttttgtttaa ctttaagaag gagatatacc                        160

SEQ ID NO: 16          moltype = DNA  length = 48
FEATURE                Location/Qualifiers
source                 1..48
                       mol_type = other DNA
                       organism = synthetic construct
SEQUENCE: 16
agcggcagcg agactcccgg gacctcagag tccgccacac ccgaaagt                48

SEQ ID NO: 17          moltype = AA  length = 16
FEATURE                Location/Qualifiers
source                 1..16
                       mol_type = protein
                       organism = synthetic construct
SEQUENCE: 17
SGSETPGTSE SATPES                                                   16

SEQ ID NO: 18          moltype = DNA  length = 624
FEATURE                Location/Qualifiers
source                 1..624
                       mol_type = other DNA
                       organism = Petromyzon marinus
SEQUENCE: 18
atgaccgacg ctgagtacgt gagaatccat gagaagttgg acatctacac gtttaagaaa  60
cagtttttca acaacaaaaa atccgtgtcg catagatgct acgttctctt tgaattaaaa  120
cgacggggtg aacgtagagc gtgtttttgg ggctatgctg tgaataaacc acagagcggg  180
acagaacgtg gcattcacgc cgaaatcttt agcattagaa aagtcgaaga atacctgcgc  240
gacaaccccg gacaattcac gataaattgg tactcatcct ggagtccttg tgcagattgc  300
gctgaaaaga tcttagaatg gtataaccag gagctgcggg ggaacggcca cactttgaaa  360
atctgggctt gcaaactcta ttacgagaaa aatgcgagga atcaaattgg gctgtggaat  420
ctcagagata acggggttgg gttgaatgta atggtaagtg aacactacca atgttgcagg  480
aaaatattca tccaatcgtc gcacaatcaa ttgaatgaga atagatggct tgagaagact  540
ttgaagcgag ctgaaaaacg acggagcgag ttgtccatta tgattcaggt aaaaatactc  600
cacaccacta agagtcctgc tgtt                                         624

SEQ ID NO: 19          moltype = AA  length = 208
FEATURE                Location/Qualifiers
source                 1..208
                       mol_type = protein
                       organism = Petromyzon marinus
SEQUENCE: 19
MTDAEYVRIH EKLDIYTFKK QFFNNKKSVS HRCYVLFELK RRGERRACFW GYAVNKPQSG  60
TERGIHAEIF SIRKVEEYLR DNPGQFTINW YSSWSPCADC AEKILEWYNQ ELRGNGHTLK  120
IWACKLYYEK NARNQIGLWN LRDNGVGLNV MVSEHYQCCR KIFIQSSHNQ LNENRWLEKT  180
LKRAEKRRSE LSIMIQVKIL HTTKSPAV                                     208
```

```
SEQ ID NO: 20          moltype = DNA  length = 255
FEATURE               Location/Qualifiers
source                1..255
                      mol_type = other DNA
                      organism = Homo sapiens
SEQUENCE: 20
atgaccaacc tttccgacat catagagaag gaaacaggca aacagttggt catccaagag  60
tcgatactca tgcttcctga agaagttgag gaggtcattg ggaataagcc ggaaagtgac  120
attctcgtac acactgcgta tgatgagagc accgatgaga acgtgatgct gctcacgtca  180
gatgccccag agtacaaacc ctgggctctg gtgattcagg actctaatgg agagaacaag  240
atcaagatgc tataa                                                   255

SEQ ID NO: 21          moltype = AA  length = 84
FEATURE               Location/Qualifiers
source                1..84
                      mol_type = protein
                      organism = Homo sapiens
SEQUENCE: 21
MTNLSDIIEK ETGKQLVIQE SILMLPEEVE EVIGNKPESD ILVHTAYDES TDENVMLLTS  60
DAPEYKPWAL VIQDSNGENK IKML                                         84

SEQ ID NO: 22          moltype = DNA  length = 30
FEATURE               Location/Qualifiers
source                1..30
                      mol_type = other DNA
                      organism = synthetic construct
SEQUENCE: 22
tctggtggat ctggaggttc tggtggatct                                   30

SEQ ID NO: 23          moltype = AA  length = 10
FEATURE               Location/Qualifiers
source                1..10
                      mol_type = protein
                      organism = synthetic construct
SEQUENCE: 23
SGGSGGSGGS                                                         10

SEQ ID NO: 24          moltype = DNA  length = 213
FEATURE               Location/Qualifiers
source                1..213
                      mol_type = genomic DNA
                      organism = Escherichia coli
SEQUENCE: 24
gaccaaagcc atgacaaaaa cgcgtaacaa aagtgtctat aatcacggca gaaaagtcca  60
cattgattat ttgcacggcg tcacactttg ctatgccata gcatttttat ccataagatt  120
agcggatcct acctgacgct ttttatcgca actctctact gtttctccat acccgttttt  180
ttgggaattc gagctctaag gaggttataa aaa                               213

SEQ ID NO: 25          moltype = DNA  length = 32
FEATURE               Location/Qualifiers
source                1..32
                      mol_type = other DNA
                      organism = synthetic construct
SEQUENCE: 25
ggagacgtca tgtcaagctc ataggcgtct cg                                32

SEQ ID NO: 26          moltype = DNA  length = 32
FEATURE               Location/Qualifiers
source                1..32
                      mol_type = other DNA
                      organism = synthetic construct
SEQUENCE: 26
acatacgctt cttgctgagt acgtgagttc ac                                32

SEQ ID NO: 27          moltype = DNA  length = 32
FEATURE               Location/Qualifiers
source                1..32
                      mol_type = other DNA
                      organism = synthetic construct
SEQUENCE: 27
cagattgctg gtcaggagca tattgatccg ct                                32

SEQ ID NO: 28          moltype = DNA  length = 32
FEATURE               Location/Qualifiers
source                1..32
                      mol_type = other DNA
                      organism = synthetic construct
SEQUENCE: 28
aaggagatat accatggagc ttttcactgg cg                                32
```

```
SEQ ID NO: 29          moltype = DNA  length = 32
FEATURE                Location/Qualifiers
source                 1..32
                       mol_type = other DNA
                       organism = synthetic construct
SEQUENCE: 29
ttcagcgtgt ccggcgaggg cgagggcgat gc                               32

SEQ ID NO: 30          moltype = DNA  length = 32
FEATURE                Location/Qualifiers
source                 1..32
                       mol_type = other DNA
                       organism = synthetic construct
SEQUENCE: 30
ctgcccgtgc cctggcccac cctcgtgacc ac                               32

SEQ ID NO: 31          moltype = DNA  length = 32
FEATURE                Location/Qualifiers
source                 1..32
                       mol_type = other DNA
                       organism = synthetic construct
SEQUENCE: 31
gagaagcgcg atcacatggt cctgctggag tt                               32

SEQ ID NO: 32          moltype = DNA  length = 32
FEATURE                Location/Qualifiers
source                 1..32
                       mol_type = other DNA
                       organism = synthetic construct
SEQUENCE: 32
taccagatgg cattgcgcca tctggcagag tg                               32

SEQ ID NO: 33          moltype = DNA  length = 32
FEATURE                Location/Qualifiers
source                 1..32
                       mol_type = other DNA
                       organism = synthetic construct
SEQUENCE: 33
aaagtcaggt tgcgcaggca gggtaatcgg gg                               32

SEQ ID NO: 34          moltype = DNA  length = 32
FEATURE                Location/Qualifiers
source                 1..32
                       mol_type = other DNA
                       organism = synthetic construct
SEQUENCE: 34
tcacgtactc agcaagaagc gtatgtgttt gc                               32

SEQ ID NO: 35          moltype = DNA  length = 32
FEATURE                Location/Qualifiers
source                 1..32
                       mol_type = other DNA
                       organism = synthetic construct
SEQUENCE: 35
acctctgtca gctcgctgac attccccgcc ag                               32

SEQ ID NO: 36          moltype = DNA  length = 32
FEATURE                Location/Qualifiers
source                 1..32
                       mol_type = other DNA
                       organism = synthetic construct
SEQUENCE: 36
ttaaacaaaa ttattgctag ctgcaaccat ta                               32

SEQ ID NO: 37          moltype = DNA  length = 32
FEATURE                Location/Qualifiers
source                 1..32
                       mol_type = other DNA
                       organism = synthetic construct
SEQUENCE: 37
ctccatggta tatctccttc ttaaagttaa ac                               32

SEQ ID NO: 38          moltype = DNA  length = 32
FEATURE                Location/Qualifiers
source                 1..32
                       mol_type = other DNA
                       organism = synthetic construct
SEQUENCE: 38
```

```
cactgcacgc cgtaggtcag ggtggtcacg ag                                 32

SEQ ID NO: 39           moltype = DNA  length = 32
FEATURE                 Location/Qualifiers
source                  1..32
                        mol_type = other DNA
                        organism = synthetic construct
SEQUENCE: 39
tccagcagga ccatgtgatc gcgcttctcg tt                                 32

SEQ ID NO: 40           moltype = DNA  length = 32
FEATURE                 Location/Qualifiers
source                  1..32
                        mol_type = other DNA
                        organism = synthetic construct
SEQUENCE: 40
cactctgcca gatggcgcaa tgccatctgg ta                                 32

SEQ ID NO: 41           moltype = DNA  length = 32
FEATURE                 Location/Qualifiers
source                  1..32
                        mol_type = other DNA
                        organism = synthetic construct
SEQUENCE: 41
ctgactttgt tgtcggcccg gcgggcactc aa                                 32

SEQ ID NO: 42           moltype =   length =
SEQUENCE: 42
000

SEQ ID NO: 43           moltype = DNA  length = 31
FEATURE                 Location/Qualifiers
source                  1..31
                        mol_type = other DNA
                        organism = synthetic construct
SEQUENCE: 43
ctcagtagat gttttcttgg gtctaccgtt a                                  31

SEQ ID NO: 44           moltype = DNA  length = 618
FEATURE                 Location/Qualifiers
source                  1..618
                        mol_type = other DNA
                        organism = Tequatrovirus T4
SEQUENCE: 44
atgaaaagcg gaatttatca gattaaaaat actttaaaca ataaagtata tgtaggaagt  60
gctaaagatt ttgaaaagag atggaagagg cattttaaag atttagaaaa aggatgccat  120
tcttctataa aacttcagag gtcttttaac aaacatggta atgtgtttga atgttctatt  180
ttggaagaaa ttccatatga gaaagatttg attattgaac gagaaaattt ttggattaaa  240
gagcttaatt ctaaaattaa tggatacaat attgctgatg caacgtttgg tgatacatgt  300
tctacgcatc cattaaaaga agaaattatt aagaaacgtt ctgaaactgt taaagctaag  360
atgcttaaac ttggacctga tggtcggaaa gctctttaca gtaaacccgg aagtaaaaac  420
gggcgttgga atccagaaac ccataagttt tgtaagtgcg gtgttcgcat acaaacttct  480
gcttatactt gtagtaaatg cagaaatcgt tcaggtgaaa ataattcatt ctttaatcat  540
aagcattcag acataactaa atctaaaata tcagaaaaga tgaaaggtaa aaagcctagt  600
aatattaaaa agatttca                                                 618

SEQ ID NO: 45           moltype = AA  length = 206
FEATURE                 Location/Qualifiers
source                  1..206
                        mol_type = protein
                        organism = Tequatrovirus T4
SEQUENCE: 45
MKSGIYQIKN TLNNKVYVGS AKDFEKRWKR HFKDLEKGCH SSIKLQRSFN KHGNVFECSI  60
LEEIPYEKDL IIERENFWIK ELNSKINGYN IADATFGDTC STHPLKEEII KKRSETVKAK  120
MLKLGPDGRK ALYSKPGSKN GRWNPETHKF CKCGVRIQTS AYTCSKCRNR SGENNSFFNH  180
KHSDITKSKI SEKMKGKKPS NIKKIS                                        206

SEQ ID NO: 46           moltype = DNA  length = 31
FEATURE                 Location/Qualifiers
source                  1..31
                        mol_type = other DNA
                        organism = synthetic construct
SEQUENCE: 46
ctcagtagat gttttcttgg gtctaccgtt a                                  31

SEQ ID NO: 47           moltype = DNA  length = 29
FEATURE                 Location/Qualifiers
source                  1..29
                        mol_type = other DNA
```

```
                       organism = synthetic construct
SEQUENCE: 47
ctcagtagat gttttcttgg gtctaccgt                             29

SEQ ID NO: 48          moltype = DNA  length = 27
FEATURE                Location/Qualifiers
source                 1..27
                       mol_type = other DNA
                       organism = synthetic construct
SEQUENCE: 48
ctcagtagat gttttcttgg gtctacc                               27

SEQ ID NO: 49          moltype = DNA  length = 25
FEATURE                Location/Qualifiers
source                 1..25
                       mol_type = other DNA
                       organism = synthetic construct
SEQUENCE: 49
ctcagtagat gttttcttgg gtcta                                 25

SEQ ID NO: 50          moltype = DNA  length = 23
FEATURE                Location/Qualifiers
source                 1..23
                       mol_type = other DNA
                       organism = synthetic construct
SEQUENCE: 50
ctcagtagat gttttcttgg gtc                                   23

SEQ ID NO: 51          moltype = DNA  length = 21
FEATURE                Location/Qualifiers
source                 1..21
                       mol_type = other DNA
                       organism = synthetic construct
SEQUENCE: 51
ctcagtagat gttttcttgg g                                     21

SEQ ID NO: 52          moltype = DNA  length = 19
FEATURE                Location/Qualifiers
source                 1..19
                       mol_type = other DNA
                       organism = synthetic construct
SEQUENCE: 52
ctcagtagat gttttcttg                                        19

SEQ ID NO: 53          moltype = DNA  length = 17
FEATURE                Location/Qualifiers
source                 1..17
                       mol_type = other DNA
                       organism = synthetic construct
SEQUENCE: 53
ctcagtagat gttttct                                          17

SEQ ID NO: 54          moltype = DNA  length = 15
FEATURE                Location/Qualifiers
source                 1..15
                       mol_type = other DNA
                       organism = synthetic construct
SEQUENCE: 54
ctcagtagat gtttt                                            15

SEQ ID NO: 55          moltype = DNA  length = 13
FEATURE                Location/Qualifiers
source                 1..13
                       mol_type = other DNA
                       organism = synthetic construct
SEQUENCE: 55
ctcagtagat gtt                                              13

SEQ ID NO: 56          moltype = DNA  length = 11
FEATURE                Location/Qualifiers
source                 1..11
                       mol_type = other DNA
                       organism = synthetic construct
SEQUENCE: 56
ctcagtagat g                                                11

SEQ ID NO: 57          moltype =   length =
SEQUENCE: 57
000
```

```
SEQ ID NO: 58          moltype =   length =
SEQUENCE: 58
000

SEQ ID NO: 59          moltype =   length =
SEQUENCE: 59
000

SEQ ID NO: 60          moltype = DNA  length = 33
FEATURE                Location/Qualifiers
source                 1..33
                       mol_type = other DNA
                       organism = synthetic construct
SEQUENCE: 60
ctcagtagat gttttcttgg gtctaccgtt acg                                  33

SEQ ID NO: 61          moltype = DNA  length = 35
FEATURE                Location/Qualifiers
source                 1..35
                       mol_type = other DNA
                       organism = synthetic construct
SEQUENCE: 61
ctcagtagat gttttcttgg gtctaccgtt acgga                                35

SEQ ID NO: 62          moltype = DNA  length = 37
FEATURE                Location/Qualifiers
source                 1..37
                       mol_type = other DNA
                       organism = synthetic construct
SEQUENCE: 62
ctcagtagat gttttcttgg gtctaccgtt acggatt                              37

SEQ ID NO: 63          moltype = DNA  length = 39
FEATURE                Location/Qualifiers
source                 1..39
                       mol_type = other DNA
                       organism = synthetic construct
SEQUENCE: 63
ctcagtagat gttttcttgg gtctaccgtt acggattag                            39

SEQ ID NO: 64          moltype = DNA  length = 28
FEATURE                Location/Qualifiers
source                 1..28
                       mol_type = other DNA
                       organism = synthetic construct
SEQUENCE: 64
ctcagtagat gttttcttgg gtctaccg                                        28

SEQ ID NO: 65          moltype = DNA  length = 30
FEATURE                Location/Qualifiers
source                 1..30
                       mol_type = other DNA
                       organism = synthetic construct
SEQUENCE: 65
ctcagtagat gttttcttgg gtctaccgtt                                      30

SEQ ID NO: 66          moltype = DNA  length = 32
FEATURE                Location/Qualifiers
source                 1..32
                       mol_type = other DNA
                       organism = synthetic construct
SEQUENCE: 66
ctcagtagat gttttcttgg gtctaccgtt ac                                   32

SEQ ID NO: 67          moltype = DNA  length = 34
FEATURE                Location/Qualifiers
source                 1..34
                       mol_type = other DNA
                       organism = synthetic construct
SEQUENCE: 67
ctcagtagat gttttcttgg gtctaccgtt acgg                                 34

SEQ ID NO: 68          moltype = DNA  length = 36
FEATURE                Location/Qualifiers
source                 1..36
                       mol_type = other DNA
                       organism = synthetic construct
SEQUENCE: 68
```

```
ctcagtagat gttttcttgg gtctaccgtt acggat                          36

SEQ ID NO: 69           moltype = DNA  length = 32
FEATURE                 Location/Qualifiers
source                  1..32
                        mol_type = other DNA
                        organism = synthetic construct
SEQUENCE: 69
tcgtgttgtc cacggttacc cgctggctgg aa                              32

SEQ ID NO: 70           moltype = DNA  length = 29
FEATURE                 Location/Qualifiers
source                  1..29
                        mol_type = other DNA
                        organism = synthetic construct
SEQUENCE: 70
gtattccccc cgcatgcggg ggttatcgg                                  29
```

TYPE OF CRISPR/CAS SYSTEM

CROSS REFERENCE TO RELATED APPLICATIONS

This application is a continuation of PCT Application No. PCT/EP2023/073881, filed on Aug. 31, 2023, which claims priority to and benefit of GB Patent Application No. 2212688.2 filed on Aug. 31, 2022, the disclosures of which are herein incorporated by reference in their entirety.

REFERENCE TO AN ELECTRONIC SEQUENCE LISTING

The contents of the electronic sequence listing (786212002001seqlist.xml; Size: 73,833 bytes; and Date of Creation: Mar. 28, 2024) is herein incorporated by reference in its entirety.

TECHNICAL FIELD

The technology described herein relates to new and synthetic CRISPR/Cas systems and components thereof, vectors, proteins, ribonucleoprotein complexes and methods of using the new system and components.

We term the new system a "Type-S" CRISPR/Cas system.

BACKGROUND

Currently, Types I-VI CRISPR/Cas systems are known. It would be desirable to provide a new system and components thereof that can increase the toolbox and utilities for CRISPR/Cas targeting generally and that can bring in new types of functionalities for these useful systems.

SUMMARY

The invention fulfils these needs by proving a new system, Type-S CRISPR/Cas. The base components of this system do not rely on the signature genes of any of the Type I-VI systems that have already been elucidated. Type-S does not use a Cas3 (the signature protein of Type I systems), a Cas9 (the signature protein of Type II systems), a Cas10 (the signature protein of Type III systems), a Cas12 (the signature protein of Type V systems) or a Cas13 (the signature protein of Type VI systems). We have described the new system as Type-S.

Furthermore, we identified that the base components (Cas-S1, Cas-S2, Cas-S3, Cas-S4 and Cas-S5) do not comprise an RNA-guided DNA nuclease. Nevertheless, we surprisingly found that a ribonucleoprotein complex of these components with a crRNA is able to effectively and specifically target a predetermined site on DNA. Using this system, it was also surprisingly possible to modify a cell without inducing dsDNA breaks. We could also surprisingly use the system to inhibit growth of bacterial cells. We fused several base components of the system to a base editor and found that it was able to perform base editing in an effective manner. We also fused several base components of the system to a DNA nuclease and found that it was able to perform DNA cutting in an effective manner. Armed with this knowledge, we can see many applications of the new system. It is possible, for example, to provide one or more other effector proteins or domains (e.g. a nuclease, base editor or prime editor) together with one or more the components of the system to produce synthetic systems that can modify cells and nucleic acid in a RNA-directed manner. DNA binding of the Type-S system does not require the presence of all of the base components (Cas-S1, Cas-S2, Cas-S3, Cas-S4 and Cas-S5). When fused to a base editor or DNA nuclease, again, surprisingly, the synthetic system does not require the presence of all of the base components (Cas-S1, Cas-S2, Cas-S3, Cas-S4 and Cas-S5) of the Type-S system to effective perform the functions of the effector domains.

The system and its components, therefore, provide new means to carry out nucleic acid editing and cell targeting in environmental, medical and other settings.'

To this end, there is provided:-

In a First Configuration

In a First Aspect:-

A Cas-S1 protein or a nucleic acid encoding a Cas-S1.

A Cas-S2 protein or a nucleic acid encoding a Cas-S2.

A Cas-S3 protein or a nucleic acid encoding a Cas-S3.

A Cas-S4 protein or a nucleic acid encoding a Cas-S4.

A Cas-S5 protein or a nucleic acid encoding a Cas-S5.

One or more nucleic acids encoding a Cas-S1, S2, S3, S4 and S5 protein.

One or more nucleic acids encoding a Cas-S4 and S5 protein.

One or more nucleic acids encoding a Cas-S3, S4 and S5 protein.

One or more nucleic acids encoding a Cas-S2, S3, S4 and S5 protein.

One or more nucleic acids encoding a Cas-S1 and S2 protein.

One or more nucleic acids encoding a Cas-S1, S2 and S3 protein.

One or more nucleic acids encoding a Cas-S1, S2, S3 and S4 protein.

One or more nucleic acids comprising SEQ ID NOs: 7-11.

One or more nucleic acids comprising SEQ ID NOs: 8-11.

One or more nucleic acids comprising SEQ ID NOs: 9-11.

One or more nucleic acids comprising SEQ ID NOs: 10 and 11.

One or more nucleic acids comprising SEQ ID NOs: 7-10.

One or more nucleic acids comprising SEQ ID NOs: 7-9.

One or more nucleic acids comprising SEQ ID NOs: 7 and 8.

A nucleic acid comprising SEQ ID NO:7.

A nucleic acid comprising SEQ ID NO:8.

A nucleic acid comprising SEQ ID NO:9.

A nucleic acid comprising SEQ ID NO:10.

A nucleic acid comprising SEQ ID NO:11.

In an embodiment, each said sequence is operably connected to a heterologous promoter (i.e. a promoter that is not naturally operably connected to the sequence). In an embodiment, each said sequence is operably connected to a promoter that is a eukaryotic promoter, or virus (e.g. phage) promoter, In a Second Aspect:-

A protein or ribonucleoprotein complex comprising 1, 2, 3, 4 or all of a Cas-S1, S2, S3, S4 and S5 protein.

A protein or ribonucleoprotein complex comprising a Cas-S1, S2, S3, S4 and S5 protein.

A protein or ribonucleoprotein complex comprising a Cas-S4 and S5 protein.

A protein or ribonucleoprotein complex comprising a Cas-S3, S4 and S5 protein.

A protein or ribonucleoprotein complex comprising a Cas-S2, S3, S4 and S5 protein.

In a Second Configuration

In a First Aspect:-

A (i) nucleic acid vector or a plurality of nucleic acid vectors or (ii) a nucleic acid or a plurality of nucleic acids, comprising expressible nucleotide sequences, wherein the sequences comprise a) a nucleotide sequence that encodes a polypeptide which comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:1;

b) a nucleotide sequence that encodes a polypeptide which comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:2;

c) a third nucleotide sequence that encodes a polypeptide which comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:3;

d) a nucleotide sequence that encodes a polypeptide which comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:4; and e) a nucleotide sequence that encodes a polypeptide which comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:5.

In another embodiment of the First Aspect, there is provided a i) nucleic acid vector or a plurality of nucleic acid vectors or (ii) a nucleic acid or a plurality of nucleic acids, comprising expressible nucleotide sequences, wherein the sequences comprise a) a nucleotide sequence that encodes a polypeptide which comprises an amino acid that is at least 94, 95, 96, 97, 98 or 99% identical to SEQ ID NO: 1; and/or b) a nucleotide sequence that encodes a polypeptide which comprises an amino acid that is at least 88, 89, 90, 91, 92, 93, 94, 95, 96, 97, 98 or 99% identical to SEQ ID NO:2; and/or c) a nucleotide sequence that encodes a polypeptide which comprises an amino acid that is at least 98 or 99% identical to SEQ ID NO:3; and/or d) a nucleotide sequence that encodes a polypeptide which comprises an amino acid that is at least 99% identical to SEQ ID NO:4; and e) a nucleotide sequence that encodes a polypeptide which comprises an amino acid that is at least 98 or 99% identical to SEQ ID NO:5.

In a Second Aspect:-

A nucleic acid vector or a nucleic acid comprising an expressible nucleotide sequence selected from a) a nucleotide sequence that encodes a polypeptide which comprises an amino acid that is at least (about) 80% identical to SEQ ID NO:1;

b) a nucleotide sequence that encodes a polypeptide which comprises an amino acid that is at least (about) 80% identical to SEQ ID NO:2;

c) a nucleotide sequence that encodes a polypeptide which comprises an amino acid that is at least (about) 80% identical to SEQ ID NO:3;

d) a nucleotide sequence that encodes a polypeptide which comprises an amino acid that is at least (about) 80% identical to SEQ ID NO:4; and e) a nucleotide sequence that encodes a polypeptide which comprises an amino acid that is at least (about) 80% identical to SEQ ID NO:5.

In a Third Aspect:-

A (i) nucleic acid vector or a plurality of nucleic acid vectors or (ii) a nucleic acid or a plurality of nucleic acids according to the First or Second Aspect, wherein said polypeptide(s) encoded by the vector(s) are operable for use with a crRNA to form a ribonucleoprotein complex for protospacer targeting in a polynucleotide, wherein the complex is operable with a protospacer adjacent motif (PAM) having the sequence 5'-AAG-3'.

The crRNA may be as described in any Configuration, Concept, aspect, example, embodiment, option or other feature herein. The PAM may alternatively be any one of the PAMs described in any Configuration, Concept, aspect, example, embodiment, option or other feature herein.

In a Fourth Aspect:-

A kit comprising a) One or more polypeptides described herein, or one, or more nucleic acids encoding such polypeptide(s); and b) A crRNA, or one or more nucleic acids encoding a crRNA), wherein the crRNA is cognate to PAM having the sequence 5'-AAG-3';

wherein said polypeptide(s) are operable for use with the crRNA to form a ribonucleoprotein complex for protospacer targeting in a polynucleotide.

The polypeptides may comprise Cas-S1, S2, S3, S4 and S5. The polypeptides may be any polypeptide, protein, fusion protein or complex described in any Configuration, Concept, aspect, example, embodiment, option or other feature herein. The crRNA may be as described in any Configuration, Concept, aspect, example, embodiment, option or other feature herein. The PAM may alternatively be any one of the PAMs described in any Configuration, Concept, aspect, example, embodiment, option or other feature herein.

In a Fifth Aspect:-

A ribonucleoprotein complex comprising a) One or more polypeptides described herein, or one, or more nucleic acids encoding such polypeptide(s); and b) A crRNA, or one or more nucleic acids encoding a crRNA), wherein the crRNA is cognate to PAM having the sequence 5'-AAG-3'.

The polypeptides may be any polypeptide, protein, fusion protein or complex described in any Configuration, Concept, aspect, example, embodiment, option or other feature herein. The crRNA may be as described in any Configuration, Concept, aspect, example, embodiment, option or other feature herein. The PAM may alternatively be any one of the PAMs described in any Configuration, Concept, aspect, example, embodiment, option or other feature herein, In a Sixth Aspect:-

One or more nucleic acid vectors or one or more nucleic acids comprising at least one nucleotide sequence selected from SEQ ID NOs: 7-11, wherein a said nucleotide sequence is a) operably connected to a heterologous promoter, synthetic promoter, eukaryotic promoter or non-bacterial promoter; and/or b) comprised by a cell that is a eukaryotic cell, a non-bacterial cell, or a cell that is not a bacterial cell (e.g. an *E coli*, Psurdomonas or *Klebsiella* cell) that comprises endogenous nucleotide sequence comprising SEQ ID NOs: 7-11.

In a Third Configuration

In a First Aspect:-

A fusion protein comprising a polypeptide (Px), wherein Px a) comprises an amino acid sequence that is at least (about) 80% identical to a sequence selected from SEQ ID Nos: 1-5; and b) is fused to a heterologous polypeptide (Py).

Py may be as described in any Configuration, Concept, aspect, example, embodiment, option or other feature herein, In a Second Aspect:-

A protein or plurality of proteins operable for use with a crRNA to form a ribonucleoprotein complex for protospacer targeting in a polynucleotide, the protein(s) comprising one, more or all polypeptides selected from a) a polypeptide that comprises an amino acid that is at least (about) 80% identical to SEQ ID NO:1;

b) a polypeptide that comprises an amino acid that is at least (about) 80% identical to SEQ ID NO:2;

c) a polypeptide that comprises an amino acid that is at least (about) 80% identical to SEQ ID NO:3;

d) a polypeptide that comprises an amino acid that is at least (about) 80% identical to SEQ ID NO:4; and e) a polypeptide that comprises an amino acid that is at least (about) 80% identical to SEQ ID NO:5;

wherein the complex is operable with a protospacer adjacent motif (PAM) having the sequence 5'-AAG-3'.

The crRNA may be as described in any Configuration, Concept, aspect, example, embodiment, option or other feature herein. The PAM may alternatively be any one of the PAMs described in any Configuration, Concept, aspect, example, embodiment, option or other feature herein.

In a Fourth Configuration

A cell, wherein the cell is a) a eukaryotic cell comprising the vector(s) or protein of the first, second or third configuration;

b) an animal, plant, insect or fungus cell comprising the vector(s) or protein of the first, second or third configuration; or c) a prokaryotic cell comprising the vector(s) or protein of the first, second or third configuration, wherein the cell is not a bacterial cell (e.g, an *E coli, Pseudomonas* or *Klebsiella* cell) that comprises endogenous nucleotide sequences that encode the polypeptides of part a) to e) as recited in the second Configuration.

In a Fifth Configuration

In a First Aspect:-

A composition (optionally an in vitro composition or wherein the composition is comprised by a medical container) comprising a crRNA or nucleic acid encoding the crRNA or guide RNA; and one, more or all of a) a polypeptide that comprises an amino acid that is at least (about) 80% identical to SEQ ID NO:1;

b) a polypeptide that comprises an amino acid that is at least (about) 80% identical to SEQ ID NO:2;

c) a polypeptide that comprises an amino acid that is at least (about) 80% identical to SEQ ID NO:3;

d) a polypeptide that comprises an amino acid that is at least (about) 80% identical to SEQ ID NO:4; and e) a polypeptide that comprises an amino acid that is at least (about) 80% identical to SEQ ID NO:5 wherein

A: the crRNA comprises a spacer that is cognate to a first protospacer, wherein the protospacer is f) not found in *E coli,* g) is a eukaryotic cell protospacer; or h) an animal (optionally mammal or human), plant, fungus cell protospacer;

or

B: a protospacer of an *E coli* that is devoid of endogenous nucleotide sequences that encode the polypeptides of a) to e).

The crRNA may be as described in any Configuration, Concept, aspect, example, embodiment, option or other feature herein.

In a Second Aspect:-

A composition (optionally an in vitro composition or wherein the composition is comprised by a medical container) comprising a crRNA or nucleic acid encoding the crRNA; and nucleic acid encoding one, more or all of a) a polypeptide that comprises an amino acid that is at least (about) 80% identical to SEQ ID NO:1;

b) a polypeptide that comprises an amino acid that is at least (about) 80% identical to SEQ ID NO:2;

c) a polypeptide that comprises an amino acid that is at least (about) 80% identical to SEQ ID NO:3;

d) a polypeptide that comprises an amino acid that is at least (about) 80% identical to SEQ ID NO:4; and e) a polypeptide that comprises an amino acid that is at least (about) 80% identical to SEQ ID NO:5 wherein A: the crRNA comprises a spacer that is cognate to a first protospacer, wherein the protospacer is f) not found in *E coli,* g) is a eukaryotic cell protospacer; or h) an animal (optionally mammal or human), plant, fungus cell protospacer;

or

B: a protospacer of an *E coli* that is devoid of endogenous nucleotide sequences that encode the polypeptides of a) to e).

The crRNA may be as described in any Configuration, Concept, aspect, example, embodiment, option or other feature herein.

In a Sixth Configuration

In a First Aspect:-

A method of modifying a nucleic acid target site in a cell, the method comprising a) contacting the cell with the vector(s) wherein the vector(s) comprise(s) one or more nucleotide sequences for producing a crRNA, wherein the crRNA comprises a spacer that is cognate to a first protospacer, wherein the protospacer is:

not found in *E. coli*, a eukaryotic cell protospacer; or an animal (optionally human), plant, insect, fungus cell protospacer;

b) allowing introduction into the cell of (i) the vector(s), whereby the polypeptide(s) and the crRNA are expressed in the cell, or (ii) the cRNA of the composition (or nucleic acids encoding the crRNA or guide RNA whereby the cRNA are expressed in the cell) and the nucleic acid of the composition encoding the polypeptide(s), whereby the polypeptide(s) are expressed in the cell;

c) wherein the crRNA guide form a complex with the polypeptide(s) to guide the complex to the target site.

The vector(s) and crRNA may be as described in any Configuration, Concept, aspect, example, embodiment, option or other feature herein. The polypeptides may be any polypeptide, protein, fusion protein or complex described in any Configuration, Concept, aspect, example, embodiment, option or other feature herein.

In a Second Aspect:-

A method of treating or preventing a disease or condition that is mediated by target cells in a subject, the method comprising carrying out any of the methods described herein to modify the target cells, wherein said contacting comprises administering the vector(s) or composition to the subject and wherein the modification treats or prevents the disease or condition.

The vector(s) and composition(s) may be as described in any Configuration, Concept, aspect, example, embodiment, option or other feature herein.

In a Third Aspect:-

A method of introducing a targeted edit in a target polynucleotide, the method comprising contacting the target polynucleotide with a CRISPR/Cas system comprising crRNA and a protein complex comprising one, more or all polypeptides selected from a) a polypeptide that comprises an amino acid that is at least (about) 80% identical to SEQ ID NO:1;

b) a polypeptide that comprises an amino acid that is at least (about) 80% identical to SEQ ID NO:2;

c) a polypeptide that comprises an amino acid that is at least (about) 80% identical to SEQ ID NO:3;

d) a polypeptide that comprises an amino acid that is at least (about) 80% identical to SEQ ID NO:4; and e) a polypeptide that comprises an amino acid that is at least (about) 80% identical to SEQ ID NO:5 wherein the crRNA comprises a spacer that is cognate to a first protospacer comprised by the polynucleotide, wherein the crRNA hybridizes to the protospacer to guide the complex whereby the complex edits the polynucleotide.

In a Fourth Aspect:-

A method of targeting a polynucleotide (optionally in a cell or in vitro), the method comprising a) contacting the polynucleotide with the protein(s) and crRNA of the Second Aspect of the Third Configuration;

b) allowing the formation of a ribonucleoprotein complex comprising the protein(s) and crRNA, wherein the complex is guided to a target site comprised by the polynucleotide to modify the polynucleotide or replication thereof, In a Fifth Aspect:-

A method of transcriptional control or replication of a target DNA, comprising contacting the target DNA with the complex, wherein the complex is devoid of a DNA nuclease and the complex binds to the target DNA, thereby controlling the transcription or replication of the target DNA, In a Sixth Aspect:-

A method of controlling replication of a target RNA, comprising contacting the target RNA or a DNA encoding the RNA with the complex, wherein the complex binds to the target RNA or DNA, thereby controlling the transcription of the target RNA.

In a Seventh Aspect:-

A method of editing a target DNA, comprising contacting the target DNA with the complex, wherein the complex binds to the target DNA, thereby editing the target DNA.

In an Eighth Aspect:-

A method for cleaving a double stranded DNA (dsDNA), comprising contacting said dsDNA with the complex, wherein the complex comprises a nuclease, wherein the dsDNA comprises a protospacer sequence flanked at its 5' by a PAM having the sequence 5'-AAG-3' or a PAM that is identical except for one base change, whereby the nuclease cleaves the DNA in the region defined by complementary binding of a spacer sequence of the crRNA to the protospacer.

The PAM may alternatively be any one of the PAMs described in any Configuration, Concept, aspect, example, embodiment, option or other feature herein.

In a Ninth Aspect:-

A method for cleaving a single stranded DNA (ssDNA), comprising contacting said DNA with the complex, wherein the complex comprises a nickase, wherein the DNA comprises a protospacer sequence flanked at its 5' by a PAM having the sequence 5'-AAG-3' or a PAM that is identical except for one base change, whereby the nuclease cleaves a single strand of the DNA in the region defined by complementary binding of a spacer sequence of the crRNA to the protospacer.

The PAM may alternatively be any one of the PAMs described in any Configuration, Concept, aspect, example, embodiment, option or other feature herein.

In a Tenth Aspect:-

A method of marking or identifying a region of a DNA, comprising contacting said DNA with the complex, wherein the DNA comprises a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, and optionally wherein the complex comprises a detectable label.

The PAM may alternatively be any one of the PAMs described in any Configuration, Concept, aspect, example, embodiment, option or other feature herein.

In a Eleventh Aspect:-

A method of modifying transcription of a region of a DNA, comprising contacting said DNA with the complex, wherein the DNA comprises a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, whereby the complex up- or down-regulates transcription of the region of DNA or an adjacent gene.

The PAM is not CGG. Optionally,

The PAM can be AAN, ANG, NAG; or

The PAM can be AAG with no or one nucleotide change.

The PAM may alternatively be any one of the PAMs described in any Configuration, Concept, aspect, example, embodiment, option or other feature herein, In a Twelfth Aspect:-

A method of modifying a target dsDNA of a cell without introducing dsDNA breaks, the method comprising producing in the cell the complex, wherein the complex targets a target DNA comprised by the cell, the target DNA comprising a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, whereby the DNA is modified without introducing breaks in the DNA.

The PAM may alternatively be any one of the PAMs described in any Configuration, Concept, aspect, example, embodiment, option or other feature herein.

In a Thirteenth Aspect:-

A method of inhibiting the growth or proliferation of a cell without introducing lethal dsDNA breaks, the method comprising producing in the cell the complex, wherein the complex targets a target DNA comprised by the cell, the target DNA comprising a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, whereby replication of the DNA is inhibited without introducing breaks in the DNA, thereby inhibiting the growth or proliferation of a cell.

The PAM may alternatively be any one of the PAMs described in any Configuration, Concept, aspect, example, embodiment, option or other feature herein.

In a Fourteenth Aspect:-

A method of treating or preventing a disease or condition in a human, animal, plant or fungus subject, the method comprising carrying out the method of any of the Fifth to Thirteenth Aspects, wherein cells of the subject comprise said DNA or RNA and the cells mediate the disease or condition.

In a Seventh Configuration

A nucleic acid vector or a nucleic acid that comprises SEQ ID NO:12 or a DNA sequence that is at least (about) 70 or 80% identical to SEQ ID NO:12.

In an Eighth Configuration

In a First Aspect:-

One or more nucleic acids encoding a plurality of Cas proteins and comprising at least one nucleotide sequence for producing a crRNA, wherein the Cas proteins and RNA are capable of forming a ribonucleoprotein CRISPR/Cas complex wherein the RNA is capable of guiding the complex to a protospacer comprised by a target DNA, wherein the 5'end of the protospacer is flanked by a protospacer adjacent motif (PAM) having the sequence 5'-AAG-3', wherein a) the complex is devoid of a DNA nuclease and is capable of modifying DNA without introducing a double stranded DNA break;

b) the Cas proteins do not comprise a DinG, a Cas3 and a Cas10; and c) the complex does not comprise all of the Cas proteins of a Type I, II, III, V or VI CRISPR/Cas complex.

The PAM may alternatively be any one of the PAMs described in any Configuration, Concept, aspect, example, embodiment, option or other feature herein.

In a Second Aspect:-

A ribonucleoprotein CRISPR/Cas complex comprising a plurality of Cas proteins and a crRNA, wherein the RNA is capable of guiding the complex to a protospacer comprised by a target DNA, wherein the 5'end of the protospacer is flanked by a protospacer adjacent motif (PAM) having the sequence 5'-AAG-3', wherein a) the complex is devoid of a DNA nuclease and is capable of modifying DNA without introducing a double stranded DNA break;

b) the complex is devoid of a DinG, a Cas3 and a Cas10; and c) the complex does not comprise all of the Cas proteins of a Type I, II, III, V or VI CRISPR/Cas complex.

The PAM may alternatively be any one of the PAMs described in any Configuration, Concept, aspect, example, embodiment, option or other feature herein.

In a Third Aspect:-

A cell comprising the nucleic acid(s) or complex described herein, wherein the DNA is comprised by a chromosome of the cell.

In a Fourth Aspect:-

A cell comprising the nucleic acid(s) or complex described herein, wherein the DNA is comprised by a plasmid in the cell.

In a Fifth Aspect:-

A method of modifying a DNA, the method comprising a) contacting the DNA with the nucleic acid(s) or vector(s) described herein;

b) allowing the formation of a ribonucleoprotein complex comprising the Cas protein(s) and crRNA, wherein the complex is guided to a target site comprised by the DNA to modify the DNA.

The crRNA and Cas protein(s) may be as described in any Configuration, Concept, aspect, example, embodiment, option or other feature herein.

In a Sixth Aspect:-

A method of inhibiting the replication of a plasmid comprising DNA, the method comprising a) contacting the DNA with the nucleic acid(s) or vector(s) described herein;

b) allowing the formation of a ribonucleoprotein complex comprising the Cas protein(s) and crRNA, wherein the complex is guided to a target site comprised by the DNA to inhibit replication of the plasmid.

The crRNA and Cas protein(s) may be as described in any Configuration, Concept, aspect, example, embodiment, option or other feature herein.

In a Seventh Aspect:-

A method of inhibiting the transcription of a nucleotide sequence comprised by a DNA, the method comprising a) contacting the DNA with the nucleic acid(s) or vector(s) described herein;

b) allowing the formation of a ribonucleoprotein complex comprising the Cas protein(s) and crRNA, wherein the complex is guided to a target site comprised by the nucleotide sequence to inhibit transcription thereof.

The crRNA and Cas protein(s) may be as described in any Configuration, Concept, aspect, example, embodiment, option or other feature herein.

In an Eighth Aspect:-

A method of inhibiting the growth or proliferation of a cell (optionally a prokaryotic cell, such as a bacterial cell) comprising DNA, the method comprising a) contacting the DNA with the nucleic acid(s) or vector(s) described herein;

b) allowing the formation of a ribonucleoprotein complex comprising the Cas protein(s) and crRNA, wherein the complex is guided to a target site comprised by the DNA to inhibit growth or proliferation of the cell.

The crRNA and Cas protein(s) may be as described in any Configuration, Concept, aspect, example, embodiment, option or other feature herein.

In a Ninth Aspect:-

A method of treating or preventing a disease or condition that is mediated by target cells in a human or animal subject, the method comprising carrying out any of the methods described herein to modify the target cells, wherein said contacting comprises administering the nucleic acid(s) to the subject and wherein the modification treats or prevents the disease or condition.

In a Tenth Aspect:-

One or more nucleic acid(s) of the First Aspect for use in a method of treating or preventing a disease or condition that is mediated by target cells in a human or animal subject, the method comprising carrying out any of the methods described herein to modify the target cells, wherein said contacting comprises administering the nucleic acid(s) to the subject and wherein the modification treats or prevents the disease or condition.

Figure 1:
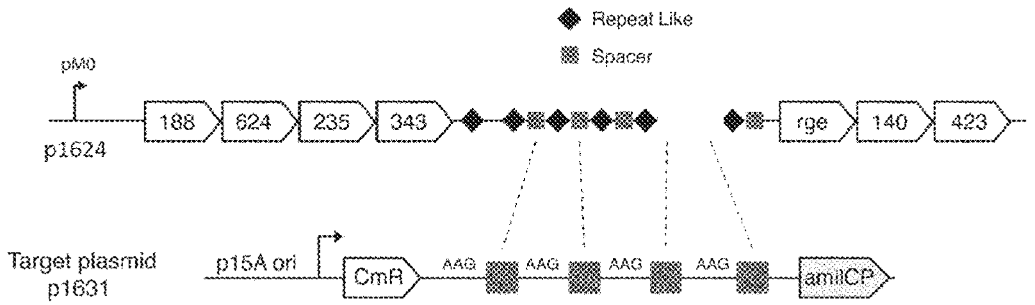
FIG. 1: Cloning components of a Type-S CRISPR system. A plasmid (p1624) was constructed carrying a pSC101 replication origin and a tetracycline resistance marker as well as DNA sequences encoding an RNA guided endonuclease (rge), two ORFs downstream of the rge gene, a cognate CRISPR array and four ORFs immediately upstream of the CRISPR array. ORFs 140 and 423 were predicted to code for an error prone DNA polymerase, while ORFs 624 and 188 were predicted to code for a helicase and an RNA endonuclease respectively. The target plasmid p1631 was constructed by first creating a synthetic DNA fragment containing spacer like sequences from the Type-S CRISPR/Cas system separated by the predicted PAM sequence (AAG), and then inserting this sequence into a plasmid containing a p15A replication origin, a chloramphenicol resistance marker (CmR), and the amilCP gene producing a purple colour.
Figure 2:
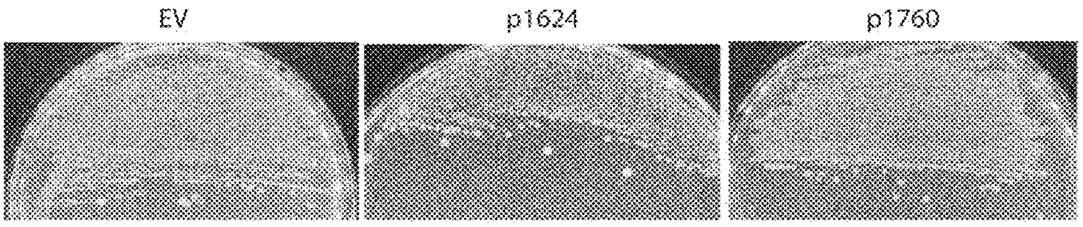

FIG. 2: CRISPR-Cas system inhibits the growth of colonies transformed with the p1631 target plasmid. Strain bSNP3127 was transformed with either p1760 (right, see FIG. 3 for content), or p1624 (middle, see FIG. 1 for content) or a no plasmid control (left). Each of the resulting strains was transformed with a 1:1 mixture of target (purple) and non-target (white) plasmids and streaked on LB plates supplemented with the appropriate antibiotics for selection. No purple colonies were observed in the presence of p1760.

Figure 3:
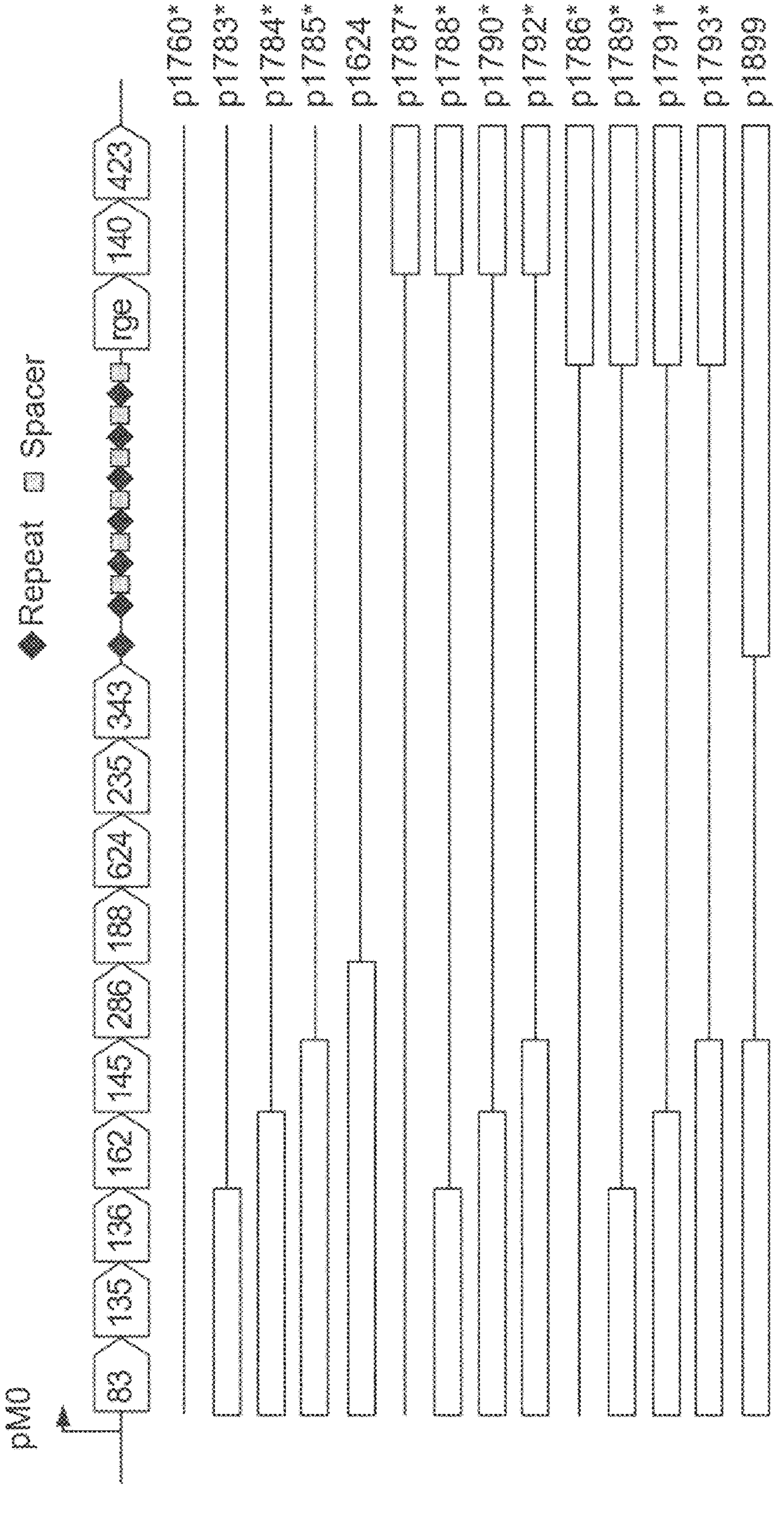

FIG. 3: Schematic representation of the plasmid library constructed upon deletion of a series of genes in p1760 (see FIG. 3 for content). Boxes indicate gene deletions. The constructs that showed plasmid inhibition are indicated with *.

Figure 4:
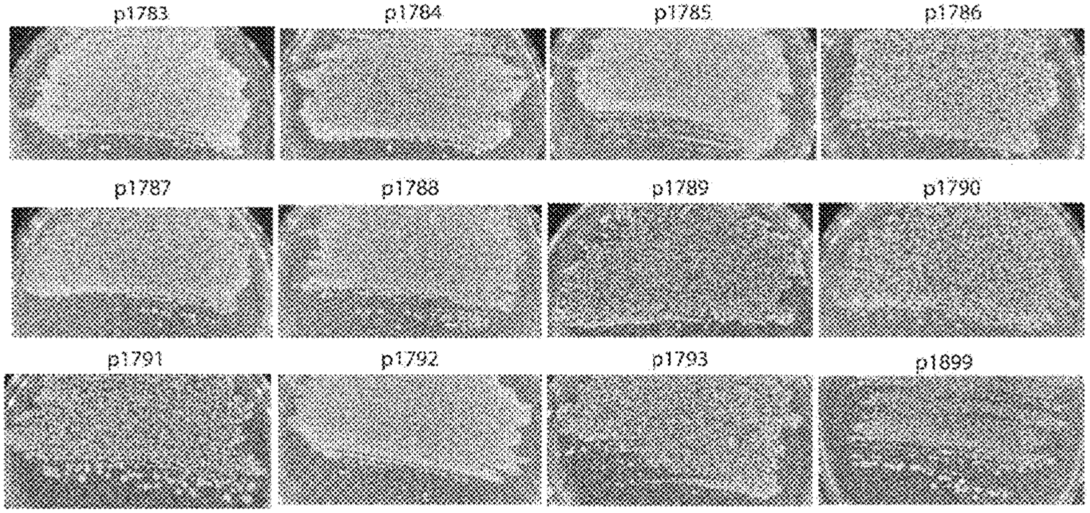

FIG. 4: Five genes and a CRISPR array comprise the Type-S CRISPR-Cas system. The bSNP3127 strains carrying some of the plasmids shown in FIG. 3 are transformed with a 1:1 mixture of target p1631 (purple) and non-target (colourless) plasmids. Purple colonies with the tested plasmids were observed only in the absence of the CRISPR array.

Figure 5:
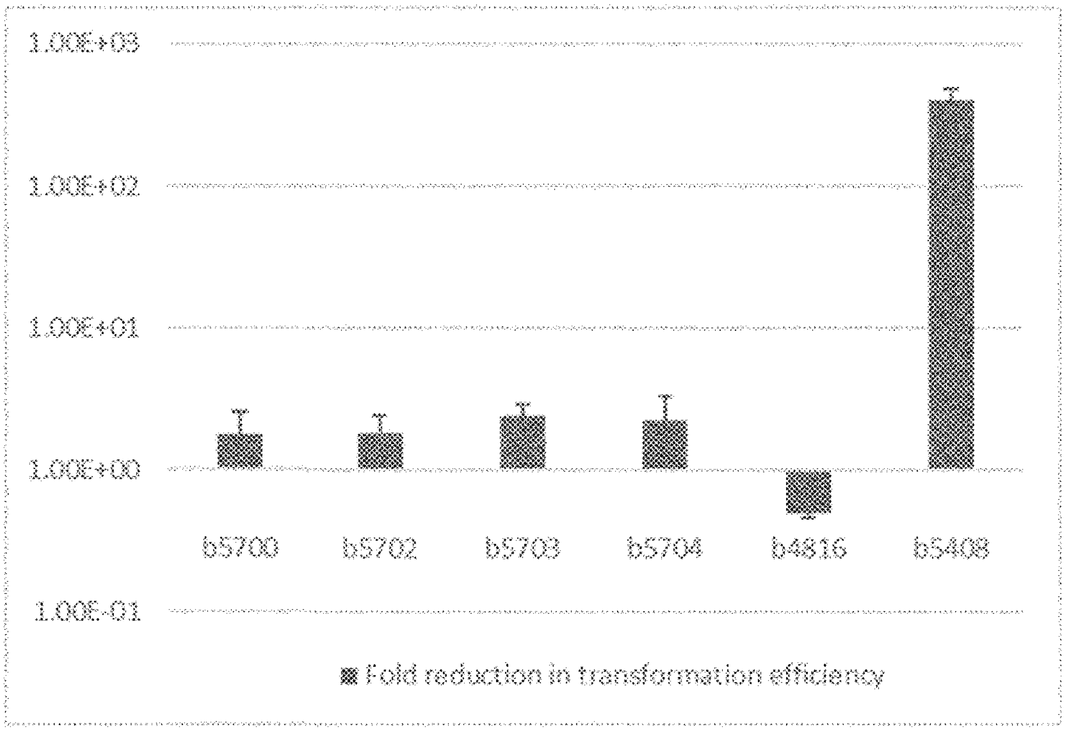

FIG. 5: The CRISPR-Cas system uses all five genes (S1-S5) and a CRISPR array for plasmid inhibition. Strains b5700 (ΔCas-S1), b5702 (ΔCas-S3), b5703 (ΔCas-S4), b5704 (ΔCas-S5) carried plasmids with single gene deletions of the Type-S CRISPR-Cas genes. These strains, together with strains b4816 (negative control, no Type-S CRISPR-Cas system) and b5408 (positive control, full Type-S CRISR-Cas system present) were transformed with either the p1631 target plasmid or the p144 non-target plasmid. The fold reduction in the transformation efficiencies of each strain is presented in this graphical representation.

Figure 6:
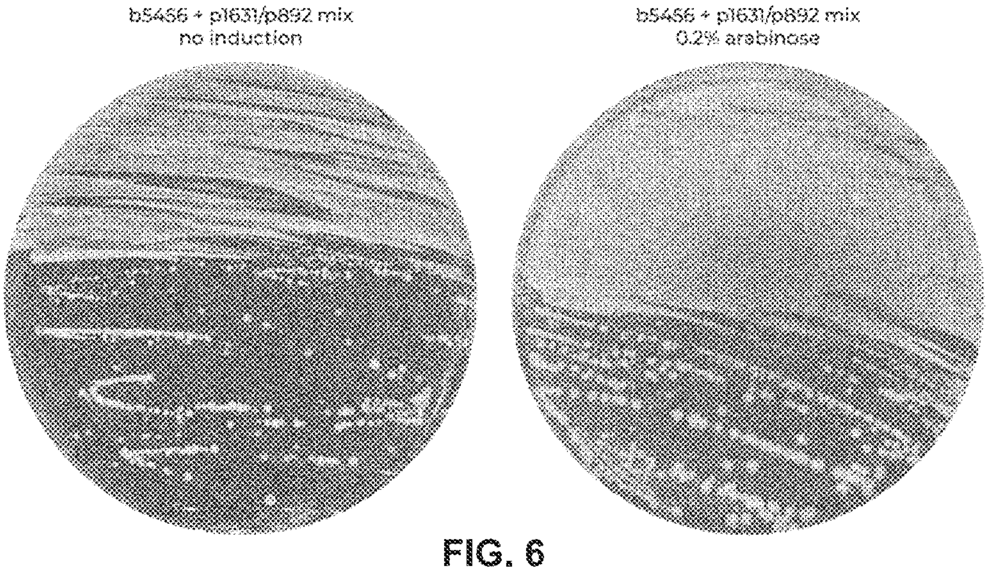

FIG. 6: Controlled induction of the Type-S CRISPR-Cas system hinders the growth of colonies with the p1631 target plasmid.

Figure 7:
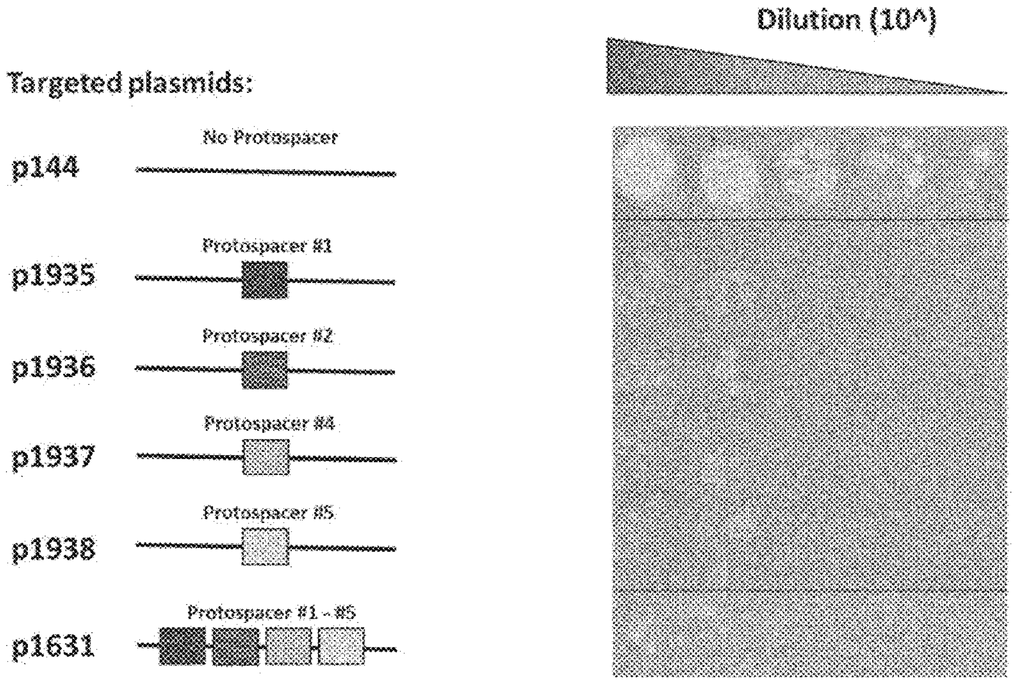

FIG. 7: Plasmid clearance assays for evaluation of the targeting activity of each spacer in the Type-S CRISPR array. All four tested spacers display similar targeting efficiency.

Figure 8:
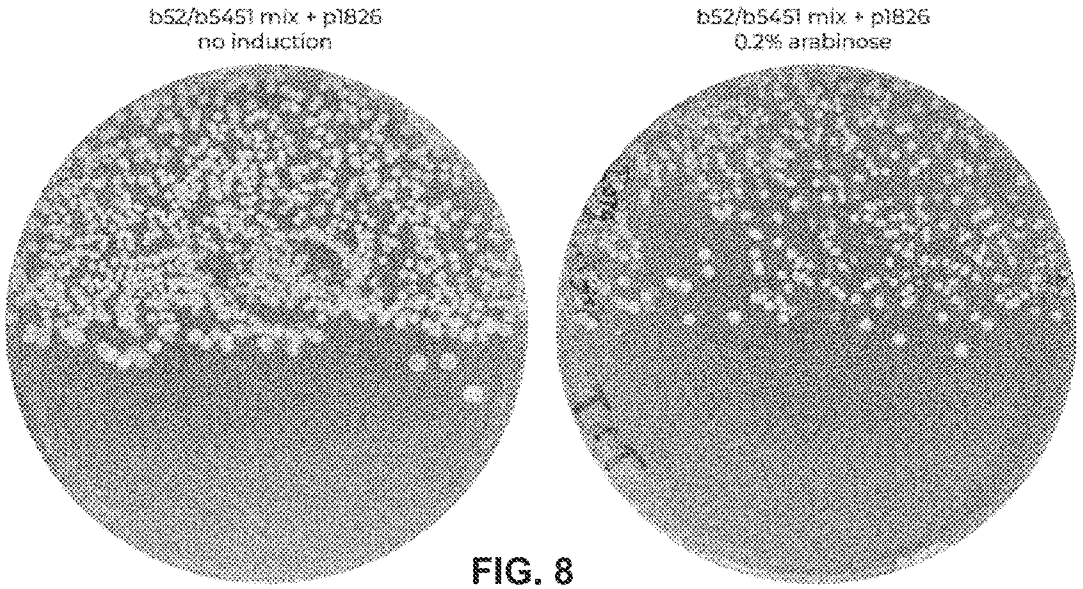

FIG. 8: The Type-S CRISPR-Cas system does not induce lethal dsDNA breaks in the chromosome of *E. coli.*

Figure 9:
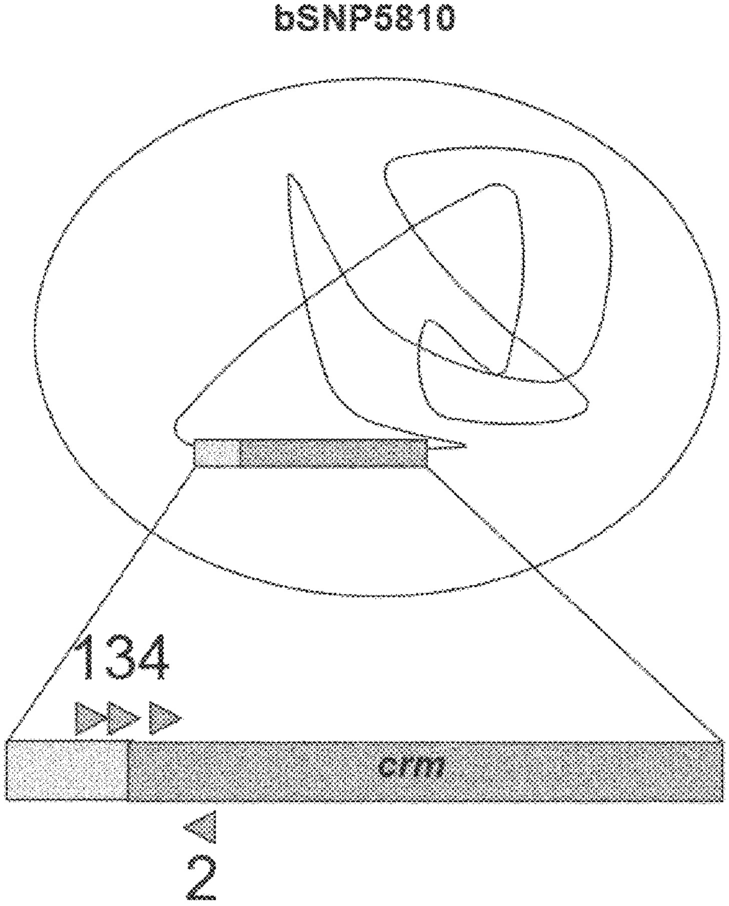

FIG. 9: Schematic representation of the positions of the protospacers employed for the Type-S CRISPR-Cas binding assays.

Figure 10A:
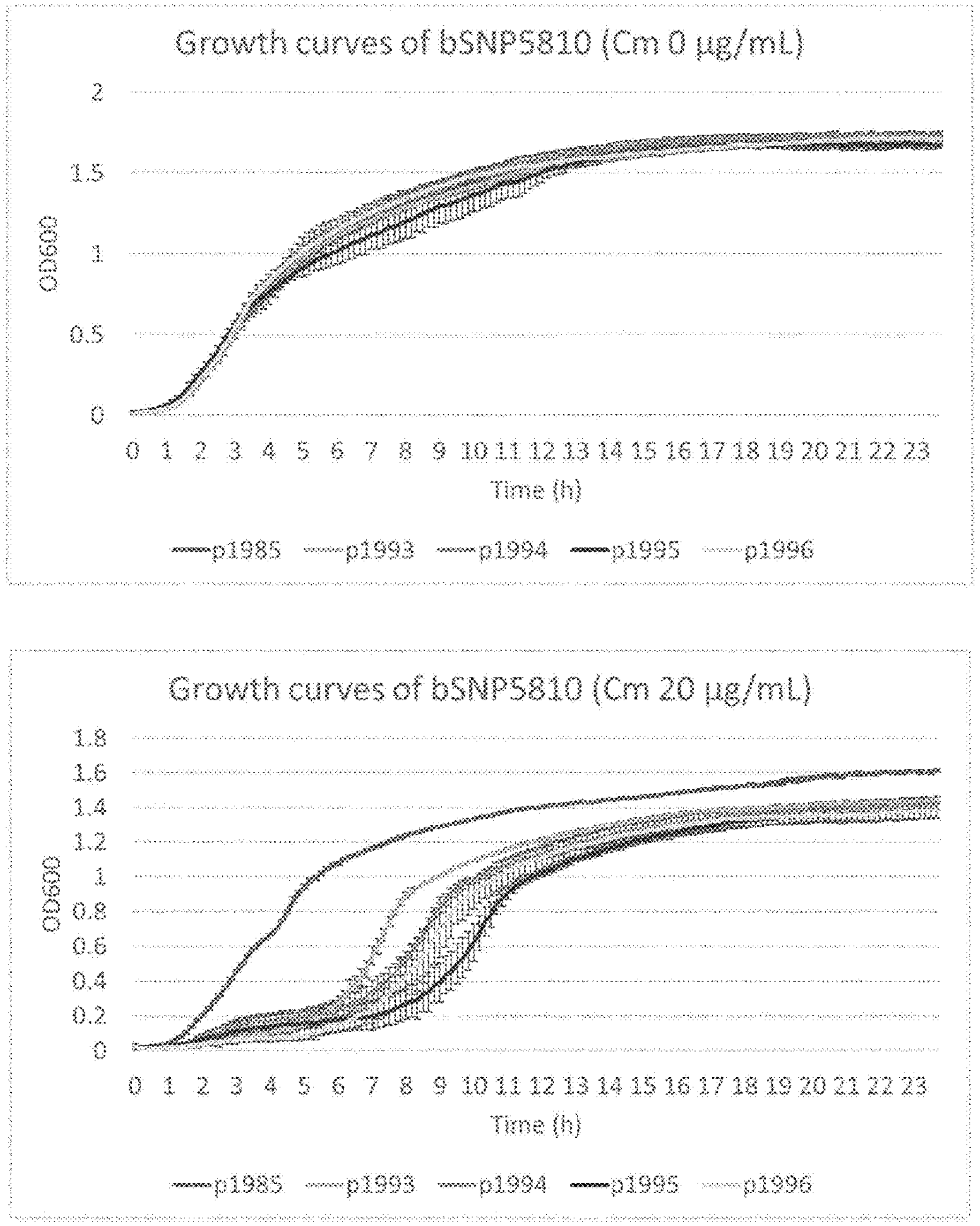
Figure 10C:
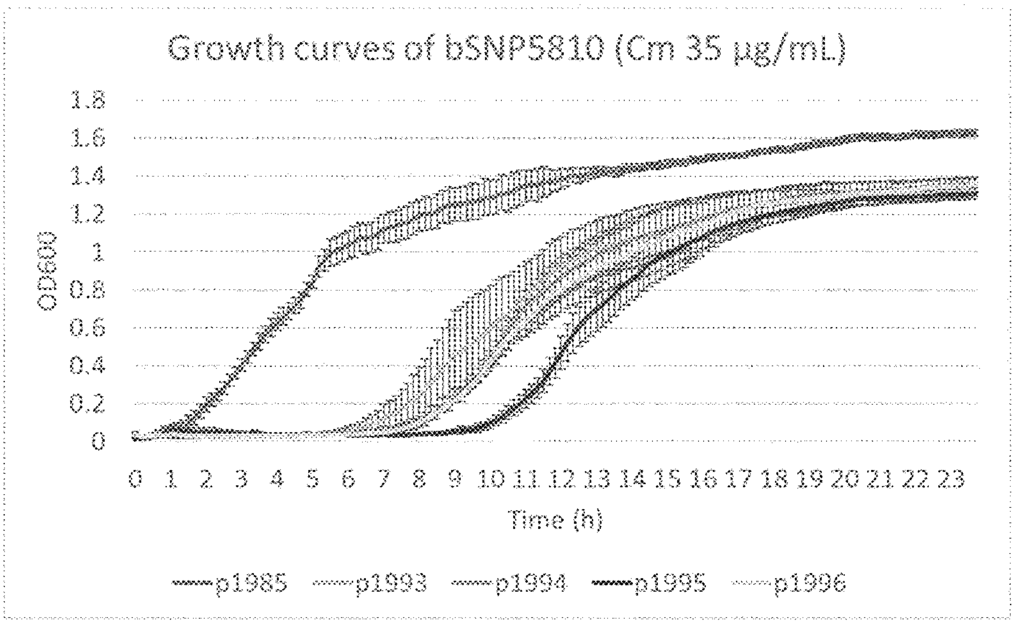

FIGS. 10A-10C: Type-S CRISPR-Cas binds to chromosomal DNA. Growth curves of the bSNP5810 derivative strains in the presence of increasing chloramphenicol concentrations.

Figure 11:
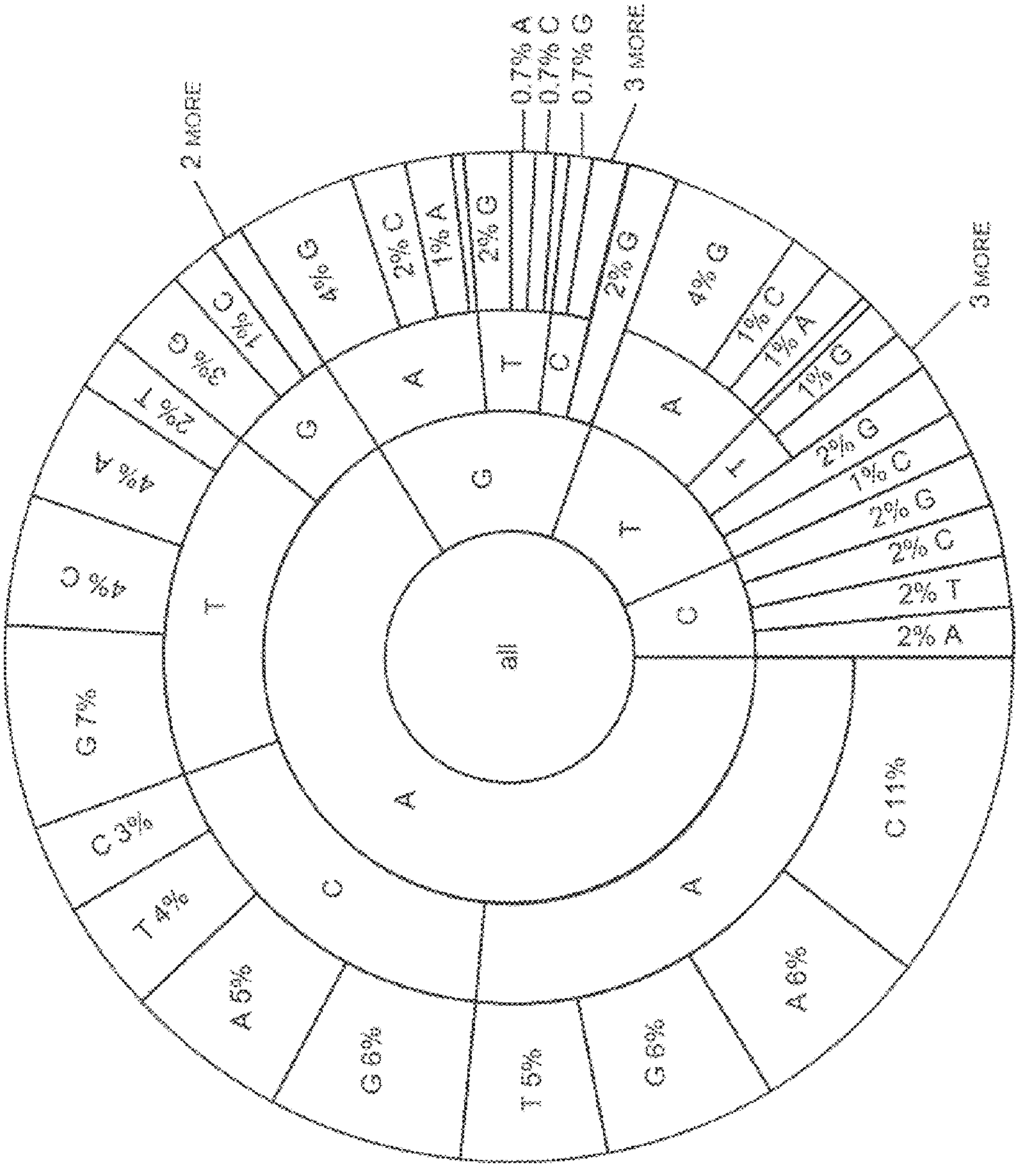

FIG. 11: Graphical representation of the Type-S CRISPR-Cas PAM preferences in a 'PAM wheel' form (see Leenay et al., Technology, 62 (1), 137-147, 2016, doi: doi.org/10.1016/j.molcel.2016.02.031). The inner ring corresponds to the $3^{rd}$ nucleotide position upstream (5') of the protospacer, the middle ring corresponds to the $2^{nd}$ nucleotide position upstream (5') of the protospacer and the outer ring corresponds to the $1^{st}$ nucleotide position upstream (5') of the protospacer. In the wheel, every sequence occupies a sector, with an area proportional to the relative enrichment of the sequence.

Figure 12:
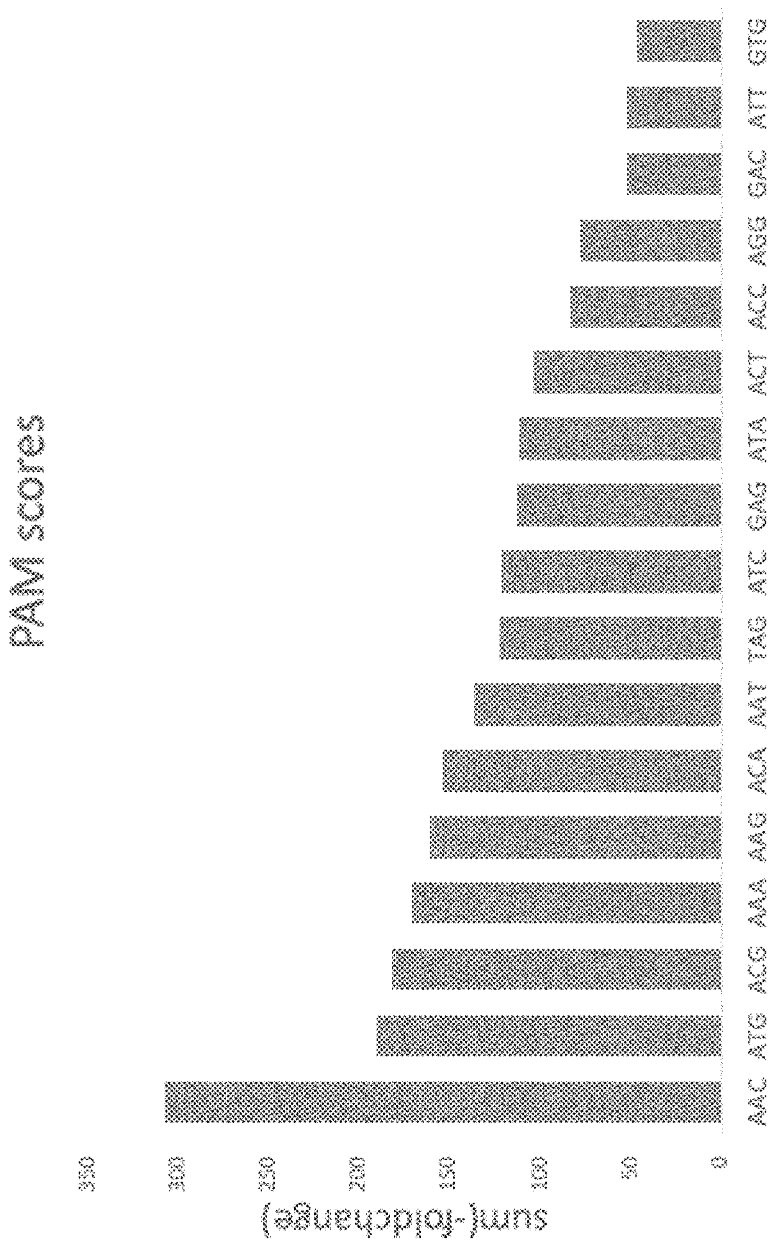

FIG. 12: Graphical representation of the Type-S CRISPR/Cas targeting efficiency on the most preferred PAMs. The x-axis notes the PAMs of the most targeted p2259 library members, according to the generated NGS data. The y-axis depicts the fold reduction of sequencing reads for each PAM, when comparing the NGS data generated by strain b5408 (Cas-S targeting) to the NGS data generated by strain b6259 (control Cas-S).

FIGS. 13A-13F: Graphical representation of the b5408 (wt Type-S) transformation efficiency with each member of the p1935 plasmid library compared to its transformation efficiency with the negative control p2361 plasmid (No PAM). The wild type protospacer is depicted at the top of each graph. The complementary spacer-protospacer sections for each tested protospacer are indicated with dots. The mutated protospacer sections are indicated with the corresponding single letter nucleotide codes. Its tested protospacer has a unique code that is denoted at the left side of the graphs.

(FIG. 13A) PAM proximal mismatches (stretches); (FIG. 13B) PAM distal mismatches (stretches); (FIG. 13C) PAM proximal single mismatches; (FIG. 3D) PAM proximal double mismatches; (FIG. 13E) PAM proximal triple mismatches; (FIG. 13F) PAM proximal quadruple mismatches.

Note: the 'cross(es)' symbols indicate presence of low (single cross) or high (double cross) number of—not possible to count—"micro-colonies" at the corresponding transformation plates. The micro-colonies possibly indicate inefficient Type-S CRISPR/Cas targeting that does not completely stop plasmid replication. As a result, colonies grow with a significantly slower rate on selection medium.

Figure 14:
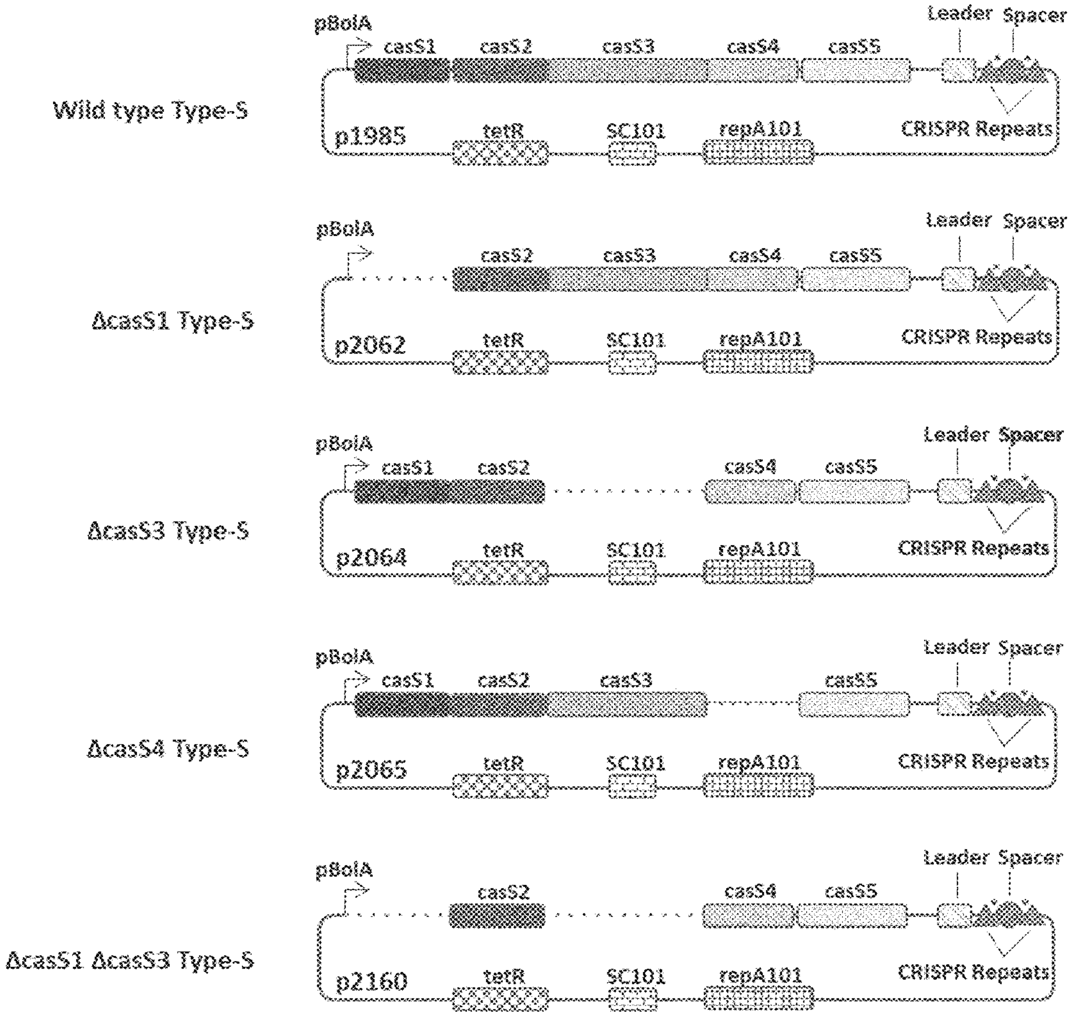

FIG. 14: Graphical representation of the plasmids used in Examples 4 and 5, The Type-S variant that each plasmid expresses is noted at the left side of the figure. The name of each plasmid is noted at the bottom left side of each plasmid. The Type-S genes are presented as boxes with solid fills and the corresponding gene names are noted above each box. Dotted lines correspond to deleted Type-S genes. The expression of the Type-S genes was driven by the pBolA promoter, which is presented as an arrow that points to the direction of the transcription. The expression of the crRNA module was driven by the 'Leader' sequence, presented as a box filled with diagonal stripes and is located right upstream (5') of the crRNA expressing module. The CRISPR repeats (SEQ ID No:6) of the crRNA expressing module are presented as triangles and the spacer is presented as a circle. The locations of the BsmBI recognition sites are indicated with asterisk (*) signs. The tetracycline resistance marker gene, the SC101 origin of replication and the repA101 replication protein gene are presented as boxes with checker, brick and grid fills respectively.

Figure 15:
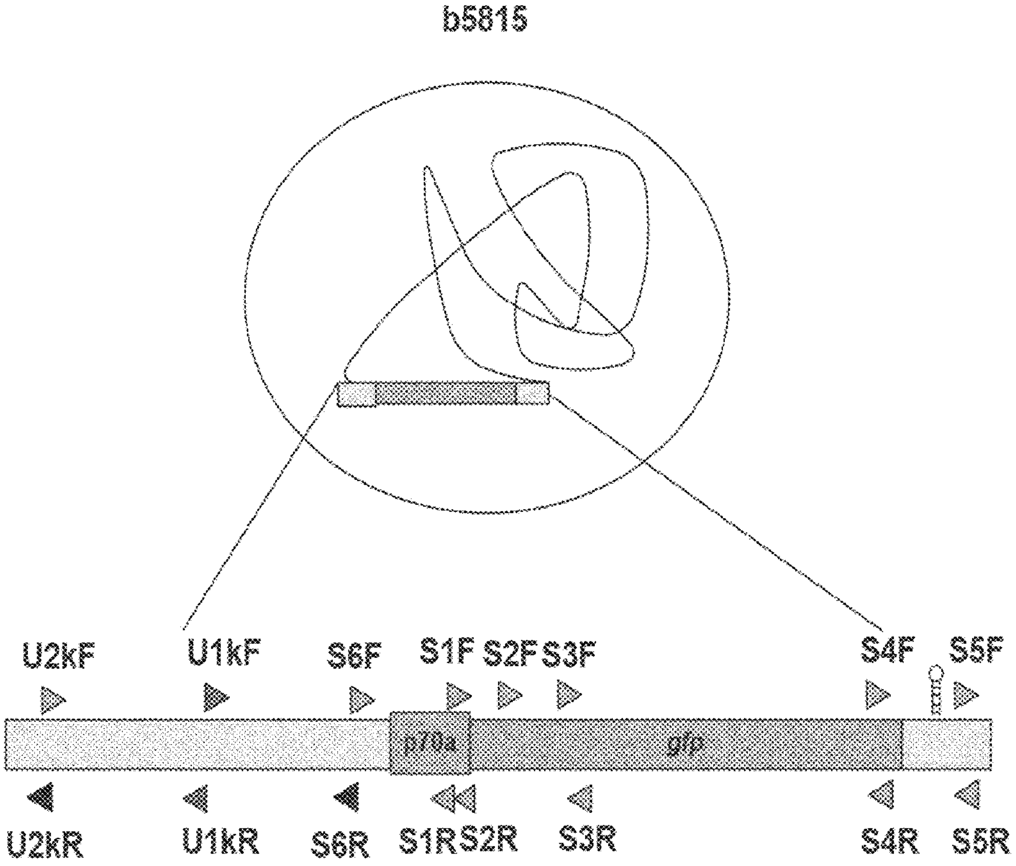

FIG. 15: Schematic representation of the positions of the protospacers employed for the Type-S CRISPRi assays for downregulation of the GFP expression from strain b5815 that contains chromosomally integrated gfp gene. Each protospacer position is indicated with a triangle and the ID of each protospacer is noted above the triangle.

Figure 16A:
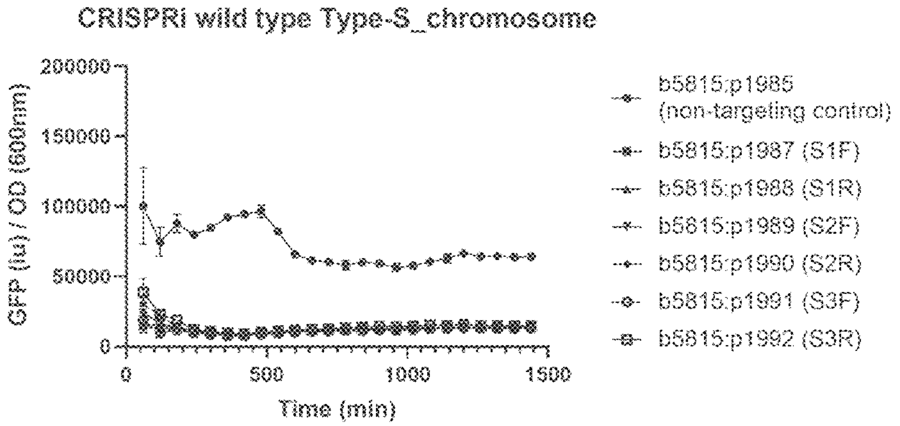
Figure 16B:
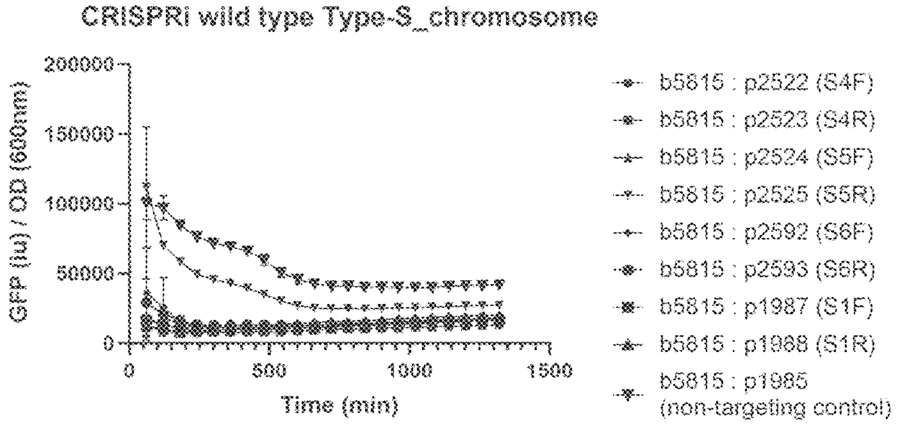
Figure 16C:
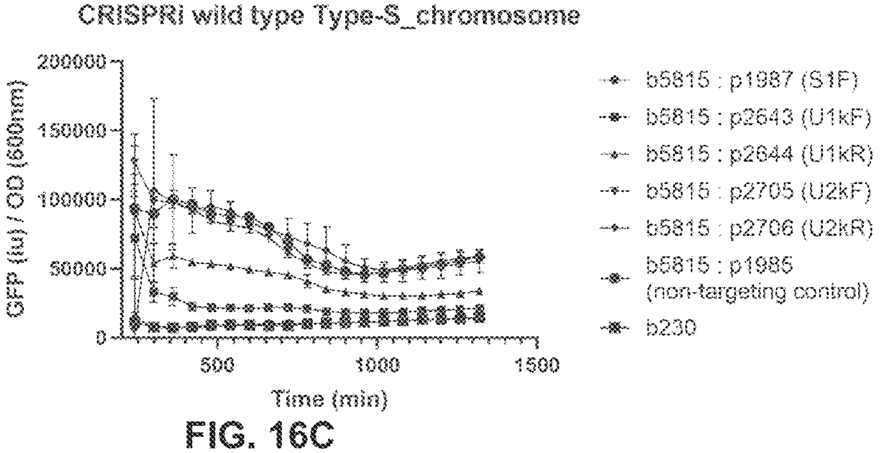

FIGS. 16A-16C: Graphical representation of the chromosomal CRISPRi activity of the wild type Type-S system on the GFP expression of strain b5815 over a 24-hour period. The targeted protospacers were located FIG. 16A) at the beginning of the gfp orf and in the p70a promoter region (Protospacers indicated in brackets: S1F, S1R, S2F, S2R, S3F, S3R), FIG. 16B) at the end of the gfp orf and the 200 bp regions upstream and downstream of gfp (Protospacers indicated in brackets S4F, S4R, S5F, S6F, S6R) FIG. 16C) 1 kb upstream (Protospacers indicated in brackets: U1kF, U1kR) and 2 kb upstream (Protospacers indicated in brackets: U2kF, U2KR) of the gfp orf.

Figure 17A:
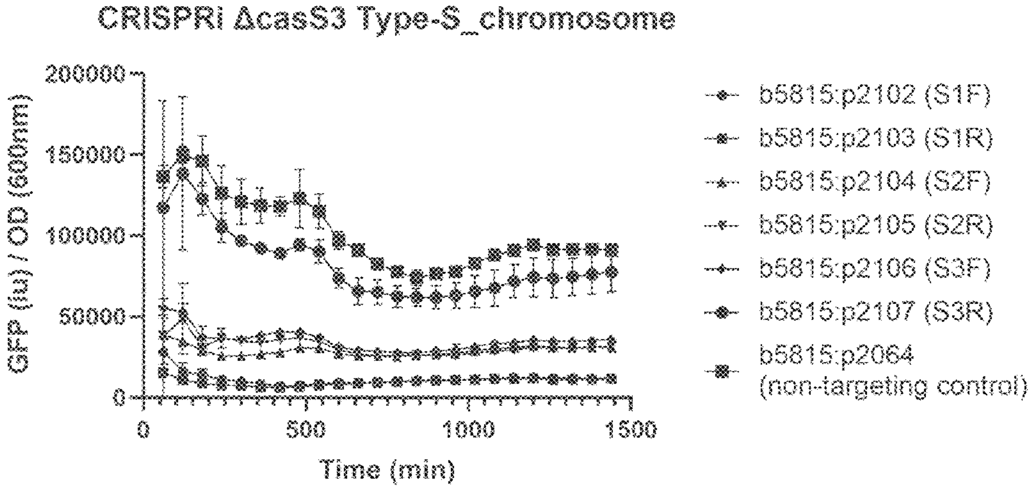
Figure 17B:
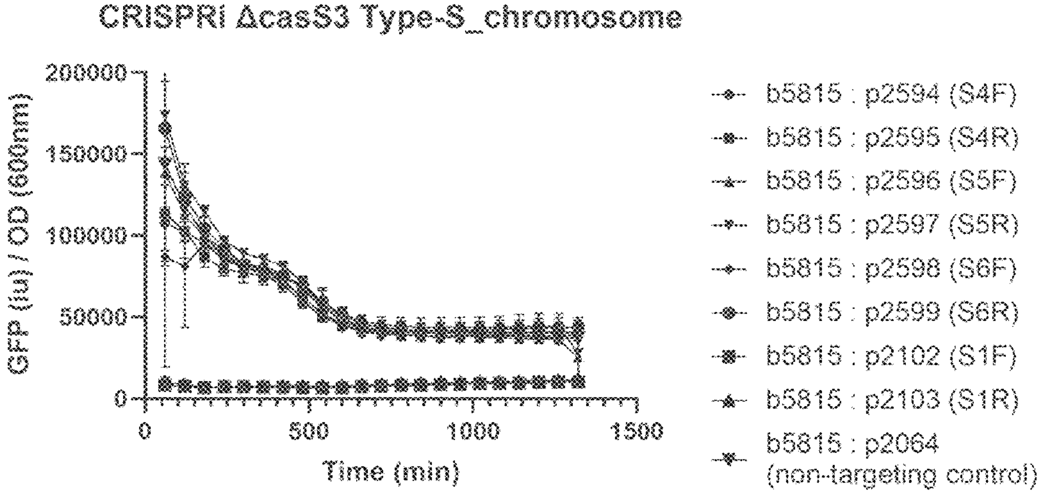

FIGS. 17A-17B: Graphical representation of the chromosomal CRISPRi activity of the ΔcasS3 Type-S system on the GFP expression of strain b5815 over a 24-hour period. The targeted protospacers were located FIG. 17A) at the beginning of the gfp orf and in the p70a promoter region (Protospacers S1F, SIR, S2F, S2R, S3F, S3R), FIG. 17B) at the end of the gfp orf and the 200 bp regions upstream and downstream of gfp (Protospacers S4F, S4R, S5F, S6F, S6R).

Figure 18A:
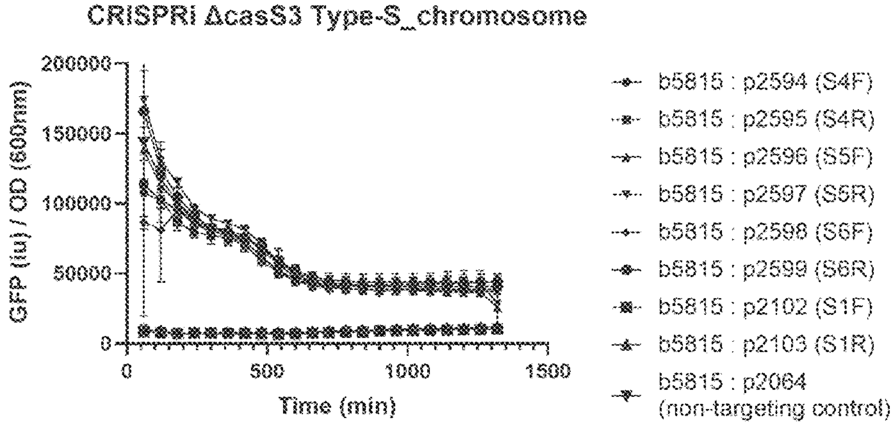
Figure 18B:
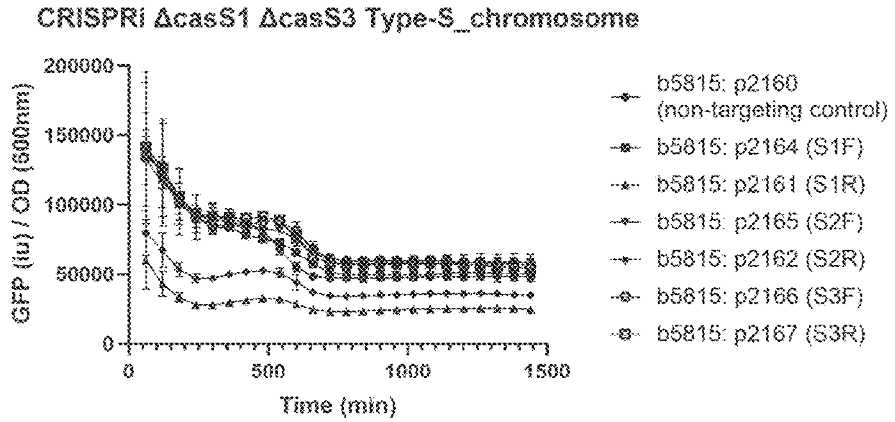
Figure 18C:
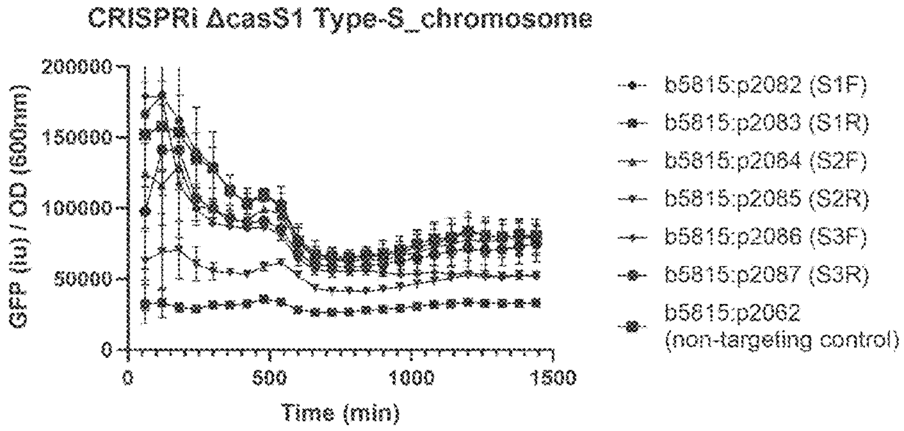

FIGS. 18A-18C: Graphical representation of the chromosomal CRISPRi activity of the FIG. 18A) ΔcasS3 Type-S system, FIG. 18B) ΔcasS14casS3 Type-S system and FIG. 18C) ΔcasS1 Type-S system on the GFP expression of strain b5815 over a 24-hour period. The targeted protospacers were located at the beginning of the gfp orf and in the p70a promoter region (Protospacers SIF, SIR, S2F, S2R, S3F, S3R). The plasmids employed for the transformation of b5815 strain is denoted with (:).

FIGS. 19A-19D: Graphical representation of on-plasmid CRISPRI activity of the FIG. 19A) ΔcasS3 Type-S system, FIG. 19B) ΔcasS4 Type-S system, FIG. 19C) ΔcasS4 Type-S system and FIG. 19D) ΔcasS1ΔcasS3 Type-S system on the GFP expression of strain b6386 over a 24-hour period. The targeted protospacers were located at the beginning of the gfp orf and in the p70a promoter region (Protospacers SIF, SIR, S2F, S2R, S3F, S3R), FIG. 20: Schematic representation of the plasmid combinations employed for the A) CasS1, B) CasS1 (ΔCasS3), C) CasS3 and D) CasS4 base editing assays. The asterix (*) indicates that the spacer is directed against one of: a non-targeting control, S1F, SIR, S2F, S2R, S3F or S3R.

FIGS. 21A-21G: Heatmap based visualization of representative sequencing results from the Type-S CRISPR/Cas base editing assays. The PmCDA1 cytidine deaminase is fused to the C-terminus of FIG. 21A) the Cas-S1 subunit of the wild type Type-S CRISPR/Cas system, FIG. 218) the Cas-S1 subunit of the ΔCas-S3 Type-S CRISPR/Cas system, FIGS. 21C-21F) the Cas-S3 subunit of the wild type Type-S CRISPR/Cas system, FIG. 21G) the Cas-S2 subunit of the wild type Type-S CRISPR/Cas system. On the top side of each box are noted i) the code of the tested protospacer and ii) the nucleotide sequence of the protospacer (highlighted with a boxy arrow that additionally shows the direction of the protospacer) together with the sequence of the immediately neighboring genomic regions where base-editing modifications were detected. On the bottom side of each box are noted i) the codes of unique Sanger sequencing results (each from a distinct colony) and ii) all the C-to-T modifications, or G-to-A modifications when the reverse strand was targeted and modified, that were detected in the sequencing results. The color intensity of each heatmap cell represents the relative C to T (or G to A) abundance for each position, according to the height ratio of the corresponding C and T peaks from the Sanger sequencing results. For example, black boxes represent colonies with 100% C to T mutated genotype for the corresponding positions, whereas off-white boxes correspond to 95% to 5% (reliable limit of detection for Sanger sequencing) C to T mixed mutant genotypes for the corresponding positions.

Figure 22:
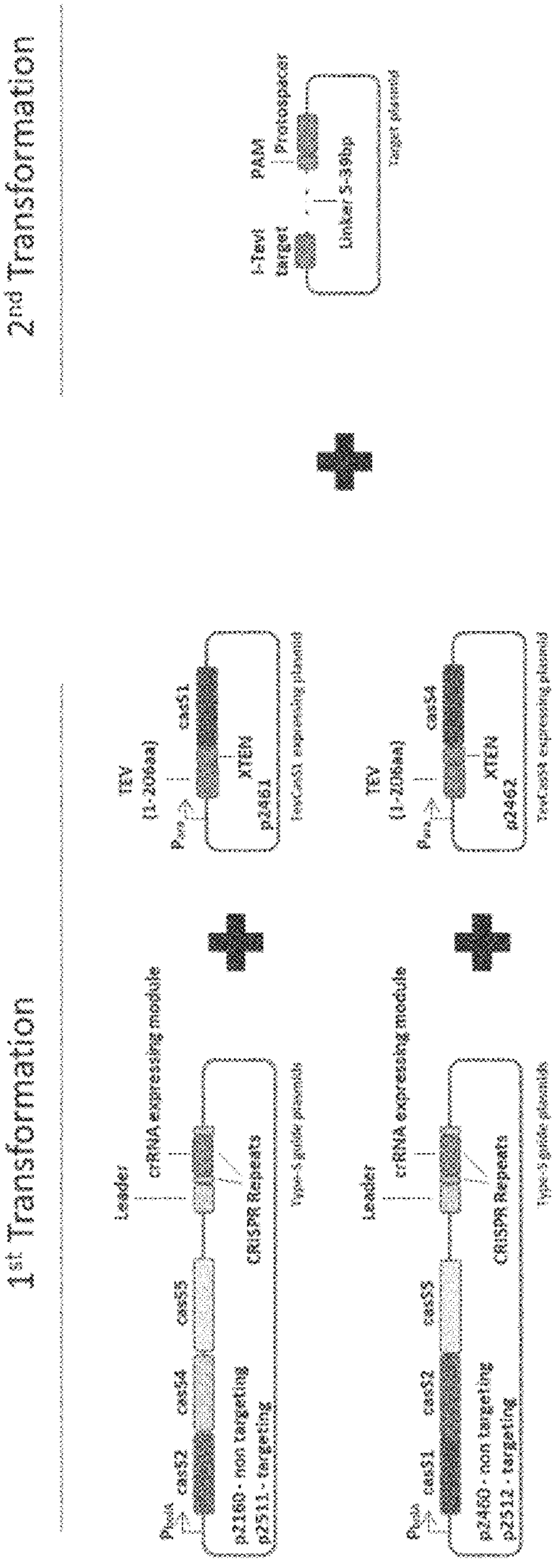

FIG. 22: Schematic representation of the plasmid combinations employed for the TevCasS plasmid targeting assays, FIG. 23: Graphical representation of the results from the TevCasS plasmid targeting assays. The x-axis corresponds to the drop in the transformation efficiency of a MG1655 strain that expresses TevCasS1 and targets the target sequence on a TevCasS target plasmid relative to the transformation efficiency of a MG1655 strain that expresses TevCasS1 and does not target the target sequence on a TevCasS target plasmid. The y-axis corresponds to the size of the I-TevI spacer sequence in the target sequence of a TevCasS target plasmid.

Figure 24:
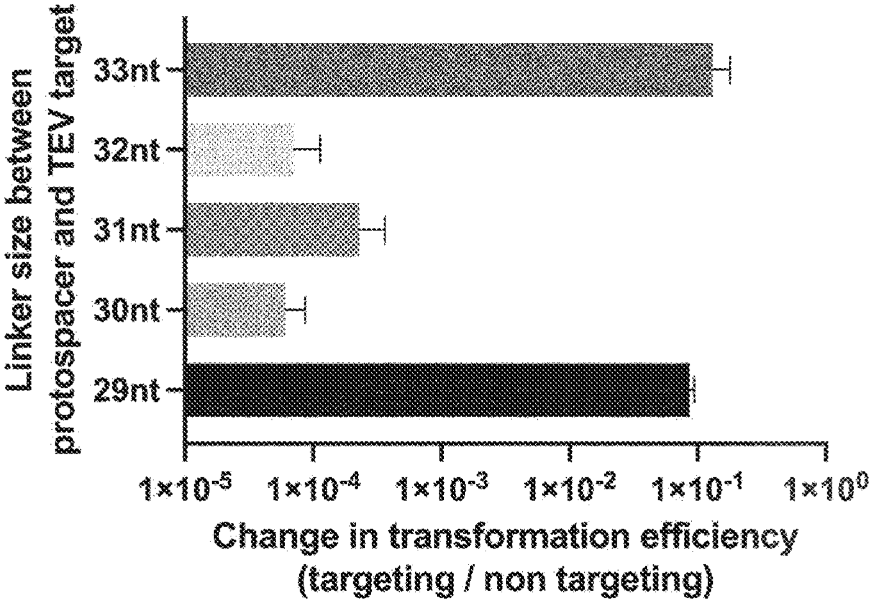

FIG. 24: Graphical representation of the results from the TevCasS chromosomal targeting assays. The x-axis corresponds to the drop in the transformation efficiency of a MG1655 strain that expresses TevCasS1 and targets a chromosomal TevCasS target sequence relative to the transformation efficiency of a MG1655 strain that expresses TevCasS1 and does not target a chromosomal TevCasS target sequence. The y-axis corresponds to the size of the I-TevI spacer sequence in the target sequence of a chromosomal TevCasS target sequence.

Figure 25:
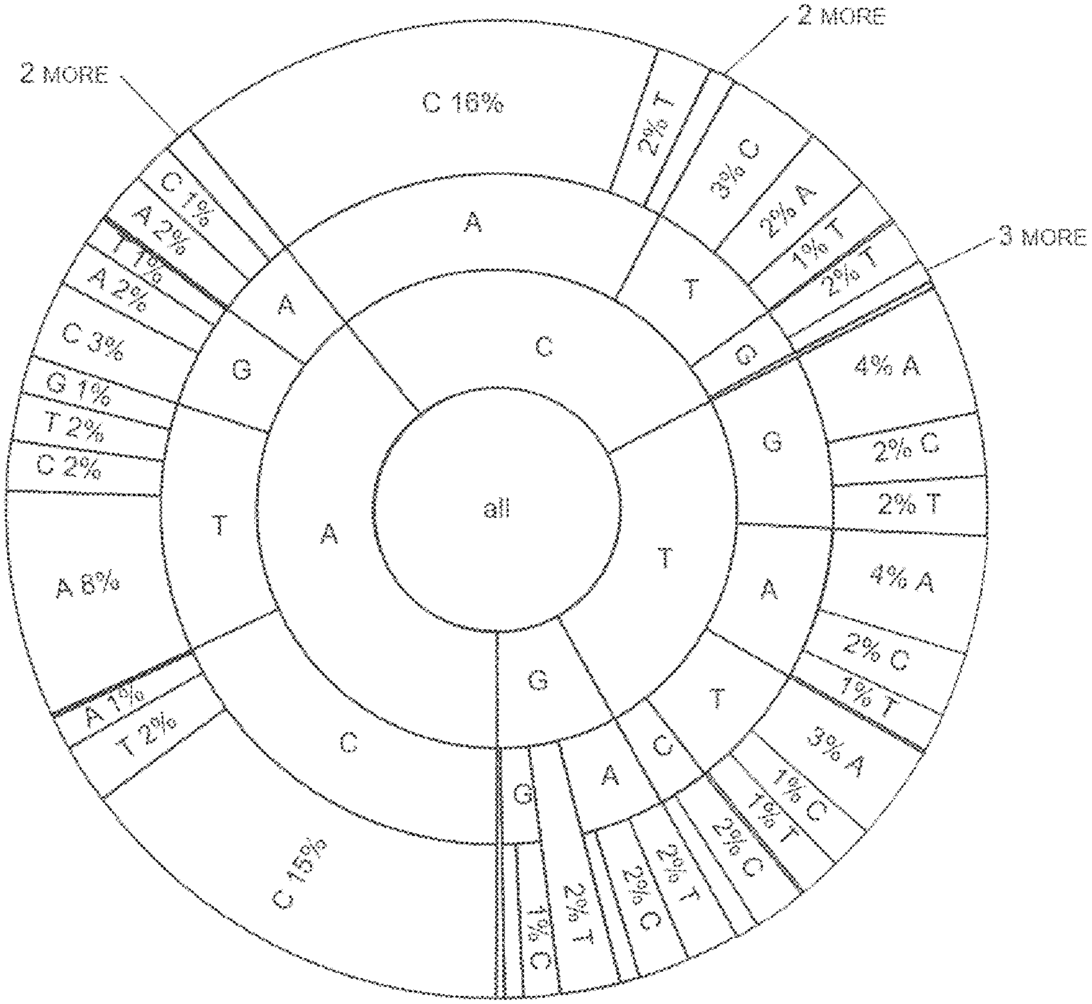

FIG. 25: Graphical representation of the TevCasS target cleavage site preferences in a 'Krona plot' form. The sequence of the TevCasS target cleavage site is 5'C$N_1N_2N_3$G-3', The inner ring corresponds to $N_1$, the middle ring corresponds to $N_2$ nucleotide and the outer ring corresponds to $N_3$. In the wheel, every sequence occupies a sector, with an area proportional to the relative enrichment of the sequence.

DETAILED DESCRIPTION

The technology described herein relates to new and synthetic CRISPR/Cas systems and components thereof, vectors, proteins, ribonucleoprotein complexes and methods of using the new system and components.

We term the new system "CRISPR-S" and we refer to it as a "Type-S CRISPR/Cas" system.

The base components of this system do not rely on the signature genes of any of the Type I-III, or V or VI systems that have already been elucidated. Type-S does not use a Cas3 (the signature protein of Type I systems), a Cas9 (the signature protein of Type II systems), a Cas10 (the signature protein of Type III systems), a Cas12 (the signature protein of Type V systems) or a Cas13 (the signature protein of Type VI systems). The basic components do not comprise a IscB, IsrB or IshB protein (IscBs and IsrBs share a common evolutionary history with Cas9). We refer to the new system as Type-S. Thus, in an embodiment, the vector(s) herein does not encode a Cas3, 9, 10, 12 and/or 13. The nucleic acid herein may not encode a Cas3, 9, 10, 12 and/or 13. The complex herein may not comprise a Cas3, 9, 10, 12 and/or 13. The method herein may not use a Cas3, 9, 10, 12 and/or 13. In an embodiment, the vector(s) or nucleic acid(s) herein do not encode a TnpB. In an embodiment, the complexes described herein do not comprise a TnpB. In an embodiment, the vector(s) or nucleic acid(s) herein do not encode a HD-nuclease domain. In an embodiment, the complexes herein do not comprise a HD-nuclease domain. In an example, the vector(s) or nucleic acid(s) herein encodes a Cas8. In an example, the complexes herein comprise a Cas8.

The complexes may comprise a protein for PAM identification, a protein for interaction with a Cas8, a protein for processing pre-crRNA, and a scaffolding protein, wherein the complexes comprises a Cas-S1 to Cas-S5 protein. The complexes may comprise a protein for PAM identification, a protein for interaction with a Cas8, and a scaffolding protein, wherein the complex comprises a Cas-S1, Cas-S2, Cas-S4 and Cas-S5 protein.

In an example, the vector(s) or nucleic acid(s) comprise a CRISPR array for producing the crRNA. The array may comprise one or more repeat sequences and one or more spacer sequences. The spacer sequences may be complementary (as defined elsewhere herein) to a first protospacer sequence. In some embodiments, the spacer sequences of the array may be complementary to a second, third, fourth . . . etc protospacer in a target sequence, for example if multiplex editing or modification is desired. For example, the repeat sequence is SEQ ID NO:6 or SEQ ID No:70 or a sequence that is identical except for 1, 2, 3, 4, or 5 changes, in particular 1 or 2, e.g. 1 change.

The vector(s) or nucleic acid(s) herein may comprise a Type-S array, i.e. an array that encodes a crRNA that is operable with at least Cas-S1, 2, 3, 4 and 5 to target a first protospacer (or e.g. a first and second protospacer) of a nucleic acid or target sequence. The vector(s) or nucleic acid(s) herein may comprise a Type-S array, i.e. an array that encodes a crRNA that is operable with at least Cas-S1, 2, 4 and 5 to target a first protospacer (or e.g. a first and second protospacer) of a nucleic acid or target sequence. The vector(s) or nucleic acid(s) herein may comprise a Type-S array, i.e. an array that encodes a crRNA that is operable with at least Cas-S2, 3, 4 and 5 to target a first protospacer (or e.g. a first and second protospacer) of a nucleic acid or target sequence. The vector(s) or nucleic acid(s) herein may comprise a Type-S array, i.e. an array that encodes a crRNA that is operable with at least Cas-S2, 4 and 5 to target a first protospacer (or e.g. a first and second protospacer) of a nucleic acid or target sequence.

The protospacer is downstream of a 5'-AAG-3' PAM in the nucleic acid or target sequence. Alternatively, the the PAM can be AAN, ANG, NAG; or the PAM can be AAG with no or one nucleotide change.

The PAM is not CGG.

Alternatively, the PAM can be AHN, KAG, AGG, GAC or GTG.

Alternatively, the PAM is selected from 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3', 5'-TAG-3', 5'-ACC-3', 5'-AGG-3', 5'-ATT-3', 5'-GAC-3' and 5'-GTG-3'. For example, the PAM is selected from 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3' and 5'-TAG-3'. For example, the PAM is selected from 5'-AAC-3', 5'-ATG-3', 5'-AAA-3', 5'-AAG-3', 5'-ACG-3', 5'-AAT-3' and 5'-ACA-3', e.g. 5'-AAC-3' and 5'-ATG-3'. In particular the PAM is 5'-AAC-3'.

Significantly, we identified that the Type-S system components (Cas-S1, Cas-S2, Cas-S3, Cas-S4 and Cas-S5) do not comprise an RNA-guided DNA nuclease. Nevertheless, we surprisingly found that a ribonucleoprotein complex of these components with a crRNA is able to effectively and specifically target a predetermined site on DNA. Using this system, it was also surprisingly possible to modify a cell without inducing dsDNA breaks, see Example 1.3.4 hereinbelow. Armed with this knowledge, we can see many applications of the new system. It is possible, for example, to provide one or more proteins or domains with effector activity (e.g. nuclease (see Example 5 hereinbelow), base editing (see Example 4 hereinbelow) or prime editing activity) together with one or more the components of the system to produce synthetic systems that can modify cells and nucleic acid in a RNA-directed or DNA-directed manner.

The Type-S system and its components, therefore, provide new means to carry out nucleic acid editing and cell targeting in environmental, medical and other settings.

In a First Aspect there is Provided the Following Aspects of the Novel Type-S System:-

A Cas-S1 protein or a nucleic acid encoding a Cas-S1.

A Cas-S2 protein or a nucleic acid encoding a Cas-S2.

A Cas-S3 protein or a nucleic acid encoding a Cas-S3.

A Cas-S4 protein or a nucleic acid encoding a Cas-S4.

A Cas-S5 protein or a nucleic acid encoding a Cas-S5.

One or more nucleic acids encoding a Cas-S1, S2, S3, S4 and S5 protein.

One or more nucleic acids encoding a Cas-S4 and S5 protein.

One or more nucleic acids encoding a Cas-S3, S4 and S5 protein.

One or more nucleic acids encoding a Cas-S2, S3, S4 and S5 protein.

One or more nucleic acids encoding a Cas-S1, S2, S4 and S5 protein.

One or more nucleic acids encoding a Cas-S2, S3, S4 and S5 protein.

One or more nucleic acids encoding a Cas-S2, S4 and S5 protein.

A vector or nucleic acid encoding a Cas-S1, S2, S3, S4 and S5 protein, wherein the vector or nucleic acid comprises SEQ ID NO:12 or a DNA sequence that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:12.

A nucleic acid vector or a nucleic acid that comprises SEQ ID NO:12 or a DNA sequence that is at least (about) 80% (or at least about 80%, 85%, 90%, 91, 92, 93, 94, 95, 96, 97, 98 or at least about 99%) identical to SEQ ID NO:12.

In an embodiment, each said sequence is operably connected to a heterologous promoter (i.e. a promoter that is not naturally operably connected to the sequence). In an embodiment, each said sequence is operably connected to a promoter that is a eukaryotic promoter, or virus (e.g. phage) promoter. The promoter may be a constitutive promoter. The promoter may be an inducible promoter. Promoters may be as described in any Configuration, Concept, aspect, example, embodiment, option or other feature described herein.

Optionally, none of the nucleic acid(s) or vector(s) encode a Cas nuclease. The nucleic acid(s) may encode a non-Cas effector protein or domain, such as a nuclease that is not a Cas nuclease.

In a Second Aspect:-

A protein or ribonucleoprotein complex comprising 1, 2, 3, 4 or all of a Cas-S1, S2, S3, S4 and S5 protein.

A protein or ribonucleoprotein complex comprising a Cas-S1, S2, S3, S4 and S5 protein.

A protein or ribonucleoprotein complex comprising a Cas-S4 and S5 protein.

A protein or ribonucleoprotein complex comprising a Cas-S3, S4 and S5 protein.

A protein or ribonucleoprotein complex comprising a Cas-S2, S3, S4 and S5 protein.

A protein or ribonucleoprotein complex comprising a Cas-S1, S2, S4 and S5 protein.

A protein or ribonucleoprotein complex comprising a Cas-S2, S3, S4 and S5 protein.

A protein or ribonucleoprotein complex comprising a Cas-S2, S4 and S5 protein.

Optionally, the complex does not comprise a Cas nuclease. The complex may comprise a non-Cas effector protein or domain, such as a nuclease that is not a Cas nuclease.

The Type-S proteins are capable of RNA-directed modification of a DNA sequence, optionally without creating a break in the DNA. As used herein:

Cas-S1 proteins: Cas-S1 is a Cas protein that comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:1. Preferably, the identity is at least (about) 80%. Even more preferably, the identity is at least (about) 90 or 95%. In another embodiment, the identity is at least about 96%. In another embodiment, the identity is at least about 97%. In another embodiment, the identity is at least about 98%. In another embodiment, the identity is at least about 99%. Preferably, the Cas-S1 is Cas-S1.1. Cas-S1.1 is a Cas protein that comprises the amino acid of SEQ ID NO:1.

Cas-S2 proteins: Cas-S2 is a Cas protein that comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:2. Preferably, the identity is at least (about) 80%. Even more preferably, the identity is at least (about) 90 or 95%. In another embodiment, the identity is at least about 96%. In another embodiment, the identity is at least about 97%. In another embodiment, the identity is at least about 98%. In another embodiment, the identity is at least about 99%. Preferably, the Cas-S2 is Cas-S2.1. Cas-S2.1 is a Cas protein that comprises the amino acid of SEQ ID NO:2.

Cas-S3 proteins: Cas-S3 is a Cas protein that comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:3. Preferably, the identity is at least (about) 80%. Even more preferably, the identity is at least (about) 90 or 95%. In another embodiment, the identity is at least about 96%. In another embodiment, the identity is at least about 97%, In another embodiment, the identity is at least about 98%. In another embodiment, the identity is at least about 99%. Preferably, the Cas-S3 is Cas-S3.1. Cas-S3.1 is a Cas protein that comprises the amino acid of SEQ ID NO:3.

Cas-S4 proteins: Cas-S4 is a Cas protein that comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:4. Preferably, the identity is at least (about) 80%. Even more preferably, the identity is at least (about) 90 or 95%. In another embodiment, the identity is at least about 96%. In another embodiment, the identity is at least about 97%. In another embodiment, the identity is at least about 98%. In another embodiment, the identity is at least about 99%. Preferably, the Cas-S4 is Cas-S4.1. Cas-S4.1 is a Cas protein that comprises the amino acid of SEQ ID NO:4.

Cas-S5 proteins: Cas-S5 is a Cas protein that comprises an amino acid that is at least (about) 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identical to SEQ ID NO:5. Preferably, the identity is at least (about) 80%. Even more preferably, the identity is at least (about) 90 or 95%. In another embodiment, the identity is at least about 96%. In another embodiment, the identity is at least about 97%. In another embodiment, the identity is at least about 98%. In another embodiment, the identity is at least about 99%. Preferably, the Cas-S5 is Cas-S5.1. Cas-S5.1 is a Cas protein that comprises the amino acid of SEQ ID NO:5.

For example, any percentage identity herein is at least (about) 70%, For example, any percentage identity herein is at least (about) 80%. For example, any percentage identity herein is at least (about) 90%. For example, any percentage identity herein is at least 95%. For example, any percentage identity herein is at least about 96%. For example, any percentage identity herein is at least about 97%. For example, any percentage identity is at least about 98%, For example, any percentage identity herein is at least about 99%.

Percent Identity for Amino Acid Sequences are Determined Using the blastP Algorithm with the Following Parameters:-

The default parameters are adjusted for short input sequences, the expect threshold is set at 0.05 and the length of the seed sequence that initiates an alignment is set at 6. Regions of low compositional complexity are masked. The employed scoring matrix is 'BLOSUM62', with scoring costs to create and extend a gap being 11 and 1 respectively. Conditional compositional score matrix adjustment is employed to compensate for amino acid composition of compared sequences.

Percent Identity for Nucleotide Sequences are Determined Using the Blastn Algorithm with the Following Parameters:-

The default parameters are automatically adjusted for short input sequences, the expect threshold is set at 0.05 and the length of the seed sequence that initiates an alignment is set at 28. Regions of low compositional complexity are masked. The query sequence is masked while producing seed sequences used to scan databases, but not masked for extensions. Matches are scored as +1 and mismatches are scored as −2.

For example, an amino acid sequence described herein is identical to the reference SEQ ID NO except for 1, 2, 3, 4, 5, 6, 7, 8, 9 or 10 amino acid changes, in particular 1 to 5, for example 1 to 3, such as 1 or 2, e.g. 1 amino acid change. For example, a nucleic acid sequence described herein is identical to the reference SEQ ID NO except for 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotide changes. For example, an amino acid sequence of the polypeptide is identical to SEQ ID NO:1 except for 1, 2, 3, 4, 5, 6, 7, 8, 9 or 10 amino acid changes, in particular 1 to 5, for example 1 to 3, such as 1 or 2, e.g. 1 amino acid change. For example, an amino acid sequence of the polypeptide is identical to SEQ ID NO: 2 except for 1, 2, 3, 4, 5, 6, 7, 8, 9 or 10 amino acid changes, in particular 1 to 5, for example 1 to 3, such as 1 or 2, e.g. 1 amino acid change. For example, an amino acid sequence of the polypeptide is identical to SEQ ID NO:3 except for 1, 2, 3, 4, 5, 6, 7, 8, 9 or 10 amino acid changes, in particular 1 to 5, for example 1 to 3, such as 1 or 2, e.g. 1 amino acid change. For example, an amino acid sequence of the polypeptide is identical to SEQ ID NO:4 except for 1, 2, 3, 4, 5, 6, 7, 8, 9 or 10 amino acid changes, in particular 1 to 5, for example 1 to 3, such as 1 or 2, e.g. 1 amino acid change. For example, an amino acid sequence of the polypeptide is identical to SEQ ID NO:5 except for 1, 2, 3, 4, 5, 6, 7, 8, 9 or 10 amino acid changes, in particular 1 to 5, for example 1 to 3, such as 1 or 2, e.g. 1 amino acid change.

For example, an amino acid sequence described herein is identical to the reference SEQ ID NO except for a total number of amino acid changes wherein the total number is no more than (about) 5, 10, 15, 20, 25 or 30% of the number of amino acids in the reference sequence. For example, a nucleotide sequence described herein is identical to the reference SEQ ID NO except for a total number of nucleotide changes wherein the total number is no more than (about) 5, 10, 15, 20, 25 or 30% of the number of nucleotides in the reference sequence. Thus, in an example, the amino acid sequence of the polypeptide is SEQ ID NO:1 or an amino acid sequence that is identical to SEQ ID NO: 1 except for a total number of amino acid changes wherein the total number is no more than (about) 5, 10, 15, 20, 25 or 30% of the number of amino acids in SEQ ID NO:1, in particular no more than (about) 20%, such as no more than (about) 10% of the number of amino acids in SEQ ID NO:1. Thus, in an example, the amino acid sequence of the polypeptide is SEQ ID NO:2 or an amino acid sequence that is identical to SEQ ID NO:2 except for a total number of amino acid changes wherein the total number is no more than (about) 5, 10, 15, 20, 25 or 30% of the number of amino acids in SEQ ID NO:2, in particular no more than (about) 20%, such as no more than (about) 10% of the number of amino acids in SEQ ID NO:2. Thus, in an example, the amino acid sequence of the polypeptide is SEQ ID NO:3 or an amino acid sequence that is identical to SEQ ID NO:3 except for a total number of amino acid changes wherein the total number is no more than (about) 5, 10, 15, 20, 25 or 30% of the number of amino acids in SEQ ID NO:3, in particular no more than (about) 20%, such as no more than (about) 10% of the number of amino acids in SEQ ID NO:3. Thus, in an example, the amino acid sequence of the polypeptide is SEQ ID NO:4 or an amino acid sequence that is identical to SEQ ID NO:4 except for a total number of amino acid changes wherein the total number is no more than (about) 5, 10, 15, 20, 25 or 30% of the number of amino acids in SEQ ID NO:4, in particular no more than (about) 20%, such as no more than (about) 10% of the number of amino acids in SEQ ID NO:4. Thus, in an example, the amino acid sequence of the polypeptide is SEQ ID NO:5 or an amino acid sequence that is identical to SEQ ID NO:5 except for a total number of amino acid changes wherein the total number is no more than (about) 5, 10, 15, 20, 25 or 30% of the number of amino acids in SEQ ID NO:5, in particular no more than (about) 20%, such as no more than (about) 10% of the number of amino acids in SEQ ID NO:5.

In an embodiment, the vector(s) herein encode Cas-S1, 2, 3, 4 and 5.

In an embodiment, the vector(s) herein encode Cas-S4 and 5.

In an embodiment, the vector(s) herein encode Cas-S3, 4 and 5.

In an embodiment, the vector(s) herein encode Cas-S2, 3, 4 and 5.

In an embodiment, the vector(s) herein encode Cas-S1 and 2.

In an embodiment, the vector(s) herein encode Cas-S1, 2 and 3.

In an embodiment, the vector(s) herein encode Cas-S1, 2, 3 and 4.

In an embodiment, the vector(s) herein encode Cas-S1, 2, 4 and 5.

In an embodiment, the vector(s) herein encode Cas-S2, 4 and 5. In an embodiment, the vector(s) herein encode Cas-S1.1, 2.1, 3.1, 4.1 and 5.1.

In an embodiment, the vector(s) herein encode Cas-S4.1 and 5.1.

In an embodiment, the vector(s) herein encode Cas-S3.1, 4.1 and 5.1.

In an embodiment, the vector(s) herein encode Cas-S2.1, 3.1, 4.1 and 5.1.

In an embodiment, the vector(s) herein encode Cas-S1.1 and 2.1.

In an embodiment, the vector(s) herein encode Cas-S1.1, 2.1 and 3.1.

In an embodiment, the vector(s) herein encode Cas-S1.1, 2.1, 3.2 and 4.1.

In an embodiment, the vector(s) herein encode Cas-S1.1, 2.1, 4.1 and 5.1.

In an embodiment, the vector(s) herein encode Cas-S2.1, 4.1 and 5.1.

In an embodiment, the complex herein comprises Cas-S1, 2, 3, 4 and 5.

In an embodiment, the complex herein comprises Cas-S4 and 5.

In an embodiment, the complex herein comprises Cas-S3, 4 and 5.

In an embodiment, the complex herein comprises Cas-S2, 3, 4 and 5.

In an embodiment, the complex herein comprises Cas-S1 and 2.

In an embodiment, the complex herein comprises Cas-S1, 2 and 3.

In an embodiment, the complex herein comprises Cas-S1, 2, 3 and 4.

In an embodiment, the complex herein comprises Cas-S1, 2, 4 and 5.

In an embodiment, the complex herein comprises Cas-S2, 4 and 5.

In an embodiment, the complex herein comprises Cas-S1.1, 2.1, 3.1, 4.1 and 5.1.

In an embodiment, the complex herein comprises Cas-S4.1 and 5.1.

In an embodiment, the complex herein comprises Cas-S3.1, 4.1 and 5.1.

In an embodiment, the complex herein comprises Cas-S2.1, 3.1, 4.1 and 5.1.

In an embodiment, the complex herein comprises Cas-S1.1 and 2.1.

In an embodiment, the complex herein comprises Cas-S1.1, 2.1 and 3.1.

In an embodiment, the complex herein comprises Cas-S1.1, 2.1, 3.1 and 4.1.

In an embodiment, the complex herein comprises Cas-S1.1, 2.1, 4.1 and 5.1.

In an embodiment, the complex herein comprises Cas-S2.1, 4.1 and 5.1.

In an embodiment, the fusion protein herein comprises Cas-S1.1, 2.1, 3.1, 4.1 or 5.1.

In an embodiment, the fusion protein herein comprises Cas-S1.1, 2.1, 3.1, 4.1 and 5.1.

In an embodiment, the fusion protein herein comprises Cas-S4.1 and 5.1.

In an embodiment, the fusion protein herein comprises Cas-S3.1, 4.1 and 5.1.

In an embodiment, the fusion protein herein comprises Cas-S2.1, 3.1, 4.1 and 5.1.

In an embodiment, the fusion protein herein comprises Cas-S1.1 and 2.1.

In an embodiment, the fusion protein herein comprises Cas-S1.1, 2.1 and 3.1.

In an embodiment, the fusion protein herein comprises Cas-S1.1, 2.1, 3.1 and 4.1.

In an embodiment, the fusion protein herein comprises Cas-S1.1, 2.1, 4.1 and 5.1.

In an embodiment, the fusion protein herein comprises Cas-S2.1, 4.1 and 5.1.

In an embodiment, the method herein uses Cas-S1.1, 2.1, 3.1, 4.1 or 5.1.

In an embodiment, the method herein uses Cas-S1.1, 2.1, 3.1, 4.1 and 5.1.

In an embodiment, the method herein uses Cas-S4.1 and 5.1.

In an embodiment, the method herein uses Cas-S3.1, 4.1 and 5.1.

In an embodiment, the method herein uses Cas-S2.1, 3.1, 4.1 and 5.1.

In an embodiment, the method herein uses Cas-S1.1 and 2.1.

In an embodiment, the method herein uses Cas-S1.1, 2.1 and 3.1.

In an embodiment, the method herein uses Cas-S1.1, 2.1, 3.1 and 4.1.

In an embodiment, the method herein uses Cas-S1.1, 2.1, 4.1 and 5.1.

In an embodiment, the method herein uses Cas-S2.1, 4.1 and 5.1.

In an aspect there is provided one or more vectors and nucleic acids comprising one or more nucleotide sequences selected from SEQ ID NOs: 7-11.

There is Provided:-

One or more nucleic acids comprising SEQ ID NOs: 7-11.

One or more nucleic acids comprising SEQ ID NOs: 8-11.

One or more nucleic acids comprising SEQ ID NOs: 9-11.

One or more nucleic acids comprising SEQ ID NOs: 10 and 11.

One or more nucleic acids comprising SEQ ID Nos: 7, 8, 10 and 11.

One or more nucleic acids comprising SEQ ID Nos: 8, 9, 10 and 11.

One or more nucleic acids comprising SEQ ID Nos: 8, 10 and 11.

A nucleic acid comprising SEQ ID NO:7.

A nucleic acid comprising SEQ ID NO:8.

A nucleic acid comprising SEQ ID NO:9.

A nucleic acid comprising SEQ ID NO:10.

A nucleic acid comprising SEQ ID NO:11.

A nucleic acid comprising SEQ ID Nos: 7-11.

A nucleic acid comprising SEQ ID Nos: 7, 8, 10 and 11.

A nucleic acid comprising SEQ ID Nos: 8, 9, 10 and 11.

A nucleic acid comprising SEQ ID Nos: 8, 10 and 11.

One or more nucleic acid vectors comprising SEQ ID NOs: 7-11.

One or more nucleic acid vectors comprising SEQ ID NOs: 8-11.

One or more nucleic acid vectors comprising SEQ ID NOs: 9-11.

One or more nucleic acid vectors comprising SEQ ID NOs: 10 and 11.

One or more nucleic acid vectors comprising SEQ ID Nos: 7, 8, 10 and 11.

One or more nucleic acid vectors comprising SEQ ID Nos: 8, 9, 10 and 11.

One or more nucleic acid vectors comprising SEQ ID Nos: 8, 10 and 11.

A nucleic acid vector comprising SEQ ID NO:7.

A nucleic acid vector comprising SEQ ID NO:8.

A nucleic acid vector comprising SEQ ID NO:9.

A nucleic acid vector comprising SEQ ID NO: 10.

A nucleic acid vector comprising SEQ ID NO:11.

A nucleic acid vector comprising SEQ ID Nos: 7-11.

A nucleic acid vector comprising SEQ ID Nos: 7, 8, 10 and 11.

A nucleic acid vector comprising SEQ ID Nos: 8, 9, 10 and 11.

A nucleic acid vector comprising SEQ ID Nos: 8, 10 and 11.

A vector comprising SEQ ID NO: 12.

A nucleic acid comprising SEQ ID NO: 12.

Optionally, said recited nucleotide sequence or at least one of said recited nucleotide sequences is operably connected to a promoter that is a) heterologous to the nucleotide sequence(s);
b) not an *E coli* or *Klebsiella* promoter;
c) a eukaryotic cell promoter;
d) an animal promoter (optionally a mammalian or human promoter);
e) a plant promoter;
f) a fungus promoter (optionally a yeast promoter);
g) an insect promoter;
h) a virus promoter (optionally a virus, AAV or lentivirus promoter); or
i) a synthetic promoter.

Any promoter described herein can be used with the vectors and nucleic acids described herein.

In an embodiment, the vector(s) or nucleic acid(s) is comprised by a cell that is not an *E. coli* or *Klebsiella* (e.g. not in a *K. pneumoniae*) cell. In an embodiment, the vector(s) or nucleic acid(s) is comprised by a cell that is not a *Pseudomonas* cell. In an embodiment, the vector(s) or nucleic acid(s) is comprised by a cell that is not an *E. coli* or *Klebsiella* cell that comprises endogenous nucleotide sequence comprising SEQ ID NOs: 7-11. In an embodiment, the vector(s) or nucleic acid(s) is comprised by a cell (e.g. a bacterial cell) that does not comprise endogenous nucleotide sequence comprising SEQ ID NOs: 7-11. In an embodiment, the vector(s) or nucleic acid(s) is comprised by a eukaryotic cell. In an embodiment, the vector(s) or nucleic acid(s) is comprised by a human cell. In an embodiment, the vector(s) or nucleic acid(s) is comprised by an animal cell. In an embodiment, the vector(s) or nucleic acid(s) is comprised by a plant cell. In an embodiment, the vector(s) or nucleic acid(s) is comprised by a fungal cell.

There is also provided:

One or more nucleic acid vectors or one or more nucleic acids comprising at least one nucleotide sequence selected from SEQ ID NOs: 7-11, wherein a said nucleotide sequence is a) operably connected to a heterologous promoter, synthetic promoter, eukaryotic promoter or non-bacterial promoter; and/or
b) comprised by a cell that is a eukaryotic cell, a non-bacterial cell, or a cell that is not a bacterial cell (e.g. an *E. coli, Pseudomonas* or *Klebsiella* cell) that comprises endogenous nucleotide sequence comprising SEQ ID NOs: 7-11.

One or more nucleic acid vectors or one or more nucleic acids comprising at least one nucleotide sequence selected from SEQ ID NOs: 7-11, wherein a said nucleotide sequence is comprised by a cell (e.g. a bacterial cell) that does not comprise endogenous nucleotide sequence comprising SEQ ID NOs: 7-11.

Optionally, any vector or nucleic acid or nucleotide sequence herein is codon optimized for use in a human, animal (e.g. mammalian, rodent, mouse or rat), plant or fungus cell. Optionally, any vector or nucleic acid or nucleotide sequence herein is codon optimized for use in a eukaryotic cell. Vectors and nucleic acid sequences for use in eukaryotic cells may comprise nuclear localisation sequences (NLSs). The NLSs facilitate entry of the proteins and polypeptides described herein into eukaryotic cells.

Optionally, any vector or nucleic acid or nucleotide sequence herein is codon optimized for use in a prokaryotic cell, e.g. a bacterial or archaeal cell. For example, the bacterial cell is not an *E. coli* cell. For example, the bacterial cell is not a *Klebsiella* (e.g. *K. pneumoniae*) cell. For example, the bacterial cell is not a *Pseudomonas* cell. In an example, the cell comprises a DNA or polynucleotide that is modified or targeted by the methods described herein.

In an example, the cell herein is a human, animal (e.g. mammalian, rodent, mouse or rat), plant or fungus cell. In an example, the cell herein is a *Homo sapiens, Drosophila melanogaster, Mus musculus, Rattus norvegicus, Caenorhabditis elegans*, or *Arabidopsis thaliana* cell. In an example, the cell herein is a prokaryotic cell, e.g. a bacterial or archaeal cell. For example, the bacterial cell is not an *E. coli* cell. For example, the bacterial cell is not a *Klebsiella* cell. For example, the bacterial cell is not a *Pseudomonas* cell.

In an example, an animal or mammal herein is a vertebrate.

Optionally, the crRNA disclosed herein (see, e.g. Concept 10 below) is 15-100 nucleotides long and comprises a sequence (e.g. a spacer sequence) of at least 10 contiguous nucleotides that is complementary to the target sequence. For example, the crRNA is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. For example, the crRNA comprises a sequence (e.g. a spacer sequence) of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to the target sequence.

In one embodiment, the crRNA is as described elsewhere herein. The crRNA may comprise two repeat sequences. The crRNA may comprise at least one repeat sequence having the nucleotide sequence of SEQ ID No:6. The crRNA may comprise two repeat sequences (e.g. having the nucleotide sequence of SEQ ID No:6) and one spacer sequence which hybridizes to a first protospacer sequence in a target sequence. The crRNA may comprise at least one repeat sequence having the nucleotide sequence of SEQ ID No:70. The crRNA may comprise two repeat sequences (e.g. having the nucleotide sequence of SEQ ID No:70) and one spacer sequence which hybridizes to a first protospacer sequence in a target sequence.

The spacer sequence may be from about 25 to 39 nucleotides in length. The spacer sequence may be from about 29 to 35 (e.g. from about 30 to 34, or from about 31 to 33) nucleotides in length. The spacer sequence may be about 32 nucleotides in length. The spacer sequence may be 32 nucleotides in length. The spacer may be (about) 70% (such as (about) 80%, or (about) 90%, or (about) 95%) complementary to the protospacer sequence in the target sequence. The spacer may be 100% complementary to the protospacer sequence in the target sequence. The spacer and/or protospacer may be as described in Concept 10 herein.

The target sequence may be an RNA. The target sequence may be a single stranded DNA.

In a particular embodiment, the target sequence may be a sequence of a dsDNA. The target sequence may be a sequence in the genome of a mammal, e.g. a human. Optionally, the target sequence comprises a sequence associated with a disease or disorder in a human or animal subject.

Optionally, the target sequence comprises a point mutation associated with a disease or disorder and the complex edits a point mutation in the target sequence. Alternatively, the target sequence is comprised by a gene whose expression is errant (e.g. is present, or over-expressed) in a disease or disorder, and the complex introduces a point mutation (or introduces one or more mutations in a region of the target sequence) which disrupts or prevents expression of the gene. The (one or more) point mutation(s) may be located between about 10 to about 20 nucleotides upstream (5') of a 5'-AAG-3' PAM in the target sequence. The (one or more) point mutation(s) may be located between about 10 to about 400 nucleotides, or between about 10 and 350 nucleotides, or between about 10 and 300 nucleotides, or between about 10 and 250 nucleotides, or between about 10 and 200 nucleotides, or between about 10 and 150 nucleotides upstream (5') or downstream (3') (e.g. downstream) of a PAM in the target sequence. The (one or more) point mutation(s) may be located between about 30 and 120 nucleotides (for example between about 50 and 100 nucleotides) upstream (5') or downstream (3') (e.g. downstream) of a PAM in the target sequence. Alternatively, the the PAM can be AAN, ANG, NAG; or the PAM can be AAG with no or one nucleotide change.

Alternatively, the PAM can be AHN, KAG, AGG, GAC or GTG.

Alternatively, the PAM is selected from 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3', 5'-TAG-3', 5'-ACC-3', 5'-AGG-3', 5'-ATT-3', 5'-GAC-3' and 5'-GTG-3', For example, the PAM is selected from 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3' and 5'-TAG-3'. For example, the PAM is selected from 5'-AAC-3', 5'-ATG-3', 5'-AAA-3', 5'-AAG-3', 5'-ACG-3', 5'-AAT-3' and 5'-ACA-3', e.g. 5'-AAC-3' and 5'-ATG-3'. In particular the PAM is 5'-AAC-3'.

For example, the mutation is a C to T point mutation (or the one or more mutations are C-to-T point mutations), wherein the complex deaminates the target C point mutation, and wherein the deamination results in a sequence that is not associated with a disease or disorder. For example, the target C point mutation (or the one or more mutations are target C point mutations) is (are) present in the DNA strand that is not complementary to the crRNA. For example, the (one or more) C to T point mutation(s) is introduced by a cytidine deaminase (e.g. a PmCDA1 cytidine deaminase as described elsewhere herein), which is fused (e.g. to the C-terminus) of a Cas-S1, Cas-S3 or Cas-S4 protein, in particular Cas-S1 or Cas-S3. The fusion protein may comprise all of Cas-S1, Cas-S2, Cas-S3, Cas-S4 and Cas-S5. Alternatively, the fusion protein comprising the cytidine deaminase fused to a Cas-S1 protein may be devoid of a Cas-S3 protein. The fusion protein may further comprises a UGI protein.

There is thus provided a fusion protein complex comprising a fusion protein in a complex with further proteins, and wherein the fusion protein comprises a protein of the formula A-B-C-D-E (in 5' to 3' orientation), wherein:

A is a CasS protein selected from a Cas-S1, Cas-S3 or Cas-S4 (in particular, Cas-S1);

B is optionally present, and when present comprises a linker (for example any of the linkers as described herein, in particular an XTEN linker, for example having the amino acid sequence of SEQ ID No:17);

C is a base editor, such as a cytidine deaminase (e.g. a PmCDA1 cytidine deaminase as described elsewhere herein, for example having the amino acid sequence of SEQ ID No: 19);

D is optionally present and when present comprises a linker (for example any of the linkers as described herein, in particular the 10 amino acid linker of SEQ ID No:23);

E is a uracil DNA glycosylase inhibitor (UGI) protein (as described in more detail elsewhere herein, for example having the amino acid sequence of SEQ ID No:21); and the further proteins in complex with the fusion protein comprise a Cas-S2 and a Cas-S5 protein and a Cas-S1 and/or a Cas-S4 protein as required such that the fusion protein complex comprises at least a Cas-S1, Cas-S2, Cas-S4 and a Cas-S5 protein.

In an embodiment, the fusion protein complex may further comprise a Cas-S3 protein. There is also provided a first vector which expresses the fusion protein of the formula A-B-C-D-E and a second vector which expresses the further proteins of the fusion protein complex.

In an embodiment, the fusion protein complex may further comprise a crRNA as described elsewhere herein.

In another example, the mutation is a A to G point mutation, wherein the complex deaminates the target A point mutation, and wherein the deamination results in a sequence that is not associated with a disease or disorder. For example, the target A point mutation is present in the DNA strand that is not complementary to the crRNA.

In an example, there is provided isolated composition, vector(s), nucleic acid(s) or protein(s) as described herein. Isolation may, for example, mean that the composition, vector(s), nucleic acid or protein(s) are provided to the exclusion of an *E. coli* cell.

Optionally, the target sequence is comprised by a gene whose expression is errant (e.g. is present, or over-expressed) in a disease or disorder, and the complex introduces a double-stranded (or single stranded) break in the target sequence thereby disrupting or preventing expression of the gene. Optionally, the target sequence is comprised by a pathogenic bacterium which causes a disease or disorder, and the complex introduces a double-stranded break (or single stranded break) in the chromosome of the bacterium thereby killing (e.g. selectively killing) the bacterium. Optionally, the target sequence is comprised by an antibiotic resistance gene comprised by a pathogenic bacterium which causes a disease or disorder, and the complex introduces a double-stranded break (or a single stranded break) in the target sequence thereby disrupting or preventing expression of the antibiotic gene and results in re-sensitisation of the bacterium to the antibiotic. The double-stranded break (or single stranded break) may be located upstream (5') of a PAM sequence (for example between about 29 to about 40 nucleotides (e.g. between 30 and 32 nucleotides) upstream (5') of a PAM sequence) in the target sequence. The PAM sequence may be any as described herein, for example selected from AHN, KAG, AGG, GAC and GTG (also see Concept 39 herein). Double stranded breaks may be introduced by fusion proteins as described elsewhere herein in which Py is a nuclease (e.g. any nuclease described herein), Single stranded breaks in a chromosome (or in double stranded DNA) may be introduced by fusion proteins as described elsewhere herein in which Py is a nickase (e.g. any nickase described herein).

For example, the double stranded break is introduced by a nuclease. For example, a single stranded break is introduced by a nickase. For example, the double stranded break is introduced by an I-Tev nuclease (e.g. an I-TevI nuclease as described elsewhere herein), which is fused (e.g. to the N-terminus) of a Cas-S1 or Cas-S4 protein, in particular Cas-S1. The fusion protein complex may comprise all of Cas-S1, Cas-S2, Cas-S4 and Cas-S5, and optionally may further comprise a Cas-S3.

There is thus provided a fusion protein complex comprising a fusion protein in a complex with further proteins, and wherein the fusion protein comprises a protein of the formula A-B-C(in 5' to 3' orientation), wherein:

A is an I-Tev nuclease (for example any of the I-TevI proteins described herein, for example having the amino acid sequence of SEQ ID No:45);

B is optionally present, and when present comprises a linker (for example any of the linkers as described herein, in particular an XTEN linker, for example having the amino acid sequence of SEQ ID No:17);

C is a CasS protein selected from Cas-S1 and Cas-S4; and the further proteins in complex with the fusion protein comprise a Cas-S2 and Cas-S5 protein and a Cas-S1 or Cas-S4 protein as required such that the fusion protein complex comprises at least a Cas-S1, Cas-S2, Cas-S4 and a Cas-S5 protein.

In an embodiment, the fusion protein complex may further comprise a Cas-S3 protein. There is also provided a first vector which expresses the fusion protein of the formula A-B-C and a second vector which expresses the further proteins of the fusion protein complex.

In an embodiment, the fusion protein complex may further comprise a crRNA as described elsewhere herein.

In an embodiment, the fusion protein complex comprising an I-Tev nuclease recognizes and cleaves a target sequence comprising, in 5' to 3' orientation:

a) an I-TevI cleavage site nucleotide sequence (as described elsewhere herein, but in particular wherein the cleavage site nucleotide sequence is 5'-CNNNG-3', such as wherein the I-TevI cleavage site nucleotide sequence has the nucleotide sequence of SEQ ID No:42);

b) an I-TevI spacer nucleotide sequence (as described elsewhere herein, but in particular wherein the I-TevI spacer nucleotide sequence is about 31 nucleotides in length, for example wherein the I-TevI spacer nucleotide sequence is at least (about) 80% (e.g. (about) 90%) identical to the nucleotide sequence of SEQ ID No:43 (e.g. is 100% identical to the nucleotide sequence of SEQ ID No:43));

c) a PAM sequence (as described elsewhere herein, but in particular wherein the PAM is selected from 5'-AAC-3', 5'-ATG-3', 5'-AAA-3', 5'-AAG-3', 5'-ACG-3', 5'-AAT-3' and 5'-ACA-3', e.g. 5'-AAC-3' and 5'-ATG-3', for example wherein the PAM is 5'-AAC-3'); and d) a protospacer sequence (as described elsewhere herein, but in particular wherein the protospacer is spacer sequence is about 32 nucleotides in length, and optionally wherein sequences a) to d) are each immediately adjacent to each other.

In an embodiment, the fusion protein complex comprising an I-Tev nuclease introduces a double stranded break within the cleavage site nucleotide sequence. For example, when the cleavage site nucleotide sequence comprises the sequence of SEQ ID No:42, the fusion protein introduces a break after the second C on the forward strand of the target sequence and after the first T on the reverse strand of the target sequence (as the cleavage site nucleotide sequence on the reverse strand comprises the sequence 5'-CGTTG-3'). The I-TevI nuclease nicks the forward strand immediately after the second C, and immediately after the first T on the reverse strand. The double nicking of the cleavage site results in a staggered double stranded DNA break and each site of the break harbours single stranded, dinucleotide overhangs; 5'-AC-3' for the forward strand and 5'-GT-3' for the reverse strand.

In an example, the vector(s), complexes, nucleic acid(s) or protein(s) are not comprised by a cell, wherein the cell comprises endogenous nucleotide sequences encoding Cas-S1, S2, S3, S4 and S5 proteins. In an example, the vector(s), complexes, nucleic acid(s) or protein(s) are not comprised by a cell of a species selected from the species in Table 3. For example, the vector(s), complexes, nucleic acid(s) or protein(s) are not comprised by an *E. coli* cell. For example, the vector(s), complexes, nucleic acid(s) or protein(s) are not comprised by a Ktedonobacter, e.g. Ktedonobacter racemifer cell. For example, the vector(s), complex, nucleic acid or protein(s) are not comprised by an *Allochromatium*, e.g. *Allochromatium warmingii* cell. For example, the vector(s), complexes, nucleic acid(s) or protein(s) are not comprised by an Ignatius, e.g. Ignatius *tetrasporus* cell.

In an example, the vector(s), complexes, nucleic acid(s) or protein(s) are not comprised by a cell, wherein the cell comprises endogenous nucleotide sequences encoding a polypeptide comprising SEQ ID NO: 1, a polypeptide comprising SEQ ID NO: 2, a polypeptide comprising SEQ ID NO: 3, a polypeptide comprising SEQ ID NO: 4 and a polypeptide comprising SEQ ID NO: 5.

Concepts:

There is also provided the following numbered Concepts relating to the new system, their components and uses. Any Concept is combinable with any Configuration, aspect, example, embodiment, option or other feature disclosed herein.

Concept 1A. A nucleic acid vector or a plurality of nucleic acid vectors comprising expressible nucleotide sequences, wherein the sequences comprise a) a nucleotide sequence that encodes a polypeptide which comprises an amino acid sequence that is at least (about) 80% (such as about 90%) identical to SEQ ID NO: 1;
b) a nucleotide sequence that encodes a polypeptide which comprises an amino acid sequence that is at least (about) 80% (such as about 90%) identical to SEQ ID NO: 2;
c) a nucleotide sequence that encodes a polypeptide which comprises an amino acid sequence that is at least (about) 80% (such as about 90%) identical to SEQ ID NO: 3;
d) a nucleotide sequence that encodes a polypeptide which comprises an amino acid sequence that is at least (about) 80% (such as about 90%) identical to SEQ ID NO: 4; and
e) a nucleotide sequence that encodes a polypeptide which comprises an amino acid sequence that is at least (about) 80% (such as about 90%) identical to SEQ ID NO: 5.

Concept 1B. A nucleic acid vector or a plurality of nucleic acid vectors comprising expressible nucleotide sequences, wherein the sequences comprise a) a nucleotide sequence that encodes a polypeptide which comprises an amino acid sequence that is at least 94% (such as 95%) identical to SEQ ID NO: 1;
b) a nucleotide sequence that encodes a polypeptide which comprises an amino acid sequence that is at least 98% (such as 99%) identical to SEQ ID NO: 2;
c) a nucleotide sequence that encodes a polypeptide which comprises an amino acid sequence that is at least 99% (such as 100%) identical to SEQ ID NO: 3;
d) a nucleotide sequence that encodes a polypeptide which comprises an amino acid sequence that is at least 98% (such as 99%) identical to SEQ ID NO: 4; and
e) a nucleotide sequence that encodes a polypeptide which comprises an amino acid sequence that is at least 88% (such as 89%) identical to SEQ ID NO: 5.

Concept 1C. A nucleic acid vector or a plurality of nucleic acid vectors comprising expressible nucleotide sequences, wherein the sequences comprise a) a nucleotide sequence that encodes a polypeptide which comprises an amino acid sequence that is at least 98% (such as 99%) identical to SEQ ID NO: 2;
b) a nucleotide sequence that encodes a polypeptide which comprises an amino acid sequence that is at least 98% (such as 99%) identical to SEQ ID NO: 4; and
c) a nucleotide sequence that encodes a polypeptide which comprises an amino acid sequence that is at least 88% (such as 89%) identical to SEQ ID NO: 5.

Concept 1C-1. A nucleic acid vector or a plurality of nucleic acid vectors according to Concept 1C, wherein the vector(s) further comprise(s) a nucleotide sequence that encodes a polypeptide which comprises an amino acid sequence that is at least 94% (such as 95%) identical to SEQ ID NO:1.

Concept 1C-2. A nucleic acid vector or a plurality of nucleic acid vectors according to Concept 1C or 1C-1, wherein the vector(s) further comprise(s) a nucleotide sequence that encodes a polypeptide which comprises an amino acid sequence that is at least 99% (such as 100%) to SEQ ID NO:3.

Concept 1D. A nucleic acid vector or a plurality of nucleic acid vectors comprising expressible nucleotide sequences, wherein the sequences comprise a) a nucleotide sequence that encodes a polypeptide which comprises an amino acid sequence that is at least about 80% (such as about 90%) identical to SEQ ID NO: 2;
b) a nucleotide sequence that encodes a polypeptide which comprises an amino acid sequence that is at least about 80% (such as about 90%) identical to SEQ ID NO: 4; and
c) a nucleotide sequence that encodes a polypeptide which comprises an amino acid sequence that is at least about 80% (such as about 90%) identical to SEQ ID NO: 5.

Concept 1D-1. A nucleic acid vector or a plurality of nucleic acid vectors according to Concept 1D, wherein the vector(s) further comprise(s) a nucleotide sequence that encodes a polypeptide which comprises an amino acid sequence that is at least about 80% (such as about 90%) identical to SEQ ID NO:1.

Concept 1D-2. A nucleic acid vector or a plurality of nucleic acid vectors according to Concept 1D or 1D-1, wherein the vector(s) further comprise(s) a nucleotide sequence that encodes a polypeptide which comprises an amino acid sequence that is at least about 80% (such as about 90%) to SEQ ID NO:3.

Instead of vector(s) in these Concepts, there is alternatively provided one or more nucleic acids comprising the recited components. The disclosures relating to vector(s) herein are also to be read as applying mutatis *mutandis* to nucleic acid(s). For example, the nucleic acid may be comprised by a chromosome of a cell, e.g. a prokaryotic cell. For example, the nucleic acid may be comprised by a plasmid. For example, the modifying may be modifying of said chromosome or plasmid, in particular the chromosome. Thus, the crRNA may comprise a spacer that is capable of hybridizing to a protospacer comprised by the chromosome or plasmid, in particular the chromosome. Thus, the crRNA may comprise a spacer that is cognate to a protospacer comprised by the chromosome or plasmid, in particular the chromosome.

Concept 2. The vector(s) of Concept 1, wherein at least one of the nucleotide sequences is operably connected to a promoter that is a) heterologous to the at least one nucleotide sequence(s);
b) not an *E. coli* or *Klebsiella* promoter;
c) a eukaryotic cell promoter;
d) an animal promoter (optionally a mammalian or human promoter);
e) a plant promoter;
f) a fungus promoter (optionally a yeast promoter);
g) an insect promoter;
h) a virus promoter (optionally a virus, AAV or lentivirus promoter); or
i) a synthetic promoter.

In any Configuration, Concept, aspect, example, embodiment, option or other feature herein relating to promoters, the promoter may be a constitutive promoter. In any Configuration, Concept, aspect, example, embodiment, option or other feature herein relating to promoters, the promoter may be an inducible promoter. Suitable promoters are well known to those in the art. Inducible promoters may be particularly useful when it is desired to express the Type-S protein(s) and complexes only under certain defined parameters. In other circumstances where it is desired to constantly produce the Type-S protein(s) and complexes described herein, constitutive promoters may be employed.

In any Configuration, Concept, aspect, example, embodiment, option or other feature herein relating to promoters, the promoter may be a BolA promoter, e.g. a pBolA promoter comprising the nucleotide sequence of SEQ ID No:14. In any Configuration, Concept, aspect, example, embodiment, option or other feature herein relating to promoters, the promoter may be a p70a promoter, e.g. a p70a promoter comprising the nucleotide sequence of SEQ ID No: 15. In any Configuration, Concept, aspect, example, embodiment, option or other feature herein relating to promoters, the promoter may be an arabinose-inducible promoter, e.g. a pBAD promoter comprising the nucleotide sequence of SEQ ID No:24.

Concept 3. The vector(s) of Concept 1 or Concept 2, wherein at least one of the nucleotide sequences is operably connected to a constitutive promoter.

In an embodiment, all of the nucleotides sequences are operably connected to a constitutive promoter. In an embodiment, all of the nucleotides are comprised by a single operon under the control of a single constitutive promoter.

Concept 4. The vector(s) of Concept 1 or Concept 2, wherein at least one of the nucleotide sequences is operably connected to an inducible promoter.

In an embodiment, all of the nucleotides sequences are operably connected to a inducible promoter. In an embodiment, all of the nucleotides are comprised by a single operon under the control of a single inducible promoter.

Concept 5. The vector(s) of any one of Concepts 1 to 4, wherein the vector(s) is/are devoid of the nucleotide sequence that encodes the polypeptide of part c) of Concept 1A or 1B.

Concept 6. The vector(s) of any one of Concepts 1 to 5, wherein the vector(s) is/are devoid of the nucleotide sequence that encodes a polypeptide of part a) of Concept 1A or 1B.

Concept 7A: A nucleic acid vector comprising an expressible nucleotide sequence which comprises a) a nucleotide sequence that encodes a polypeptide which comprises an amino acid sequence that is at least (about) 90% identical to SEQ ID NO:2;
b) a nucleotide sequence that encodes a polypeptide which comprises an amino acid sequence that is at least (about) 90% identical to SEQ ID NO:4; and
c) a nucleotide sequence that encodes a polypeptide which comprises an amino acid sequence that is at least (about) 90% identical to SEQ ID NO:5.

Concept 7B. A nucleic acid vector comprising an expressible nucleotide sequence selected from a) a nucleotide sequence that encodes a polypeptide, which comprises an amino acid sequence that is at least (about) 80% (such as about 90%) identical to SEQ ID NO: 1;
b) a nucleotide sequence that encodes a polypeptide which comprises an amino acid sequence that is at least (about) 80% (such as about 90%) identical to SEQ ID NO: 2;
c) a nucleotide sequence that encodes a polypeptide which comprises an amino acid sequence that is at least (about) 80% (such as about 90%) identical to SEQ ID NO: 3;
d) a nucleotide sequence that encodes a polypeptide which comprises an amino acid sequence that is at least (about) 80% (such as about 90%) identical to SEQ ID NO: 4; and
e) a nucleotide sequence that encodes a polypeptide which comprises an amino acid sequence that is at least (about) 80% (such as about 90%) identical to SEQ ID NO: 5.

Concept 8A. The vector of Concept 7A, wherein the vector further comprises a nucleotide sequence that encodes a polypeptide which comprises an amino acid sequence that is at least (about) 90% identical to SEQ ID NO:1.

Concept 8B. The vector of Concept 7A or 7B, wherein the vector further comprises a nucleotide sequence that encodes a Cas protein domain which is operable with the polypeptides of parts a), b) and c) to bind to a nucleotide sequence selected from double stranded DNA, single stranded DNA and RNA.

Such Cas proteins may be selected from Cas proteins of naturally occurring Type I, II, III, IV, V or VI CRISPR/Cas complexes, which are well known to those skilled in the art. Methods provided herein can be used to identify proteins which are operable with the Cas-S2, Cas-S4 and Cas-S5 proteins to provide additional activities.

Concept 9. The vector of Concept 7A or Concept 8A or 8B, wherein the vector further comprises a nucleotide sequence that encodes a polypeptide which comprises an amino acid sequence that is at least (about) 90% identical to SEQ ID NO:3

Concept 10. The vector(s) of any preceding Concept, wherein the vector(s) comprise(s) one or more nucleotide sequences for producing a crRNA, wherein the crRNA comprises a spacer that is cognate to a first protospacer in a target sequence, optionally wherein the protospacer is a) not found in *E coli,*
b) an eukaryotic cell protospacer; or
c) an animal (optionally human), plant, insect, or fungus cell protospacer.

The protospacer may not be found in a bacterium which comprises endogenous nucleotide sequences that encode the polypeptides of a) to e) as recited in Concept 1.

The crRNA optionally comprises a spacer having at least 10 consecutive nucleotide sequences which are complementary to the protospacer. The crRNA optionally comprises a spacer having at least 15 consecutive nucleotide sequences which are complementary to the protospacer. The crRNA optionally comprises a spacer having at least 20 consecutive nucleotide sequences which are complementary to the protospacer. The crRNA optionally comprises a spacer having at least 25 consecutive nucleotide sequences which are complementary to the protospacer. The crRNA optionally comprises a spacer having at least 28 consecutive nucleotide sequences which are complementary to the protospacer.

In any Configuration, Concept, aspect, example, embodiment, option or other feature herein relating to protospacers and spacers, the spacer and protospacer may be from about 10 to 40 nucleotides in length. For example, the spacer and protospacer may be between about 25 and 40 nucleotides, such as between about 25 and 38 nucleotides, such as between about 28 and 35 nucleotides. The spacer and protospacer may be from about 25 to 39 nucleotides in length. The spacer and protospacer may be from about 29 to 35 (e.g. from about 30 to 34, or from about 31 to 33) nucleotides in length. For example, the spacer and protospacer may be about 32 nucleotides in length. For example, the spacer and protospacer may be about 28 nucleotides in length. For example, the spacer and protospacer may be 32 nucleotides in length. For example, the spacer and protospacer may be 28 nucleotides in length. The spacer and/or protospacer may have any of the features described in any Configuration, Concept, aspect, example, embodiment, option or other feature herein.

In any Configuration, Concept, aspect, example, embodiment, option or other feature herein relating to protospacers and spacers, the spacer may be (about) 90% complementary to the protospacer. The spacer may be (about) 70% complementary to the protospacer. The spacer may be (about) 80% complementary to the protospacer. The spacer may be (about) 95% complementary to the protospacer. The spacer may 100% complementary to the protospacer across its entire length.

In an embodiment, when the protospacer is about 32 (e.g. is 32) nucleotides (or longer) in length, nucleotides 1 to 28 of the spacer which are 5' of the PAM sequence are complementary to the protospacer sequence.

In any Configuration, Concept, aspect, example, embodiment, option or other feature herein relating to crRNA, the crRNA comprises at least one repeat sequence. For example the crRNA comprises two repeat sequences. The repeat sequence may be any sequence which is capable of forming a hairpin loop and being recognised by the Type-S system. The repeat sequence may be about 20 to 25 nucleotides (e.g. 22 or 23 nucleotides) in length. The repeat sequence may be a nucleotide sequence which is at least about 80%, e.g. about 90% (such as at least about 95, 96, 97 or 98%) identical to the nucleotide sequence of SEQ ID No:6. The repeat sequence may be a nucleotide sequence of SEQ ID No:6. The repeat sequence may be a nucleotide sequence which is at least about 80%, e.g. about 90% (such as at least about 95, 96, 97 or 98%) identical to the nucleotide sequence of SEQ ID No:70. The repeat sequence may be a nucleotide sequence of SEQ ID No:70.

In any nucleic acid or vector described herein, the crRNA may be encoded by a CRISPR array (for example a CRISPR array as described elsewhere herein).

According to any Configuration, Concept, aspect, example, embodiment, option or other feature herein, a plant may be a monocot or a dicot. Optionally, the plant is selected from the group consisting of maize, soybean, cotton, wheat, canola, oilseed rape, sorghum, rice, rye, barley, millet, oats, sugarcane, turfgrass, switchgrass, alfalfa, sunflower, tobacco, peanut, potato, *Arabidopsis*, safflower and tomato.

As the skilled person will know, "cognate to" or "cognate with" or "complementary to" refers to components that are operable together. For example, a crRNA is known to operate with a PAM to guide Cas to a protospacer in a target nucleic acid. In this sense, the crRNA is cognate to the PAM and is cognate to the protospacer.

Concept 11. The vector(s) of any preceding Concept, wherein the vector(s) comprise(s)

a) a nuclear localization sequence (NLS);
b) a phage packaging sequence (optionally a pac or cos site);
c) a plasmid origin of replication;
d) a plasmid origin of transfer;
e) a bacterial plasmid backbone;
f) a eukaryotic plasmid backbone;
g) a human virus (optionally AAV or lentivirus) structural protein gene;
h) a virus (optionally AAV or lentivirus) rep and/or cap sequence;
i) a selection marker or sequence encoding a selectable marker;
j) a eukaryotic promoter; or
k) a nucleotide sequence of a human, animal, plant or fungus gene.

When the target sequence is in a eukaryotic cell, in any Configuration, Concept, aspect, example, embodiment, option or other feature the vector(s), proteins or complexes herein further comprise an NLS. NLSs are known to those skilled in the art, and include, but are not limited to monopartite or bipartite NLSs. The NLS sequence may be from an SV40 Large T-antigen (see Kalderon et al., Cell, 39 (3), 499-509, 1984, doi: doi.org/10.1016/0092-8674 (84) 90457-4, which is incorporated herein by reference in its entirety), from nucleoplamin, importin a, c-myc, EGL-13, TUS-protein, hnRNP A1 or yeast transcription repressor Mata2.

Any of the vector(s) as described herein may be delivered to bacterial cells via a phage particle. Any of the vector(s) as described herein may be delivered to bacterial cells via a phagemid particle packaged within a phage particle. Any of the vector(s) as described herein may be delivered to bacterial cells via a conjugative plasmid.

Concept 12. The vector(s) of any preceding Concept, wherein each vector is a) a plasmid vector (optionally a conjugative plasmid)
b) a transposon vector (optionally a conjugative transposon);
c) a virus vector (optionally a phage, AAV or lentivirus vector);
d) a phagemid (optionally a packaged phagemid); or
e) a nanoparticle (optionally a lipid nanoparticle).

Concept 13A. One or more polypeptide(s) as recited in any preceding Concept.

Concept 13B. One or more polypeptide(s) expressed from the vector(s) recited in any preceding Concept.

Concept 13C. One or more polypeptide(s) as recited in any preceding claim expressed from the vector(s) of any preceding Concept.

Concept 14A. A fusion protein comprising a polypeptide (Px), wherein Px a) comprises an amino acid sequence that is at least (about) 80% identical (e.g. (about) 90% identical) to a sequence selected from SEQ ID Nos: 1-5; and
b) is fused to a heterologous polypeptide (Py).

The 14th Concept Also Provides:-

A fusion protein comprising a Cas-S1 fused to a heterologous polypeptide (Py).

A fusion protein comprising a Cas-S2 fused to a heterologous polypeptide (Py).

A fusion protein comprising a Cas-S3 fused to a heterologous polypeptide (Py).

A fusion protein comprising a Cas-S4 fused to a heterologous polypeptide (Py).

A fusion protein comprising a Cas-S5 fused to a heterologous polypeptide (Py).

Concept 14B. A fusion protein complex comprising:

(i) a fusion protein polypeptide (Px), wherein Px
 a) comprises an amino acid sequence that is at least (about) 80% identical (e.g. (about) 90% identical) to a sequence selected from SEQ ID Nos: 1, 3, and 4; and
 b) is fused to a heterologous polypeptide (Py);

(ii) a polypeptide which comprises an amino acid sequence that is at least (about) 80% identical (e.g. (about) 90% identical) to SEQ ID No:2;

(iii) a polypeptide which comprises an amino acid sequence that is at least (about) 80% identical (e.g. (about) 90% identical) to SEQ ID No:5;

(iv) a crRNA comprising a spacer sequence that is cognate to a first protospacer in a target sequence; and (v) optionally a polypeptide which is at least (about) 80% identical (e.g. (about) 90% identical) to a sequence selected from SEQ ID Nos: 1, 3, and 4 and is not based on the amino acid sequence of the polypeptide recited in part (i) a); and (vi) optionally a polypeptide which is at least (about) 80% identical (e.g. (about) 90% identical) to a sequence selected from SEQ ID Nos: 1, 3, and 4 and is not based on the amino acid sequence of the polypeptide recited in part (I) a), and, if present, is not based on the amino acid sequence of the polypeptide recited in part (v).

Concept 14C. A fusion protein complex comprising:

(i) a fusion protein polypeptide (Px), wherein Px
 a) comprises a Cas-S1, Cas-S3 or Cas-S4 protein; and
 b) is fused to a heterologous polypeptide (Py);

(ii) a Cas-S2 protein;

(iii) a Cas-S5 protein;

(iv) a crRNA comprising a spacer sequence that is cognate to a first protospacer in a target sequence; and (v) optionally a protein which is selected from a Cas-S1, Cas-S3 and Cas-S4 protein, and is of a different CasS protein class to the protein recited in part (i) a); and (vi) optionally a protein which is selected from a Cas-S1, Cas-S3 and Cas-S4 protein, and is of a different CasS protein class to the protein recited in part (i) a), and, if present, is of a different CasS protein class to the protein recited in part (v).

In an example, the fusion protein comprises 2 or more of Cas-S1 to S5, e.g. comprises Cas-S1 and S2, or S4 and S5.

In any Configuration, Concept, aspect, example, embodiment, option or other feature relating to fusion proteins, Py may be fused (directly or indirectly) to the N-terminus of the CasS protein. In any Configuration, Concept, aspect, example, embodiment, option or other feature relating to fusion proteins, the Py may be fused (directly or indirectly) to the C-terminus of the CasS protein.

Fusion may be direct or indirect (e.g. via a peptide linker, such as a $(G_4S)_n$ linker, wherein n=1, 2, 3, 4, 5, 6, 7, 8, 9 or 10). A peptide linker may be from about 10 to 20 amino acids (e.g. about 16 amino acids) in length. A peptide linker may be from about 8 to 12 amino acids (e.g. about 10 amino acids) in length. A peptide linker may have the amino acid sequence of SEQ ID No: 17. A peptide linker may have the amino acid sequence of SEQ ID No:23. Linkers may be as described elsewhere herein (e.g. in Concepts 27 or 29 herein).

Here, "heterologous" refers to a polypeptide that is not naturally found fused to Px. In an example, Py comprises an I-Tev nuclease or mutH protein.

In any Configuration, Concept, aspect, example, embodiment, option or other feature, Py is an I-Tev nuclease, such as an I-TevI nuclease, for example as described elsewhere herein. In an example, the I-TevI nuclease is a protein comprising the amino acid sequence of SEQ ID No:45. In one embodiment, the I-TevI nuclease is encoded by a nucleic acid sequence which encodes an amino acid sequence comprising the amino acids of SEQ ID: No: 45. In one embodiment, the I-TevI nuclease is encoded by a nucleic acid sequence of SEQ ID: No: 46. In an example, the I-TevI nuclease is a protein which has an amino acid sequence which is at least about 80% identical (e.g. is about 85%, 90%, 95%, 96%, 97% or 98% identical) to the amino acid of SEQ ID No:45 and is capable of cleaving an I-TevI cleavage site nucleotide sequence having the nucleotide sequence of SEQ ID No:42 and is capable of recognising an I-TevI spacer nucleotide sequence having the nucleotide sequence of SEQ ID No:43.

Generally, when one component is heterologous to another component, the components do not naturally occur in nature, or in the same cell.

For example, the selected sequence is SEQ ID NO: 1. For example, the selected sequence is SEQ ID NO: 2. For example, the selected sequence is SEQ ID NO: 3. For example, the selected sequence is SEQ ID NO: 4. For example, the selected sequence is SEQ ID NO: 5.

Py may comprise an effector domain. For example, the effector domain is a domain that comprises nuclease activity, nickase activity, recombinase activity, reverse transcriptase, helicase, deaminase activity, methyltransferase activity, methylase activity, acetylase activity, acetyltransferase activity, transcriptional activation activity, or transcriptional repression activity.

Py may be naturally occurring. Py may be a synthetic sequence. Py may be a synthetically mutated derivative of a naturally occurring sequence.

Optionally, the effector domain is a nucleic acid editing domain. For example, the nucleic acid editing domain comprises a deaminase domain. The deaminase domain may be a cytidine deaminase domain. The cytidine deaminase domain may be an apolipoprotein B mRNA-editing complex (APOBEC) family deaminase. The cytidine deaminase domain may be at least (about) 80%, at least (about) 85%, at least (about) 90%, at least (about) 92%, at least (about) 95%, at least (about) 96%, at least (about) 97%, at least (about) 98%, at least (about) 99%, or at least (about) 99.5% identical to the cytidine deaminase domain of any one of SEQ ID NOs: 350-389 disclosed in U.S. application Ser. No. 16/976,047 or WO2019/168953, which sequences are explicitly incorporated herein by reference.

Optionally, Py comprises a uracil glycosylase inhibitor (UGI) domain. The UGI domain may comprise the amino acid sequence of SEQ ID NO:500 disclosed in U.S. application Ser. No. 16/976,047 or WO2019/168953, which sequence is explicitly incorporated herein by reference. The UGI domain may have the amino acid sequence of SEQ ID No:21. The UGI domain may have the nucleotide sequence of SEQ ID No:20.

Optionally, Py comprises the amino acid sequence of SEQ ID NO:534. Optionally, Py may comprise the amino acid sequence of SEQ ID NO:538. These sequences being disclosed in U.S. application Ser. No. 16/976,047 or WO2019/168953, which sequences are explicitly incorporated herein by reference.

Optionally, Py comprises the fusion protein further comprises a second UGI domain. Optionally, Py comprises the amino acid sequence of SEQ ID NO:540. Optionally, Py comprises the amino acid sequence of SEQ ID NO:541. These sequences being disclosed in U.S. application Ser. No. 16/976,047 or WO2019/168953, which sequences are explicitly incorporated herein by reference.

Optionally, the deaminase domain is an adenosine deaminase domain. The fusion protein may comprise a second adenosine deaminase domain. For example, the first adenosine deaminase domain and the second adenosine deaminase domain comprises an ecTadA domain, or variant thereof. The first adenosine deaminase domain and the second adenosine deaminase domain may comprise the amino acid sequence of any one of SEQ ID NOs: 400-458. The first adeosine deaminase may comprise the amino acid sequence of SEQ ID NO:400. The second adeosine deaminase may comprise the amino acid sequence of SEQ ID NO:458. Optionally, Py comprises the amino acid sequence of SEQ ID NO:535 or 539. These sequences being disclosed in U.S. application Ser. No. 16/976,047 or WO2019/168953, which sequences are explicitly incorporated herein by reference.

Base editors that may be used with the Cas-S system are well known in the art. Base editors include systems where a CasS protein is fused to a cytosine or adenosine deaminase domain and directed to the target sequence to make the desired modification.

In one embodiment, the base editor is selected from:

1) Cytosine Base Editors (CBEs) that convert C:G into T:A (Komar et al., Nature, 533:420-4, 2016, incorporated herein by reference in its entirety)
2) Adenine Base Editors (ABEs) that convert A:T into G:C (Gaudelli et al., Nature, 551 (7681), 464-471, 2017, incorporated herein by reference in its entirety)
3) Cytosine Guanine Base Editors (CGBEs) that convert C:G into G:C (Chen et al., Biorxiv, 2020; Kurt et al., Nature Biotechnology, 2020, both incorporated herein by reference in its entirety)
4) Cytosine Adenine Base Editors (CABEs) that convert C:G into A:T (Zhao et al., Nature Biotechnology, 2020, incorporated herein by reference in its entirety)
5) Adenine Cytosine Base Editors (ACBEs) that convert A:T into C:G (WO2020/181180, incorporated herein by reference in its entirety)
6) Adenine Thymine Base Editors (ATBEs) that convert A:T into T:A (WO2020/181202, incorporated herein by reference in its entirety)
7) Thymine Adenine Base Editor (TABE) that convert T:A into A:T (WO2020/181193 (or US2022/0170013); WO2020/181178; WO2020/181195, each of which is incorporated herein by reference in its entirety).

Base editors differ in the base modification enzymes. CBEs rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA 1), evoCDA 1, FERNY, evoFERNY.

ABEs rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Examples of DNA-based editor proteins include, but are not limited to BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa (KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa (KKH)-ABE, ABE8e, SpRY-ABE, SpRYCBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3 and AncBE4.

In one embodiment, Py is a cytidine deaminase. The cytidine deaminase may be a PmCDA1 cytidine deaminase. The cytidine deaminase may be from sea lamprey. In one embodiment, the PmCDA1 cytidine deaminase comprises the amino acid sequence of SEQ ID No:19. In one embodiment, the PmCDA1 cytidine deaminase is encoded by a nucleic acid sequence which encodes an amino acid sequence comprising the amino acids of SEQ ID No:19. In one embodiment, the PmCDA1 cytidine deaminase is encoded by a nucleic acid sequence of SEQ ID No: 18. In an example, the PmCDA1 cytidine deaminase is a protein which has an amino acid sequence which is at least about 80% identical (e.g. is about 85%, 90%, 95%, 96%, 97% or 98% identical) to the amino acid of SEQ ID No:19 and is capable of making a C to T mutation in the target nucleic acid.

Concept 15. The fusion protein of Concept 14, wherein the fusion protein is in the form of a fusion protein complex which comprises at least two further polypeptides, wherein the two further polypeptides each have an amino acid sequence that is at least 90% identical to a sequence selected from the sequences of SEQ ID No:2, SEQ ID No:4 and SEQ ID No: 5, and wherein the fusion protein complex comprises amino acid sequences that are at least 90% identical to each of the sequences of SEQ ID No:2, SEQ ID No:4 and SEQ ID No:5.

Px can comprise an amino acid sequence that is at least 90% identical to the sequence of SEQ ID No:2, and the further polypeptides comprise an amino acid sequence that is at least 90% Identical to each of the sequences of SEQ ID No:4 and SEQ ID No:5. Px can comprise an amino acid sequence that is at least 90% identical to the sequence of SEQ ID No:4, and the further polypeptides comprise an amino acid sequence that is at least 90% identical to each of the sequences of SEQ ID No:2 and SEQ ID No:5. Px can comprise an amino acid sequence that is at least 90% identical to the sequence of SEQ ID No:5, and the further polypeptides comprise an amino acid sequence that is at least 90% identical to each of the sequences of SEQ ID No:2 and SEQ ID No:4.

Concept 16. The fusion protein complex of Concept 15, wherein the protein complex comprises at least 3 further polypeptides, and wherein the fusion protein complex comprises amino acid sequences that are at least 90% identical to each of the sequences of SEQ ID No:2, SEQ ID No:3, SEQ ID No:4 and SEQ ID No:5.

Px can comprise an amino acid sequence that is at least 90% identical to the sequence of SEQ ID No:2, and the further polypeptides comprise an amino acid sequence that is at least 90% identical to each of the sequences of SEQ ID No: 3, SEQ ID No:4 and SEQ ID No:5. Px can comprise an amino acid sequence that is at least 90% identical to the sequence of SEQ ID No:3, and the further polypeptides comprise an amino acid sequence that is at least 90% identical to each of the sequences of SEQ ID No:2, SEQ ID No:4 and SEQ ID No:5. Px can comprise an amino acid sequence that is at least 90% identical to the sequence of SEQ ID No:4, and the further polypeptides comprise an amino acid sequence that is at least 90% identical to each of the sequences of SEQ ID No: 2, SEQ ID No:3 and SEQ ID No:5. Px can comprise an amino acid sequence that is at least 90% identical to the sequence of SEQ ID No:5, and the further polypeptides comprise an amino acid sequence that is at least 90% identical to each of the sequences of SEQ ID No:2, SEQ ID No:3 and SEQ ID No:4.

Concept: 17A. The fusion protein complex of Concept 15, wherein the protein complex comprises at least 3 further polypeptides, and wherein the fusion protein complex comprises amino acid sequences that are at least 90% identical to each of the sequences of SEQ ID No:1, SEQ ID No:2, SEQ ID No:4 and SEQ ID No:5.

Px can comprise an amino acid sequence that is at least 90% identical to the sequence of SEQ ID No:1, and the further polypeptides comprise an amino acid sequence that is at least 90% identical to each of the sequences of SEQ ID No: 2, SEQ ID No:4 and SEQ ID No:5, Px can comprise an amino acid sequence that is at least 90% identical to the sequence of SEQ ID No:2, and the further polypeptides comprise an amino acid sequence that is at least 90% identical to each of the sequences of SEQ ID No:1, SEQ ID No:4 and SEQ ID No:5. Px can comprise an amino acid sequence that is at least 90% identical to the sequence of SEQ ID No:4, and the further polypeptides comprise an amino acid sequence that is at least 90% identical to each of the sequences of SEQ ID No:1, SEQ ID No:2 and SEQ ID No:5. Px can comprise an amino acid sequence that is at least 90% identical to the sequence of SEQ ID No:5, and the further polypeptides comprise an amino acid sequence that is at least 90% identical to each of the sequences of SEQ ID No:1, SEQ ID No:2 and SEQ ID No:4.

Concept 17B. The fusion protein complex of Concept 15, wherein the protein complex comprises at least 4 further polypeptides, and wherein the fusion protein complex comprises amino acid sequences that are at least 90% identical to each of the sequences of SEQ ID No:1, SEQ ID No:2, SEQ ID No:3, SEQ ID No:4 and SEQ ID No:5.

Px can comprise an amino acid sequence that is at least 90% identical to the sequence of SEQ ID No:1, and the further polypeptides comprise an amino acid sequence that is at least 90% Identical to each of the sequences of SEQ ID No: 2, SEQ ID No:3, SEQ ID No:4 and SEQ ID No:5. Px can comprise an amino acid sequence that is at least 90% identical to the sequence of SEQ ID No: 2, and the further polypeptides comprise an amino acid sequence that is at least 90% identical to each of the sequences of SEQ ID No:1, SEQ ID No:3, SEQ ID No:4 and SEQ ID No:5. Px can comprise an amino acid sequence that is at least 90% identical to the sequence of SEQ ID No:3, and the further polypeptides comprise an amino acid sequence that is at least 90% identical to each of the sequences of SEQ ID No:1, SEQ ID No:2, SEQ ID No:4 and SEQ ID No:5. Px can comprise an amino acid sequence that is at least 90% identical to the sequence of SEQ ID No:4, and the further polypeptides comprise an amino acid sequence that is at least 90% identical to each of the sequences of SEQ ID No:1, SEQ ID No:2, SEQ ID No:3 and SEQ ID No:5. Px can comprise an amino acid sequence that is at least 90% identical to the sequence of SEQ ID No:5, and the further polypeptides comprise an amino acid sequence that is at least 90% identical to each of the sequences of SEQ ID No:1, SEQ ID No:2, SEQ ID No:3 and SEQ ID No:4.

Concept 18. The fusion protein of Concept 14, wherein Px comprises an amino acid sequence that is selected from an amino acid sequence that is at least 90% identical to the sequence selected from the sequences of SEQ ID Nos: 1, 3, and 4;

wherein the fusion protein is in the form of a fusion protein complex which comprises at least two further polypeptides, wherein the two further polypeptides each have an amino acid sequence that is at least 90% identical to a sequence selected from the sequences of SEQ ID No:2 and Seq ID No:5, and (i) optionally a polypeptide which is at least 90% identical to a sequence selected from SEQ ID Nos: 1, 3, and 4 and is not based on the amino acid sequence of the polypeptide recited in part I; and (ii) optionally a polypeptide which is at least 90% identical to a sequence selected from SEQ ID Nos: 1, 3, and 4 and is not based on the amino acid sequence of the polypeptide recited in part I, and, if present, is not based on the amino acid sequence of the polypeptide recited in part (i).

Concept 19. The fusion protein or fusion protein complex of any one of Concepts 14 to 18, wherein Py is fused to the C-terminus of the amino acid sequence of part I.

Alternatively, Py is fused to the N-terminus of the amino acid sequence of part I.

Concept 20. The fusion protein or fusion protein complex of any one of Concepts 14 to 19, wherein Py is an enzyme, optionally selected from a deaminase (such as a cytosine or adenine deaminase), a base editor, a prime editor, helicase, a reverse transcriptase, a methyltransferase, methylase, acetylase, acetyltransferase, a transcription activator or deactivator, a translation activator or deactivator or a nuclease (such as a DNA nuclease, an RNA nuclease, a nickase or a dead nuclease, e.g. dCas).

In any Configuration, Concept, aspect, example, embodiment, option or other feature, Py is a nuclease, such as any of the nucleases disclosed herein, in particular an I-TevI nuclease. Py may be a DNA nuclease. Py may be an RNA nuclease. Py may be a nickase or a dead nuclease In one embodiment, Py is a base editor, such as any of the base editors disclosed herein, in particular an a PmCDA1 cytidine deaminase. In one embodiment, Py is a prime editor.

Concept 21. The fusion protein or fusion protein complex of Concept 20, wherein Py is a nuclease which is an I-TevI nuclease.

In any Configuration, Concept, aspect, example, embodiment, option or other feature, in Part I, the I-TevI nuclease is fused to the N-terminus of an amino acid sequence (e.g. any CasS protein described herein). In one embodiment, in Part I, the I-TevI nuclease is fused to the N-terminus of an amino acid sequence that is at least (about) 80% (e.g. (about) 90%) identical to the sequence of SEQ ID No:1. The I-TevI nuclease may be as described elsewhere herein (e.g. as in Concept 14).

Concept 22. The fusion protein or fusion protein complex of Concept 21, wherein the I-TevI nuclease does not comprise a complete DNA binding domain.

I-TevI comprises 245 amino acids, and consists of an N-terminal catalytic domain and a C-terminal DNA-binding domain that are connected by a long, flexible linker. The crystal structure of the DNA-binding domain of I-TevI (comprising residues 130 to 245) complexed with the 20-bp primary binding region of its DNA target, reveals the presence of a zinc finger (comprising residues 151 to 167)

that makes backbone contacts with the DNA from the minor groove, an elongated segment containing a minor groove-binding α-helix (comprising residues 183 to 194) and a helix-turn-helix (comprising residues 204 to 245). The N-terminal catalytic domain was shown to comprise residues 1-92. Biochemical data have shown that the zinc finger does not contribute to the DNA-binding affinity or to the specificity of the enzyme, but rather that it has a novel function and acts as a distance determinant that controls the relative positions of the catalytic and DNA-binding domains, see for example, Roey et al., 2005, DOI: 10.1007/0-387-27421-9_7, which is incorporated herein by reference in its entirety.

Kleinstiver et al., G3 Genes|Genomes|Genetics, 4 (6), 1155-1165, 2014, doi: doi.org/10.1534/g3.114.011445 (which is incorporated herein by reference in its entirety) showed that various truncations of the N-terminal catalytic domain retain activity when fused in TALEN construct. The largest construct was residues 1 to 206 of I-TevI. The smallest that was functional when fused to a TALEN was resides 1 to 162.

Thus, in one embodiment, the I-TevI does not comprise a complete helix-turn-helix domain. The I-TevI may comprise the amino acid sequence of SEQ ID No:45. The I-TevI may not comprise a helix-turn-helix domain. The I-TevI may comprise amino acids 1 to 195-203 of SEQ ID No: 45. The I-TevI may not comprise the minor groove-binding-helix. The I-TevI may comprise amino acids 1 to 167 of SEQ ID No:45. The I-TevI may not comprise a complete zinc finger domain. The I-TevI may comprise amino acids 1 to 162 of SEQ ID No:45.

Concept 23. The fusion protein or fusion protein complex of Concept 21 or 22, wherein the I-TevI nuclease comprises an N-terminal catalytic domain.

Thus, the I-TevI may comprise amino acids 1 to 92 of SEQ ID No:45. The I-TevI may comprise the amino acid sequence of SEQ ID No:45.

Concept 24. The fusion protein or fusion protein complex of any one of Concepts 21 to 23, wherein the I-TevI nuclease is a bacteriophage I-TevI nuclease.

In any Configuration, Concept, aspect, example, embodiment, option or other feature, the I-TevI nuclease may be a T4 bacteriophage I-TevI. The I-TevI nuclease may be from a T4 bacteriophage. The I-TevI nuclease may be encoded by the intron of bacteriophage T4, The I-TevI nuclease may comprise amino acids 1 to 206 of a naturally occurring I-TevI nuclease. The I-TevI nuclease may comprise an amino acid sequence of SEQ ID No:45. The I-TevI nuclease may be encoded by a nucleotide sequence of SEQ ID No:44.

Concept 25. The fusion protein or fusion protein complex of claim 20, wherein Py comprises a base editor selected from an adenine base editor (ABE, e.g. an adenosine deaminase), a cytosine base editor (CBE, e.g. a cytidine deaminase or an apolipoprotein B mRNA-editing complex (APOBEC) family deaminase), a cytosine guanine base editor (CGBE), a cytosine adenine base editor (CABE), an adenine cytosine base editor (ACBE), an adenine thymine base editor (ATBE), a thymine adenine base editor (TABE), and a uracil DNA glycosylase inhibitor (UGI) protein.

In any Configuration, Concept, aspect, example, embodiment, option or other feature relating to fusion proteins or fusion protein complexes, Py is a CBE. In one embodiment, Py is a PmCDA1 cytidine deaminase (as described elsewhere herein, for example in Concept 14). In one embodiment, Py is a PmCDA1 cytidine deaminase in combination with a UGI protein. In one embodiment, Py is a CBE linked via a linker (as described elsewhere herein) to a UGI protein. In one embodiment, Py is a PmCDA1 cytidine deaminase linked via a linker (as described elsewhere herein) to a UGI protein. In one embodiment, Py is a CBE linked via a linker (as described elsewhere herein) to a UGI protein, and the CBE is linked to a CasS protein described herein via a linker (as described elsewhere herein). In one embodiment, Py is a PmCDA1 cytidine deaminase linked via a linker (as described elsewhere herein) to a UGI protein, and the PmCDA1 is linked to a CasS protein described herein via a linker (as described elsewhere herein). In one embodiment, Py is a CBE linked via a linker (as described elsewhere herein) to a UGI protein, and the UGI protein is linked to a CasS protein described herein via a linker (as described elsewhere herein). In one embodiment, Py is a PmCDA1 cytidine deaminase linked via a linker (as described elsewhere herein) to a UGI protein, and the UGI protein is linked to a CasS protein described herein via a linker (as described elsewhere herein). In one embodiment, the CasS protein is selected from a CasS1 protein, a CasS3 protein and a CasS4 protein.

Concept 26. The fusion protein or fusion protein complex of Concept 25, wherein the base editor is a sea lamprey base editor.

In any Configuration, Concept, aspect, example, embodiment, option or other feature, the base editor is a PmCDA1 cytidine deaminase having the amino acid sequence encoded by SEQ ID No: 19. In one embodiment, the base editor is from sea lamprey.

Concept 27. The fusion protein or fusion protein complex of Concept 25 or Concept 26, wherein the base editor is fused to the C-terminus of the amino acid sequence of part I.

In any Configuration, Concept, aspect, example, embodiment, option or other feature, the base editor (e.g. PmCDA1 cytidine deaminase) is fused via a peptide linker to the amino acid sequence of Part I. The peptide linker may be as described in Concept 14 or Concept 29. In any Configuration, Concept, aspect, example, embodiment, option or other feature, the base editor (e.g. PmCDA1 cytidine deaminase) is fused via a peptide linker to a CasS protein. The linker may from (about) 10 to 20 amino acids in length. The linker may be from (about) 10 to 22, from (about) 11 to 21, from (about) 12 to 20, from (about) 13 to 19, from (about) 14 to 18, from (about) 15 to 17 amino acids in length. The linker may be (about) 16 amino acids in length. The linker may be a linker having the amino acid sequence of SEQ ID No:17. The linker may be any linker described herein.

Concept 28. The fusion protein or fusion protein complex of Concept 27, wherein a UGI protein is fused to the base editor.

In any Configuration, Concept, aspect, example, embodiment, option or other feature, the UGI protein has an amino acid sequence of SEQ ID No:21. The UGI protein may be as described elsewhere herein (e.g. in Concept 14). The UGI protein may be fused directly to the base editor. The UGI protein may be fused to the base editor via a linker, e.g. a peptide linker as described elsewhere herein.

Concept 29. The fusion protein or fusion protein complex of Concept 28, where the UGI protein is fused to the base editor via a peptide linker.

In any Configuration, Concept, aspect, example, embodiment, option or other feature, the UGI protein is fused to the base editor via a peptide linker of from (about) 8 to 12 amino acids in length. The peptide linker may be from (about) 9 to 11 amino acids in length. The linker may be (about) 10 amino acids in length. The linker may have the amino acid sequence of SEQ ID No:23. The linker may be fused to the C-terminus of the base editor, and the UGI protein is fused to the C-terminus of the linker. The linker may be fused to the N-terminus of the base editor, and the UGI protein is fused to the N-terminus of the linker. The linker may be as described elsewhere herein (e.g. in Concept 14 or 27).

Concept 30. The fusion protein or fusion protein complex of any one of Concepts 14 to 29, wherein the fusion protein or fusion protein complex is in combination with a crRNA which comprises a spacer that is cognate to a first protospacer in a target sequence.

The crRNA, spacer and/or protospacer sequence may have any of the features described elsewhere herein (e.g. in Concept 10, or in the First Aspect of the Detailed Description). In any Configuration, Concept, aspect, example, embodiment, option or other feature, the protospacer is not found in a bacterium which comprises endogenous nucleotide sequences that encode the polypeptides of a) to e) as recited in Concept 1A or 1B. In any Configuration, Concept, aspect, example, embodiment, option or other feature, the protospacer is a eukaryotic cell protospacer. In any Configuration, Concept, aspect, example, embodiment, option or other feature, the protospacer is heterologous to the source of Py. For example, when Py is a naturally occurring polypeptide, the protospacer is from a different species (or genera) to the Py. In any Configuration, Concept, aspect, example, embodiment, option or other feature, the protospacer is an animal (optionally human), plant, insect, fungus cell protospacer.

In one embodiment, the fusion protein complex forms a ribonucleoprotein complex with a crRNA which comprises a spacer that is cognate to a first protospacer in a target sequence. In one embodiment, the fusion protein forms a ribonucleoprotein complex with a crRNA which comprises a spacer that is cognate to a first protospacer in a target sequence. The Concept 31. One or more nucleic acid vector(s) comprising one or more nucleotide sequence(s) encoding a fusion protein or fusion protein complex as recited in any one of Concepts 14 to 30.

The vector(s) may further encode a crRNA as described elsewhere herein (e.g. in the First Aspect of Detailed Description, in Concept 10 or in Concept 30). In one embodiment, there is provided a first and second vector which encode a fusion protein complex as described elsewhere herein. In one embodiment, the first vector encode the fusion protein Px and the second vector encodes the further proteins of the fusion protein complex.

The vector(s) may encode a second, third, fourth . . . etc, crRNA which comprises a spacer that is cognate to a second, third, fourth . . . etc, protospacer in a target sequence. Expression of multiple crRNAs may be useful for multiplex editing, for example for targeting multiple genes in a cell or organism.

Concept 32. The vector(s) of Concept 31, wherein the fusion protein is encoded by a single first nucleotide sequence and wherein the at least two further polypeptides are encoded by a second nucleotide sequence.

In one embodiment, the fusion proteins described herein are encoded by a single first nucleotide sequence comprised by a first vector, and the at least two further CasS polypeptides of the complex are encoded by a second nucleotide sequence comprised by a second vector. In one embodiment, all of the further CasS polypeptides of the fusion protein complexes described herein are encoded by a second nucleotide sequence. In one embodiment, all of the further CasS polypeptides of the complexes described herein are encoded by a second nucleotide sequence comprised by a second vector.

Concept 33. The vector(s) of Concept 31, wherein the fusion protein complex is encoded by:

a) a first nucleotide sequence encoding Py fused to an amino acid sequence that is at least (about) 80% (e.g. (about) 90%) identical to the sequence of SEQ ID No:1, SEQ ID No: 3 or Seq ID No:4; and
b) a second nucleotide sequence encoding the at least two further polypeptides encoding amino acid sequences that are at least (about 80% (e.g. (about) 90%) identical to the sequences of SEQ ID Nos: 1, 2, 3, 4 and/or 5.

In any Configuration, Concept, aspect, example, embodiment, option or other feature, the fusion protein complexes described herein comprise polypeptides comprising amino acid sequences at least (about) 80% (e.g. (about) 90%) identical to the each of the sequences of SEQ ID Nos: 1, 2, 3, 4 and 5. In any Configuration, Concept, aspect, example, embodiment, option or other feature, the fusion protein complexes described herein comprise polypeptides comprising amino acid sequences at least (about) 80% (e.g. (about) 90%) identical to the each of the sequences of SEQ ID Nos: 2, 4 and 5. In any Configuration, Concept, aspect, example, embodiment, option or other feature, the fusion protein complexes described herein comprise polypeptides comprising amino acid sequences at least (about) 80% (e.g. (about) 90%) identical to the each of the sequences of SEQ ID Nos: 2, 3, 4 and 5. In any Configuration, Concept, aspect, example, embodiment, option or other feature, the fusion protein complexes described herein comprise polypeptides comprising amino acid sequences at least (about) 80% (e.g. (about) 90%) identical to the each of the sequences of SEQ ID Nos: 1, 2, 4 and 5.

Concept 34A, The vector(s) of Concept 32 or Concept 33, wherein the crRNA is encoded by the first nucleotide sequence.

Concept 34B. The vector(s) of Concept 32 or Concept 33, wherein the crRNA or is encoded by the second nucleotide sequence.

Where multiple crRNAs are encoded to target multiple protospacers, they may all be encoded by the first nucleotide sequence. Where multiple crRNAs are encoded to target multiple protospacers, they may all be encoded by the second nucleotide sequence.

Concept 35A. The vector(s) of any one of Concepts 31 to 34, wherein at least one of the nucleotide sequences is operably connected to a promoter that is heterologous to the at least one nucleotide sequence(s).

Concept 35B. The vector(s) of any one of Concepts 31 to 34, wherein at least one of the nucleotide sequences is operably connected to a promoter that is a eukaryotic cell promoter.

The eukaryotic cell promoter may be any of those described herein.

Concept 35C. The vector(s) of any one of Concepts 31 to 34, wherein at least one of the nucleotide sequences is operably connected to a promoter that is an animal promoter.

In one embodiment, the promoter is a mammalian or human promoter. The animal, mammalian or human promoter may be any of those described herein.

Concept 35D. The vector(s) of any one of Concepts 31 to 34, wherein at least one of the nucleotide sequences is operably connected to a promoter that is a plant promoter.

The plant promoter may be any of those described herein.

Concept 35E. The vector(s) of any one of Concepts 31 to 34, wherein at least one of the nucleotide sequences is operably connected to a promoter that is a fungal promoter.

In one embodiment, the promoter is a yeast promoter. The fungal or yeast promoter may be any of those described herein.

Concept 35F. The vector(s) of any one of Concepts 31 to 34, wherein at least one of the nucleotide sequences is operably connected to a promoter that is an insect promoter.

The insect promoter may be any of those described herein.

Concept 35G. The vector(s) of any one of Concepts 31 to 34, wherein at least one of the nucleotide sequences is operably connected to a promoter that is a viral promoter.

In one embodiment, the promoter is a viral, AAV or lentiviral promoter. The viral, AAV or lentiviral promoter may be any of those described herein.

Concept 35H. The vector(s) of any one of Concepts 31 to 34, wherein at least one of the nucleotide sequences is operably connected to a promoter that is a synthetic promoter.

The synthetic promoter may be any of those described herein.

Concept 36. The vector(s) of any one of Concepts 31 to 35, wherein at least one of the nucleotide sequences is operably connected to a constitutive promoter.

Concept 37. The vector(s) of any one of Concepts 31 to 35, wherein at least one of the nucleotide sequences is operably connected to an inducible promoter.

Concept: 38A. The vector(s), protein(s), fusion protein(s) or fusion protein complexes described in any Configuration, Concept, aspect, example, embodiment, option or other feature which comprises a crRNA, wherein the crRNA comprises two repeat sequences (e.g. two repeat sequences).

The crRNA and other features of the repeat sequences may have the other features as described elsewhere herein (for example in the First Aspect of Detailed Description, or in Concept 10).

Concept 38B. The vector(s), protein(s), fusion protein(s) or fusion protein complexes described in any Configuration, Concept, aspect, example, embodiment, option or other feature which comprises a crRNA, wherein the crRNA comprises at least one repeat sequence comprising the nucleotide sequence of SEQ ID No:6.

Concept 38C. The vector(s), protein(s), fusion protein(s) or fusion protein complexes described in any Configuration, Concept, aspect, example, embodiment, option or other feature which comprises a crRNA, wherein the crRNA comprises two repeat sequences comprising the nucleotide sequence of SEQ ID No:6.

Concept 38D. The vector(s), protein(s), fusion protein(s) or fusion protein complexes described in any Configuration, Concept, aspect, example, embodiment, option or other feature which comprises a crRNA, wherein the crRNA comprises at least one repeat sequence comprising the nucleotide sequence of SEQ ID No:70.

Concept 38E. The vector(s), protein(s), fusion protein(s) or fusion protein complexes described in any Configuration, Concept, aspect, example, embodiment, option or other feature which comprises a crRNA, wherein the crRNA comprises two repeat sequences comprising the nucleotide sequence of SEQ ID No:70.

Concept 39. The vector(s), protein(s), fusion protein(s) or fusion protein complexes described in any Configuration, Concept, aspect, example, embodiment, option or other feature which comprises a crRNA which comprises a spacer that is cognate to a first protospacer in a target sequence, wherein the protospacer is immediately adjacent to a Protospacer Adjacent Motif (PAM) sequence in the target sequence selected from 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3', 5'-TAG-3', 5'-ACC-3', 5'-AGG-3', 5'-ATT-3', 5'-GAC-3' and 5'-GTG-3'.

In any Configuration, Concept, aspect, example, embodiment, option or other feature which comprises a crRNA which comprises a spacer that is cognate to a first protospacer in a target sequence, the protospacer may be immediately adjacent to a Protospacer Adjacent Motif (PAM) sequence in the target sequence selected from 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3' and 5'-TAG-3'. In any Configuration, Concept, aspect, example, embodiment, option or other feature which comprises a crRNA which comprises a spacer that is cognate to a first protospacer in a target sequence, the protospacer may be immediately adjacent to a Protospacer Adjacent Motif (PAM) sequence in the target sequence selected from 5'-AAC-3', 5'-ATG-3', 5'-AAA-3', 5'-AAG-3', 5'-ACG-3', 5'-AAT-3' and 5'-ACA-3'. In any Configuration, Concept, aspect, example, embodiment, option or other feature which comprises a crRNA which comprises a spacer that is cognate to a first protospacer in a target sequence, the protospacer may be immediately adjacent to a Protospacer Adjacent Motif (PAM) sequence in the target sequence selected from 5'-AAC-3' and 5'-ATG-3'. In any Configuration, Concept, aspect, example, embodiment, option or other feature which comprises a crRNA which comprises a spacer that is cognate to a first protospacer in a target sequence, the protospacer may be immediately adjacent to a Protospacer Adjacent Motif (PAM) sequence in the target sequence which is 5'-AAC-3'. In any Configuration, Concept, aspect, example, embodiment, option or other feature which comprises a crRNA which comprises a spacer that is cognate to a first protospacer in a target sequence, the protospacer may be immediately adjacent to a Protospacer Adjacent Motif (PAM) sequence having any of the features described elsewhere herein.

Concept 40. The vector(s), protein(s), fusion protein(s) or fusion protein complexes described in any Configuration, Concept, aspect, example, embodiment, option or other feature which comprises a crRNA which comprises a spacer that is cognate to a first protospacer in a target sequence, wherein the spacer sequence is from (about) 25 to 39 nucleotides in length.

The spacer sequence may be from (about) 28 to 32 nucleotides in length. The spacer sequence may be about 32 nucleotides in length. The spacer sequence may be 32 nucleotides in length.

In any Configuration, Concept, aspect, example, embodiment, option or other feature which comprises a crRNA which comprises a spacer that is cognate to a first protospacer in a target sequence, the spacer sequence may be 32 nucleotides in length. In any Configuration, Concept, aspect, example, embodiment, option or other feature which comprises a crRNA which comprises a spacer that is cognate to a first protospacer in a target sequence, the spacer sequence may have any of the features described elsewhere herein (e.g. in the First Aspect of Detailed Description, in Concept 10 and in Concept 30).

Concept 41. The vector(s), protein(s), fusion protein(s) or fusion protein complexes described in any Configuration, Concept (e.g. as in Concept 40), aspect, example, embodiment, option or other feature which comprises a crRNA which comprises a spacer that is cognate to a first protospacer in a target sequence, wherein nucleotides 1 to 28 of the spacer are identical to the complement of nucleotides 1 to 28 of the protospacer sequence which is immediately 5' of the PAM sequence in the target sequence.

The protospacer may have any of the features described elsewhere herein (e.g. in the First Aspect of Detailed Description, in Concept 10 and in Concept 30).

Concept 42. The vector(s), protein(s), fusion protein(s) or fusion protein complexes described in any Configuration, Concept, aspect, example, embodiment, option or other feature which comprises a crRNA which comprises a spacer that is cognate to a first protospacer in a target sequence, wherein the spacer is identical to the complement of the protospacer in the target sequence.

The spacer may be identical to the complement of the protospacer in the target sequence across its entire length. The spacer may be (about) 80% (for example (about) 90%) identical to the complement of the protospacer in the target sequence across its entire length. The spacer may be identical to the complement of the protospacer in the target sequence across the first 1 to 28 nucleotides which are immediately 5' of the PAM sequence in the target sequence, and (about) 80% (e.g. (about) 90%) identical across the rest of the nucleotides in the protospacer.

Concept 43. The vector(s), fusion protein(s) or fusion protein complexes described in any Configuration, Concept, aspect, example, embodiment, option or other feature which comprise a fusion protein in which Py is a nuclease which is an I-TevI nuclease, wherein the I-TevI nuclease recognises an I-TevI cleavage site nucleotide sequence which is 5' or 3' (e.g. 5') of the protospacer in the target sequence.

The I-TevI cleavage site nucleotide sequence may be as described elsewhere herein. In one embodiment, the I-TevI cleavage site nucleotide sequence is 5' of the protospacer in the target sequence. The I-TevI cleavage site nucleotide sequence may be is between (about) 3 and 7 nucleotides in length, for example between (about) 4 and 6 nucleotides in length. The I-TevI cleavage site nucleotide sequence may be about 5 nucleotides in length. The I-TevI cleavage site nucleotide sequence may comprise the motif 5'-CNNNG-3'. The I-TevI cleavage site nucleotide sequence may be selected from 5'-CCACG-3', 5'-CACCG-3', 5'-CATAG-3', 5'-CTAAG-3', 5'-CTGAG-3', 5'-CTTAG-3', 5'-CCTCG-3', 5'-CAGCG-3', 5'-CACTG-3', 5'-CGACG-3', 5'-CGATG-3', 5'-CTOCG-3', 5'-CTACG-3', 5'-CTGTG-3', 5'-CTGCG-3', 5'-CCGTG-3', 5'-CCTAG-3', 5'-CCATG-3', 5'-CAAAG-3', 5'-CAGAG-3', 5'-CATTG-3' and 5'-CATCG-3'. The I-TevI cleavage site nucleotide sequence may be selected from 5'-CCACG-3', 5'-CACCG-3', 5'-CATAG-3', 5'-CTAAG-3', 5'-CTGAG-3', 5'-CTTAG-3', 5'-CCTCG-3' and 5'-CAGCG-3', or is selected from 5'-CCACG-3', 5'-CACCG-3', 5'-CATAG-3', 5'-CTAAG-3' and 5'-CTGAG-3'. The I-TevI cleavage site nucleotide sequence may be selected from 5'-CCACG-3', 5'-CACCG-3' and 5'-CATAG-3'. The I-TevI cleavage site nucleotide sequence may be selected from 5'-CCACG-3' and 5'-CACCG-3'. The I-TevI cleavage site nucleotide sequence may have the nucleotide sequence of SEQ ID No:42.

Concept 44. The vector(s), fusion protein(s) or fusion protein complexes described in any Configuration, Concept, aspect, example, embodiment, option or other feature which comprise a fusion protein in which Py is a nuclease which is an I-TevI nuclease, wherein the I-TevI nuclease recognises an I-TevI spacer nucleotide sequence which is 5' or 3' (e.g. 5') of the protospacer in the target sequence, The I-TevI spacer nucleotide sequence may be as described elsewhere herein. In one embodiment, the I-TevI spacer nucleotide sequence is 5' of the protospacer in the target sequence. The I-TevI spacer nucleotide sequence may be between (about) 10 and 35 nucleotides in length, such as from 15 to 35, or from 20 to 35 in length. The I-TevI spacer nucleotide sequence may be between (about) 29 and 33 nucleotides in length. The I-TevI spacer nucleotide sequence may be between (about) 30 and 32 nucleotides in length. The I-TevI spacer nucleotide sequence may be (about) 31 nucleotides in length. The I-TevI spacer nucleotide sequence may at least (about) 80% (e.g. (about) 90%) identical to the nucleotide sequence of SEQ ID No:43. The I-TevI spacer nucleotide sequence may be 100% identical to the nucleotide sequence of SEQ ID No:43.

Concept 45. The vector(s), fusion protein(s) or fusion protein complexes described in any Configuration, Concept, aspect, example, embodiment, option or other feature which comprise a fusion protein in which Py is a nuclease which is an I-TevI nuclease, wherein the target sequence comprises, in 5' to 3' orientation:

a) an I-TevI cleavage site nucleotide sequence;

b) an I-TevI spacer nucleotide sequence;

c) a PAM sequence; and d) a protospacer sequence.

In one embodiment, sequences a) to d) are each immediately adjacent to each other. The I-TevI cleavage site nucleotide sequence is as described elsewhere herein (e.g. as described in Concept 43). The I-TevI spacer nucleotide sequence is as described elsewhere herein (e.g. as described in Concept 44). The PAM sequence is as described elsewhere herein (e.g. as described in Concept 39). The protospacer sequence is as described elsewhere herein (e.g. as in the First Aspect of Detailed Description, or in Concept 10, or Concept 30).

Concept 46A. A cell which comprises one or more vector(s), fusion protein(s) or fusion protein complexes described in any Configuration, Concept, aspect, example, embodiment, option or other feature as described elsewhere herein.

Concept 46B. A eukaryotic cell which comprises one or more vector(s), fusion protein(s) or fusion protein complexes described in any Configuration, Concept, aspect, example, embodiment, option or other feature as described elsewhere herein.

Concept 46C. An animal, plant, insect or fungus cell which comprises one or more vector(s), fusion protein(s) or fusion protein complexes described in any Configuration, Concept, aspect, example, embodiment, option or other feature as described elsewhere herein.

Concept 46D. A prokaryotic cell comprising one or more vector(s), fusion protein(s) or fusion protein complexes described in any Configuration, Concept, aspect, example, embodiment, option or other feature as described elsewhere herein.

Concept 46E. A prokaryotic cell comprising one or more vector(s), fusion protein(s) or fusion protein complexes described in any Configuration, Concept, aspect, example, embodiment, option or other feature as described elsewhere herein, wherein the cell is not a bacterial cell (for example an *E. coli, Pseudomonas* or *Klebsiella* cell) that comprises endogenous nucleotide sequences that encode the polypeptides of a) to e) as recited in Concept 1A.

In one embodiment, the cell is a vertebrate, mammal or human cell.

Concept 47A. A composition comprising one or more vector(s), fusion protein(s) or fusion protein complexes described in any Configuration, Concept, aspect, example, embodiment, option or other feature as described elsewhere herein.

The composition may be as described elsewhere herein. In one embodiment, a composition described herein may be an in vitro composition. In one embodiment, a composition described herein may be comprised by a medical container.

There is also provided a pharmaceutical composition comprising one or more vector(s), fusion protein(s) or fusion protein complexes described in any Configuration, Concept, aspect, example, embodiment, option or other feature as described elsewhere herein and further comprising a diluent, excipient or carrier. The pharmaceutical compositions are for use in any of the methods of medical treatment described herein.

There is also provided one or more vector(s), fusion protein(s) or fusion protein complexes described in any Configuration, Concept, aspect, example, embodiment, option or other feature as described elsewhere herein for use in therapy.

There is also provided one or more vector(s), fusion protein(s) or fusion protein complexes described in any Configuration, Concept, aspect, example, embodiment, option or other feature as described elsewhere herein for use in the treatment of any disease described herein by carrying out any of the methods described herein.

The pharmaceutical compositions may be comprised within a medical device (such as an ampoule, a syringe, or an inhaler). The pharmaceutical compositions may be formulated in a tincture, a capsule or a slow-release formulation. The pharmaceutical compositions may be an oral tablet, comprised within a blister pack.

In one embodiment, the pharmaceutical composition comprising one or more vector(s), fusion protein(s) or fusion protein complexes as described herein is formulated for oral or rectal administration. In one embodiment, the pharmaceutical composition is formulated for oral administration. In one embodiment, the pharmaceutical composition is formulated as a capsule or coated tablet.

The formulation comprising the one or more vector(s), fusion protein(s) or fusion protein complexes described herein may be freeze dried prior to encapsulation. In one embodiment, the pharmaceutical composition comprising one or more vector(s), fusion protein(s) or fusion protein complexes as described herein is a lyophilised formulation. In one embodiment, the pharmaceutical composition comprising one or more vector(s), fusion protein(s) or fusion protein complexes as described herein is an encapsulated formulation to be released in the lower gut of a subject.

Concept 47B. A composition (optionally an in vitro composition or wherein the composition is comprised by a medical container) comprising a crRNA or nucleic acid encoding the crRNA; and one, more or all of a) a polypeptide that comprises an amino acid that is at least (about) 80% identical to SEQ ID NO:1;
b) a polypeptide that comprises an amino acid that is at least (about) 80% identical to SEQ ID NO:2;
c) a polypeptide that comprises an amino acid that is at least (about) 80% identical to SEQ ID NO:3;
d) a polypeptide that comprises an amino acid that is at least (about) 80% identical to SEQ ID NO:4; and
e) a polypeptide that comprises an amino acid that is at least (about) 80% identical to SEQ ID NO:5 wherein A: the crRNA comprises a spacer that is cognate to a first protospacer, wherein the protospacer is f) not found in *E. coli,*
g) is a eukaryotic cell protospacer; or
h) an animal (optionally mammal or human), plant or fungus cell protospacer; or B: a protospacer of an *E. coli* that is devoid of endogenous nucleotide sequences that encode the polypeptides recited in parts a) to e) above.

In an example, the composition comprises (a)-(e). In an example, the composition comprises (a)-(d). In an example, the composition comprises (a)-(c). In an example, the composition comprises (a)-(b). In an example, the composition comprises (d)-(e). In an example, the composition comprises (c)-(e). In an example, the composition comprises (b)-(e).

In an example, the composition comprises (a), In an example, the composition comprises (b). In an example, the composition comprises (c). In an example, the composition comprises (d). In an example, the composition comprises (e).

The crRNA is operable in a cell to guide the polypeptide(s), protein(s), fusion protein(s) and complexes described herein to a target sequence comprised by a nucleic acid in the cell. There is provided a complex that comprises one, more or all of polypeptides (a)-(e) and the crRNA, wherein the crRNA is capable of guiding the complex to a protospacer comprised by a target DNA. For example, the complex comprises (a)-(e).

Concept 47C, A composition (optionally an in vitro composition or wherein the composition is comprised by a medical container) comprising a crRNA or nucleic acid encoding the crRNA; and nucleic acid encoding one, more or all of a) a polypeptide that comprises an amino acid that is at least (about) 80% identical to SEQ ID NO:1;
b) a polypeptide that comprises an amino acid that is at least (about) 80% identical to SEQ ID NO:2;
c) a polypeptide that comprises an amino acid that is at least (about) 80% identical to SEQ ID NO:3;
d) a polypeptide that comprises an amino acid that is at least (about) 80% identical to SEQ ID NO:4; and
e) a polypeptide that comprises an amino acid that is at least (about) 80% identical to SEQ ID NO:5 wherein A: the crRNA comprises a spacer that is cognate to a first protospacer, wherein the protospacer is f) not found in *E. coli,*
g) is a eukaryotic cell protospacer; or
h) an animal (optionally mammal or human), plant or fungus cell protospacer; or B: a protospacer of an *E. coli* that is devoid of endogenous nucleotide sequences that encode the polypeptides recited in parts a) to e) above.

In an example, the composition comprises a vector that encodes at least 2, 3 or 4, of said polypeptides. In an example, (a)-(e) are encoded by the same vector. In an example, the composition comprises a vector encoding all of (a)-(e).

In an example, the composition nucleic acid encodes (a)-(e). In an example, the composition nucleic acid encodes (a)-(d), In an example, the composition nucleic acid encodes (a)-(c). In an example, the composition nucleic acid encodes (a)-(b). In an example, the composition nucleic acid encodes (d)-(e). In an example, the composition nucleic acid encodes (c)-(e). In an example, the composition nucleic acid encodes (b)-(e).

The crRNA is operable in a cell to guide the polypeptide (s) to a target sequence comprised by a nucleic acid in the cell. There is provided a complex that comprises one, more or all of polypeptides (a)-(e) and the crRNA, wherein the crRNA is capable of guiding the complex to a protospacer comprised by a target DNA. For example, the complex comprises (a)-(e).

There are also provided methods. Any method herein may be an in vitro method. Optionally, the method is carried out on a cell comprised by a subject, such as a human, animal (e.g. a mammal, e.g. a rodent, mouse or rat), plant, insect or fungus (e.g. yeast).

Herein, modifying (e.g. modifying a target sequence of a DNA, polynucleotide or cell) may be wherein the modifying cuts, edits, blocks, marks or labels the target sequence.

Concept 48A. A method of modifying a nucleic acid target sequence in a cell, the method comprising

- (I) contacting the cell with one or more vector(s), protein(s), fusion protein(s), fusion protein complexes or with a composition as described in any Configuration, Concept, aspect, example, embodiment, option or other feature which comprises a crRNA which comprises a spacer that is cognate to a first protospacer in a target sequence;
- (II) allowing introduction into the cell of
  - (i) the vector(s) protein(s), fusion protein(s) or fusion protein complexes, whereby the polypeptide(s) and the crRNA are expressed in the cell, or
  - (ii) the cRNA of the composition (or nucleic acids encoding the crRNA whereby the CRNA are expressed in the cell) and the nucleic acid of the composition encoding the polypeptide(s) or protein(s), whereby the polypeptide(s) or protein(s) are expressed in the cell;
- (III) wherein the crRNA form a complex with the polypeptide(s) or protein(s) to guide the complex to the target sequence.

When the method comprises introduction of vector(s) which express CasS protein(s) or introduction of CasS protein(s), the modifying may be downregulation of a gene comprising the target sequence. When the method comprises introduction of vector(s) which express CasS protein(s) or introduction of CasS protein(s), the modifying may be downregulation of a gene adjacent to (e.g. within 2 kb of) the target sequence.

When the method comprises introduction of vector(s) which express fusion protein(s) or fusion protein complexes, or introduction of fusion protein(s) or fusion protein complexes, the modifying may be cutting the target sequence (e.g. when Py comprises a nuclease or a nickase).

When the method comprises introduction of vector(s) which express fusion protein(s) or fusion protein complexes, or introduction of fusion protein(s) or fusion protein complexes, the modifying may be introduction of one or more mutations in the target sequence (e.g. when Py comprises a nuclease, nickase, prime editor or base editor).

When the method comprises introduction of vector(s) which express fusion protein(s) or fusion protein complexes, or introduction of fusion protein(s) or fusion protein complexes, the modifying may be performing base editing in the target sequence (e.g. when Py is a base editor).

When the method comprises introduction of vector(s) which express fusion protein(s) or fusion protein complexes, or introduction of fusion protein(s) or fusion protein complexes, the modifying may be performing prime editing in the target sequence (e.g. when Py is a prime editor).

When the method comprises introduction of vector(s) which express fusion protein(s) or fusion protein complexes, or introduction of fusion protein(s) or fusion protein complexes, the modifying may be deaminating one or more nucleotides in the target sequence (e.g. when Py is a deaminase, such as a cytosine or adenine deaminase).

When the method comprises introduction of vector(s) which express fusion protein(s) or fusion protein complexes, or introduction of fusion protein(s) or fusion protein complexes, the modifying may be methylating one or more nucleotides in the target sequence (e.g. when Py is a methyltransferase).

When the method comprises introduction of vector(s) which express fusion protein(s) or fusion protein complexes, or introduction of fusion protein(s) or fusion protein complexes, the modifying may be methylasing one or more nucleotides in the target sequence (e.g. when Py is a methylase).

When the method comprises introduction of vector(s) which express fusion protein(s) or fusion protein complexes, or introduction of fusion protein(s) or fusion protein complexes, the modifying may be acetylasing one or more nucleotides in the target sequence (e.g. when Py is a acetylase).

When the method comprises introduction of vector(s) which express fusion protein(s) or fusion protein complexes, or introduction of fusion protein(s) or fusion protein complexes, the modifying may be subjecting DNA of the target sequence to acetyltransferase activity (e.g. when Py is an acetyltransferase).

When the method comprises introduction of vector(s) which express fusion protein(s) or fusion protein complexes, or introduction of fusion protein(s) or fusion protein complexes, the modifying may be reverse transcribing the target sequence, or reverse transcribing an RNA in the cell to produce a DNA that is inserted at the target sequence (e.g. when Py is a reverse transcriptase).

When the method comprises introduction of vector(s) which express fusion protein(s) or fusion protein complexes, or introduction of fusion protein(s) or fusion protein complexes, the modifying may be activating transcription of a gene in the cell, such as a gene comprising or adjacent to the target sequence (e.g. when Py is a transcription activator).

When the method comprises introduction of vector(s) which express fusion protein(s) or fusion protein complexes, or introduction of fusion protein(s) or fusion protein complexes, the modifying may be de-activating transcription of a gene in the cell, such as a gene comprising or adjacent to the target sequence (e.g. when Py is a transcription deactivator).

When the method comprises introduction of vector(s) which express fusion protein(s) or fusion protein complexes, or introduction of fusion protein(s) or fusion protein complexes, the modifying may be activating translation of a gene in the cell, such as a gene comprising or adjacent to the target sequence (e.g. when Py is a translation activator).

When the method comprises introduction of vector(s) which express fusion protein(s) or fusion protein complexes, or introduction of fusion protein(s) or fusion protein complexes, the modifying may be de-activating translation of a gene in the cell, such as a gene comprising or adjacent to the target sequence (e.g. when Py is a translation deactivator).

Concept 48B. A method of modifying a nucleic acid target sequence in a cell, the method comprising

- a) contacting the cell with the vector(s) of Concept 10 or any one of Concepts 11 to 12 when dependent on Concept 10, or a composition according to Concept 47;
- b) allowing introduction into the cell of
  - (i) the vector(s), whereby the polypeptide(s) and the crRNA are expressed in the cell, or (ii) the cRNA of the composition (or nucleic acids encoding the crRNA whereby the CRNA are expressed in the cell) and the nucleic acid of the composition encoding the polypeptide(s), whereby the polypeptide(s) are expressed in the cell;

c) wherein the crRNA form a complex with the polypeptide(s) to guide the complex to the target sequence.

It is noteworthy that we found that the orientation of the spacers does not influence the efficiency of the Type-S CRISPR-Cas system to downregulate the transcription of a targeted gene, which is not the case for other CRISPR-Cas systems that must target either the coding or the non-coding region of a gene to efficiently downregulate its transcription. Thus, the complex, for example, modifies (e.g. cuts or edits) a coding target sequence coding or a non-coding target sequence, optionally wherein (i) a coding strand but not non-coding strand of DNA is modified or (ii) a non-coding strand but not coding strand of DNA is modified. The modifying herein may usefully modify (i) a coding strand but not non-coding strand of DNA or (ii) a non-coding strand but not coding strand of DNA.

Concept 48C. The method of Concept 48B, wherein the complex is guided to the target sequence and modifies the target sequence, optionally wherein the complex comprises a component selected from a) a nuclease which cuts the target sequence;

b) a deaminase (such as a cytosine or adenine deaminase) which carries out deamination of the target sequence;

c) a base editor which base edits the target sequence;

d) a prime editor which prime edits the target sequence;

e) a reverse transcriptase which reverse transcribes the target sequence or which reverse transcribes an RNA in the cell to produce a DNA that is inserted at the target sequence;

f) a methyltransferase that methylates DNA in the cell;

g) a methylase that methylases DNA in the cell;

h) an acetylase that acetylases DNA in the cell;

i) an acetyltransferase that subjects DNA in the cell to acetyltransferase activity;

j) a transcription activator that activates transcription of a gene in the cell, such as a gene comprising or adjacent to the target sequence; and k) a transcription deactivator that de-activates transcription of a gene in the cell, such as a gene comprising or adjacent to the target sequence;

optionally wherein the component is encoded by the vector(s) or nucleic acid of the composition.

In any Configuration, Concept, aspect, example, embodiment, option or other feature relating to modifying target DNA or RNA, the complex further comprises a base editor (e.g. as described elsewhere herein).

In any Configuration, Concept, aspect, example, embodiment, option or other feature relating to modifying target DNA or RNA, the complex further comprises a prime editor (e.g. as described elsewhere herein).

In any Configuration, Concept, aspect, example, embodiment, option or other feature relating to modifying target DNA or RNA, the complex further comprises a nuclease (e.g. as described elsewhere herein).

Concept 49A. The method of Concept 48C, wherein the cell is a eukaryotic, animal, plant, insect or fungus cell.

Concept 49B. The method of Concept 48, wherein the cell is a prokaryotic cell.

In one embodiment, the cell is a prokaryotic cell wherein the cell is not a prokaryotic cell (e.g. an *E. coli, Pseudomonas* or *Klebsiella* cell) that comprises endogenous nucleotide sequences that encode polypeptides a) to e) as recited in Concept 1.

In any Configuration, Concept, aspect, example, embodiment, option or other feature herein, an animal herein is a non-human mammal or vertebrate. Optionally an animal cell herein is a non-human mammal or vertebrate cell. Optionally the cell is a plant cell, bacteria cell, fungal cell, mammalian cell, insect cell, or archaeon cell. A cell herein may be ex vivo or in vivo.

In any Configuration, Concept, aspect, example, embodiment, option or other feature herein, a cell herein is a pluripotent cell, such as a pluripotent stem cell. Optionally, a cell herein is stem cell, such as an embryonic stem cell. Optionally, a cell herein is a totipotent cell. In an embodiment of these options, the cell is a human cell. Alternatively, the cell is not a human cell and not comprised by a human or human embryo.

Optionally, any method herein is not any of the following:

(a) a process for cloning a human being;

(b) a process for modifying the germ line genetic identity of a human being;

(c) a use of a human embryo;

(d) a process for modifying the genetic identity of an animals which is likely to cause it suffering without any substantial medical benefit to man or animal.

Optionally, any method herein is not a method of treatment on the human or animal body. Optionally, any method herein is not a surgical method.

Concept 50. The method of Concept 48 or 49, wherein the target sequence is comprised by a chromosome or episome in the cell.

In any Configuration, Concept, aspect, example, embodiment, option or other feature herein, the target sequence is comprised by a chromosome. In any Configuration, Concept, aspect, example, embodiment, option or other feature herein, the target sequence is comprised by a plasmid. In any Configuration, Concept, aspect, example, embodiment, option or other feature herein, the target sequence is not comprised by a plasmid.

Concept 51. The method of Concept 50, wherein the method inhibits chromosome or episome replication in the cell.

In an example, inhibition is at least (about) 20, 30, 40, 50, 60, 70, 80, 90 or 95% compared to replication in an identical cell that has not been exposed to the vector(s) or composition. In an example, inhibition is 100%.

Concept 52. The method of any one of Concepts 48 to 51, wherein the target sequence is within (about) 2 kb upstream or downstream of a gene of interest.

In any Configuration, Concept, aspect, example, embodiment, option or other feature relating to a target sequence, the target sequence is within (about) 2 kb upstream (5) or downstream (3') of a gene of interest. The target sequence may be upstream (5') of the gene of interest. The target sequence may be downstream (3') of the gene of interest. The target sequence may be within (about) 1.75 kb, within (about) 1.5 kb, within (about) 1.25 kb, within (about) 1 kb, within (about) 0.75 kb, within (about) 0.5 kb, or within (about) 0.25 kb upstream (5') or downstream (3') of a gene of interest. The target sequence may be within a gene of interest, for example may be within the promoter, exon(s) and/or intron(s) of the gene of interest. In one embodiment, the target sequence is within the promoter of the gene of interest.

Concept 53. The method of Concept 52, wherein the target sequence of the gene of interest is at least 2 kb upstream and downstream of any promoter, exon and intron of any other gene.

As shown in Example 4 herein, the CasS3 protein can have a wide range of influence, with binding effects being shown within approximately 2 kb either side (i.e. 5' and 3') of the protospacer sequence in the target sequence. Thus, for applications where the CasS system is used for CRISPRi (i.e. in any method described herein of upregulation or downregulation of a gene of interest), it may be beneficial to avoid off target effects if the protospacer in the target sequence is at least 2 kb upstream (5') and downstream (3') of any other gene (i.e. promoter, exon or intron).

Concept 54. The method of any one of Concepts 48 to 53, wherein the modifying is a substitution, deletion or insertion of one or more nucleotides.

In one embodiment, the modifying is a substitution of one or more nucleotides in the target sequence. In one embodiment, the modifying is one or more C to T substitutions in the nucleotides of the target sequence when Py is a CBE. In one embodiment, the CBE is a PmCDA1 cytidine deaminase, for example as described elsewhere herein.

Concept 55. A method of treating or preventing a disease or condition that is mediated by target cells in a subject, the method comprising carrying out a method as described in any Configuration, Concept, aspect, example, embodiment, option or other feature herein (for example as described in any one of Concepts 48 to 54) to modify the target cells, wherein said contacting comprises administering the vector(s), protein(s) (including fusion protein(s) or fusion protein complexes) or composition to the subject and wherein the modification treats or prevents the disease or condition.

Target cells may be, for example, pathogenic bacterial cells. They may be antibiotic resistance bacterial cells and the modification re-sensitises the bacterial cell to the antibiotic.

Concept 56. The method of Concept 55, wherein the subject is a human, animal or plant.

Concept 57. The method of Concept 56, wherein the target cells are cells of the subject that comprise a nucleic acid defect and the modification corrects the defect.

For example, certain diseases are known to be causes by single nucleotide polymorphisms (SNP) s (e.g. progeria syndrome and mandibuloacral dysplasia are caused by a missense SNP c.1580G>T SNP in the LMNA gene encoding the lamin A/C protein, and an SNP in the F5 gene causes Factor V Leiden thrombophilia). Correction of these SNPs by targets substitutions could be used to ameliorate diseases. In 2012, there were 124 genetic diseases that have been demonstrated to be caused by retrotransposon insertions, including cystic fibrosis (Alu), hemophilia A (L1) and X-linked dystonia-parkinsonism (SVA), see Hancks et al., Curr, Opin. Genet. Dev., 22, 191-203, 2012, doi: 10.1016/j.gde.2012.02.006, which is incorporated herein by reference in its entirety. It is possible to use certain targeted edits to correct these types of insertions an ameliorate the associated disease(s).

Concept 58A. The method of Concept 56 or 57, wherein the modification adds a new functionality to the cells.

In one embodiment, the modification upregulates or downregulates expression of a gene in the cells. In one embodiment, the modification downregulates expression of a gene in the cells. In one embodiment, the modification inhibits expression of a gene in the cells. In one embodiment, the modification blocks expression of a gene in the cells.

In another embodiment, the modification is insertion of a new gene or pathway of genes (e.g. an operon), which may be used to produce substances which are beneficial to the cells. For example, the new genes may produce beneficial metabolites, or therapeutics. In another embodiment, the modification is insertion of a new gene or pathway of genes (e.g. an operon), which may be used to remove substances which are detrimental to the cells. For example, the new genes may metabolites harmful toxins.

Concept 58B. The method of Concept 56 or 57, wherein the modification adds a new nucleotide sequence to the genomes of the cells for expression of a protein encoded by the new sequence.

For example, the protein is a heterologous protein. For example, the protein is a therapeutic protein, e.g. an antibody, antibody fragment (such as an antibody single variable domain), TCR (T-cell receptor) binding site, TCR variable domain, hormone, incretin, growth factor, anti-cancer agent, neurotransmitter or enzyme.

Concept 58C. The method of Concept 56 or 57, wherein the modification modulates the expression of a nucleotide sequence comprised by a chromosome or episome of the cell.

In one embodiment, the modification modulates the expression of a nucleotide sequence comprised by a plasmid. In one embodiment, the modification modulates the expression of a nucleotide sequence which is not comprised by a plasmid. For example, the expression is upregulated. For example, the expression is downregulated.

Concept 59. Vector(s), a protein(s) (inclusion fusion protein(s) and fusion protein complexes), cell(s) or composition as described in any Configuration, Concept, aspect, example, embodiment, option or other feature herein (for example as described in any one of Concepts 1-58) for use in a method of treating or preventing a disease or condition in a human or animal, wherein the method as described in any Configuration, Concept, aspect, example, embodiment, option or other feature herein (for example as described in any one of Concepts 55 to 58).

Any vector herein (in any Configuration, Concept, aspect, example, embodiment, option or other feature herein) may be a) a plasmid vector (optionally a conjugative plasmid)
b) a transposon vector (optionally a conjugative transposon);
c) a virus vector (optionally a phage, AAV or lentivirus vector);
d) a phagemid (optionally a packaged phagemid); or
e) a nanoparticle (optionally a lipid nanoparticle).

Concept 60. A method of introducing a targeted edit in a target polynucleotide, the method comprising contacting the target polynucleotide with a fusion protein or fusion protein complex as described in any Configuration, Concept, aspect, example, embodiment, option or other feature herein, wherein the protein or fusion protein complex is in combination with a crRNA which comprises a spacer that is cognate to a first protospacer in a target sequence (for example as described in the First Aspect of Detailed Description, Concept 10 or in Concept 30 or in any one of Concepts 38 to 45 when dependent on Concept 30)

wherein the first protospacer in the target sequence is comprised by the polynucleotide, wherein the crRNA hybridizes to the protospacer to guide the protein (e.g.

the ribonucleoprotein complex) whereby the protein (e.g. the ribonucleoprotein complex) edits the polynucleotide.

The method may be carried out in a parental cell that comprises the polynucleotide. There is further provided a progeny cell or organism that is derived from the edited parental cell, wherein the progeny cell or organism retains the edit in its genome. The method may comprise one or more steps of culturing the edited cell to produce said progeny cell or a plurality of such progeny cells.

Concept 61A. The method of Concept 60, wherein the method inserts, deletes or substitutes a base or nucleic acid sequence in the polynucleotide.

Concept 61B. The vector(s) of Concepts 10 or Concept 11 or 12 when dependent from Concept 10, method of any one of Concepts 48-54, or method of Concept 60 or 61, wherein the crRNA is cognate to a protospacer adjacent motif (PAM) having the sequence 5'-AAG-3'.

Alternatively, the PAM may be any one of the PAMs described in any Configuration, Concept, aspect, example, embodiment, option or other feature herein (for example having one of the sequences recited in Concept 39).

Concept 62A. A container comprising a plurality of proteins operable for use with a crRNA to form a ribonucleoprotein complex for protospacer targeting in a polynucleotide, the protein(s) s comprising any of the protein(s) described in any Configuration, Concept, aspect, example, embodiment, option or other feature herein (for example as described in Concept 13), wherein the complex is operable with any of the protospacer adjacent motifs (PAMs) described in any Configuration, Concept, aspect, example, embodiment, option or other feature herein (for example having one of the sequences recited in Concept 39), and the container is not a cell, and the proteins are mixed with an in vitro buffer.

Concept 62B. A container comprising a plurality of proteins operable for use with a crRNA to form a ribonucleoprotein complex for protospacer targeting in a polynucleotide, the proteins comprising any of the fusion protein(s) or fusion protein complexes described in any Configuration, Concept, aspect, example, embodiment, option or other feature herein (for example as described in any one of Concepts 14 to 29), wherein the complex is operable with any of the protospacer adjacent motifs (PAMs) described in any Configuration, Concept, aspect, example, embodiment, option or other feature herein (for example having one of the sequences recited in Concept 39), and the container is not a cell, and the proteins are mixed with an in vitro buffer.

Concept 62C. A container comprising a protein or plurality of proteins operable for use with a crRNA to form a ribonucleoprotein complex for protospacer targeting in a polynucleotide, the protein(s) comprising one, more or all polypeptides selected from a) a polypeptide that comprises an amino acid that is at least (about) 80% identical to SEQ ID NO:1;
b) a polypeptide that comprises an amino acid that is at least (about) 80% identical to SEQ ID NO:2;
c) a polypeptide that comprises an amino acid that is at least (about) 80% identical to SEQ ID NO:3;
d) a polypeptide that comprises an amino acid that is at least (about) 80% identical to SEQ ID NO:4; and
e) a polypeptide that comprises an amino acid that is at least (about) 80% identical to SEQ ID NO:5 wherein the complex is operable with a protospacer adjacent motif (PAM) having the sequence 5'-AAG-3', the container is not a cell, and the proteins are mixed with an in vitro buffer.

Alternatively, the PAM may be any one of the PAMs described in any Configuration, Concept, aspect, example, embodiment, option or other feature herein (for example having one of the sequences recited in Concept 39)

There is Also Provided:-

A protein or plurality of proteins operable for use with a crRNA to form a ribonucleoprotein complex for protospacer targeting in a polynucleotide, the protein(s) comprising one, more or all polypeptides selected from a) a polypeptide that comprises an amino acid that is at least (about) 80% identical to SEQ ID NO:1;
b) a polypeptide that comprises an amino acid that is at least (about) 80% identical to SEQ ID NO:2;
c) a polypeptide that comprises an amino acid that is at least (about) 80% identical to SEQ ID NO:3;
d) a polypeptide that comprises an amino acid that is at least (about) 80% identical to SEQ ID NO:4; and
e) a polypeptide that comprises an amino acid that is at least (about) 80% identical to SEQ ID NO:5 wherein the complex is operable with a protospacer adjacent motif (PAM) having the sequence 5'-AAG-3'.

Alternatively, the PAM may be any one of the PAMs described in any Configuration, Concept, aspect, example, embodiment, option or other feature herein (for example having one of the sequences recited in Concept 39)

Concept 63. A nucleic acid vector or a plurality of nucleic acid vectors as described in any Configuration, Concept, aspect, example, embodiment, option or other feature herein (for example according to any one of Concepts 1 to 12, or any one of Concepts 31 to 45), wherein said polypeptide(s) or protein(s) (including fusion protein(s) and fusion protein complexes) encoded by the vector(s) are operable for use with a crRNA to form a ribonucleoprotein complex for protospacer targeting in a polynucleotide, wherein the complex is operable with any of the protospacer adjacent motifs (PAMs) described in any Configuration, Concept, aspect, example, embodiment, option or other feature herein (for example having one of the sequences recited in Concept 39).

In one embodiment, the protospacer adjacent motif (PAM) has the sequence 5'-AAG-3'.

Concept 64. A method of targeting a polynucleotide, the method comprising a) contacting the polynucleotide with the protein(s), (including fusion protein(s) and fusion protein complexes) as described in any Configuration, Concept, aspect, example, embodiment, option or other feature herein, wherein the protein(s) is/are in combination with a crRNA which comprises a spacer that is cognate to a first protospacer in a target sequence;
b) allowing the formation of a ribonucleoprotein complex comprising the protein(s) and crRNA, wherein the complex is guided to a target sequence comprised by the polynucleotide to modify the polynucleotide or replication thereof.

The targeting may be in a cell. The targeting may be in vitro.

Concept 65. The method of Concept 64, wherein the polynucleotide is comprised by a chromosome or an episome.

In one embodiment, the polynucleotide is comprised by a chromosome. In one embodiment, the polynucleotide is comprised by a plasmid. In one embodiment, the polynucleotide is not comprised by a plasmid.

Concept 66A. The method of Concept 65, wherein the method inhibits replication of the polynucleotide.

Concept 66B. The method of Concept 65, wherein the method edits the polynucleotide.

The editing may insert a base or nucleic acid sequence in the polynucleotide. The editing may delete a base or nucleic acid sequence in the polynucleotide. The editing may substitute a base or nucleic acid sequence in the polynucleotide.

Concept: 67A. A kit comprising a) One or more protein(s) described in any Configuration, Concept, aspect, example, embodiment, option or other feature herein (for example as described in Concept 13); and b) A crRNA, (or one or more nucleic acids encoding a crRNA), wherein the crRNA is cognate to any of the (PAMs) described in any Configuration, Concept, aspect, example, embodiment, option or other feature herein (for example a PAM having one of the sequences recited in Concept 39);

wherein said polypeptide(s) are operable for use with the crRNA to form a ribonucleoprotein complex for protospacer targeting in a polynucleotide.

Concept 67B. A kit comprising a) One or more fusion protein(s) or fusion protein complexes described in any Configuration, Concept, aspect, example, embodiment, option or other feature herein (for example as described in any one of Concepts 14 to 29), or one, or more nucleic acids encoding such polypeptide(s); and b) A crRNA, or one or more nucleic acids encoding a crRNA), wherein the crRNA is cognate to any of the (PAMs) described in any Configuration, Concept, aspect, example, embodiment, option or other feature herein (for example a PAM having one of the sequences recited in Concept 39);

wherein said polypeptide(s) are operable for use with the crRNA to form a ribonucleoprotein complex for protospacer targeting in a polynucleotide.

Concept 67C. A kit comprising a) One or more vector(s) as described in any Configuration, Concept, aspect, example, embodiment, option or other feature herein (for example as described in any one of Concepts 1 to 12, or any one of Concepts 31 to 45), or one, or more nucleic acids encoding such polypeptide(s); and b) A crRNA, or one or more nucleic acids encoding a crRNA), wherein the crRNA is cognate to any of the (PAMs) described in any Configuration, Concept, aspect, example, embodiment, option or other feature herein (for example a PAM having one of the sequences recited in Concept 39);

wherein said polypeptide(s) are operable for use with the crRNA to form a ribonucleoprotein complex for protospacer targeting in a polynucleotide.

Concept 67D. A kit comprising a) One or more polypeptides as recited in Concept 7, or one, or more nucleic acids encoding such polypeptide(s); and b) A crRNA, (or one or more nucleic acids encoding a crRNA, wherein the crRNA is cognate to PAM having the sequence 5'-AAG-3;

wherein said polypeptide(s) are operable for use with the crRNA or guide RNA to form a ribonucleoprotein complex for protospacer targeting in a polynucleotide.

There is provided a complex as described herein. In an example, the complex further comprises one or more Cascade Cas proteins, e.g. one, more or all of a Type I CasA-E proteins. The complex may further comprise a Cas3 and optionally one or more cognate Type I Cascade proteins. The complex may further comprise a Cas3, 9, 10, 12 or 13. Thus, function of a Type-S system or components can be provided together with function on one or more proteins of a different Type of CRISPR/Cas system. The complex may comprise a helicase fused to a nuclease. The nuclease may be, for example, a Cas3, 9, 10, 12 or 13. For example, the nuclease is a Cas3. For example, the nuclease is a Cas9.

In an example, the complex further comprises a TevI nuclease, e.g. an I-TevI nuclease domain. The I-TevI may be as described in any Configuration, Concept, aspect, example, embodiment, option or other feature herein (e.g. in Concept 14, or Concepts 21 to 24, or in Concepts 43 to 45).

In an example, the complex further comprises a MutH protein.

In an example, the complex is an isolated complex. The complex may be in vitro. The complex may be comprised by a medical container, such as an IV bag, medical vial or medical injection device.

Concept 68A. A ribonucleoprotein complex comprising a) One or more protein(s) as described in any Configuration, Concept, aspect, example, embodiment, option or other feature herein (for example as described in Concept 13); and b) A crRNA which is cognate to any of the (PAMs) described in any Configuration, Concept, aspect, example, embodiment, option or other feature herein (for example having one of the sequences recited in Concept 39).

Concept 68B. A ribonucleoprotein complex comprising a) One or more fusion protein(s) or fusion protein complexes described in any Configuration, Concept, aspect, example, embodiment, option or other feature herein (for example as described in any one of Concepts 14 to 29); and b) A crRNA which is cognate to any of the (PAMs) described in any Configuration, Concept, aspect, example, embodiment, option or other feature herein (for example having one of the sequences recited in Concept 39).

Concept 68C. A ribonucleoprotein complex comprising a) One or more polypeptides as recited in Concept 5, or one, or more nucleic acids encoding such polypeptide(s); and b) A crRNA, or one or more nucleic acids encoding a crRNA), wherein the crRNA is cognate to PAM having the sequence 5'-AAG-3'.

Concept 68D. The complex of Concept 68C, wherein the complex is devoid of a) a Cas nuclease;

b) a DNA nuclease or RNA nuclease; or c) a nuclease.

Concept 69. A method of transcriptional control or replication of a target DNA, comprising contacting the target DNA with any of the complexes described herein (for example with the complex of Concept 68), wherein the complex is devoid of a DNA nuclease and the complex binds to the target DNA, thereby controlling the transcription or replication of the target DNA.

Concept 70A. A method of controlling replication of a target RNA, comprising contacting the target RNA or a DNA encoding the RNA with any of the complexes described herein (for example with the complex of Concept 68), wherein the complex binds to the target RNA or DNA, thereby controlling the transcription of the target RNA.

Concept 70B. A method of controlling transcription of a target RNA, comprising contacting the target RNA or a DNA encoding the RNA with any of the complexes described herein (for example with the complex of Concep 68), wherein the complex binds to the target RNA or DNA, thereby controlling the transcription of the target RNA.

Concept 71. The method of Concept 69 or 70, wherein the DNA is comprised by a chromosome or an episome (optionally a plasmid).

In one embodiment, the DNA is comprised by a chromosome. In one embodiment, the DNA is comprised by a plasmid. In one embodiment, the DNA is not comprised by a plasmid.

Concept 72. A method of editing a target DNA, comprising contacting the target DNA with any of the complexes described herein (for example with the complex of Concept 68), wherein the complex binds to the target DNA, thereby editing the target DNA.

Concept 73A. A method for cleaving a double stranded DNA (dsDNA), comprising contacting said dsDNA with any of the complexes described herein (for example with the complex of Concept 68), wherein the complex comprises a fusion protein in which Py comprises a nuclease, wherein the dsDNA comprises a protospacer sequence flanked at its 5' by any one of the (PAMs) described in any Configuration, Concept, aspect, example, embodiment, option or other feature herein (for example having one of the sequences recited in Concept 39), whereby the nuclease cleaves the DNA in the region defined by complementary binding of a spacer sequence of the crRNA to the protospacer.

Concept 73B. A method for cleaving RNA, comprising contacting said RNA with any of the complexes described herein (for example with the complex of Concept 68), wherein the complex comprises a fusion protein in which Py comprises an RNA nuclease, wherein the RNA comprises a protospacer sequence flanked at its 5' by any one of the (PAMs) described in any Configuration, Concept, aspect, example, embodiment, option or other feature herein (for example having one of the sequences recited in Concept 39), whereby the nuclease cleaves the RNA in the region defined by complementary binding of a spacer sequence of the crRNA to the protospacer.

Concept 73C. A method for cleaving a double stranded DNA (dsDNA), comprising contacting said dsDNA with the complex of Concept 68C or 68D, wherein the complex comprises a nuclease, wherein the dsDNA comprises a protospacer sequence flanked at its 5' by a PAM having the sequence 5'-AAG-3' or a PAM that is identical except for one base change, whereby the nuclease cleaves the DNA in the region defined by complementary binding of a spacer sequence of the crRNA to the protospacer.

Alternatively, the the PAM can be AAN, ANG, NAG; or the PAM can be AAG with no or one nucleotide change.

The nuclease may be any nuclease described herein (such as an I-TevI nuclease as described elsewhere herein). The nuclease may be a DNA nuclease. The nuclease may be an RNA nuclease. The nuclease may be a TALEN. The nuclease may be a zinc finger protein. The nuclease may be a Cas nuclease from any naturally occurring system. The nuclease may be a synthetic Cas nuclease.

Concept 74A. A method for cleaving a single stranded DNA (ssDNA), comprising contacting said ssDNA with any of the complexes described herein (for example with the complex of Concept 68), wherein the complex comprises a fusion protein in which Py comprises a nickase, wherein the ssDNA comprises a protospacer sequence flanked at its 5' by any one of the (PAMs) described in any Configuration, Concept, aspect, example, embodiment, option or other feature herein (for example having one of the sequences recited in Concept 39), whereby the nickase cleaves a single strand of the ssDNA in the region defined by complementary binding of a spacer sequence of the crRNA to the protospacer.

Concept 74B. A method for cleaving a single strand in a double stranded DNA (dsDNA), comprising contacting said dsDNA with any of the complexes described herein (for example with the complex of Concept 68), wherein the complex comprises a fusion protein in which Py comprises a nickase, wherein the dsDNA comprises a protospacer sequence flanked at its 5' by any one of the (PAMs) described in any Configuration, Concept, aspect, example, embodiment, option or other feature herein (for example having one of the sequences recited in Concept 39), whereby the nickase cleaves a single strand of the dsDNA in the region defined by complementary binding of a spacer sequence of the crRNA to the protospacer.

Concept 74C. A method for cleaving a single stranded DNA (ssDNA), comprising contacting said DNA with the complex of Concept 68C or 68D, wherein the complex comprises a nickase, wherein the DNA comprises a protospacer sequence flanked at its 5' by a PAM having the sequence 5'-AAG-3' or a PAM that is identical except for one base change, whereby the nickase cleaves a single strand of the DNA in the region defined by complementary binding of a spacer sequence of the crRNA to the protospacer.

The nickase may be any nuclease described herein. The nickase may be a DNA nickase. The nickase may be selected from Nt.BstNBI, Nb.BsrDI, Nb.BtsI, Nt.AlwI, Nb.BbvCI, Nt.BbvCI, and Nb.BsmI (available from New England BioLabs), The nickase a synthetic Cas nickase (e.g. nCas9 or Cas9D10A).

Concept 75A. A method of marking or identifying a region of a DNA, comprising contacting said DNA with any of the complexes described herein (for example with the complex of Concept 68), wherein the DNA comprises a protospacer sequence flanked at its 5' by any one of the (PAMs) described in any Configuration, Concept, aspect, example, embodiment, option or other feature herein (for example having one of the sequences recited in Concept 39), whereby the complex binds to the DNA in the region defined by complementary binding of a spacer sequence of the crRNA to the protospacer, and optionally wherein the complex comprising a fusion protein in which Py comprises a detectable label.

Concept 75B. A method of marking or identifying a region of a DNA, comprising contacting said DNA with the complex of Concept 68C or 68D, wherein the DNA comprises a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, and optionally wherein the complex comprises a detectable label.

Concept 76A. A method of modifying transcription of a region of a DNA, comprising contacting said DNA with any of the complexes described herein (for example with the complex of Concept 68), wherein the DNA comprises a protospacer sequence flanked at its 5' by any one of the (PAMs) described in any Configuration, Concept, aspect, example, embodiment, option or other feature herein (for example having one of the sequences recited in Concept 39), whereby the complex binds to the DNA in the region defined by complementary binding of a spacer sequence of the crRNA to the protospacer, whereby the complex up- or down-regulates transcription of the region of DNA or an adjacent gene.

Concept 76B. A method of modifying transcription of a region of a DNA, comprising contacting said DNA with the complex of Concept 68C or 68D, wherein the DNA comprises a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, whereby the complex up- or down-regulates transcription of the region of DNA or an adjacent gene.

In one embodiment, the complex down-regulates transcription. Down-regulation may be at least about 50% compared to transcription without the complex present. In an embodiment, the downregulation is at least about 60%, 70%, 80% or 90%. In another embodiment, the down-regulation is at least about 95%, 96%, 97%, 98% or 99%. In another embodiment, the down-regulation is 100%, i.e. transcription of the region of DNA is blocked completely.

In some embodiments, downregulation may be desirable when a gene is overexpressed and is causative of a negative phenotype, but complete removal of the protein would be detrimental. Downregulation of a target gene can be useful in making and studying knockout phenotypes where generation of a complete knockout would be lethal to the cell or organism.

In some embodiments, blocking transcription of an essential gene in a pathogenic bacteria can be used to kill the pathogenic bacterium whilst leaving other, beneficial bacteria unaffected. Equally, pathogenic bacteria can be killed by blocking the transcription of the origin of replication. Blocking non-essential genes in a cell or organism is useful for studying knock-outs and phenotype behaviour(s).

Concept 77A. A method of modifying a target dsDNA of a cell without introducing dsDNA breaks, the method comprising producing in the cell with any of the complexes described herein (for example with the complex of Concept 68), wherein the complex targets a target dsDNA comprised by the cell, the target dsDNA comprising a protospacer sequence flanked at its 5' by any one of the (PAMs) described in any Configuration, Concept, aspect, example, embodiment, option or other feature herein (for example having one of the sequences recited in Concept 39), whereby the complex binds to the dsDNA in the region defined by complementary binding of a spacer sequence of the crRNA to the protospacer, whereby the dsDNA is modified without introducing dsDNA breaks.

Concept 77B. A method of modifying a target dsDNA of a cell without introducing dsDNA breaks, the method comprising producing in the cell with the complex of Concept 68C or 68D, wherein the complex targets a target DNA comprised by the cell, the target DNA comprising a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, whereby the DNA is modified without introducing breaks in the DNA.

Concept 78. The method of Concept 77, wherein the method edits the DNA, such as wherein the editing inserts, deletes or substitutes a base or nucleic acid sequence in the DNA.

The modifying may be the introduction of one or more substitutions when the complex is a complex of Concept 68B and Py is a base editor or a prime editor (such as any of the base editors or prime editors described elsewhere herein). The modifying may be the introduction of one or more insertions and/or deletions (INDELS) when the complex is a complex of Concept 68B and Py is a nuclease or nickase and the cell is a cell which is able to repair the dsDNA break or the ssDNA break via the NHEJ mechanism.

Concept 79A. A method of inhibiting the growth or proliferation of a cell without introducing lethal dsDNA breaks, the method comprising producing in the cell any of the complexes described herein (for example a complex of Concept 68), wherein the complex targets a target DNA comprised by the cell, the target DNA comprising a protospacer sequence flanked at its 5' by any one of the (PAMs) described in any Configuration, Concept, aspect, example, embodiment, whereby the complex binds to the DNA in the region defined by complementary binding of a spacer sequence of the crRNA to the protospacer, whereby replication of the DNA is inhibited without introducing lethal dsDNA breaks in the DNA, thereby inhibiting the growth or proliferation of a cell.

Concept 79B. A method of inhibiting the growth or proliferation of a cell without introducing lethal dsDNA breaks, the method comprising producing in the cell the complex of Concept 68C or 68D, wherein the complex targets a target DNA comprised by the cell, the target DNA comprising a protospacer sequence flanked at its 5' by a PAM having the sequence 5'-AAG-3' or a PAM that is identical except for one base change, whereby the complex binds to the DNA in the region defined by complementary binding of a spacer sequence of the crRNA to the protospacer, whereby replication of the DNA is inhibited without introducing breaks in the DNA, thereby inhibiting the growth or proliferation of a cell.

The growth or proliferation of a cell may be inhibited by the introduction of one or more insertions and/or deletions (INDELS) when the complex is a complex of Concept 68B and Py is a nickase which introduces single stranded breaks in DNA and the cell is a cell which is able to repair the dsDNA break or the ssDNA break via the NHEJ mechanism. The growth or proliferation of a cell may be inhibited by downregulating or blocking the transcription of an essential gene in the cell when the complex is a complex of Concept 68A. Essential genes are well-known to those skilled in the art. The growth or proliferation of a cell may be inhibited by downregulating or blocking the transcription of a chromosomal origin of replication in the cell when the complex is a complex of Concept 68A.

Concept 80. A method of treating or preventing a disease or condition in a human, animal, plant or fungus subject, the method comprising carrying out the method of any one of Concepts 69 to 79, wherein cells of the subject comprise said DNA or RNA and the cells mediate the disease or condition.

Concept 81A. The method of Concept 81, wherein the complex modifies a coding target sequence or a non-coding target sequence.

In one embodiment, a coding strand but not non-coding strand of DNA is modified. In another embodiment, a non-coding strand but not coding strand of DNA is modified.

Concept 81B. The method of any one of Concepts 69 to 80, wherein the complex modifies (e.g. cuts, edits, blocks, marks or labels) a coding target sequence coding or a non-coding target sequence, optionally wherein (i) a coding strand but not non-coding strand of DNA is modified or (ii) a non-coding strand but not coding strand of DNA is modified.

Concept 82. The method of Concept 81, wherein the modifying cuts, edits, blocks, marks or labels the target sequence.

When the complex is a complex of Concept 68A, the modifying may be blocking. When the complex is a complex of Concept 68A, the modifying may be downregulating transcription of a coding target sequence. When the complex is a complex of Concept 68B in which Py is a nuclease or nickase, the modifying may be cutting a coding target sequence. When the complex is a complex of Concept 68B in which Py is a base editor or prime editor, the modifying may be editing a coding target sequence. The base editor may introduce one or more substitutions in the coding target sequence.

Concept 83A. One or more nucleic acid vectors or one or more nucleic acids comprising at least one nucleotide sequence selected from SEQ ID NOs: 7-11, wherein a said nucleotide sequence is operably connected to a heterologous promoter, synthetic promoter, eukaryotic promoter or non-bacterial promoter.

Concept 83B. One or more nucleic acid vectors or one or more nucleic acids comprising at least one nucleotide sequence selected from SEQ ID NOs: 7-11, wherein a said nucleotide sequence is comprised by a cell that is a eukaryotic cell, a non-bacterial cell, or a cell that is not a bacterial cell (e.g. an *E. coli, Pseudomonas* or *Klebsiella* cell) that comprises endogenous nucleotide sequence comprising SEQ ID NOS: 7-11.

Concept 83C. One or more nucleic acid vectors or one or more nucleic acids comprising at least one nucleotide sequence selected from SEQ ID NOs: 7-11, wherein a said nucleotide sequence is operably connected to a heterologous promoter, synthetic promoter, eukaryotic promoter or non-bacterial promoter and a said nucleotide sequence is comprised by a cell that is a eukaryotic cell, a non-bacterial cell, or a cell that is not a bacterial cell (e.g. an *E coli, Pseudomonas* or *Klebsiella* cell) that comprises endogenous nucleotide sequence comprising SEQ ID NOs: 7-11.

Concept 84. A nucleic acid vector or a nucleic acid that comprises SEQ ID NO: 12 or a DNA sequence that is at least (about) 80% identical to SEQ ID NO:12.

Concept 85. One or more nucleic acids encoding a plurality of Cas proteins and comprising at least one nucleotide sequence for producing a crRNA, wherein the Cas proteins and RNA are capable of forming a ribonucleoprotein CRISPR/Cas complex wherein the RNA is capable of guiding the complex to a protospacer comprised by a target DNA, wherein the 5'end of the protospacer is flanked by any one of the protospacer adjacent motifs (PAMs) described in any Configuration, Concept, aspect, example, embodiment, option or other feature herein (for example having one of the sequences recited in Concept 39), wherein

- a) the complex is devoid of a DNA nuclease and is capable of modifying DNA without introducing a double stranded DNA break;
- b) the Cas proteins do not comprise a DinG, Cas3 and Cas10; and
- c) the complex does not comprise all of the Cas proteins of a Type I, II, III, IV, V or VI CRISPR/Cas complex.

Concept 86. The nucleic acid(s) of Concept 85, wherein the nucleic acid is comprised by a vector or the nucleic acids are comprised by one or more vectors.

Concept 87. The nucleic acid(s) of Concept 85 or 86, wherein the DNA is comprised by a chromosome.

Concept 88. A ribonucleoprotein CRISPR/Cas complex comprising a plurality of Cas proteins and a crRNA, wherein the RNA is capable of guiding the complex to a protospacer comprised by a target DNA, wherein the 5'end of the protospacer is flanked by any one of the protospacer adjacent motifs (PAMs) described in any Configuration, Concept, aspect, example, embodiment, option or other feature herein (for example having one of the sequences recited in Concept 39)', wherein

- a) the complex is devoid of a DNA nuclease and is capable of modifying DNA without introducing a double stranded DNA break;
- b) the complex is devoid of a Cas3, and a Cas10; and
- c) the complex does not comprise all of the Cas proteins of a Type I, II, III, IV, V or VI CRISPR/Cas complex.

Concept 89. The nucleic acid(s) of any one of Concepts 85-87 or the complex of Concept 88, wherein the crRNA is not a Type I, II, III, V or VI crRNA respectively.

Concept 90. The nucleic acid(s) or complex of any one of Concepts 85 to 89, wherein the complex is capable of modifying (i) a coding strand but not non-coding strand of DNA or (ii) a non-coding strand but not coding strand of DNA.

Concept 91. The nucleic acid(s) or complex of any one of Concepts 85 to 90, wherein the complex modifies (e.g. cuts, edits, blocks, marks or labels) a coding target sequence or a non-coding target sequence of the DNA.

Concept 92. The nucleic acid(s) or complex of any of Concepts 85 to 91, wherein the plurality of Cas proteins comprises a Cas-S1, S2, S3, S4 and S5.

For example, the plurality of Cas proteins comprises Cas-S1.1, S2.1, S3.1, S4.1 and S5.1.

Concept 93. The nucleic acid(s) or complex of any of Concepts 85 to 92, wherein the complex further comprises an effector protein domain for modifying DNA, optionally wherein the effector domain comprises nuclease activity, nickase activity, recombinase activity, reverse transcriptase, helicase, deaminase activity, methyltransferase activity, methylase activity, acetylase activity, acetyltransferase activity, transcriptional activation activity, or transcriptional repression activity.

In an example, the complex comprises a component selected from

- a) a nuclease which cuts the target site;
- b) a deaminase (such as a cytosine or adenine deaminase) which carries out deamination of the target site;
- c) a base editor which base edits the target site;
- d) a prime editor which prime edits the target site;
- e) a reverse transcriptase which reverse transcribes the target site or which reverse transcribes an RNA in the cell to produce a DNA that is inserted at the target site;
- f) a methyltransferase that methylates DNA in the cell;
- g) a methylase that methylases DNA in the cell;
- h) an acetylase that acetylases DNA in the cell;
- i) an acetyltransferase that subjects DNA in the cell to acetyltransferase activity;
- j) a transcription activator that activates transcription of a gene in the cell, such as a gene comprising or adjacent to the target site; and
- k) a transcription deactivator that de-activates transcription of a gene in the cell, such as a gene comprising or adjacent to the target site.

Concept 94. A cell comprising the nucleic acid(s) or complex of any one of Concepts 85 to 93, wherein the DNA is comprised by a chromosome of the cell.

Concept 95. A cell comprising the nucleic acid(s) or complex of any one of Concepts85 to 93, wherein the DNA is comprised by a plasmid in the cell.

Concept 96. The cell of Concept 95, wherein the complex is capable of inhibiting growth or proliferation of the cell.

Concept 97. A method of modifying a DNA, the method comprising a) contacting the DNA with the nucleic acid(s) defined in any one of Concepts 85 to 87 and 89 to 93;

b) allowing the formation of a ribonucleoprotein complex comprising the Cas protein(s) and crRNA, wherein the complex is guided to a target site comprised by the DNA to modify the DNA.

Concept 98. A method of inhibiting the replication of a plasmid comprising DNA, the method comprising a) contacting the DNA with the nucleic acid(s) defined in any one of Concepts 85 to 87 and 89 to 93;

b) allowing the formation of a ribonucleoprotein complex comprising the Cas protein(s) and crRNA, wherein the complex is guided to a target site comprised by the DNA to inhibit replication of the plasmid.

Concept 99. A method of inhibiting the transcription of a nucleotide sequence comprised by a DNA, the method comprising a) contacting the DNA with the nucleic acid(s) defined in any one of Concepts 85 to 87 and 89 to 93;

b) allowing the formation of a ribonucleoprotein complex comprising the Cas protein(s) and crRNA, wherein the complex is guided to a target site comprised by the nucleotide sequence to inhibit transcription thereof.

Concept 100. A method of inhibiting the growth or proliferation of a cell (optionally a prokaryotic cell, such as a bacterial cell) comprising DNA, the method comprising a) contacting the DNA with the nucleic acid(s) defined in any one of Concepts 85 to 87 and 89 to 93;

b) allowing the formation of a ribonucleoprotein complex comprising the Cas protein(s) and crRNA, wherein the complex is guided to a target site comprised by the DNA to inhibit growth or proliferation of the cell.

Concept 101. A method of treating or preventing a disease or condition that is mediated by target cells in a human or animal subject, the method comprising carrying out the method of any one of Concepts 97 to 100 to modify the target cells, wherein said contacting comprises administering the nucleic acid(s) to the subject and wherein the modification treats or prevents the disease or condition.

Concept 102. The method of Concept 101, wherein the target cells are cells of the subject that comprise a nucleic acid defect and the modification corrects the defect.

Concept 103. The method of Concept 101 or 102, wherein the modification a) adds a new functionality to the cells, optionally the modification upregulates or downregulates expression of a gene in the cells or adds a new nucleotide sequence to the genomes of the cells for expression of a protein encoded by the sequence; or b) modulates the expression of a nucleotide sequence comprised by a chromosome or episome (optionally a plasmid) of the cell; or c) inhibits growth or proliferation of the cells.

The cell may be a bacterial cell of any genus or species in Table 3. The method may modify a cell of any genus or species in Table 3. The DNA or polynucleotide may be comprised by a cell of any genus or species in Table 3. The method may kill or inhibit the growth or proliferation of a cell of any genus or species in Table 3. The cell may be a cell of a genus or species that is different from one of the genera or species respectively in Table 3, for example, the cell is not an *E. coli* cell, or the cell is not a *Klebsiella* cell. The cell may be an archaea, such as a methanogen. The method may kill or inhibit the growth or proliferation of the archaea. The method may edit the genome of the bacterial or archaeal cell. Any prokaryotic cell (e.g. bacterial or archaeal cell) or fungal cell herein may be comprised by a microbiome, such as a microbiome of a human, animal, plant or environment (such as soil or a waterway). For, example, the microbiome is comprised by the gastrointestinal tract (GI tract) of a human or animal. For, example, the microbiome is comprised by the urinary system of a human or animal, e.g. comprised by a bladder, kidney or urethra. For, example, the microbiome is comprised by the blood of a human or animal. For, example, the microbiome is comprised by the eye or nose or ear of a human or animal. For, example, the microbiome is comprised by the hair of a human or animal. For, example, the microbiome is comprised by the skin of a human or animal. For, example, the microbiome is comprised by a leaf, root, stem or seed of a plant.

A disease or condition herein may be selected from any of the following:

| | |
|---|---|
| A neurodegenerative disease or condition; | A sexually-transmissible disease or condition, e.g. gonorrhea, HIV infection, syphilis or Chlamydia infection; |
| A brain disease or condition; | An ear disease or condition; |
| A CNS disease or condition; | A skin disease or condition; |
| Memory loss or impairment; | A heart disease or condition; |
| A heart or cardiovascular disease or condition, e.g. heart attack, stroke or atrial fibrillation; | A nasal disease or condition |
| A liver disease or condition; | A haematological disease or condition, e.g. anaemia, e.g. anaemia of chronic disease or cancer; |
| A kidney disease or condition, e.g. chronic kidney disease (CKD); | A viral infection; |
| A pancreas disease or condition; | A pathogenic bacterial infection; |
| A lung disease or condition, e.g. cystic fibrosis or COPD; | A cancer; |
| A gastrointestinal disease or condition; | An autoimmune disease or condition, e.g. SLE; |
| A throat or oral cavity disease or condition; | An inflammatory disease or condition, e.g. rheumatoid arthritis, psoriasis, eczema, asthma, ulcerative colitis, colitis, Crohn's disease or IBD; |
| An ocular disease or condition; | Autism; |
| A genital disease or condition, e.g. a vaginal, labial, penile or scrotal disease or condition; | ADHD; |
| ALS [Amyotrophic Lateral Sclerosis]; | Bipolar disorder; |
| Osteoarthritis; | Conception disorder, e.g. infertility or low fertility; |
| A congenital or development defect or condition; | Jaundice; |

-continued

| | |
|---|---|
| Miscarriage; | Skin rash; |
| A blood clotting condition; | Kawasaki Disease; |
| Bronchitis; | Lyme Disease; |
| Dry or wet AMD; | An allergy, eg, a nut, grass, pollen, dust |
| Neovascularisation (e.g. of a tumour or in | mite, cat or dog fur or dander allergy; |
| the eye); | Malaria, typhoid fever, tuberculosis or |
| Common cold; | cholera; |
| Epilepsy; | Depression; |
| Fibrosis, e.g. liver or lung fibrosis; | Mental retardation; |
| A fungal disease or condition, e.g. | Microcephaly; |
| thrush; | Malnutrition; |
| A metabolic disease or condition, e.g. | Conjunctivitis; |
| obesity, anorexia, diabetes, Type I or | Pneumonia; |
| Type II diabetes. | Pulmonary embolism; |
| Ulcer(s), e.g. gastric ulceration or skin | Pulmonary hypertension; |
| ulceration; | A bone disorder; |
| Dry skin; | Sepsis or septic shock; |
| Sjogren's syndrome; | Sinusitus; |
| Cytokine storm; | Stress (eg, occupational stress); |
| Deafness, hearing loss or impairment; | Thalassaemia, anaemia, von Willebrand |
| Slow or fast metabolism (ie, slower or | Disease, or haemophilia; |
| faster than average for the weight, sex | Shingles or cold sore; |
| and age of the subject); | Menstruation; and |
| | Low sperm count. |

Neurodegenerative or CNS Diseases or Conditions for Treatment or Prevention by the Method In an example, the neurodegenerative or CNS disease or condition is selected from the group consisting of Alzheimer disease, geriopsychosis, Down syndrome, Parkinson's disease, Creutzfeldt-Jakob disease, diabetic neuropathy, Parkinson syndrome, Huntington's disease, Machado-Joseph disease, amyotrophic lateral sclerosis, diabetic neuropathy, and Creutzfeldt-Jakob disease. For example, the disease is Alzheimer disease. For example, the disease is Parkinson syndrome.

In an example, any of the methods described herein is practised on a human or animal subject for treating a CNS or neurodegenerative disease or condition, the method causes downregulation of Treg cells in the subject, thereby promoting entry of systemic monocyte-derived macrophages and/or Treg cells across the choroid plexus into the brain of the subject, whereby the disease or condition (e.g. Alzheimer's disease) is treated, prevented or progression thereof is reduced. In an embodiment the method causes an increase of IFN-gamma in the CNS system (e.g. in the brain and/or CSF) of the subject. In an example, the method restores nerve fibre and/or reduces the progression of nerve fibre damage. In an example, the method restores nerve myelin and//or reduces the progression of nerve myelin damage. In an example, any of the methods described herein treats or prevents a disease or condition disclosed in WO2015/136541 and/or the method can be used with any method disclosed in WO2015/136541 (the disclosure of this document is incorporated by reference herein in its entirety, e.g. for providing disclosure of such methods, diseases, conditions and potential therapeutic agents that can be administered to the subject for effecting treatment and/or prevention of CNS and neurodegenerative diseases and conditions, e.g. agents such as immune checkpoint inhibitors, e.g. anti-PD-1, anti-PD-L1, anti-TIM3 or other antibodies disclosed therein).

Cancers for Treatment or Prevention by the Method

Cancers that may be treated include tumours that are not vascularized, or not substantially vascularized, as well as vascularized tumours. The cancers may comprise non-solid tumours (such as haematological tumours, for example, leukaemias and lymphomas) or may comprise solid tumours. Types of cancers to be treated by the methods, protein(s) (including fusion protein(s) and fusion protein complexes), vector(s), complexes and composition(s) described herein include, but are not limited to, carcinoma, blastoma, and sarcoma, and certain leukaemia or lymphoid malignancies, benign and malignant tumours, and malignancies e.g. sarcomas, carcinomas, and melanomas. Adult tumours/cancers and paediatric tumours/cancers are also included.

Haematologic cancers are cancers of the blood or bone marrow. Examples of haematological (or haematogenous) cancers include leukaemias, including acute leukaemias (such as acute lymphocytic leukaemia, acute myelocytic leukaemia, acute myelogenous leukaemia and myeloblasts, promyelocytic, myelomonocytic, monocytic and erythroleukaemia), chronic leukaemias (such as chronic myelocytic (granulocytic) leukaemia, chronic myelogenous leukaemia, and chronic lymphocytic leukaemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukaemia and myelodysplasia.

Solid tumours are abnormal masses of tissue that usually do not contain cysts or liquid areas. Solid tumours can be benign or malignant. Different types of solid tumours are named for the type of cells that form them (such as sarcomas, carcinomas, and lymphomas). Examples of solid tumours, such as sarcomas and carcinomas, include fibrosarcoma, myxosarcoma, liposarcoma, chondrosarcoma, osteosarcoma, and other sarcomas, synovioma, mesothelioma, Ewing's tumour, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumour, cervical cancer, testicular tumour, seminoma, blad der carcinoma, melanoma, and CNS tumours (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

| AUTOIMMUNE DISEASES FOR TREATMENT OR PREVENTION BY THE METHOD | |
|---|---|
| Acute Disseminated Encephalomyelitis (ADEM) | Autoimmune myocarditis |
| Acute necrotizing hemorrhagic leukoencephalitis | Autoimmune oophoritis |
| Addison's disease | Autoimmune pancreatitis |
| Agammaglobulinemia | Autoimmune retinopathy |
| Alopecia areata | Autoimmune thrombocytopenia purpura (ATP) |
| Amyloidosis | Autoimmune thyroid disease |
| Ankylosing spondylitis | Autoimmune urticaria |
| Anti-GBM/Anti-TBM nephritis | Axonal & neuronal neuropathies |
| Antiphospholipid syndrome (APS) | Balo disease |
| Autoimmune angioedema | Behcet's disease |
| Autoimmune aplastic anemia | Bullous pemphigoid |
| Autoimmune dysautonomia | Cardiomyopathy |
| Autoimmune hepatitis | Castleman disease |
| Autoimmune hyperlipidemia | Celiac disease |
| Autoimmune immunodeficiency | Chagas disease |
| Autoimmune inner ear disease (AIED) | Chronic fatigue syndrome |
| Chronic inflammatory demyelinating polyneuropathy (CIDP) | Guillain-Barre syndrome |
| Chronic recurrent multifocal ostomyelitis (CRMO) | Hashimoto's encephalitis |
| Churg-Strauss syndrome | Hashimoto's thyroiditis |
| Cicatricial pemphigoid/benign mucosal pemphigoid | Hemolytic anemia |
| Crohn's disease | Henoch-Schonlein purpura |
| Cogans syndrome | Herpes gestationis |
| Cold agglutinin disease | Hypogammaglobulinemia |
| Congenital heart block | Idiopathic thrombocytopenia purpura (ITP) |
| Coxsackie myocarditis | IgA nephropathy |
| CREST disease | IgG4-related sclerosing disease |
| Essential mixed cryoglobulinemia | Immunoregulatory lipoproteins |
| Demyelinating neuropathies | Inclusion body myositis |
| Dermatitis herpetiformis | Interstitial cystitis |
| Dermatomyositis | Juvenile arthritis |
| Devic's disease (neuromyelitis optica) | Juvenile diabetes (Type 1 diabetes) |
| Discoid lupus | Juvenile myositis |
| Dressler's syndrome | Kawasaki syndrome |
| Endometriosis | Lambert-Eaton syndrome |
| Eosinophilic esophagitis | Leukocytoclastic vasculitis |
| Eosinophilic fasciitis | Lichen planus |
| Erythema nodosum | Lichen sclerosus |
| Experimental allergic encephalomyelitis | Ligneous conjunctivitis |
| Evans syndrome | Linear IgA disease (LAD) |
| Fibromyalgia | Lupus (SLE) |
| Fibrosing alveolitis | Lyme disease, chronic |
| Giant cell arteritis (temporal arteritis) | Meniere's disease |
| Giant cell myocarditis | Microscopic polyangiitis |
| Glomerulonephritis | Mixed connective tissue disease (MCTD) |
| Goodpasture's syndrome | Mooren's ulcer |
| Granulomatosis with Polyangiitis (GPA) (formerly called Wegener's Granulomatosis) | Mucha-Habermann disease |
| Graves' disease | Multiple sclerosis |
| Ocular cicatricial pemphigoid | Myasthenia gravis |
| Optic neuritis | Myositis |
| Palindromic rheumatism | Narcolepsy |
| PANDAS (Pediatric Autoimmune Neuropsychiatric Disorders Associated with Streptococcus) | Neuromyelitis optica (Devic's) |
| Paraneoplastic cerebellar degeneration | Neutropenia |
| Paroxysmal nocturnal hemoglobinuria (PNH) | Reactive Arthritis |
| Parry Romberg syndrome | Reflex sympathetic dystrophy |
| Parsonnage-Turner syndrome | Reiter's syndrome |
| Pars planitis (peripheral uveitis) | Relapsing polychondritis |
| Pemphigus | Restless legs syndrome |
| Peripheral neuropathy | Retroperitoneal fibrosis |
| Perivenous encephalomyelitis | Rheumatic fever |
| Pernicious anemia | Rheumatoid arthritis |
| POEMS syndrome | Sarcoidosis |
| Polyarteritis nodosa | Schmidt syndrome |
| Type I, II, & III autoimmune polyglandular | Scleritis |
| | Scleroderma |
| | Sjogren's syndrome |
| | Sperm & testicular autoimmunity |
| | Stiff person syndrome |
| | Subacute bacterial endocarditis (SBE) |
| | Susac's syndrome |
| | Sympathetic ophthalmia |
| | Takayasu's arteritis |
| | Temporal arteritis/Giant cell arteritis |

-continued

| AUTOIMMUNE DISEASES FOR TREATMENT OR PREVENTION BY THE METHOD | |
|---|---|
| syndromes | Thrombocytopenia purpura (TTP) |
| Polymyalgia rheumatica | Tolosa-Hunt syndrome |
| Polymyositis | Transverse myelitis |
| Postmyocardial infarction syndrome | Type 1 diabetes |
| Postpericardiotomy syndrome | Ulcerative colitis |
| Progesterone dermatitis | Undifferentiated connective tissue disease (UCTD) |
| Primary biliary cirrhosis | Uveitis |
| Primary sclerosing cholangitis | Vasculitis |
| Psoriasis | Vesiculobullous dermatosis |
| Psoriatic arthritis | Vitiligo |
| Idiopathic pulmonary fibrosis | Wegener's granulomatosis (now termed Granulomatosis with Polyangiitis (GPA) |
| Pyoderma gangrenosum | |
| Pure red cell aplasia | |
| Raynauds phenomenon | |

Inflammatory Diseases for Treatment or Prevention by the Method

| INFLAMMATORY DISEASES FOR TREATMENT OR PREVENTION BY THE METHOD | |
|---|---|
| Alzheimer's | arthritis (osteoarthritis, rheumatoid arthritis (RA), psoriatic arthritis) |
| ankylosing spondylitis | hepatitis |
| asthma | irritable bowel syndrome (IBS) |
| atherosclerosis | systemic lupus erythematous (SLE) |
| Crohn's disease | nephritis |
| colitis | Parkinson's disease |
| dermatitis | ulcerative colitis. |
| diverticulitis | |
| fibromyalgia | |

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. Reference is made to the publications mentioned herein and equivalent publications by the US Patent and Trademark Office (USPTO) or WIPO, the disclosures of which 25 are incorporated herein by reference for providing disclosure that may be used in the present invention and/or to provide one or more features (e.g. of a vector) that may be included in one or more claims herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non-limiting Examples.

EXAMPLES

Example 1

1.1 Executive Summary

This Example describes the in-silico identification and in-vivo (in *E. coli*) functional characterization of the previously uncharacterized CRISPR-Cas system that its targeting activity does not rely on a predicted RNA guided Cas endonuclease. We demonstrated that the system i) successfully targets plasmid DNA, with an unknown mechanism, hindering plasmid-induced antibiotic resistance, and ii) efficiently binds to chromosomal DNA without inducing cell death. We term this system a "Type-S CRISPR/Cas system".

1.1.1 Objectives

Characterize a CRISPR system that is different from the currently known functionally characterized systems.

1.2 Materials and Methods 1.2.1 Plasmid and Strain Construction

Plasmids and strains used in this study are listed in the Appendix (see section 1.5 below), Plasmids were constructed from PCR generated DNA fragments by InFusion HD™ cloning (Takara). Insertion of the target sequences into the chromosome of *E. coli* C-1 strain was performed using lambda-red mediated recombineering. The resulting strain is b5451 (ΔlacZ).

1.2.2 Transformation Assay for Sequence Specific Plasmid Inhibition

Cells were first transformed with the p1624 plasmid shown in FIG. 1 and the plasmids shown in FIG. 3, carrying components of a novel CRISPR/Cas system (which we call a Type-S CRISPR/Cas system herein). Next, to evaluate the functionality of the plasmids that carried components of the Type-S system, *E coli* cells were separately transformed with these plasmids and subsequently were transformed with a 1:1 mixture of two plasmids, p1631 and p892. Target plasmid p1631 carried all the natural target sequences (5 protospacers) of the CRISPR array of the system and the amilCP gene, providing a purple color to the colonies that carried the plasmid. Plasmid p892 served as a non-target control, it had the same replication origin (p15A) and antibiotic marker gene (CmR) as the target plasmid but did not carry the target sequences and the amilCP gene.

Cells that did not carry any components of the Type-S system were also transformed with the p1631/p892 plasmid mixture as a control for evaluating the ratio of the two plasmids in the mixture.

Transformed cells were plated on LB agar plates containing appropriate antibiotics to select for the presence of the plasmids. Plates were incubated at 37° C. overnight and the ratio of purple and white colonies, carrying the target and non-target plasmid, respectively, was determined.

1.2.3 Plasmid Inhibition Using Controlled Expression of the Type-S System Components Strain b5456 carrying plasmid p1826, which is identical to p1793 (FIG. 3) but contains the Type-S system under the control of an arabinose inducible promoter (instead of pBolA), was transformed by electroporation with a 1:1 mixture of two plasmids, p1631 and p892. Cells were left to recover for 1.5 hours and plated on LB agar containing appropriate antibiotics, with and without 0.2% arabinose.

1.2.4 Growth Inhibition Assay

A 1:1 mixture of *E. coli* C-1 and b5451 competent cells was transformed with plasmid p1826 containing the required components of the Type-S CRISPR-Cas system and left to recover for 1.5 hour before plating on LB agar containing 20 μg/mL tetracycline to select for transformants carrying the plasmids. Plates also contained X-gal (20 ng/mL) and IPTG (1 mM) to distinguish colonies of *E. coli* C-1 (lacZ+, blue) and b5451 (lacZ-, white).

1.2.5 Plasmid Clearance Assays

Strain b5408 was separately transformed with plasmids p1935, p1936, p1937, p1938, p1631 and p144 (see Table 2 and FIG. 7). Serial dilutions of the recovered transformation solutions were plated on LB agar plates supplemented with 10 μg/mL tetracycline and 20 μg/mL chloramphenicol. The plates were incubated overnight at 37° C. and the resulting colony forming units were counted to calculate the effect of the Type-S system on the transformation efficiency of the b5408 strain.

1.2.6 Chromosomal Binding Assays

Strain b5872 was transformed with the p1985, p1993, p1994, p1995 and p1996 plasmids (see Table 2). The transformation mixtures were plated on LB agar plates supplemented with 10 ng/ml tetracycline and were incubated overnight at 37° C. Three randomly selected single colonies per transformation were used for inoculation of LB cultures supplemented with 10 ng/ml tetracycline. The cultures were allowed to reach late stationary phase upon incubation at 37° C. for 20 hours with rigorous shaking at 220 rpm. 1 μL from each culture was added to 99 μL of LB medium supplemented with 10 ng/ml tetracycline and either 0 μg/mL, 20 μg/mL, 25 μg/mL, 30 μg/mL or 35 μg/ml chloramphenicol. The cultures were transferred to the wells of a microtiter plate and they were incubated in a plate reader at 37° C. for 24 hours with rigorous shaking (900 rpm). The optical densities of the cultures were monitored throughout the incubation period with readings at 600 nm every 10 minutes.

1.3 Results 1.3.1 Type-S CRISPR/Cas Systems

We Cloned into a Low Copy Plasmid DNA that Encoded an RNA Guided Endonuclease (Rge), two open reading frames (ORFs) downstream of the rge gene, a cognate CRISPR array and four ORFs immediately upstream (5') of the CRISPR array (FIG. 1). ORFs 140 and 423 were predicted to code for an error prone DNA polymerase, while ORFs 624 and 188 were predicted to code for a helicase and an RNA endonuclease respectively. The generated p1624 plasmid sets the inserted genes under the transcriptional control of a constitutive promoter. Meanwhile, the CRISPR array carried five spacers. The corresponding protospacers were preceded by a 5'-AAG-3' protospacer adjacent motif (PAM) of the Type-S CRISPR-Cas system. We constructed a target plasmid (p1631), which carried four of the predicted protospacers (correspond to spacers #1, #2, #4 and #5) flanked at their 5'-end by the 5'-AAG-3' PAM (FIG. 1).

We subsequently tested the in vivo functionality of the system on p1624. The p1624 and p1631 plasmids were employed for sequence specific plasmid inhibition assays, described in the 'Materials and methods' section 1.2.2. In brief, cells carrying plasmid p1624 were transformed with a 1:1 mixture of the p1631 target plasmid and a control (non-target) plasmid. p1631 expresses a purple-coloured protein, facilitating screening. Both target and non-target plasmids were transformed with similar efficiencies, demonstrating that the current set-up of the system was not inducing plasmid targeting. Hence, it was hypothesized that the system requires additional subunits to be active. We extended our study by cloning six additional ORFs (ORFs 83, 135, 136, 162, 145 and 286, see FIG. 3) into p1624 upstream (5') of ORF 188. All additional ORFs were transcribed in the same direction as the previously cloned ORFs and the CRISPR array. We used the resulting p1760 plasmid in place of p1624 to repeat the plasmid inhibition assay. p1760 inhibited the growth of colonies transformed with the p1631 target plasmid but allowed the growth of colonies transformed with the non-target plasmid, as all colonies appeared white (FIG. 2). The result indicated that p1760 carried an active CRISPR-Cas system.

1.3.2 Deletion Analysis for Identification of the Minimal Functional System

We aimed to identify the minimal number of elements required for sequence specific plasmid inhibition/targeting by the CRISPR-Cas system. We created a library of plasmids performing a series of gene deletions in p1760 (FIG. 3), and we repeated the plasmid inhibition assay (Materials and methods, Section 1.2.3).

Eleven out of the twelve new constructs that we tested displayed target plasmid inhibition (FIG. 4). No plasmid inhibition was observed in the absence of the CRISPR array, as demonstrated by the assays using p1899 (bottom row, right panel of FIG. 4). Plasmid inhibition was observed with the assays that used p1793 (bottom row, third panel of FIG. 4), which contain an operon of just five genes (encoding Cas that we term Cas-S1, Cas-S2, Cas-S3, Cas-S4 and Cas-S5).

Separate deletion of each one of these genes from p1793 resulted in the construction of plasmids p2009 (ΔCas-S1), p2011 (ΔCas-S3), p2012 (ΔCas-S4) and p2013 (ΔCas-S5) (see Table 2). The plasmids were transformed in *E. coli* NEB10b cells, generating strains b5700 (ΔCas-S1), b5702 (ΔCas-S3), b5703 (ΔCas-S4) and b5704 (ΔCas-S5) respectively (see Table 1). Each one of these strains, together with the negative and positive targeting control strains b4816 and b5408, were transformed with target plasmid p1631 and plated on agar plates with appropriate antibiotic selection. The transformation efficiency of b5408 dropped approximately 3 orders of magnitude whereas the transformation efficiency of all other strains did not drop (see FIG. 5). These results demonstrate that Type-S CRISPR-Cas system requires all 5 subunits for plasmid inhibition. It is noteworthy that there is no predicted RNA-guided DNA endonuclease gene amongst these five genes, which indicates that the mechanism of action of the CRISPR-Cas system probably does not rely on DNA cleavage.

To further confirm the functionality of the Type-S CRISPR-Cas system, we cloned the DNA fragment containing the minimal system and the CRISPR array downstream of an arabinose inducible promoter. The resulting plasmid (p1826) could be maintained together with the p1631 target plasmid in the same cell in the absence of arabinose (FIG. 6, left panel). In the presence of arabinose, the CRISPR-Cas system was expressed resulting in the inhibition of p1631 and surprisingly inhibition of bacterial growth (FIG. 6, right panel).

1.3.3 the Spacers in the Type-S CRISPR Array Exhibit Similar Targeting Efficiencies We evaluated the targeting efficiency of each spacer in the CRISPR array that we used in these experiments in the Type-S CRISPR-Cas system. The array contained five spacers and the p1631 target plasmid contained protospacers for 4 out of these 5 spacers. Using p1631 as our basis, we constructed four additional target plasmids, namely p1935, p1936, p1937 and p1938, each containing only one protospacer (see Table 2 and FIG. 7, left panel). We separately transformed all 5 target plasmids and the non-target p144 plasmid (see Table 2) in strain b5408 and we plated serial dilutions of the transformation mixtures on appropriate selection plates (FIG. 7, right panel). The following day, colony forming units were counted for analysis; all 4 tested spacers demonstrated similar targeting efficiencies, reducing the transformation efficiencies of the corresponding target plasmids by 3 orders of magnitude, relative to the non-target plasmid. Moreover, the combined targeting efficiency of all 4 spacers was not significantly higher than the efficiency of each spacer separately.

1.3.4 the Type-S CRISPR-Cas System Binds to Chromosomal DNA

We determined that the Type-S CRISPR-Cas system does not contain a predicted RNA-guided DNA-endonuclease. Hence, we decided to examine whether the subunits of the system contain a novel dsDNA cleaving domain, which can efficiently introduce lethal dsDNA breaks to the *E. coli* chromosome, We constructed the b5451 strain by moving the 4 previously tested protospacers from p1631 to the chromosome of *E. coli* C-1, inactivating the lacZ gene. The resulting strain can be distinguished from the original, non-target. *E. coli* C-1 strain on X-gal plates as the latter strain metabolizes X-gal and converts it into a blue dye. Both the constitutive and the arabinose inducible Type-S CRISPR-Cas expression systems were tested as described in the 'Materials and Methods' section 1.2.6. In brief, a 1:1 mixture of *E. coli* C-1 and b5451 competent cells was transformed with the p1826 plasmid, that contained the Type-S CRISPR-Cas system under the control of an arabinose inducible promoter. The ratio of white to blue colonies remained 1:1 under appropriate antibiotic selection conditions, regardless of the induction conditions (FIG. 8). This result further supported the probable absence of a dsDNA endonuclease domain in the system.

We subsequently wondered whether the Type-S CRISPR-Cas system has DNA binding function or its mode of action is on the RNA level. We constructed the bSNP5810 strain by introducing the crm gene in an intergenic region of *E. coli* C-1. We subsequently constructed one negative control strain, denoted as p1985, and four crm targeting plasmids, denoted as p1993, p1994, p1995 and p1996 (see Table 2). For this purpose, we substituted the spacers within the CRISPR array of p1793 either with a non-targeting spacer or with single spacers that target four different positions in the promoter or the coding region of the crm gene (FIG. 9). We transformed the bSNP5810 strain with each of p1993, p1994, p1995 and p1996 and we cultured the cells in media supplemented with different chloramphenicol concentrations. In the absence of chloramphenicol, the growth rates of all the strains with the crm targeting spacers were similar to the growth rate of the control strain (FIG. 10A, first graph). Nonetheless, increasing chloramphenicol concentrations reduced the growth rates of all the targeted strains in a proportional manner (FIGS. 10A-10C, $2^{nd}$-$4^{th}$ graphs). The growth rate of the control strain remained unaffected by the presence of chloramphenicol in the media. These results demonstrate that the Type-S CRISPR-Cas system steadily binds to the chromosome and acts as a surprisingly efficient transcriptional inhibitor. It is noteworthy that the orientation of the crm targeting spacers does not influence the binding efficiency of the Type-S CRISPR-Cas system and the subsequent downregulation of the crm expression, which is not the case for other previously known CRISPR-Cas systems that must target either the coding or the non-coding region (system dependent characteristic) of a gene to efficiently downregulate its transcription (see Qi et al, Cell, 152 (5), 1173-1183, 2013, doi: doi.org/10.1016/j.cell.2013.02.022, Rath et al., NAR, 43 (1), 237-246, 2015, doi: doi.org/10.1093/nar/gku1257 and Luo et al., NAR, 43 (1), 674-681, 2015, doi: doi.org/10.1093/nar/gku971).

1.4 Conclusions

A nuclease-deficient CRISPR-Cas system (which we call Type-S CRISPR/Cas) was characterized and its minimal functional elements determined. Our studies revealed that Type-S CRISPR/Cas for comprises five Cas proteins (we call Cas-S1 to S5) and a cognate CRISPR array. None of the Cas proteins was shown to have a DNA nuclease activity. The system surprisingly inhibits the growth of bacterial cells that contain at least one target sequence adjacent to an AAG PAM. Additionally, the system could be programmed to efficiently bind to chromosomal targets and act as a transcriptional inhibitor, without inducing lethal dsDNA breaks. With these findings we have identified and characterized a functional, novel CRISPR/Cas system that can be used in its minimal form to inhibit plasmids, reduce bacterial cell growth and inhibit transcription from a chromosome. We can see applications for individual Cas of the system, such as by creating fusion of a Type-S Cas with a nuclease domain, in order to produce targeted cutting of DNA. Other fusion partners include base editors, prime editors, deaminases and reverse transcriptases.

1.5 Appendix

TABLE 1

Bacterial strains used in this study

| Strain number | Relevant characteristics |
|---|---|
| b5451 | *E. coli* C-1 carrying target sequences from p1631 inserted with cmR in lacZ, lac− |
| b3127 | NEB Turbo |
| b52 | Lac+ |
| b5456 | P1826 |
| bSNP5810 | *E. coli* C-1 with the crm (chloramphenicol resistance marker) gene integrated in an intergenic region |
| b5700 | *E. coli* NEB10b carrying plasmid p2009 |
| b5702 | *E. coli* NEB10b carrying plasmid p2011 |
| b5703 | *E. coli* NEB10b carrying plasmid p2012 |
| b5704 | *E. coli* NEB10b carrying plasmid p2013 |
| b4816 | *E. coli* NEB10b carrying plasmid p1624 |
| b5408 | *E. coli* NEB10b carrying plasmid p1793 |

TABLE 2

Bacterial plasmids used in this study

| Plasmid No | Host strain number | Relevant characteristics |
|---|---|---|
| p1624 | b4816 | For gene content see FIG. 1 |
| p1631 | b4818 | Target plasmid, containing protospacers targeted by the 1$^{st}$, 2$^{nd}$, 4$^{th}$ and 5$^{th}$ spacer of the natural Type-S CRISPR array (purple colonies) |
| p892 | b2685 | Non target plasmid, contains only the p15a origin of replication and the chloramphenicol resistance marker gene |
| p144 | | Almost identical to p1631 but does not contain protospacers targeted by the natural Type-S CRISPR array (white colonies) |
| p1783 | b5398 | For gene content see FIG. 3 |
| p1784 | b5399 | For gene content see FIG. 3 |
| p1785 | b5400 | For gene content see FIG. 3 |
| p1786 | b5401 | For gene content see FIG. 3 |
| p1787 | b5402 | For gene content see FIG. 3 |
| p1788 | b5403 | For gene content see FIG. 3 |
| p1789 | b5404 | For gene content see FIG. 3 |
| p1790 | b5405 | For gene content see FIG. 3 |
| p1791 | b5406 | For gene content see FIG. 3 |
| p1792 | b5407 | For gene content see FIG. 3 |
| p1793 | b5408 | Minimal functional system for plasmid targeting + the natural Type-S CRISPR array (FIG. 3) |
| p1899 | b5538 | For gene content see FIG. 3 |
| p1826 | b5456 | System from p1793 under arabinose inducible promoter |
| p1935 | b5647 | Target plasmid, almost identical to p1631 but contains only 1 protospacer targeted by the 1$^{st}$ spacer of the natural Type-S CRISPR array (purple colonies) |
| p1936 | b5648 | Target plasmid, almost identical to p1631 but contains only 1 protospacer targeted by the 2$^{nd}$ spacer of the natural Type-S CRISPR array (purple colonies) |
| p1937 | b5649 | Target plasmid, almost identical to p1631 but contains only 1 protospacer targeted by the 4$^{th}$ spacer of the natural Type-S CRISPR array (purple colonies) |
| p1938 | b5650 | Target plasmid, almost identical to p1631 but contains only 1 protospacer targeted by the 5$^{th}$ spacer of the natural Type-S CRISPR array (purple colonies) |
| p1985 | | Almost identical to p1793 but contains a single non-targeting spacer in the CRISPR array and none of the naturally occurring spacer of the Type-S CRISPR array |

TABLE 2-continued

Bacterial plasmids used in this study

| Plasmid No | Host strain number | Relevant characteristics |
|---|---|---|
| p1993 | | Almost identical to p1793 but contains a single spacer (see #1 in FIG. 9) in the CRISPR array and none of the naturally occurring spacer of the Type-S CRISPR array. The spacer targets the forward strand of the promoter region of the crm gene in bSNP5810 strain |
| p1994 | | Almost identical to p1793 but contains a single spacer (see #2 in FIG. 9) in the CRISPR array and none of the naturally occurring spacer of the Type-S CRISPR array. The spacer targets the reverse strand of the crm gene in bSNP5810 strain |
| p1995 | | Almost identical to p1793 but contains a single spacer (see #3 in FIG. 9) in the CRISPR array and none of the naturally occurring spacer of the Type-S CRISPR array. The spacer targets the forward strand of the promoter region of the crm gene in bSNP5810 strain |
| p1996 | | Almost identical to p1793 but contains a single spacer (see #4 in FIG. 9) in the CRISPR array and none of the naturally occurring spacer of the Type-S CRISPR array. The spacer targets the forward strand of the crm gene in bSNP5810 strain |
| p2009 | b5700 | Almost identical to p1793 but CasS1 is deleted |
| p2011 | b5702 | Almost identical to p1793 but CasS3 is deleted |
| p2012 | b5703 | Almost identical to p1793 but CasS4 is deleted |
| p2013 | b5704 | Almost identical to p1793 but CasS5 is deleted |

Example 2: PAM Identification and Characterisation for the Type-S CRISPR/Cas System

2.1 Background

SNIPR Biome has identified and characterised a Type-S CRISPR/Cas system as described in Example 1.

An in silico analysis of public genome databases was performed in-house, aiming to identify a potential PAM sequence for the Type-S CRISPR/Cas system of Example 1. This analysis was based on the spacers from the wild-type Type-S CRISPR array. A few potential protospacers were discovered which all comprised a 5'-AAG-3' sequence motif at their 5' end, but no common sequence motif at their 3' end. It was hypothesized that this 5'-AAG-3' motif at the 5' end of a protospacer could serve as a valid PAM for the Type-S system. This hypothesis was confirmed with plasmid targeting/killing assays (as described in Example 1.3.1-1.3.3). Nonetheless, the PAM sequences of most CRISPR-Cas systems are promiscuous, hence it was decided to further experimentally investigate the variety of sequences that the Type-S CRISPR/Cas recognises as valid PAMs.

2.2 Experimental Design

The Type-S CRISPR/Cas system PAM identification process was based on the following plasmids:

1. PAM plasmid library (p2259); each member of this library encompasses the protospacer sequence present in the target plasmid p1935 (see Example 1.2.5) and a mixture of candidate 5-nt long PAMs at the 5' end of the protospacer.
2. Targeting Type-S plasmid (p1793); the plasmid expresses the Type-S CRISPR/Cas system (Cas-S1 to Cas-S5) and a spacer that is complementary to the protospacer of the PAM plasmid library.
3. Non-Targeting (control) Type-S plasmid (p1985); the plasmid expresses the Type-S CRISPR/Cas system (Cas-S1 to Cas-S5) and a spacer that is not complementary to the protospacer of the PAM plasmid library. Moreover, the spacer is not complementary to any part of the *E. coli* genome.

The steps of the PAM identification assay are the following:

1. Construction of the PAM plasmid library, denoted as p2259 (see section below).
2. Construction of the Targeting *E. coli* NEBTurbo strain (b5408), by transforming the NEB Turbo b3127 strain (NEB) with the p1793 (Type-S targeting) plasmid,
3. Construction of the Non-targeting *E. coli* NEBTurbo strain (b6259) by transforming the NEB Turbo b3127 strain (NEB) with the p1985 (control Type-S) plasmid.
4. Transformation of the b5408 (Type-S targeting) and b6259 (control Type-S) with the p2259 plasmid library and culturing under appropriate antibiotic selection conditions.
5. Isolation of p2259 plasmid library from both cultures and preparation of NGS fragments that contain the PAM-protospacer region.
6. NGS and analysis of the sequencing results.

2.2.1 Step 1: Construction of the PAM Library

The PAM library plasmid p2259 was designed to contain a 5nt long variable PAM region at the 5'end of the protospacer, Hence the library should be comprised of $4^5$ (1024) different PAMs.

The construction of the PAM library plasmid p2259 was based on the previously described target plasmid p1935 (see Example 1.2.5). The p1935 plasmid was employed as the PCR amplification template, with appropriately designed primers, CloneAMP PCR pre-mix (Takara) was used for the PCR reaction. The forward primer was designed to introduce a 5nt long degenerate sequence at the 5'-end of the protospacer present on the p1935 plasmid. The gel-purified PCR product was used for In-Fusion cloning, employing 5× In-Fusion HD enzyme premix (Takara). 5 μL from the In-Fusion cloning reaction was transformed by electroporation into 50 μL of NEB10b electro competent cells (NEB). The cells were subsequently left to recover in SOC medium (500 μl final volume) for 1 hour at 37° C. and shaking at 200 rpm. The recovered cells were transferred into 500 mL of LB liquid medium, supplemented with 20 μg/mL chloramphenicol. 100 μL from the 500 mL culture were removed and plated on an LB agar plate, supplemented with 20 μg/mL chloramphenicol. Culture and plate were incubated overnight at 37° C. with rigorous shaking (200 rpm). The following day, 536 colonies were counted on the plate and it was subsequently calculated that 2,680,000 successfully transformed cells were added into the 500 mL culture. For this calculation, Equation 1 was used.

$$\text{No of transformed cells in culture} = \frac{\text{Volume of culture}}{\text{Volume of plated culture}} \times \text{No of colonies on selection plate} \quad \text{Equation 1}$$

This number of transformed cells in the culture corresponds to 2,617× coverage of the PAM library members, according to Equation 2.

$$\text{Plasmid library coverage} = \frac{\text{Number of transformed cells in the culture}}{\text{Number of distinct plasmid library members}} \quad \text{Equation 2}$$

After making glycerol stocks from the 500 mL culture, the constructed p2259 plasmid library was isolated from the remaining culture using the Qiagen plasmid midi kit.

2.2.2 Step 2: Transformation of the b5408 (CRIPSR-S Targeting) and b6259 (Control Type-S) Strain with the p2259 Plasmid Library It is expected that some members of the p2259 plasmid library contain PAMs that are recognised by the Type-S CRISPR/Cas system. These PAM-positive plasmids will be successfully targeted, and their replication will be hampered by the Type-S system, Hence, b5408 (Type-S targeting) cells transformed with the PAM-positive members of the p2259 plasmid library should not survive in medium supplemented with chloramphenicol, as the p2259 plasmid library carries the chloramphenicol resistance marker gene. Meanwhile, b5408 (Type-S targeting) cells transformed with PAM-negative members of the p2259 plasmid library should survive in medium supplemented with chloramphenicol. In contrast, none of the p2259 plasmids in the library will be targeted by the Type-S CRISPR/Cas system expressed in the b6259 (control Type-S) strain, and will survive in the chloramphenicol-supplemented media.

The p2259 plasmid library was electroporated into b5408 (Type-S targeting) and b6259 (control Type-S) electrocompetent cells respectively. The electrocompetent cells from both strains were prepared using the protocol described in (barricklab.org/twiki/bin/view/Lab/ProtocolsElectrocompetentCells). Five transformation reactions per strain were performed, using 40 ng of p2259 plasmid library per reaction. The cells were allowed to recover in 500 μL of SOC medium for 1 hour at 37° C. and shaking at 200 rpm. The recoveries from each strain were combined and each of the final two recoveries (one per strain) was used for the inoculation of 500 mL of LB liquid medium cultures, supplemented with 20 μg/mL chloramphenicol and 10 μg/mL tetracycline. The cultures were incubated overnight at 37° C. with rigorous shaking at 200 rpm. The following day, glycerol stocks from each culture were prepared and the p2259 plasmid libraries from each strain were isolated using the Qiagen plasmid midi kit.

Plasmid isolation from cultures of b5408 (Type-S targeting) transformed with p2259, followed by NGS, will show which of the PAM sequences are not recognized by the Type-S CRISPR/Cas system and subsequently which are the PAM sequences that the system requires. Plasmid isolation from b6259 (control Type-S) cultures transformed with p2259, followed by NGS, will indicate the abundance of each plasmid member in the p2259 library. This information will be used for normalization of the NGS results from strain b5408 (Type-S targeting).

2.2.3 Step 3: PAM Identification Via NGS p2259 isolated from b6259 (control Type-S) should contain all members of the p2259 PAM library, providing quantitative information regarding the abundance of each PAM plasmid in the library.

The p2259 plasmids isolated from b5408 (Type-S targeting) and b6259 (control Type-S) were subjected to NGS. The 1$^{st}$ NGS PCR amplification step on both p2259 preps was performed using appropriately designed primers in 50 μL KAPA HIFI Hotstart ReadyMix reactions (Roche) (25 cycles, 30 s denaturation, 20 s annealing, 15 s extension). The reaction products were purified with AMPure XP Reagent (Beckman Coulter), Subsequently, Illumina indexes and flow cell binding sequences were added to the purified products with a 2$^{nd}$ NGS PCR amplification step. The 1st NGS PCR product from strain b5408 (Type-S targeting) was subjected to the 2$^{nd}$ NGS PCR amplification step using appropriately designed primers. The 1st NGS PCR product from strain b6259 (control CRISPR-S) was subjected to a 2$^{nd}$ NGS PCR amplification step using appropriately designed primers. Both amplifications were 50 μL KAPA HIFI Hotstart ReadyMix reactions (Roche) (10 cycles, 20 ng of template DNA, 30 s denaturation, 20 s annealing, 15 s extension).

Both reaction products were purified with AMPure XP Reagent (Beckman Coulter). The purified products were sequenced using Illumina MiSeq® with single-end 150 cycles.

2.3 Results

The NGS data were used to compare the relative abundance of each member of the p2259 library in the b5408 (Type-S targeting) and b6259 (control) strains. The data analysis revealed clear preference of the Type-S CRISPR/Cas system for the following PAM sequences (FIGS. 11 and 12):

5'-AHN-3'
5'-KAG-3'
5'-AGG-3'
5'-GAC-3'
5'-GTG-3'

Example 3: Protospacer Mismatch Tolerance in the Type S CRISPR/Cas System

3.1 Background

CRISPR/Cas systems present various spacer-protospacer complementarity requirements for DNA/RNA binding and targeting. For example, the *Escherichia coli* Type I-E CRISPR/Cas system tolerates spacer-protospacer mismatches outside the 'seed' region without compromising its function as an immune system (see Semenova et al., PNAS, 108 (25), 10098-10103, 2011, doi: doi.org/10.1073/ pnas.110414410), and *Streptococcus pyogenes* Cas9 requires 15nt spacer protospacer complementarity for in vitro DNA cleavage (see Jinek et al., Science, 337 (6096), 816-821, 2012, doi: 10.1126/science.12258) but tolerates multiple (up to 15 nucleotides) spacer-protospacer mismatches for DNA binding in bacteria (see Ciu et al., Nature Comm., 9 (1912), 2018, doi: doi.org/10.1038/s41467-018-04209-5).

The Type-S CRISPR/Cas system does not contain a predicted dsDNA nuclease domain. It was previously shown that the Type-S CRISPR/Cas system plasmid clearance activity requires the presence of the Cas-S3 helicase subunit (see Example 1.2.5). Spacer-protospacer mismatches are expected to negatively affect the DNA target binding stability of the pre-helicase Type-S CRISPR/Cas system CRISPR-Cas complex (the Type-S CRISPR-Cas complex without the helicase subunit, comprising the following subunits: Cas-S1, -S2, -S4, and -S5). It is expected that reduction in the DNA binding efficiency of the Type-S CRISPR/Cas system should result in reduced plasmid clearance. Hence, the assays described in this Example were designed to employ plasmid curing/transformation efficiency as the measurable output of the effect that spacer-protospacer mismatches have on the Type-S CRISPR/Cas system CRISPR-Cas targeting efficiency.

3.2 Experimental Design

Plasmid p1935 was previously designed (see Example 1.2.5) and constructed to contain a 32 bp protospacer and a PAM sequence (5'-AAG-3') that is targeted by the Type-S CRISPR/Cas system. In this Example, different variants of the p1935 plasmid were designed and constructed, containing various combination of mutations in the protospacer region. These mutations partially disrupt the complementarity of the protospacer to the targeting spacer. The accompanying transformation efficiency graphs (FIGS. 13A-13) depict these mutations in detail.

The various protospacer mutations were introduced into the protospacer sequence of the p1935 plasmid by Q5® Site-Directed Mutagenesis (NEB) using appropriately designed primers. The resulting PCR products were circularized using KLD Enzyme Mix (NEB) reactions. The KLD reaction mixtures were transformed into NEB-10B electrocompetent cells (NEB). The cells were subsequently let to recover in SOC medium (500 μL final volume) for 1 hour at 37° C. and shaking at 200 rpm. The recovered cells were plated on LB agar plates supplemented with 20 μg/mL chloramphenicol for plasmid selection. The plates were incubated overnight at 37° C. Single colonies from each plate were inoculated in 10 mL LB liquid medium cultures supplemented with 20 μg/mL chloramphenicol for plasmid selection. The cultures were incubated overnight at 37° C. with rigorous shaking (200 rpm). Each culture was sampled for preparation of glycerol stocks, which were stored at −80° C. The remaining culture contents were used for plasmid isolation using the Qiagen plasmid mini kit.

b5408 is a NEB Turbo *E coli* strain that contains plasmid p1793 (which contains the wild type Type-S CRISPR/Cas System, Cas-S1 to Cas-S5 including the Type-S CRISPR array). 50 ng from each member of the p1935 plasmid library were electroporated into electrocompetent b5408 (wt Type-S) cells. The electrocompetent cells from both strains were prepared using the protocol described in (barrick-lab.org/twiki/bin/view/Lab/ProtocolsElectrocompetent-Cells). The cells were allowed to recover in 500 μL of SOC medium for 1 hour at 37° C. and shaking at 200 rpm. The recoveries from each strain were used for the preparation of serial dilutions, which were subsequently spot-plated on LB agar plates supplemented with the appropriate antibiotics, 20 μg/ml chloramphenicol and 10 μg/mL tetracycline, for plasmid selection. The transformations were performed in biological triplicates. The formed colonies from each transformation were counted, and the reduction in the transformation efficiency of the b5408 (wt Type-S) strain, when compared to its transformation efficiency when transformed with a negative (non-target) control plasmid, indicated how the corresponding spacer-protospacer mismatches affect the targeting efficiency of the Type-S CRISPR/Cas system (see FIGS. 13A-13F).

Controls:

The original plasmid p1935 is the positive control plasmid, which always generated almost no transformants (just escape mutants), The plasmid p2361 is the negative control plasmid. It is identical to p1935 except for the 5'-AAG-3' PAM sequence upstream (5') of the protospacer, which is exchanged with the 5'-CGG-3' sequence that is not predicted to be a Type-S CRISPR/Cas PAM (see Example 2), Thus, the transformation efficiency of p2361 (-ve control) should be the highest of all the library members mentioned in this Example.

3.3 Results

FIGS. 13A-13F shows the analysis of the transformation efficiency for each of the mismatches.

Careful examination of the graphs yielded the following conclusions, regarding how spacer-protospacer mismatches affect the plasmid clearance efficiency of Type-S CRISPR/Cas System:

1. 5 consecutive PAM distal mismatches are well tolerated.
2. 8 consecutive PAM distal mismatches completely abolish targeting.
3. Single mismatches at the 1$^{st}$ or 2$^{nd}$ PAM proximal positions reduce targeting by 3 orders of magnitude.
4. Single mismatches at the 3$^{rd}$ to 10$^{th}$ PAM proximal positions reduce targeting by 0 to 1 orders of magnitude.
5. Double mismatches at the 1$^{st}$ to 3$^{rd}$ PAM proximal positions reduce targeting by 3 to 4 orders of magnitude.
6. Double mismatches at the 4$^{th}$ to 10$^{th}$ PAM proximal positions reduce targeting by 0 to 1 orders of magnitude.
7. Triple mismatches at the 1$^{st}$ to 5$^{th}$ PAM proximal positions reduce targeting by 3 to 4 orders of magnitude.
8. Triple mismatches at the 4$^{th}$ to 9$^{th}$ PAM proximal positions reduce targeting by 0 to 1 orders of magnitude.
9. Triple mismatches at the 8$^{th}$ to 10$^{th}$ PAM proximal positions reduce targeting by 4 orders of magnitude.
10. Quadruple mismatches at the 1$^{st}$ to 8$^{th}$ PAM proximal positions reduce targeting by 3 to 4 orders of magnitude.
11. Quadruple mismatches at the 6$^{th}$ to 9$^{th}$ PAM proximal positions reduce targeting by 1 order of magnitude.
12. Quadruple mismatches at the 7$^{th}$ to 10$^{th}$ PAM proximal positions reduce targeting by 5 orders of magnitude.

Example 4: The Type-S CRISPR/Cas System for CRISPRi Applications 4.1 Aim

This study evaluated i) the efficiency of the Type-S CRISPR/Cas system to bind to *E. coli* chromosomal and plasmid targets, acting as a CRISPRi tool, ii) which subunits are essential for DNA binding.

4.2 Introduction

We previously demonstrated that the Type-S CRISPR/Cas system drives crRNA-dependent hinderance of plasmid replication (see Example 1.3.2 and 1.3.3) while lacking a DNA nuclease domain. The crRNA-guided DNA binding activity of the Type-S CRISPR/Cas system can be exploited for the development of a CRISPR interference (CRISPRI) tool in *E. coli*. We expect that it will also be able to be used in other cell types. In this Example, the CRISPRi potential of the Type-S CRISPR/Cas system was evaluated via the targeted downregulation of the transcription, and subsequent translation, of a reporter green fluorescent protein (gfp) gene. The targeted gfp gene was either chromosomally integrated or plasmid-borne. Moreover, this Example revealed which Type-S CRISPR/Cas system subunits are essential for the DNA-binding activity of Type-S CRISPR/Cas system.

4.3 Methods and Results

Five variations of the Type-S CRISPR/Cas system were tested for their CRISPRi potential;

i) the wild type (wt) Type-S CRISPR/Cas system ii) the Cas-S1 deletion mutant (ΔCas-S1) Type-S CRISPR/Cas system iii) the Cas-S3 deletion mutant (ΔCas-S3) Type-S CRISPR/Cas system iv) the Cas-S4 deletion mutant (ΔCas-S4) Type-S CRISPR/Cas system v) the Cas-S1/Cas-S3 double deletion mutant (ΔCas-S1 ΔCas-S3) Type-S CRISPR/Cas system.

All variants were set under the transcriptional control of the pBolA promoter (SEQ ID No: 14) and were cloned together with a non-targeting crRNA expressing module, generating plasmids p1985 (wt), p2062 (ΔCas-S1), p2064 (ΔCas-S3), p2065 (ΔCas-S4) and p2160 (ΔCas-S1 ΔCas-S3) respectively (FIG. 14). The 5' and 3' end of the spacer of the crRNA module contained recognition sites for the BsmBI-v2 (NEB) restriction enzyme, which facilitated the cloning of the targeting spacers (FIG. 14). All the plasmids contained the repA101 replication protein gene, the SC101 low copy origin of replication and the tetR tetracycline resistance marker gene (FIG. 14).

4.4 Chromosomal CRISPRi

Strains MG1655 and b5815 (gfp+ve strain) were employed for the chromosomal Type-S CRISPR/Cas system CRISPRi assays, b5815 is an *E. coli* MG1655 derivative, constructed to contain the gfp gene under the control of the p70a promoter (SEQ ID No:15) and positioned in between the ybcB and ybcC genes (FIG. 15). Sixteen protospacers within or near the gfp gene of the b5815 (gfp+ve) strain were selected and targeted for the chromosomal CRISPRI assays (FIG. 15, Table 4, Seq ID Nos: 25 to 41). Eight of the protospacers were located on the gfp coding strand (namely Protospacer U2kF, U1kF, S1F, S2F, S3F, S4F, S5F, S6F) and eight on the non-coding strand (namely Protospacer U2KR, U1KR, SIR, S2R, S3R, S4R, S5R, S6R).

4.4.1 Methods

The construction of the plasmids that express the different Type-S CRISPR/Cas system variants and target the prementioned protospacers was performed by digesting the p1985 (wt), p2062 (ΔCas-S1), p2064 (ΔCas-S3), p2065 (ΔCas-S4) and p2160 (ΔCas-S1 ΔCas-S3) plasmids with the BsmBi-v2 (NEB) restriction enzyme and then ligating pre-annealed complementary ssDNA oligos that code for the corresponding spacers into the digested plasmids using T4 DNA ligase (NEB). 5 μL from each ligation reaction were transformed with electroporation into 50 μl of NEB10β electro competent cells (NEB). The cells were subsequently left to recover in SOC medium (500 μL final volume) for 1 hour at 37° C. and shaking at 200 rpm. 100 μL from each recovery were removed and plated on LB agar plates supplemented with 20 μg/mL chloramphenicol. The plates were incubated overnight at 37° C.

The following day, single colonies were randomly selected and used for inoculation of 10 mL LB liquid medium cultures supplemented with 10 g/mL tetracycline. The cultures were incubated overnight at 37° C. with rigorous shaking (200 rpm).

The following day, glycerol stocks were prepared for each culture and the remaining cultures were used for plasmid isolation with the Qiagen plasmid mini kit. Each plasmid was sequence-verified with NGS. Each of the plasmids was transformed into electrocompetent b5815 (gfp+ve strain) cells. The electrocompetent cells were prepared using the protocol described in (barricklab.org/twiki/bin/view/Lab/ProtocolsElectrocompetentCells). The transformation reactions were performed using 40 ng from each plasmid per reaction. The cells were allowed to recover in 500 μL of SOC medium for 1 hour at 37° C. and shaking at 200 rpm. 100 μL from each recovery were plated on LB agar plates supplemented with 10 g/mL tetracycline. The plates were incubated overnight at 37° C.

The following day, three single colonies were randomly selected from each transformation and they were used for inoculation of 5 mL M9 minimal medium cultures supplemented with glycerol (0.4% w/v) and 10 μg/mL tetracycline. The cultures were incubated overnight at 37° C. with rigorous shaking (200 rpm).

The following day, 2 μL from each culture were transferred to 198 μL of M9 medium supplemented with glycerol (0.4% w/v) and 10 μg/mL tetracycline. The resulting 200 μL cultures were transferred to distinct wells in Thermo Scientific™ Nunc microWell 96-well optical-bottom plates with polymer base. The plates were sealed with Breathe-Easy® sealing membranes (Sigma-Aldrich) and loaded into Synergy H1 microplate readers (Biotek) for incubation at 37° C. with continuous shaking. The optical densities (absorbance at 600 nm) and the green fluorescence emissions (excitation at 485 nm, emission at 516 nm) of the cultures were measured in 10 minute intervals for a 24-hour period. The fluorescence emissions data from each culture and each time point were normalized with the corresponding OD600 nm data. The normalized data from the cultures that belong to biological triplicates were averaged and the corresponding standard deviations were calculated. The final data were plotted in the graphs presented in FIGS. 16A-16C.

4.4.2 Results

The Type-S CRISPR/Cas system downregulated GFP expression from b5815 (gfp+ve strain) to the no-fluorescence control strain (b230) levels, when targeting protospacers at the beginning of the gfp orf and in the p70a promoter region (Protospacers S1F, S1R, S2F, S2R, S3F, S3R) (FIG. 16A) or protospacers at the end of the gfp orf and the 200 bp regions upstream and downstream of gfp (Protospacers S4F, S4R, S5F, S6F, S6R) (FIG. 16B), demonstrating extremely efficient and tight CRISPRI performance. The sole exception was the targeting of the S5R protospacer, which downregulated GFP expression by approximately 50%. The GFP expression was also downregulated when the Type-S CRISPR/Cas system targeted protospacers located 1 kb upstream of the gfp orf (Protospacers U1kF, U1kR), whereas GFP expression was completely unaffected for protospacers 2 kb upstream of the gfp orf (U2kF, U2KR) (FIG. 16C).

The helicase-deficient ΔCas-S3 Type-S CRISPR/Cas system extensively or completely downregulated GFP expression from b5815 (gfp+ve strain) when targeting the promoter p70a region or the forward strand in the gfp orf (Protospacers S1F, SIR, S2F, S2R, S3F), but did not affect the GFP expression when it targeted the reverse strand in the gfp orf (Protospacer S3R) (FIG. 17A). It was here demonstrated that Cas-S3 cannot unwind DNA, and subsequently block transcription of genes, that reside 2 kb away from the targeted protospacer.

To confirm that the Type-S CRISPR/Cas system CRISPRi function is Cas-S3-dependent when targeting protospacers at the very end of, or outside of, a gene's orf, the targeting assays on protospacers S4F, S4R, S5F, S5R, S6F and S6R were repeated employing ΔCas-S3 Type-S CRISPR/Cas system (FIG. 17B), Indeed, the GFP expression of b5815 (gfp+ve strain) was unaffected for the selected targets in the absence of Cas-S3. These results indicate that Cas-S3 is not essential for the formation of the Type-S CRISPR/Cas system RNP complex and its binding to the DNA target.

The ΔCas-S4 Type-S CRISPR/Cas system did not affect GFP expression from b5815 (gfp +ve strain), indicating that the subunit is essential for the for the formation of the Type-S CRISPR/Cas system RNP complex and/or its binding to the DNA target (FIG. 18A).

The ΔCas-S1 Type-S CRISPR/Cas system and the ΔCas-S1, ΔCas-S3 Type-S CRISPR/Cas system reduced GFP expression from b5815 (gfp+ve strain) in a similar manner and only when they targeted (completely or partially) the reverse strand of the p70a promoter (FIGS. 18B, 18C). These results indicate that Cas-S1 is not essential for the formation of the Type-S CRISPR/Cas system RNP complex and its binding to the DNA target, albeit it is important for its stability and/or the efficiency of its DNA binding activity. Moreover, these results indicate that Cas-S1 is vital for the loading of Cas-S3 to the complex.

4.5 Plasmid CRISPRi

Strain b6386 was employed for the plasmid Type-S CRISPR/Cas system CRISPRi assays. b6386 is an *E. coli* MG1655 strain transformed with the plasmid p2370 plasmid that contains the gfp gene (under the control of the p70a promoter, SEQ ID No:15), the p15a origin of replication and the cmR chloramphenicol resistance marker gene. Only four out of the five Type-S variants tested for chromosomal CRISPRi in Example 4.4 were also tested for plasmid CRISPRI. The wild type Type-S CRISPR/Cas system comprising Cas-S1-Cas-S5 was not tested, due to its proven activity to inhibit plasmid replication (see Example 1.3.2, and 1.3.3). Six protospacers within the p70a promoter region and the gfp gene in b6386 were selected and targeted for the on-plasmid CRISPRi assays, the same as for the chromosomal CRISPRi assays; three of the protospacers were located on the gfp coding strand (namely Protospacer S1F, S2F, S3F) and three on the non-coding strand (namely Protospacer S1R, S2R, S3R) (see FIG. 15).

4.5.1 Methods

The construction of the various Type-S expressing plasmids that targeted these protospacers was performed as previously described in Example 4.4.1.

The transformation of the plasmids was performed as described in Example 4.4.1, with the following two changes:

1. 100 μl from each recovery were plated on LB agar plates supplemented with 20 μg/mL chloramphenicol, instead of 10 μg/mL tetracycline
2. 2) The inoculation cultures were supplemented with 20 μg/mL chloramphenicol, instead of 10 μg/mL tetracycline.
3. The final data were plotted in the graphs presented in FIGS. 19A-19D.

4.5.2 Results

Figure 19A:
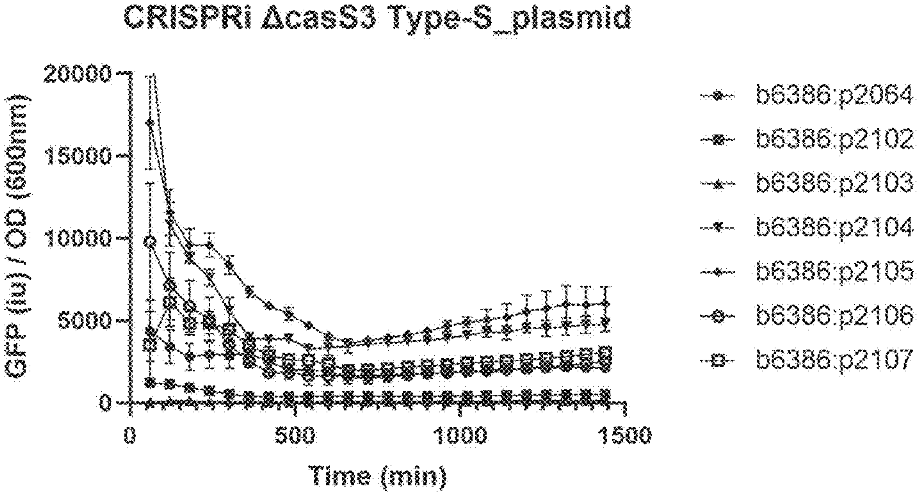
Figure 19B:
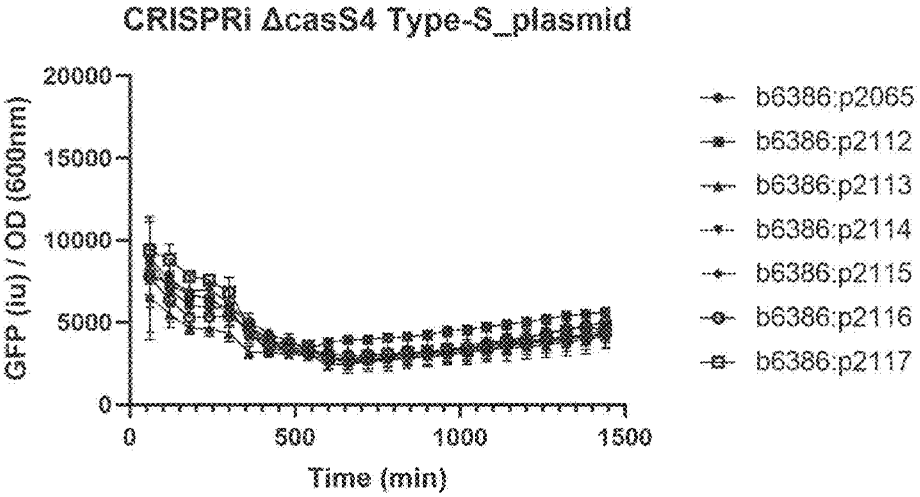
Figure 19C:
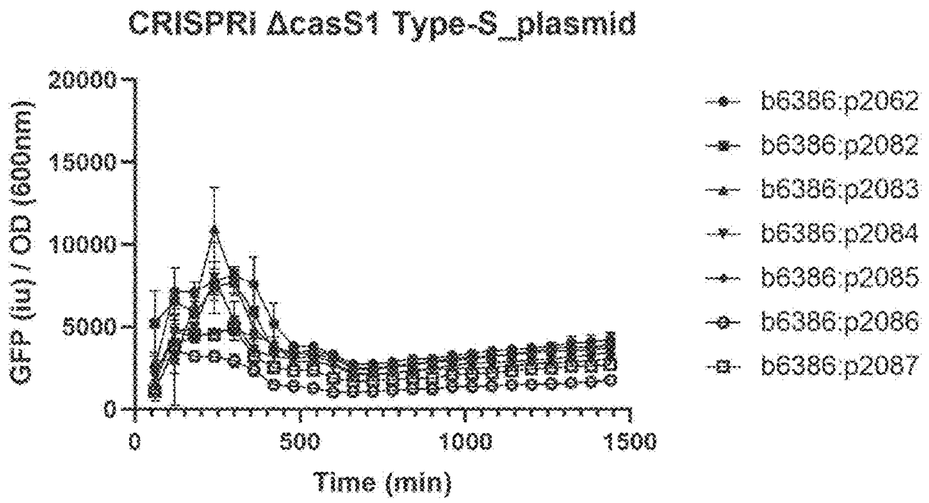
Figure 19D:
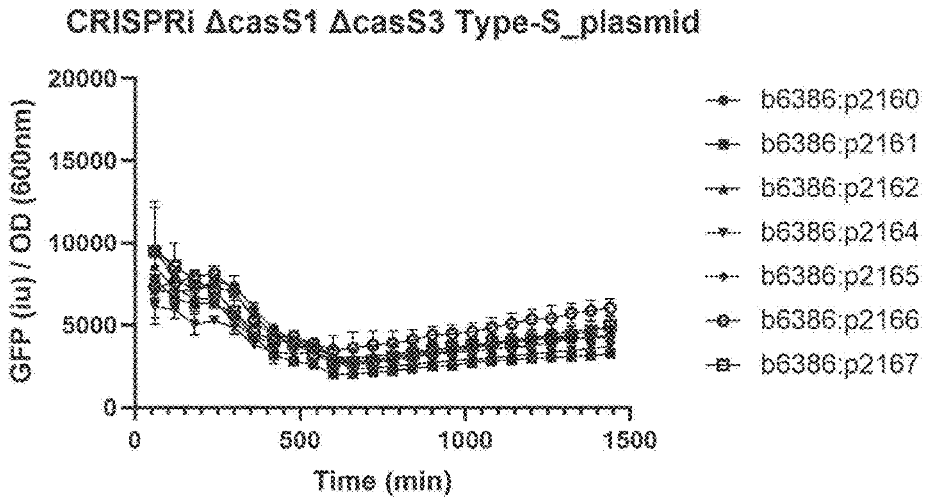

ΔCas-S3 Type-S downregulated, completely or efficiently (but not completely), GFP expression from b6386 (gfp+ve strain) only when it targeted protospacers within the promoter p70a region (S1F and S1R), regardless of the orientation of the targeted strand (FIG. 19A). None of the other tested variants downregulated GFP expression (FIG. 19B, FIG. 19C, FIG. 19D). This comes in complete contrast to the results obtained by the chromosomal CRISPRi experiments.

Example 5: Type-S CRISPR/Cas System in Base Editing Applications

5.1 Introduction

The currently developed and reported CRISPR/Cas base-editing tools rely on the single-subunit effector modules of different Class 2 CRISPR/Cas systems. Class 1 CRISPR/Cas systems have multi-subunit effector modules, complicating the development of base editing tools. Consequently, the base editing capacities of Class 1 base-editors, regarding for example editing specificity, efficiency and window, have remained unexplored.

In this Example, the potential of the Type-S CRISPR/Cas system to transform into a flexible base-editing platform was extensively studied. A collection of base editors was designed and constructed by fusing, with a 16 amino acids long XTEN linker (SEQ ID Nos: 16 and 17, see Schellenberger et al., Nat. Biotechnol., 27 (12), 1186-1190, 2009, doi: 10.1038/nbt.1588), the PmCDA1 cytidine deaminase from sea lamprey (SEQ ID Nos: 18 and 19, see Nishida et al., Science, 353 (6305), aaf8729, 2016, doi: 10.1126/science.aaf8729) to either the N- or the C-terminus of the Cas-S1, Cas-S3 or Cas-S4 subunits of the Type-S CRISPR/Cas system. The Uracil DNA glycosylase inhibitor (UGI) protein (SEQ ID Nos: 20 and 21, see Mol et al., Cell, 82 (5), 701-8, 1995, doi: 10.1016/0092-8674 (95) 90467-0) was fused to the C-terminus of each chimera with a 10 amino acids long linker (SEQ ID Nos: 22 and 23). Subsequently, these base-editors were tested for their ability to generate targeted, chromosomal C-to-T modifications.

5.2 Experimental Design 5.2.1 Overview of Screening Strain and Plasmids

A gfp gene was inserted into the chromosome of *E. coli* MG1655 under the transcriptional control of the p70a promoter (SEQ ID No:15). The resulting b5815 (gfp+ve) strain was employed as the test strain for all the base-editing assays. The six protospacer targets for the base-editing assays were selected to have a 5'-AAG-3' PAM at their 5' end and to be located within a 249 bp long region, comprised of the last 52 bp of the p70a promoter and the first 197 bp of the gfp sequence. Three of the protospacers were on the template (regarding transcription) strand and three were on the non-template strand (FIG. 15).

Figure 20:
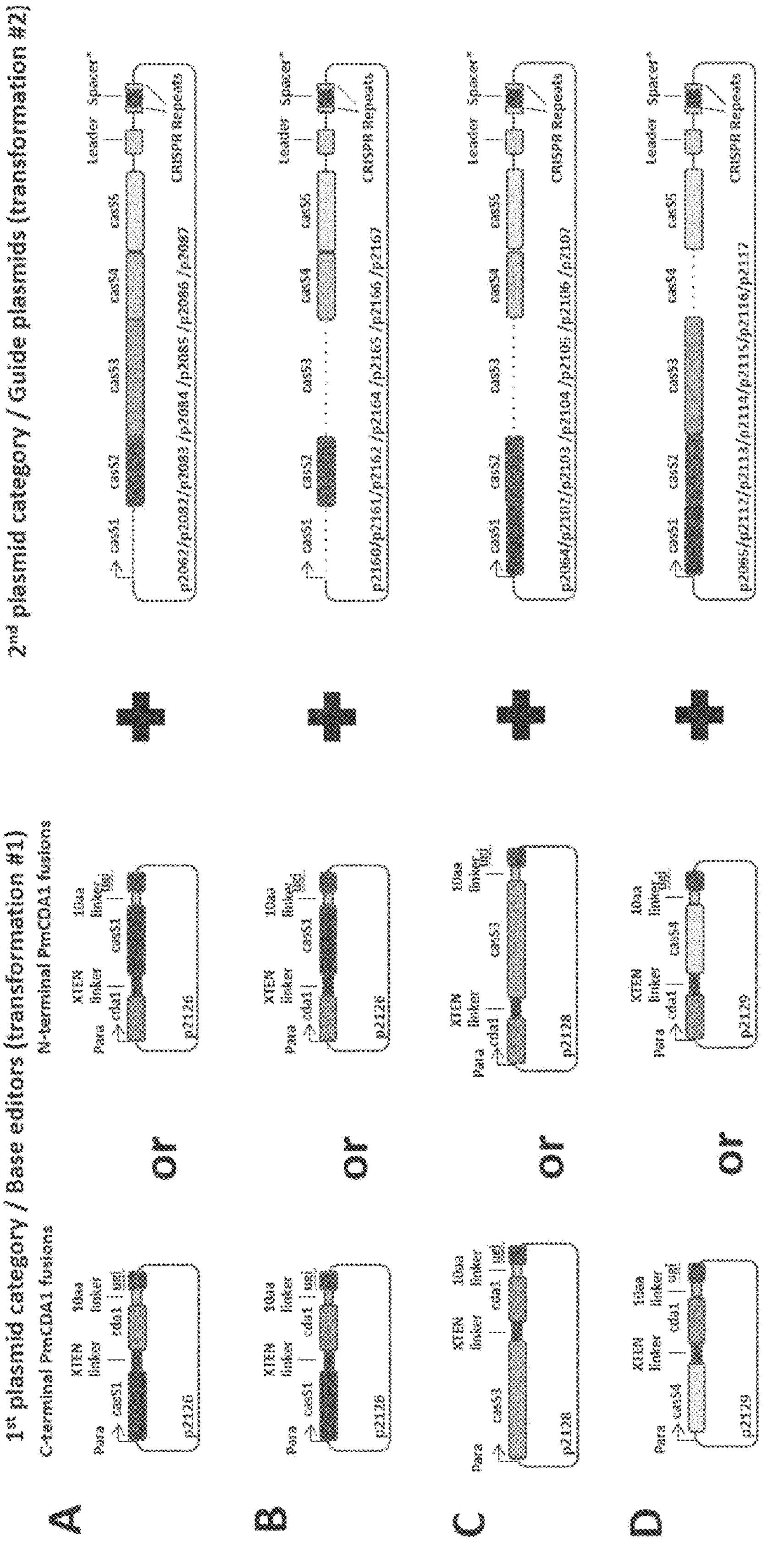

Two categories of plasmids were designed and constructed for the base editing assays:

The 1$^{st}$ category contained the 'base editor' plasmids responsible for the expression of the pm_cdal gene which was fused to either the N- or the C-terminus of either the Cas-S1, Cas-S3 or the Cas-S4 gene (see FIG. 20, left hand side). The expression of the chimeras was set under the transcriptional control of the arabinose inducible promoter (PBAD, SEQ ID No:24, see Guzman et al., J. Bacteriol., 177 (14), 4121-4130, 1995, doi: 10.1128/jb.177.14.4121-4130.1995). The backbone of the plasmids contained the chloramphenicol resistance marker gene (crm), for selection on the antibiotic chloramphenicol, and the p15a origin of replication.

All the PCR reactions were performed with Q5 Hi FI 2X Master Mix (NEB), with appropriately designed primers and PCR templates to construct the plasmids. The PCR fragments were employed for NEBuilder® HIFI DNA Assembly Master Mix reactions. 5 μL from each assembly reaction were transformed with electroporation into 50 μL of NEB10B electro competent cells (NEB). The cells were subsequently left to recover in SOC medium (500 μL final volume) for 1 hour at 37° C. and shaking at 200 rpm. 100 μL from each recovery were removed and plated on LB agar plates supplemented with 20 μg/mL chloramphenicol. The plates were incubated overnight at 37° C.

The following day, single colonies were randomly selected and used for inoculation of 10 mL. LB liquid medium cultures supplemented with 20 μg/mL chloramphenicol. The cultures were incubated overnight at 37° C. with rigorous shaking (200 rpm).

The following day, glycerol stocks were prepared for each culture and the remaining cultures were used for plasmid isolation with the Qiagen plasmid mini kit. Each plasmid was sequence verified with NGS.

The 2$^{nd}$ category contained the 'guide' plasmids responsible for the expression of 1) the crRNA expressing modules (one for each of the non-targeting control, S1F, S1R, S2F, S2R, S3F and S3R) and ii) different versions of the Type-S Cas operon with either Cas-S1, Cas-S3 or Cas-S4 genes being deleted (see FIG. 20, right hand plasmids). The expression of the crRNAs was set under the control of the original leader (promoter) sequence as it was found in the CRISPR locus of the Type-S CRISPR/Cas system. The expression of the operons was set under the transcriptional control of the constitutive promoter of the bolA gene (SEQ ID No:14) present in the *E. coli* genome (PboiA). The backbone of the plasmids contains the tetracycline resistance marker gene (tet), for selection on the antibiotic tetracycline, and the pSC101 origin of replication.

The construction methodology for the 'guide' plasmids was the same as for the 1$^{st}$ category, except that (i) 10 μg/mL tetracycline was used for plating on LB agar, instead of 20 μg/mL chloramphenicol and (ii) 10 μg/mL tetracycline was used for inoculation of the LB liquid medium, instead of 20 μg/mL chloramphenicol.

Subsequently, the p2062 (non-targeting control, ΔCas-S1), p2064 (non-targeting control, ΔCas-S3), p2065 (non-targeting control, ΔCas-S4) and p2160 (non-targeting control, ΔCas-S1, ΔCas-S3) plasmids were subjected to restriction digestion with BsmBI-v2 (NEB) and the digestion products were gel purified with the Zymoclean Gel DNA Recovery Kit (Zymoresearch). Appropriately designed oligos were annealed and ligated into the digested plasmids with T4 DNA ligase (NEB). 5 μL from each ligation reaction was transformed with electroporation into 50 μL of NEB10B electro competent cells (NEB). The cells were subsequently left to recover in SOC medium (500 μL final volume) for 1 hour at 37° C. and shaking at 200 rpm. 100 μL from each recovery were removed and plated on LB agar plates supplemented with 10 μg/ml tetracycline. The plates were incubated overnight at 37° C.

The following day, single colonies were randomly selected and used for inoculation of 10 mL LB liquid medium cultures supplemented with 10 g/mL tetracycline. The cultures were Incubated overnight at 37° C. with rigorous shaking (200 rpm).

The following day, glycerol stocks were prepared for each culture and the remaining cultures were used for plasmid isolation with the Qiagen plasmid mini kit. Each plasmid was sequence verified with NGS.

5.2.2 Base Editing Assays

Each of the 6 'base editor' plasmids having the PmCDA1 cytidine deaminase fused to either the N- or C-terminus of each of the wt Type-S subunits Cas-S1, Cas-S3 and Cas-S4 (see FIG. 20, left hand side) was transformed into electrocompetent b5815 cells. The electrocompetent cells were prepared using the protocol described in (barricklab.org/twiki/bin/view/Lab/ProtocolsElectrocompetentCells). The transformation reactions were performed using 40 ng of each plasmid per reaction. The cells were allowed to recover in 500 μl of SOC medium for 1 hour at 37° C. and shaking at 200 rpm. 100 μL from each recovery was plated on LB agar plates supplemented with 20 μg/mL chloramphenicol. The plates were incubated overnight at 37° C.

The following day, single colonies were randomly selected and used for inoculation of 10 mL LB liquid medium cultures supplemented with 20 μg/mL chloramphenicol. The cultures were incubated overnight at 37° C. with rigorous shaking (200 rpm).

The following day, electrocompetent cells were prepared for each one of the six produced b5815 strains with the base-editor plasmids, according to the protocol described in (barricklab.org/twiki/bin/view/Lab/ProtocolsElectrocompetentCells). Subsequently, each one of the six strains was electro-transformed with the corresponding group of guide plasmids, as presented on the right side of FIG. 20. These plasmids were responsible for the expression of i) Type-S subunits that are not expressed by the pairing base editor plasmids and ii) targeting and non-targeting crRNAs. The transformation reactions were performed using 40 ng from each plasmid per reaction. The cells were allowed to recover in 500 μL of SOC medium for 1 hour at 37° C. and shaking at 200 rpm. 100 μL from each recovery were plated on LB agar plates supplemented with 20 μg/mL chloramphenicol, 10 μg/ml tetracycline and 0.2% v/w arabinose. The plates were incubated overnight at 37° C.

The following day, single colonies were randomly selected and subjected to colony PCR with appropriately designed genome-specific primers. The PCR products were sequenced by Sanger sequencing and the results were analyzed for the detection of C-to-T modifications- or G-to-A modifications when the reverse strand was targeted and modified.

5.3 Results

Representative results from the base editing assays are presented in FIGS. 21A-21G.

Detailed analysis of the Sanger sequencing data from all the base editing assays is provided below:

5.3.1 PmCDA1 Linked to the N-Terminus of

- Cas-S1 (WT Type-S): no base-editing
- Cas-S3 (WT Type-S): single C-to-T mutation in only 1 of the targeted protospacers
- Cas-S4 (WT Type-S): single C-to-T mutation in only 1 of the targeted protospacers (same as for Cas-S3-N term CDA)

5.3.2 PmCDA1 Linked to the C-Terminus of

- Cas-S1:
  - Protospacer S1F: No base-editing
  - Protospacer S1R: No base-editing
  - Protospacer S2F: Multiple positions base-edited (105 nt editing window) with different levels of efficiency for each position. Not only C-to-T but also a few G-to-A conversions
  - Protospacer S2R: 4 positions base-edited (29 nt editing window) with different levels of efficiency for each position. Not only G-to-A but also 1 C-to-T conversion
  - Protospacer S3F: 8 positions base-edited (35 nt editing window) with different levels of efficiency for each position. Not only C-to-T but also 1 G-to-A conversion
  - Protospacer S3R: few positions base-edited (outside the protospacer region) with low efficiency. Streaking improved efficiency and extended editing window (96 nt). A mixture of C-to-T and G-to-A conversions were detected,
- Cas-S1 (in the absence of Cas-S3: Type-S_ΔCas-S3):
  - Protospacer S1F: No base-editing
  - Protospacer S1R: Single G-to-A modification within the protospacer
  - Protospacer S2F: Multiple positions were C-toT modified, with different levels of efficiency, within and 7 nt downstream of the protospacer region. 2 additional C-to-T conversions were detected within a 102 nt editing window upstream of the 5'end of the protospacer.
  - Protospacer S2R: 4 positions base-edited (48 nt editing window) with different levels of efficiency for each position. Only 1 weak G-to-A modification at the 3 PAM proximal position, and 3 efficient C-to-T modifications downstream of the protospacer
  - Protospacer S3F: multiple very weak modifications
  - Protospacer S3R: few very weak modifications (mixture of C-to-T and G-to-A conversions) were detected, as well as 1 very efficient C-to-T modification 40 nt downstream of the 3' end of the protospacer.
- Cas-S3:
  - Protospacer S1F: No base-editing
  - Protospacer S1R: Dominant single position was base-edited in the middle of the protospacer and a few more were inefficiently edited. Streaking extended the base editing window (50 nt), while not only G-to-A but also a few C-to-T conversions were detected
  - Protospacer S2F: No base-editing
  - Protospacer S2R: Multiple positions were inefficiently base-edited within a wide editing window (up to 208 nt). Not only G-to-A but mostly C-to-T conversions were detected. Streaking improved the efficiency as it resulted in 3 clean conversions (both G-to-A and C-to-T) within a 178 nt window.
  - Protospacer S3F: Multiple positions were base-edited (388 nt editing window). Conversions within the protospacer region were the cleanest ones. Only 2 positions were detected with G-to-A conversions.
  - Protospacer S3R: No base-editing detected initially, but the streaking generated multiple G-to-A and C-to-T conversions within a 388 nt editing window.
- Cas-S4:
  - All targeted protospacers were edited in multiple positions within the protospacer region. Exception was S2R, that was also edited downstream the protospacer region, and S3R that had a single G-to-A mutation at the $2^{nd}$ PAM distal position of the protospacer.
  - Protospacers S1F and S2R had mixtures of C-to-T and G-to-A modifications, while the rest of the protospacers had either C-to-T or G-to-A modifications, depending on the direction of the protospacer.

5.4 Conclusions

This Example generated the first reported Class I CRISPR/Cas platform for efficient base-editing. The seven developed base editors employed the PmCDA1 cytidine deaminase. Six of the base editors employed the wild type Type-S CRISPR/Cas system and one of the base editors employed the ΔCas-S3 Type-S CRISPR/Cas system.

Fusion of PmCDA1 to the N-terminus of Cas-S1 did not generate any detectable modification.

Fusion of PmCDA1 to the N-terminus of Cas-S4 and Cas-S3 generated only a single detectable, mixed (wild type/mutant genotype) modification for one of the tested spacers. These systems could be used when very specific point mutations are required. But the low number of spacers that can be used restricts the applicability of these systems.

Fusion of PmCDA1 to the C-terminus of Cas-S1, Cas-S4 and Cas-S3 generated three base editing systems with very different base editing outcomes (editing windows, editing efficiencies and edited positions) even on the same protospacers. In general, the Cas-S1- and Cas-S3-based base editors had very wide editing windows and can be very valuable in the generation of amino-acid libraries for a single protein or the introduction of stop codons. In the absence of Cas-S3, the editing window of the Cas-S1-based base editor was reduced and a shift in the edited positions was noted. The Cas-S4-based base editor had a narrower base-editing window and was the only base editor that introduced modifications into all the targeted protospacers.

Example 6: Functionalizing the Type-S CRISPR/Cas System for dsDNA Cleavage

6.1 Aim

Type-S is a nuclease deficient CRISPR-Cas system that carries no bioinformatically predicted, or experimentally determined (see Examples 1 and 4 herein) nuclease domains in any of its subunits. The aim of this study was to expand the repertoire of genome-editing reagents by creating synthetic crRNA-guided DNA nucleases upon fusing the nuclease domain of the I-TevI homing endonuclease (SEQ ID Nos: 44 and 45) to the N-termini of the CasS1 and CasS4 subunits of the hellcase-deficient Type-S system (ΔCasS3, see FIG. 22). The developed chimeras were tested on chromosomal and plasmid-borne DNA targets and a set of rules for efficient dsDNA cleavage was established.

6.2 Introduction

I-TevI is a homing endonuclease that is comprised of an N-terminal nuclease domain (1-92 amino acids (aa)), a zinc-finger containing spacer domain (92-169 aa) and a DNA-binding domain (169-245 aa) (see Edgell et al., PNAS, 98 (14), 7898-7903, 2001, doi: doi.org/10.1073/pnas.141222498 and Kleinstiver et al., PNAS, 109 (21), 8061-8066, 2012, doi: doi.org/10.1073/pnas.111798410). I-TevI binds its DNA target as a monomer, and introduces a sequence-specific, staggered dsDNA cut in the I-TevI cleavage via the GIY-YIG motif present in its N-terminal nuclease domain. The sequence of the naturally occurring I-TevI cleavage site is 5'-CAACG-3' (forward strand)/5'-CGTTG-3' (reverse strand). Nonetheless, I-TevI has been reported to recognize a more flexible 5'-CNNNG-3' (forward strand)/5'-CNNNG-3' (reverse strand) I-TevI cleavage site (see Edgell et al., 2001 and Kleinstiver et al. 2012, both supra). It was hypothesized that by fusing the N-terminal and zinc-finger/linker domains of I-TevI to the N-terminus of CasS1 or CasS4, it would be possible to create synthetic TevCasSx (x=1 or 4) crRNA-guided DNA nucleases.

In Example 4 it was demonstrated-via CRISPRI experiments—that the helicase-deficient ΔCasS3 Type-S system retains strong DNA binding activity. Moreover, in the same example, it was demonstrated that the helicase-expressing ΔCasS1 Type-S system shows the same CRISPRi/DNA-binding efficiency to the helicase-deficient ΔCasS3 Type-S system, whereas the ΔCasS1ΔCasS3 Type-S system shows reduced CRISPRI/DNA-binding activity. These results support a model in which CasS1 is involved in the recruitment of CasS3 to the Type-S complex. Hence, it was decided to employ the ΔCasS3 Type-S helicase-deficient system for the construction of the TevCasSx synthetic nucleases, aiming to avoid hinderance of the nuclease activity of the TevCasSx chimeras by the recruitment or the helicase activity of CasS3.

6.3 Experimental Design

6.3.1 TevCasS Plasmid-DNA Cleavage Assays

Three categories of plasmids were designed, constructed and employed for the TevCasS plasmid-DNA cleavage assays; i) the TevCasS target plasmids, ii) the TevCasSx expressing plasmids and ill) the Type-S guide plasmids.

23 TevCasS target plasmids (named p2497-p2510, p2575-p2578 and p2655-p2659, see FIG. 22, right hand plasmids) were designed to contain various TevCasS target sites (SEQ ID Nos: 46 to 68 respectively, see Table 4) separately cloned into a low copy plasmid backbone, comprised of the low copy number pBBR1 replicon and the kanamycin resistance marker gene. The 1$^{st}$ TevCasS target plasmid, denoted as p2497 (Table 4), was designed to encompass a 71nt long target site with the following structure—in 5' to 3' direction-: i) the 5nt long I-TevI 5'-CAACG-3' (SEQ ID No:42) cleavage site followed by ii) the 31nt long natural I-TevI DNA spacer sequence 5'-CTCAGTAGATGTTTTCTTGGGTCTACCGTTA-3' (SEQ ID No:46), that interacts with the I-TevI zinc-finger domain, followed by ill) the 3nt long Type-S PAM sequence 5'-AAG-3' (SEQ ID No:13) followed by iv) the 32nt long protospacer sequence 5'-TOGTGTTGTCCACGGTTACCCGCTGGCTGGAA-3' (SEQ ID No:69), that is complementary to the sequence of the 1$^{st}$ spacer in the natural CRISPR array of the Type-S CRISPR-Cas system. The target sites of the additional TevCasS target plasmids (Table 4, SEQ ID Nos: 46 to 68) had the same I-TevI cleavage site, PAM and protospacer portions as the target on the p2497 plasmid, but their I-TevI DNA spacer portions were different; various numbers of nucleotides were removed from or were added to the 3'-end of the I-TevI DNA spacer sequence from p2497, resulting in the construction of target plasmids with 5nt (SEQ ID No:59), 7nt (SEQ ID No:58), 9nt (SEQ ID No:57), 11nt (SEQ ID No:56), 13nt (SEQ ID No:55), 15nt (SEQ ID No:54), 17nt (SEQ ID No:53), 19nt (SEQ ID No: 52), 21nt (SEQ ID No:51), 23nt (SEQ ID No:50), 25nt (SEQ ID No:49), 27nt (SEQ ID No:48), 28nt (SEQ ID No:64), 29nt (SEQ ID No:47), 30nt (SEQ ID No:65), 31nt (SEQ ID No:46), 32nt (SEQ ID No: 66), 33nt (SEQ ID No:60), 34nt (SEQ ID No:67), 35nt (SEQ ID No:61), 36nt (SEQ ID No:68), 37nt (SEQ ID No:62) or 39nt (SEQ ID No:63) long I-TevI DNA spacer sequences).

For the construction of the I-TevI target plasmids, all the PCR reactions were performed with Q5 Hi Fi 2× Master Mix (NEB) and appropriately designed primers and PCR templates. The PCR fragments were employed for KLD Enzyme Mix (NEB) reactions. 5 μL from each reaction were transformed with electroporation into 50 μL of NEB10ß electro competent cells (NEB). The cells were subsequently left to recover in SOC medium (500 μL final volume) for 1 hour at 37° C. and shaking at 200 rpm. 100 μL from each recovery were removed and plated on LB agar plates supplemented with 50 μg/mL kanamycin. The plates were incubated overnight at 37° C.

The following day, single colonies were randomly selected and used for inoculation of 10 mL LB liquid medium cultures supplemented with 50 μg/mL kanamycin. The cultures were incubated overnight at 37° C. with rigorous shaking (200 rpm).

The following day, glycerol stocks were prepared for each culture and the remaining cultures were used for plasmid isolation with the Qiagen plasmid mini kit. Each plasmid was sequence verified with NGS.

The TevCasS1 (p2461) and TevCasS4 (p2462) (see FIG. 22, middle plasmids) expressing plasmids were designed to have the initial 618 bp of the I-tevI gene (SEQ ID No:44), that express the N-terminal 206 amino acids of the I-TevI nuclease (SEQ ID No:45), linked to the N-terminus of the casS1 and the cas4 genes with an XTEN linker expressing sequence (SEQ ID Nos: 16 and 17). The expression of the chimeras was set under the transcriptional control of the arabinose inducible promoter (PBAD, SEQ ID No:24) (see Guzman et al., J. Bacteriol., 177 (14), 4121-4130, 1995, doi: 10.1128/jb.177.14.4121-4130.1995). The backbone of the constructed plasmids contained the chloramphenicol resistance marker gene (crm), for selection on the antibiotic chloramphenicol, and the p15a origin of replication.

The construction methodology for the expressing plasmids was the same as for the target plasmids, except that (i) the for NEBuilder® HIFI DNA Assembly Master Mix was used instead of the KLD Enzyme Mix (NEB), (ii) 20 μg/mL chloramphenicol was used for plating on LB agar, instead of 50 μg/mL kanamycin, and (iii) 20 μg/mL chloramphenicol was used for inoculation of the LB liquid medium, instead of 50 g/mL kanamycin.

Four Type-S guide plasmids were designed (see FIG. 22, left hand plasmids); two non-targeting (negative) controls and two targeting plasmids. The guide plasmids were responsible for the expression of i) the crRNA expressing modules (either a non-targeting control crRNA or a crRNA that targets the protospacer within the TevCasS target sequence) and ii) either the ΔCasS1 ΔCasS3 version or the ΔCasS1 ΔCasS4 version of the Type-S Cas operon (Table 2), The expression of the crRNAs was set under the control of the original leader (promoter) sequence as it was found in the CRISPR locus of the wild type Type-S CRISPR/Cas system. The expression of the operons was set under the transcriptional control of the constitutive promoter of the bolA gene (SEQ ID No: 14) present in the *E. coli* genome (pbolA). The guide plasmids share the same backbone, that contains the tetracycline resistance marker gene (tetR), for selection on the antibiotic tetracycline, and the low copy number pSC101 origin of replication.

The construction methodology for the guide plasmids was the same as for the expression plasmids, except that (i) 10 μg/mL tetracycline was used for plating on LB agar, instead of 20 μg/mL chloramphenicol and (ii) 10 μg/mL tetracycline was used for inoculation of the LB liquid medium, instead of 20 μg/mL chloramphenicol.

For the TevCasS plasmid-DNA cleavage assays, the following plasmid combinations were transformed with electroporation into *E. coli* strain MG1655 (see also FIG. 22, left side):

1. p2461 (expressing TevCasS1) and p2160 (non-targeting control guide)
2. p2461 (expressing TevCasS1) and p2511 (TevCasS targeting guide)
3. p2462 (expressing TevCasS4) and p2460 (non-targeting control guide)
4. p2462 (expressing TevCasS4) and p2512 (TevCasS targeting guide)

The electrocompetent MG1655 cells were prepared using the protocol described in (barricklab.org/twiki/bin/view/Lab/ProtocolsElectrocompetentCells). The transformation reactions were performed using 40 ng from each plasmid per reaction. The cells were subsequently left to recover in SOC medium (500 μL final volume) for 1 hour at 37° C. and shaking at 200 rpm. 100 μL from each recovery were removed and plated on LB agar plates supplemented with 20 μg/mL chloramphenicol and 10 μg/mL tetracycline. The plates were incubated overnight at 37° C. The following day, single colonies were randomly selected and used for inoculation of 10 mL LB liquid medium cultures supplemented with 20 μg/mL chloramphenicol and 10 μg/mL tetracycline. The cultures were incubated overnight at 37° C. with rigorous shaking (200 rpm). The following day, glycerol stocks were prepared for each culture and the cultures were used for preparation of electrocompetent cells plasmid according to the protocol described in (barricklab.org/twiki/bin/view/Lab/ProtocolsElectrocompetentCells). Each one of the four strains was transformed with each one of the target plasmids (FIG. 22 right side) and the p2027 control plasmid, that is identical to the target plasmids but does not contain any TevCasS target sequence. The recoveries from each strain were used for the preparation of serial dilutions, which were subsequently spot plated on LB agar plates supplemented with 20 μg/mL chloramphenicol, 10 μg/mL tetracycline and 50 μg/mL kanamycin, for plasmid selection. The transformations were performed in biological triplicates. Successful introduction of a dsDNA break to a target plasmid would result into plasmid elimination and subsequently growth inhibition in the presence of kanamycin.

The formed colonies from each transformation were counted. The reduction in the transformation efficiencies of the two strains that express the targeting crRNA, when compared to the two strains that express the non-targeting crRNA, was calculated in 2 steps: 1) Normalization of the transformation efficiency of each strain for each target plasmid by division with the corresponding transformation efficiency of the control plasmid p2027, and 2) Division of the normalized transformation efficiencies of the strains with the targeting crRNA to the corresponding normalized transformation efficiencies of the strains with the non-targeting crRNA.

6.3.2 TevCasS Chromosomal-DNA Cleavage Assays

The TevCasS target sequences with 29nt (SEQ ID No:47), 30nt (SEQ ID No:65), 31nt (SEQ ID No: 46), 32nt (SEQ ID No:66) and 33nt (SEQ ID No:60) long I-TevI spacers were inserted into the chromosome of the *E. coli* MG1655 strain, generating five TevCasS chromosomal target strains each containing a different target. All constructed strains were transformed with the p2461 (TevCasS1 expressing) plasmid. The electrocompetent cells were prepared using the protocol described in (barricklab.org/twiki/bin/view/Lab/Protocols-ElectrocompetentCells). The transformation reactions were performed using 40 ng from each plasmid per reaction. The cells were subsequently left to recover in SOC medium (500 μl final volume) for 1 hour at 37° C. and shaking at 200 rpm. 100 μL from each recovery were removed and plated on LB agar plates supplemented with 20 μg/mL chloramphenicol. The plates were incubated overnight at 37° C.

The following day, single colonies were randomly selected and used for inoculation of 10 mL LB liquid medium cultures supplemented with 20 μg/mL chloramphenicol. The cultures were incubated overnight at 37° C. with rigorous shaking (200 rpm).

The following day, glycerol stocks were prepared for each culture and the cultures were used for preparation of electrocompetent cells plasmid according to the protocol described in (barricklab.org/twiki/bin/view/Lab/Protocols-ElectrocompetentCells). Each one of the resulting strains was transformed with the p2160 (non-targeting control guide) and the p2511 (TevCasS targeting guide) plasmids (see FIG. 22). The recoveries from each strain were used for the preparation of serial dilutions, which were subsequently spot plated on LB agar plates supplemented with 20 μg/ml chloramphenicol and 10 g/mL tetracycline. The transformations were performed in biological triplicates. Successful introduction of dsDNA breaks to the chromosomal TevCasS targets would be lethal resulting in reduced number of surviving colonies upon plating.

The formed colonies from each transformation were counted. The transformation efficiencies of the strains transformed with the targeting crRNA guide plasmid were divided by the transformation efficiencies of the strains transformed with the targeting crRNA guide plasmid. This divisions revealed the reduction in the transformation efficiencies of the strains and subsequently the targeting efficiency of the TevCasS1 system on chromosomal targets.

6.3.3 TevCasS Cleavage Site Identification

I-TevI recognizes a flexible 5'-CNNNG-3' (forward strand)/5'-CNNNG-3' (reverse strand) cleavage site. It was reasoned to identify the I-TevI cleavage sites that TevCasS1 recognizes and cleaves, via a plasmid clearance assay similar to the one described in Example 2 for the Type-S PAM identification.

A TevCasS target plasmid library was designed and constructed; each member of this library is identical to the p2497 target plasmid except for the sequence of the I-TevI cleavage site, that instead of 5'-CAACG-3' is 5'-CNNNG-3', where N is any nucleotide. Hence the library should be comprised of $4^3$ (64) different I-TevI cleavage sites.

For the construction of the library, p2497 was PCR amplified (CloneAMP PCR pre-mix) with appropriately designed primers. The gel purified PCR product was used for Infusion reaction (Takarabio) and 5 μL from the reaction mixture were transformed into 50 μL of NEB10 electro competent cells (NEB), The transformed cells were recovered in SOC medium (500 μL final volume) for 1 hour at 37° C. and 200 rpm and were subsequently transferred into 500 mL of LB medium supplemented with 50 μg/mL kanamycin. 100 μL from the 500 mL culture were plated on LB agar plates supplemented with 50 μg/ml kanamycin. Culture and plate were incubated overnight at 37° C., the former with rigorous shaking (200 rpm).

The following day, the colonies on the plate were counted (180 colonies) and it was calculated that 900,000 transformed cells were added into the 500 mL culture, using Equation 1.

With this number of transformed cells in the culture, the coverage of the library members was calculated at 14,062× according to Equation 2.

Glycerol stocks were prepared from the 500 mL culture and midi-preps were performed for isolation of the TevCasS1 target plasmid library. The plasmid library was subsequently transformed into the *E. coli* MG1655 strains that harbor the following plasmid combinations:

Strain #1. p2461 (expressing TevCasS1) and p2160 (non-targeting control guide)

Strain #2. p2461 (expressing TevCasS1) and p2511 (TevCasS targeting guide)

It is expected that some or all members of the target plasmid library contain cleavage sites that are recognized from TevCasS1. These target plasmids should be efficiently targeted upon transformation in strain #2, hampering the growth of the transformed cells under appropriate antibiotic selection conditions. None of the target library members should be targeted upon transformation of the library to strain #1.

Plasmid isolation from cultures of strain #2 transformed with the target plasmid library, followed by NGS, show which the TevCasS cleavage site sequences are not recognized by TevCasS and subsequently which are the sequences that the system recognises and cleaves.

Plasmid isolation from cultures of strain #1 transformed with the target plasmid library, followed by NGS, will indicate the abundance of each plasmid member in the target plasmid library. This information will be used for normalization of the NGS results from strain #2.

Experimentally, electrocompetent cells for both strains were prepared using the protocol described in (barrick-lab.org/twiki/bin/view/Lab/ProtocolsElectrocompetent-Cells). Five transformation reactions per strain were performed, using 40 ng of the plasmid library per reaction. The cells were subsequently left to recover in SOC medium (500 μL final volume) for 1 hour at 37° C. and shaking at 200 rpm. The recovered cells from each strain were combined and used for inoculation of 500 mL LB cultures supplemented with 50 μg/mL kanamycin (one culture per strain). The cultures were incubated overnight at 37° C. with rigorous shaking (200 rpm). The following day, the cultures were used for preparation of glycerol stocks and they were subjected to plasmid isolation. The isolated plasmids were employed for preparation of NGS samples, following the process described in Example 2, and the prepared samples were subjected to NGS.

6.4 Results

6.4.1 TevCasS Targeting Assays on Plasmid Targets

Figure 23:
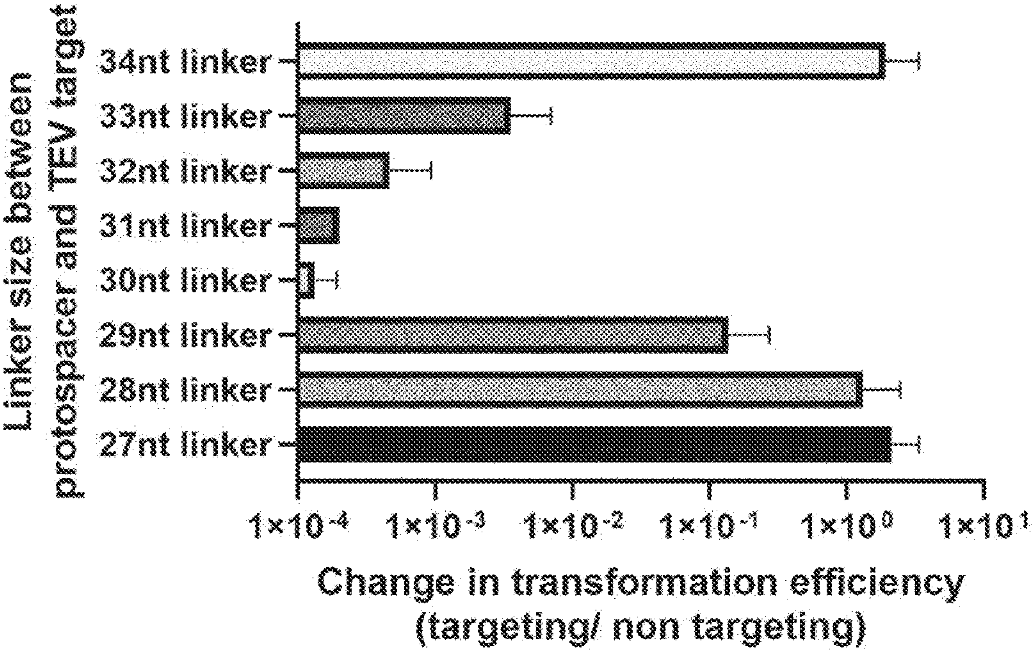

The strains that express the TevCasS1 chimera and either the targeting crRNA or the non-targeting crRNA were transformed with the TevCasS target plasmids and their transformation efficiencies were compared (FIG. 23). The transformation efficiency of the targeting strain dropped:

i) 4 orders of magnitude when transformed with target plasmids with 30nt and 31nt long I-TevI spacers, ii) 3 orders of magnitude when transformed with the target plasmid with 32nt long I-TevI spacer, iii) 2 orders of magnitude when transformed with target plasmid with 33nt long I-TevI spacer, and iv) 1 order of magnitude when transformed with the target plasmid with 29nt long I-TevI spacer (FIG. 23).

None of the remaining target plasmids were efficiently (at least 1 order of magnitude drop in the transformation efficiency) targeted by the TevCasS1 chimera. None of the target plasmids were efficiently (at least 1 order of magnitude) targeted by the TevCasS4 chimera. Hence, the TevCasS1 chimera is highly efficient in targeting plasmid-born TevCasS targets.

6.4.2 TevCasS Targeting Assays on Chromosomal Targets

Five strains with chromosomally-integrated TevCasS targets, that also carry the TevCasS1 expressing plasmid, were transformed with the either the targeting guide plasmid or the non-targeting guide plasmid and their transformations efficiencies were compared (FIG. 24). The transformation efficiencies of the strains with TevCasS targets that have:

i) 30nt, 31nt and 32nt long I-TevI spacers dropped by 4 orders of magnitude when transformed with the targeting guide plasmid.

ii) 29nt and 33nt long I-TevI spacers dropped by 1 order of magnitude when transformed with the targeting guide plasmid.

Hence, the TevCasS1 chimera is highly efficient in targeting chromosomal TevCasS targets.

6.4.3 TevCasS Cleavage Site Identification

The generated NGS data were used to compare the relative abundance of each member of the target plasmid library in strain #1 and #2. This analysis revealed the preferences of the TevCasS for specific 5'-CNNNG-3' sequences (FIG. 25):

5'-CASHG-3'
5'-CATNG-3'
5'-CAAMG-3'
5'-CCAYG-3'
5'-CCTHG-3'
5'-CCGTG-3'
5'-CTDHG-3'
5'-CTOCG-3'
5'-CGGCG-3'
5'-CGAYG-3'

TABLE 3

| EXAMPLE BACTERIA |
|---|
| Abiotrophia |
| *Abiotrophia defectiva* |
| Acaricomes |
| *Acaricomes phytoseiuli* |
| Acetitomaculum |
| *Acetitomaculum ruminis* |
| Acetivibrio |
| *Acetivibrio cellulolyticus* |
| *Acetivibrio ethanolgignens* |
| *Acetivibrio multivorans* |
| Acetoanaerobium |
| *Acetoanaerobium noterae* |
| Acetobacter |
| *Acetobacter aceti* |
| *Acetobacter cerevisiae* |
| *Acetobacter cibinongensis* |
| *Acetobacter estunensis* |
| *Acetobacter fabarum* |
| *Acetobacter ghanensis* |
| *Acetobacter indonesiensis* |
| *Acetobacter lovaniensis* |
| *Acetobacter malorum* |
| *Acetobacter nitrogenifigens* |
| *Acetobacter oeni* |
| *Acetobacter orientalis* |
| *Acetobacter orleanensis* |
| *Acetobacter pasteurianus* |
| *Acetobacter pornorurn* |
| *Acetobacter senegalensis* |
| *Acetobacter xylinus* |
| Acetobacterium |
| *Acetobacterium bakii* |
| *Acetobacterium carbinolicum* |
| *Acetobacterium dehalogenans* |
| *Acetobacterium fimetarium* |
| *Acetobacterium malicum* |
| *Acetobacterium paludosum* |
| *Acetobacterium tundrae* |
| *Acetobacterium wieringae* |
| *Acetobacterium woodii* |
| Acetofilamentum |
| *Acetofilamentum rigidum* |
| Acetohalobium |
| *Acetohalobium arabaticum* |
| Acetomicrobium |
| *Acetomicrobium faecale* |
| *Acetomicrobium flavidum* |
| Acetonema |
| *Acetonema longum* |
| Acetothermus |
| *Acetothermus paucivorans* |
| Acholeplasma |
| *Acholeplasma axanthum* |
| *Acholeplasma brassicae* |
| *Acholeplasma cavigenitalium* |
| *Acholeplasma equifetale* |
| *Acholeplasma granularum* |
| *Acholeplasma hippikon* |
| *Acholeplasma laidlawii* |
| *Acholeplasma modicum* |
| *Acholeplasma morum* |
| *Acholeplasma multilocale* |
| *Acholeplasma oculi* |
| *Acholeplasma palmae* |

TABLE 3-continued

| EXAMPLE BACTERIA |
|---|
| *Acholeplasma parvum* |
| *Acholeplasma pleciae* |
| *Acholeplasma vituli* |
| Achromobacter |
| *Achromobacter denitrificans* |
| *Achromobacter insolitus* |
| *Achromobacter piechaudii* |
| *Achromobacter ruhlandii* |
| *Achromobacter spanius* |
| Acidaminobacter |
| *Acidaminobacter hydrogenoformans* |
| Acidaminococcus |
| *Acidaminococcus fermentans* |
| *Acidaminococcus intestini* |
| Acidicaldus |
| *Acidicaldus organivorans* |
| Acidimicrobium |
| *Acidimicrobium ferrooxidans* |
| Acidiphilium |
| *Acidiphilium acidophilum* |
| *Acidiphilium angustum* |
| *Acidiphilium cryptum* |
| *Acidiphilium multivorum* |
| *Acidiphilium organovorum* |
| *Acidiphilium rubrum* |
| Acidisoma |
| *Acidisoma sibiricum* |
| *Acidisoma tundrae* |
| Acidisphaera |
| *Acidisphaera rubrifaciens* |
| Acidithiobacillus |
| *Acidithiobacillus albertensis* |
| *Acidithiobacillus caldus* |
| *Acidithiobacillus ferrooxidans* |
| *Acidithiobacillus thiooxidans* |
| Acidobacterium |
| *Acidobacterium capsulatum* |
| Acidocella |
| *Acidocella aminolytica* |
| *Acidocella facilis* |
| Acidomonas |
| *Acidomonas methanolica* |
| Acidothermus |
| *Acidothermus cellulolyticus* |
| Acidovorax |
| *Acidovorax anthurii* |
| *Acidovorax caeni* |
| *Acidovorax cattleyae* |
| *Acidovorax citrulli* |
| *Acidovorax defluvii* |
| *Acidovorax delafieldii* |
| *Acidovorax facilis* |
| *Acidovorax konjaci* |
| *Acidovorax temperans* |
| *Acidovorax valerianellae* |
| Acinetobacter |
| *Acinetobacter baumannii* |
| *Acinetobacter baylyi* |
| *Acinetobacter bouvetii* |
| *Acinetobacter calcoaceticus* |
| *Acinetobacter gerneri* |
| *Acinetobacter haemolyticus* |
| *Acinetobacter johnsonii* |
| *Acinetobacter junii* |
| *Acinetobacter lwoffi* |
| *Acinetobacter parvus* |
| *Acinetobacter radioresistens* |
| *Acinetobacter schindleri* |
| *Acinetobacter soli* |
| *Acinetobacter tandoii* |
| *Acinetobacter tjernbergiae* |
| *Acinetobacter towneri* |
| *Acinetobacter ursingii* |
| *Acinetobacter venetianus* |
| Acrocarpospora |
| *Acrocarpospora corrugata* |
| *Acrocarpospora macrocephala* |
| *Acrocarpospora pleiomorpha* |

TABLE 3-continued

| EXAMPLE BACTERIA |
|---|
| Actibacter |
| *Actibacter sediminis* |
| Actinoalloteichus |
| *Actinoalloteichus cyanogriseus* |
| *Actinoalloteichus hymeniacidonis* |
| *Actinoalloteichus spitiensis* |
| Actinobaccillus |
| *Actinobacillus capsulatus* |
| *Actinobacillus delphinicola* |
| *Actinobacillus hominis* |
| *Actinobacillus indolicus* |
| *Actinobacillus lignieresii* |
| *Actinobacillus minor* |
| *Actinobacillus muris* |
| *Actinobacillus pleuropneumoniae* |
| *Actinobacillus porcinus* |
| *Actinobacillus rossii* |
| *Actinobacillus scotiae* |
| *Actinobacillus seminis* |
| *Actinobacillus succinogenes* |
| *Actinobaccillus suis* |
| *Actinobacillus ureae* |
| Actinobaculum |
| *Actinobaculum massiliense* |
| *Actinobaculum schaalii* |
| *Actinobaculum suis* |
| *Actinomyces urinale* |
| Actinocatenispora |
| *Actinocatenispora rupis* |
| *Actinocatenispora thailandica* |
| *Actinocatenispora sera* |
| Actinocorallia |
| *Actinocorallia aurantiaca* |
| *Actinocorallia aurea* |
| *Actinocorallia cavernae* |
| *Actinocorallia glomerata* |
| *Actinocorallia herbida* |
| *Actinocorallia libanotica* |
| *Actinocorallia longicatena* |
| Actinomadura |
| *Actinomadura alba* |
| *Actinomadura atramentaria* |
| *Actinomadura bangladeshensis* |
| *Actinomadura catellatispora* |
| *Actinomadura chibensis* |
| *Actinomadura chokoriensis* |
| *Actinomadura citrea* |
| *Actinomadura coerulea* |
| *Actinomadura echinospora* |
| *Actinomadura fibrosa* |
| *Actinomadura formosensis* |
| *Actinomadura hibisca* |
| *Actinomadura kijaniata* |
| *Actinomadura atina* |
| *Actinomadura livida* |
| *Actinomadura luteofluorescens* |
| *Actinomadura macra* |
| *Actinomadura madurae* |
| *Actinomadura oligospora* |
| *Actinomadura pelletieri* |
| *Actinomadura rubrobrunea* |
| *Actinomadura rugatobispora* |
| *Actinomadura umbrina* |
| *Actinomadura verrucosospora* |
| *Actinomadura vinacea* |
| *Actinomadura viridilutea* |
| *Actinomadura viridis* |
| *Actinomadura yumaensis* |
| Actinomyces |
| *Actinomyces bovis* |
| *Actinomyces denticolens* |
| *Actinomyces europaeus* |
| *Actinomyces georgiae* |
| *Actinomyces gerencseriae* |
| *Actinomyces hordeovulneris* |
| *Actinomyces howellii* |
| *Actinomyces hyovaginalis* |
| *Actinomyces israelii* |
| *Actinomyces johnsonii* |
| *Actinomyces meyeri* |
| *Actinomyces naeslundii* |
| *Actinomyces neuii* |
| *Actinomyces odontolyticus* |
| *Actinomyces oris* |
| *Actinomyces radingae* |
| *Actinomyces slackii* |
| *Actinomyces turicensis* |
| *Actinomyces viscosus* |
| Actinoplanes |
| *Actinoplanes auranticolor* |
| *Actinoplanes brasiliensis* |
| *Actinoplanes consettensis* |
| *Actinoplanes deccanensis* |
| *Actinoplanes derwentensis* |
| *Actinoplanes digitatis* |
| *Actinoplanes durhamensis* |
| *Actinoplanes ferrugineus* |
| *Actinoplanes globisporus* |
| *Actinoplanes humidus* |
| *Actinoplanes italicus* |
| *Actinoplanes liguriensis* |
| *Actinoplanes lobatus* |
| *Actinoplanes missouriensis* |
| *Actinoplanes palleronii* |
| *Actinoplanes philippinensis* |
| *Actinoplanes rectilineatus* |
| *Actinoplanes regularis* |
| *Actinoplanes teichomyceticus* |
| *Actinoplanes utahensis* |
| Actinopolyspora |
| *Actinopolyspora halophila* |
| *Actinopolyspora mortivallis* |
| Actinosynnema |
| *Actinosynnema mirum* |
| Actinotalea |
| *Actinotalea fermentans* |
| Aerococcus |
| *Aerococcus sanguinicola* |
| *Aerococcus urinae* |
| *Aerococcus urinaeequi* |
| *Aerococcus urinaehominis* |
| *Aerococcus viridans* |
| Aeromicrobium |
| *Aeromicrobium erythreum* |
| Aeromonas |
| *Aeromonas allosaccharophila* |
| *Aeromonas bestiarum* |
| *Aeromonas caviae* |
| *Aeromonas encheleia* |
| *Aeromonas enteropelogenes* |
| *Aeromonas eucrenophila* |
| *Aeromonas ichthiosmia* |
| *Aeromonas jandaei* |
| *Aeromonas media* |
| *Aeromonas popoffii* |
| *Aeromonas sobria* |
| *Aeromonas veronii* |
| Agrobacterium |
| *Agrobacterium gelatinovorum* |
| Agrococcus |
| *Agrococcus citreus* |
| *Agrococcus jenensis* |
| Agromonas |
| *Agromonas oligotrophica* |
| Agromyces |
| *Agromyces fucosus* |
| *Agromyces hippuratus* |
| *Agromyces luteolus* |
| *Agromyces mediolanus* |
| *Agromyces ramosus* |
| *Agromyces rhizospherae* |
| Akkermansia |
| *Akkermansia muciniphila* |
| Albidiferax |
| *Albidiferax ferrireducens* |
| Albidovulum |

TABLE 3-continued

| EXAMPLE BACTERIA |
|---|
| *Albidovulum inexpectatum* |
| Alcaligenes |
| *Alcaligenes denitrificans* |
| *Alcaligenes faecalis* |
| Alcanivorax |
| *Alcanivorax borkumensis* |
| *Alcanivorax jadensis* |
| Algicola |
| *Algicola bacteriolytica* |
| Alicyclobacillus |
| *Alicyclobacillus disulfidooxidans* |
| *Alicyclobacillus sendaiensis* |
| *Alicyclobacillus vulcanalis* |
| Alishewanella |
| *Alishewanella fetalis* |
| Alkalibacillus |
| *Alkalibacillus haloalkaliphilus* |
| Alkalilimnicola |
| *Alkalilimnicola ehrlichii* |
| Alkaliphilus |
| *Alkaliphilus oremlandii* |
| *Alkaliphilus transvaalensis* |
| Allochromatium |
| *Allochromatium vinosum* |
| Alloiococcus |
| *Alloiococcus otitis* |
| Allokutzneria |
| *Allokutzneria albata* |
| Altererythrobacter |
| *Altererythrobacter ishigakiensis* |
| Altermonas |
| *Altermonas haloplanktis* |
| *Altermonas macleodii* |
| Alysiella |
| *Alysiella crassa* |
| *Alysiella filiformis* |
| Aminobacter |
| *Aminobacter aganoensis* |
| *Aminobacter aminovorans* |
| *Aminobacter niigataensis* |
| Aminobacterium |
| *Aminobacterium mobile* |
| Aminomonas |
| *Aminomonas paucivorans* |
| Ammoniphilus |
| *Ammoniphilus oxalaticus* |
| *Ammoniphilus oxalivorans* |
| Amphibacillus |
| *Amphibacillus xylanus* |
| Amphritea |
| *Amphritea balenae* |
| *Amphritea japonica* |
| Amycolatopsis |
| *Amycolatopsis alba* |
| *Amycolatopsis albidoflavus* |
| *Amycolatopsis azurea* |
| *Amycolatopsis coloradensis* |
| *Amycolatopsis lurida* |
| *Amycolatopsis mediterranei* |
| *Amycolatopsis rifamycinica* |
| *Amycolatopsis rubida* |
| *Amycolatopsis sulphurea* |
| *Amycolatopsis tolypomycina* |
| Anabaena |
| *Anabaena cylindrica* |
| *Anabaena flos-aquae* |
| *Anabaena variabilis* |
| Anaeroarcus |
| *Anaeroarcus burkinensis* |
| Anaerobaculum |
| *Anaerobaculum mobile* |
| Anaerobiospirillum |
| *Anaerobiospirillum succiniciproducens* |
| *Anaerobiospirillum thomasii* |
| Anaerococcus |
| *Anaerococcus hydrogenalis* |
| *Anaerococcus lactolyticus* |
| *Anaerococcus prevotii* |

TABLE 3-continued

| EXAMPLE BACTERIA |
|---|
| *Anaerococcus tetradius* |
| *Anaerococcus vaginalis* |
| Anaerofustis |
| *Anaerofustis stercorihominis* |
| Anaeromusa |
| *Anaeromusa acidaminophila* |
| Anaeromyxobacter |
| *Anaeromyxobacter dehalogenans* |
| Anaerorhabdus |
| *Anaerorhabdus furcosa* |
| Anaerosinus |
| *Anaerosinus glycerini* |
| Anaerovirgula |
| *Anaerovirgula multivorans* |
| Ancalomicrobium |
| *Ancalomicrobium adetum* |
| Ancylobacter |
| *Ancylobacter aquaticus* |
| Aneurinibacillus |
| *Aneurinibacillus aneurinilyticus* |
| *Aneurinibacillus migulanus* |
| *Aneurinibacillus thermoaerophilus* |
| Angiococcus |
| *Angiococcus disciformis* |
| Angulomicroblum |
| *Angulomicrobium tetraedrale* |
| Anoxybacillus |
| *Anoxybacillus pushchinoensis* |
| Aquabacterium |
| *Aquabacterium commune* |
| *Aquabacterium parvum* |
| Aquaspirillum |
| *Aquaspirillum polymorphum* |
| *Aquaspirillum putridiconchylium* |
| *Aquaspirillum serpens* |
| Aquimarina |
| *Aquimarina latercula* |
| Arcanobacterium |
| *Arcanobacterium haemolyticum* |
| *Arcanobacterium pyogenes* |
| Archangium |
| *Archangium gephyra* |
| Arcobacter |
| *Arcobacter butzleri* |
| *Arcobacter cryaerophilus* |
| *Arcobacter halophilus* |
| *Arcobacter nitrofigilis* |
| *Arcobacter skirrowii* |
| Arhodomonas |
| *Arhodomonas aquacolei* |
| Arsenophonus |
| *Arsenophonus nasoniae* |
| Arthrobacter |
| *Arthrobacter agilis* |
| *Arthrobacter albus* |
| *Arthrobacter aurescens* |
| *Arthrobacter chlorophenolicus* |
| *Arthrobacter citreus* |
| *Arthrobacter crystallopoietes* |
| *Arthrobacter cumminsii* |
| *Arthrobacter globiformis* |
| *Arthrobacter histidinolovorans* |
| *Arthrobacter ilicis* |
| *Arthrobacter luteus* |
| *Arthrobacter methylotrophus* |
| *Arthrobacter mysorens* |
| *Arthrobacter nicotianae* |
| *Arthrobacter nicotinovorans* |
| *Arthrobacter oxydans* |
| *Arthrobacter pascens* |
| *Arthrobacter phenanthrenivorans* |
| *Arthrobacter polychromogenes* |
| *Atrhrobacter protophormiae* |
| *Arthrobacter psychrolactophilus* |
| *Arthrobacter ramosus* |
| *Arthrobacter sulfonivorans* |
| *Arthrobacter sulfureus* |
| *Arthrobacter uratoxydans* |

TABLE 3-continued

| EXAMPLE BACTERIA |
|---|
| *Arthrobacter ureafaciens* |
| *Arthrobacter viscosus* |
| *Arthrobacter woluwensis* |
| Asaia |
| *Asaia bogorensis* |
| Asanoa |
| *Asanoa ferruginea* |
| Asticcacaulis |
| *Asticcacaulis biprosthecium* |
| *Asticcacaulis excentricus* |
| Atopobacter |
| *Atopobacter phocae* |
| Atopobium |
| *Atopobium fossor* |
| *Atopobium minutum* |
| *Atopobium parvulum* |
| *Atopobium rimae* |
| *Atopobium vaginae* |
| Aureobacterium |
| *Aureobacterium barkeri* |
| Aurobacterium |
| *Aurobacterium liquefaciens* |
| Avibacterium |
| *Avibacterium avium* |
| *Avibacterium gallinarum* |
| *Avibacterium paragallinarum* |
| *Avibacterium volantium* |
| Azoarcus |
| *Azoarcus indigens* |
| *Azoarcus tolulyticus* |
| *Azoarcus toluvorans* |
| Azohydromonas |
| *Azohydromonas australica* |
| *Azohydromonas lata* |
| Azomonas |
| *Azomonas agilis* |
| *Azomonas insignis* |
| *Azomonas macrocytogenes* |
| Azorhizobium |
| *Azorhizobium caulinodans* |
| Azorhizophilus |
| *Azorhizophilus paspali* |
| Azospirillum |
| *Azospirillum brasilense* |
| *Azospirillum halopraeferens* |
| *Azospirillum irakense* |
| Azotobacter |
| *Azotobacter beijerinckii* |
| *Azotobacter chroococcum* |
| *Azotobacter nigricans* |
| *Azotobacter salinestris* |
| *Azotobacter vinelandii* |
| Bacteriovorax |
| *Bacteriovorax stolpii* |
| Bacteroides |
| *Bacteroides caccae* |
| *Bacteroides coagulans* |
| *Bacteroides eggerthii* |
| *Bacteroides fragilis* |
| *Bacteroides galacturonicus* |
| *Bacteroides helcogenes* |
| *Bacteroides ovatus* |
| *Bacteroides pectinophilus* |
| *Bacteroides pyogenes* |
| *Bacteroides salyersiae* |
| *Bacteroides stercoris* |
| *Bacteroides suis* |
| *Bacteroides tectus* |
| *Bacteroides thetaiotaomicron* |
| *Bacteroides uniformis* |
| *Bacteroides ureolyticus* |
| *Bacteroides vulgatus* |
| Balnearium |
| *Balnearium lithotrophicum* |
| Balneatrix |
| *Balneatrix alpica* |
| Balneola |
| *Balneola vulgaris* |

TABLE 3-continued

| EXAMPLE BACTERIA |
|---|
| Barnesiella |
| *Barnesiella viscericola* |
| Bartonella |
| *Bartonella alsatica* |
| *Bartonella bacilliformis* |
| *Bartonella clarridgeiae* |
| *Bartonella doshiae* |
| *Bartonella elizabethae* |
| *Bartonella grahamii* |
| *Bartonella henselae* |
| *Bartonella rochalimae* |
| *Bartonella vinsonii* |
| Bavarlicoccus |
| *Bavariicoccus seileri* |
| Bdellovibrio |
| *Bdellovibrio bacteriovorus* |
| *Bdellovibrio exovorus* |
| Beggiatoa |
| *Beggiatoa alba* |
| Beijerinckia |
| *Beijerinckia derxii* |
| *Beijerinckia fluminensis* |
| *Beijerinckia indica* |
| *Beijerinckia mobilis* |
| Belliella |
| *Belliella baltica* |
| Bellilinea |
| *Bellilinea caldifistulae* |
| Belnapia |
| *Belnapia moabensis* |
| Bergeriella |
| *Bergeriella denitrificans* |
| Beutenbergia |
| *Beutenbergia cavernae* |
| Bibersteinia |
| *Bibersteinia trehalosi* |
| Bifidobacterium |
| *Bifidobacterium adolescentis* |
| *Bifidobacterium angulatum* |
| *Bifidobacterium animalis* |
| *Bifidobacterium asteroides* |
| *Bifidobacterium bifidum* |
| *Bifidobacterium boum* |
| *Bifidobacterium breve* |
| *Bifidobacterium catenulatum* |
| *Bifidobacterium choerinum* |
| *Bifidobacterium coryneforme* |
| *Bifidobacterium cuniculi* |
| *Bifidobacterium dentium* |
| *Bifidobacterium gallicum* |
| *Bifidobacterium gallinarum* |
| *Bifidobacterium indicum* |
| *Bifidobacterium longum* |
| *Bifidobacterium magnum* |
| *Bifidobacterium merycicum* |
| *Bifidobacterium minimum* |
| *Bifidobacterium pseudocatenulatum* |
| *Bifidobacterium pseudolongum* |
| *Bifidobacterium pullorum* |
| *Bifidobacterium ruminantium* |
| *Bifidobacterium saeculare* |
| *Bifidobacterium subtile* |
| *Bifidobacterium thermophilum* |
| Bilophila |
| *Bilophila wadsworthia* |
| Biostraticola |
| *Biostraticola tofi* |
| Bizionia |
| *Bizionia argentinensis* |
| Blastobacter |
| *Blastobacter capsulatus* |
| *Blastobacter denitrificans* |
| Blastococcus |
| *Blastococcus aggregatus* |
| *Blastococcus saxobsidens* |
| Blastochloris |
| *Blastochloris viridis* |
| Blastomonas |

TABLE 3-continued

| EXAMPLE BACTERIA |
|---|
| *Blastomonas natatoria* |
| Blastopirellula |
| *Blastopirellula marina* |
| Blautia |
| *Blautia coccoides* |
| *Blautia hansenii* |
| *Blautia producta* |
| *Blautia wexlerae* |
| Bogoriella |
| *Bogoriella caseilytica* |
| Bordetella |
| *Bordetella avium* |
| *Bordetella bronchiseptica* |
| *Bordetella hinzii* |
| *Bordetella holmesii* |
| *Bordetella parapertussis* |
| *Bordetella pertussis* |
| *Bordetella petrii* |
| *Bordetella trematum* |
| Borrelia |
| *Borrelia afzelii* |
| *Borrelia americana* |
| *Borrelia burgdorferi* |
| *Borrelia carolinensis* |
| *Borrelia coriaceae* |
| *Borrelia garinii* |
| *Borrelia japonica* |
| Bosea |
| *Bosea minatitlanensis* |
| *Bosea thiooxidans* |
| Brachybacterium |
| *Brachybacterium alimentarium* |
| *Brachybacterium faecium* |
| *Brachybacterium paraconglomeratum* |
| *Brachybacterium rhamnosum* |
| *Brachybacterium tyrofermentans* |
| Brachyspira |
| *Brachyspira alvinipulli* |
| *Brachyspira hyodysenteriae* |
| *Brachyspira innocens* |
| *Brachyspira murdochii* |
| *Brachyspira pilosicoli* |
| *Bradyrhizobium canariense* |
| *Bradyrhizobium elkanii* |
| *Bradyrhizobium japonicum* |
| *Bradyrhizobium liaoningense* |
| Brenneria |
| *Brenneria alni* |
| *Brenneria nigrifluens* |
| *Brenneria quercina* |
| *Brenneria quercina* |
| *Brenneria salicis* |
| Brevibacillus |
| *Brevibacillus agri* |
| *Brevibacillus borstelensis* |
| *Brevibacillus brevis* |
| *Brevibacillus centrosporus* |
| *Brevibacillus choshinensis* |
| *Brevibacillus invocatus* |
| *Brevibacillus laterosporus* |
| *Brevibacillus parabrevis* |
| *Brevibacillus reuszeri* |
| Brevibacterium |
| *Brevibacterium abidum* |
| *Brevibacterium album* |
| *Brevibacterium aurantiacum* |
| *Brevibacterium celere* |
| *Brevibacterium epidermidis* |
| *Brevibacterium frigoritolerans* |
| *Brevibacterium halotolerans* |
| *Brevibacterium iodinum* |
| *Brevibacterium linens* |
| *Brevibacterium lyticum* |
| *Brevibacterium mcbrellneri* |
| *Brevibacterium otitidis* |
| *Brevibacterium oxydans* |
| *Brevibacterium paucivorans* |
| *Brevibacterium stationis* |

TABLE 3-continued

| EXAMPLE BACTERIA |
|---|
| Brevinema |
| *Brevinema andersonii* |
| Brevundimonas |
| *Brevundimonas alba* |
| *Brevundimonas aurantiaca* |
| *Brevundimonas diminuta* |
| *Brevundimonas intermedia* |
| *Brevundimonas subvibrioides* |
| *Brevundimonas vancanneytii* |
| *Brevundimonas variabilis* |
| *Brevundimonas vesicularis* |
| Brochothrix |
| *Brochothrix campestris* |
| *Brochothrix thermosphacta* |
| Brucella |
| *Brucella canis* |
| *Brucella neotomae* |
| Bryobacter |
| *Bryobacter aggregatus* |
| Burkholderia |
| *Burkholderia ambifaria* |
| *Burkholderia andropogonis* |
| *Burkholderia anthina* |
| *Burkholderia caledonica* |
| *Burkholderia caryophylli* |
| *Burkholderia cenocepacia* |
| *Burkholderia cepacia* |
| *Burkholderia cocovenenans* |
| *Burkholderia dolosa* |
| *Burkholderia fungorum* |
| *Burkholderia glathei* |
| *Burkholderia glumae* |
| *Burkholderia graminis* |
| *Burkholderia kururiensis* |
| *Burkholderia multivorans* |
| *Burkholderia phenazinium* |
| *Burkholderia plantarii* |
| *Burkholderia pyrrocinia* |
| *Burkholderia silvatlantica* |
| *Burkholderia stabilis* |
| *Burkholderia thailandensis* |
| *Burkholderia tropica* |
| *Burkholderia unamae* |
| *Burkholderia vietnamiensis* |
| Buttiauxella |
| *Buttiauxella agrestis* |
| *Buttiauxella brennerae* |
| *Buttiauxella ferragutiae* |
| *Buttiauxella gaviniae* |
| *Buttiauxella izardii* |
| *Buttiauxella noackiae* |
| *Buttiauxella warmboldiae* |
| Butyrivibrio |
| *Butyrivibrio fibrisolvens* |
| *Butyrivibrio hungatei* |
| *Butyrivibrio proteoclasticus* |
| Bacillus |
| *B. acidiceler* |
| *B. acidicola* |
| *B. acidiproducens* |
| *B. acidocaldarius* |
| *B. acidoterrestris* |
| *B. aeolius* |
| *B. aerius* |
| *B. aerophilus* |
| *B. agaradhaerens* |
| *B. agri* |
| *B. aidingensis* |
| *B. akibai* |
| *B. alcalophilus* |
| *B. algicola* |
| *B. alginolyticus* |
| *B. alkalidiazotrophicus* |
| *B. alkalinitrilicus* |
| *B. alkalisediminis* |
| *B. alkalitelluris* |
| *B. altitudinis* |
| *B. alveayuensis* |

TABLE 3-continued

| EXAMPLE BACTERIA |
|---|
| *B. alvei* |
| *B. amyloliquefaciens* |
| *B. a.* subsp. *Amyloliquefaciens* |
| *B. a.* subsp. *Plantarum* |
| *B. dipsosauri* |
| *B. drentensis* |
| *B. edaphicus* |
| *B. ehimensis* |
| *B. eiseniae* |
| *B. enclensis* |
| *B. endophyticus* |
| *B. endoradicis* |
| *B. farraginis* |
| *B. fastidiosus* |
| *B. fengqiuensis* |
| *B. firmus* |
| *B. flexus* |
| *B. foraminis* |
| *B. fordii* |
| *B. formosus* |
| *B. fortis* |
| *B. fumarioli* |
| *B, funiculus* |
| *B. fusiformis* |
| *B. galactophilus* |
| *B. galactosidilyticus* |
| *B. galliciensis* |
| *B. gelatini* |
| *B. gibsonii* |
| *B. ginsengi* |
| *B. ginsengihumi* |
| *B. ginsengisoli* |
| *B. globisporus* (eg, *B. g.* subsp. *Globisporus;* or *B. g.* subsp. *Marinus*) |
| *B. aminovorans* |
| *B. amylolyticus* |
| *B. andreesenii* |
| *B. aneurinilyticus* |
| *B. anthracis* |
| *B. aquimaris* |
| *B. arenosi* |
| *B. arseniciselenatis* |
| *B. arsenicus* |
| *B. aurantiacus* |
| *B. arvi* |
| *B. aryabhattai* |
| *B. asahii* |
| *B. atrophaeus* |
| *B. axarquiensis* |
| *B. azotofixans* |
| *B. azotoformans* |
| *B. badius* |
| *B. barbaricus* |
| *B. bataviensis* |
| *B. beijingensis* |
| *B. benzoevorans* |
| *B. beringensis* |
| *B. berkeleyi* |
| *B. beveridgei* |
| *B. bogoriensis* |
| *B. boroniphilus* |
| *B. borstelensis* |
| *B. brevis Migula* |
| *B. butanolivorans* |
| *B. canaveralius* |
| *B. carboniphilus* |
| *B. cecembensis* |
| *B. cellulosilyticus* |
| *B. centrosporus* |
| *B. cereus* |
| *B. chagannorensis* |
| *B. chitinolyticus* |
| *B. chondroitinus* |
| *B. choshinensis* |
| *B. chungangensis* |
| *B. cibi* |
| *B. circulans* |

TABLE 3-continued

| EXAMPLE BACTERIA |
|---|
| *B. clarkii* |
| *B. clausii* |
| *B. coagulans* |
| *B. coahuilensis* |
| *B. cohnii* |
| *B. composti* |
| *B. curdlanolyticus* |
| *B. cycloheptanicus* |
| *B. cytotoxicus* |
| *B. daliensis* |
| *B. decisifrondis* |
| *B. decolorationis* |
| *B. deserti* |
| *B. glucanolyticus* |
| *B. gordonae* |
| *B. gottheilii* |
| *B. graminis* |
| *B. halmapalus* |
| *B. haloalkaliphilus* |
| *B. halochares* |
| *B. halodenitrificans* |
| *B. halodurans* |
| *B. halophilus* |
| *B. halosaccharovorans* |
| *B. hemicellulosilyticus* |
| *B. hemicentroti* |
| *B. herbersteinensis* |
| *B. horikoshii* |
| *B. horneckiae* |
| *B. horti* |
| *B. huizhouensis* |
| *B. humi* |
| *B. hwajinpoensis* |
| *B. idriensis* |
| *B. indicus* |
| *B. infantis* |
| *B. infernus* |
| *B. insolitus* |
| *B. invictae* |
| *B. iranensis* |
| *B. isabeliae* |
| *B. isronensis* |
| *B. jeotgali* |
| *B. kaustophilus* |
| *B. kobensis* |
| *B. kochii* |
| *B. kokeshiiformis* |
| *B. koreensis* |
| *B. korlensis* |
| *B. kribbensis* |
| *B, krulwichiae* |
| *B. laevolacticus* |
| *B. larvae* |
| *B. laterosporus* |
| *B. salexigens* |
| *B. saliphilus* |
| *B. schlegelii* |
| *B. sediminis* |
| *B. selenatarsenatis* |
| *B. selenitireducens* |
| *B. seohaeanensis* |
| *B. shacheensis* |
| *B. shackletonii* |
| *B. siamensis* |
| *B. silvestris* |
| *B. simplex* |
| *B. siralis* |
| *B. smithii* |
| *B. soli* |
| *B. solimangrovi* |
| *B. solisalsi* |
| *B. songklensis* |
| *B. sonorensis* |
| *B. sphaericus* |
| *B. sporothermodurans* |
| *B. stearothermophilus* |
| *B. stratosphericus* |
| *B. subterraneus* |

TABLE 3-continued

| EXAMPLE BACTERIA |
| --- |
| *B. subtilis* (eg, *B. s.* subsp. *Inaquosorum; or B. s.* subsp. *Spizizeni;* or *B. s.* subsp. *Subtilis*) |
| *B. taeanensis* |
| *B. tequilensis* |
| *B. thermantarcticus* |
| *B. thermoaerophilus* |
| *B. thermoamylovorans* |
| *B. thermocatenulatus* |
| *B. thermocloacae* |
| *B. thermocopriae* |
| *B. thermodenitrificans* |
| *B. thermoglucosidasius* |
| *B. thermolactis* |
| *B. thermoleovorans* |
| *B. thermophilus* |
| *B. thermoruber* |
| *B. thermosphaericus* |
| *B. thiaminolyticus* |
| *B. thioparans* |
| *B. thuringiensis* |
| *B. tianshenii* |
| *B. trypoxylicola* |
| *B. tusciae* |
| *B. validus.* |
| *B. vallismortis* |
| *B. vedderi* |
| *B. velezensis* |
| *B. vietnamensis* |
| *B. vireti* |
| *B. vulcani* |
| *B. wakoensis* |
| *B. weihenstephanensis* |
| *B. xiamenensis* |
| *B. xiaoxiensis* |
| *B. zhanjiangensis* |
| *B. peoriae* |
| *B. persepolensis* |
| *B. persicus* |
| *B. pervagus* |
| *B. plakortidis* |
| *B. pocheonensis* |
| *B. polygoni* |
| *B. polymyxa* |
| *B. popilliae* |
| *B. pseudalcalophilus* |
| *B. pseudofirmus* |
| *B. pseudomycoides* |
| *B. psychrodurans* |
| *B. psychrophilus* |
| *B. psychrosaccharolyticus* |
| *B. psychrotolerans* |
| *B. pulvifaciens* |
| *B. pumilus* |
| *B. purgationiresistens* |
| *B. pycnus* |
| *B. qingdaonensis* |
| *B. qingshengii* |
| *B. reuszeri* |
| *B. rhizosphaerae* |
| *B. rigui* |
| *B. ruris* |
| *B. safensis* |
| *B. salarius* |
| *B. lautus* |
| *B. lehensis* |
| *B. lentimorbus* |
| *B. lentus* |
| *B. licheniformis* |
| *B. ligniniphilus* |
| *B. litoralis* |
| *B. locisalis* |
| *B. luciferensis* |
| *B. luteolus* |
| *B. luteus* |
| *B. macauensis* |
| *B. macerans* |

TABLE 3-continued

| EXAMPLE BACTERIA |
| --- |
| *B. macquariensis* |
| *B. macyae* |
| *B. malacitensis* |
| *B. mannanilyticus* |
| *B. marisflavi* |
| *B. marismortui* |
| *B. marmarensis* |
| *B. massiliensis* |
| *B. megaterium* |
| *B. mesonae* |
| *B. methanolicus* |
| *B. methylotrophicus* |
| *B. migulanus* |
| *B. mojavensis* |
| *B. mucilaginosus* |
| *B. muralis* |
| *B. murimartini* |
| *B. mycoides* |
| *B. naganoensis* |
| *B. nanhaiensis* |
| *B. nanhaiisediminis* |
| *B. nealsonii* |
| *B. neidei* |
| *B. neizhouensis* |
| *B. niabensis* |
| *B. niacini* |
| *B. novalis* |
| *B. oceanisediminis* |
| *B. odysseyi* |
| *B. okhensis* |
| *B. okuhidensis* |
| *B. oleronius* |
| *B. oryzaecorticis* |
| *B. oshimensis* |
| *B. pabuli* |
| *B. pakistanensis* |
| *B. pallidus* |
| *B. pallidus* |
| *B. panacisoli* |
| *B. panaciterrae* |
| *B. pantothenticus* |
| *B. parabrevis* |
| *B. paraflexus* |
| *B. pasteurii* |
| *B. patagoniensis* |
| Caenimonas |
| *Caenimonas koreensis* |
| Caldalkalibacillus |
| *Caldalkalibacillus uzonensis* |
| Caldanaerobacter |
| *Caldanaerobacter subterraneus* |
| Caldanaerobius |
| *Caldanaerobius fijiensis* |
| *Caldanaerobius polysaccharolyticus* |
| *Caldanaerobius zeae* |
| Caldanaerovirga |
| *Caldanaerovirga acetigignens* |
| Caldicellulosiruptor |
| *Caldicellulosiruptor bescii* |
| *Caldicellulosiruptor kristjanssonii* |
| *Caldicellulosiruptor owensensis* |
| Campylobacter |
| *Campylobacter coli* |
| *Campylobacter concisus* |
| *Campylobacter curvus* |
| *Campylobacter fetus* |
| *Campylobacter gracilis* |
| *Campylobacter helveticus* |
| *Campylobacter hominis* |
| *Campylobacter hyointestinalis* |
| *Campylobacter jejuni* |
| *Campylobacter lari* |
| *Campylobacter mucosalis* |
| *Campylobacter rectus* |
| *Campylobacter showae* |
| *Campylobacter sputorum* |
| *Campylobacter upsaliensis* |
| Capnocytophaga |

TABLE 3-continued

| EXAMPLE BACTERIA |
|---|
| *Capnocytophaga canimorsus* |
| *Capnocytophaga cynodegmi* |
| *Capnocytophaga gingivalis* |
| *Capnocytophaga granulosa* |
| *Capnocytophaga haemolytica* |
| *Capnocytophaga ochracea* |
| *Capnocytophaga sputigena* |
| Cardiobacterium |
| *Cardiobacterium hominis* |
| Carnimonas |
| *Carnimonas nigrificans* |
| Carnobacterium |
| *Carnobacterium alterfunditum* |
| *Carnobacterium divergens* |
| *Carnobacterium funditum* |
| *Carnobacterium gallinarum* |
| *Carnobacterium maltaromaticum* |
| *Carnobacterium mobile* |
| *Carnobacterium viridans* |
| Caryophanon |
| *Caryophanon latum* |
| *Caryophanon tenue* |
| Catellatospora |
| *Catellatospora citrea* |
| *Catellatospora methionotrophica* |
| Catenococcus |
| *Catenococcus thiocycli* |
| Catenuloplanes |
| *Catenuloplanes atrovinosus* |
| *Catenuloplanes castaneus* |
| *Catenuloplanes crispus* |
| *Catenuloplanes indicus* |
| *Catenuloplanes japonicus* |
| *Catenuloplanes nepalensis* |
| *Catenuloplanes niger* |
| Chryseobacterium |
| *Chryseobacterium balustinum* |
| Citrobacter |
| *C. amalonaticus* |
| *C. braakii* |
| *C. diversus* |
| *C. farmeri* |
| *C. freundii* |
| *C. gillenii* |
| *C. koseri* |
| *C. murliniae* |
| *C. pasteurii* |
| *C. rodentium* |
| *C. sedlakii* |
| *C. werkmanii* |
| *C. youngae* |
| Coccochloris |
| *Coccochloris elabens* |
| Corynebacterium |
| *Corynebacterium flavescens* |
| *Corynebacterium variabile* |
| Curtobacterium |
| *Curtobacterium albidum* |
| *Curtobacterium citreus* |
| Clostridium |
| *Clostridium absonum*, |
| *Clostridium aceticum*, |
| *Clostridium acetireducens*, |
| *Clostridium acetobutylicum*, |
| *Clostridium acidisoli*, |
| *Clostridium aciditolerans*, |
| *Clostridium acidurici*, |
| *Clostridium aerotolerans*, |
| *Clostridium aestuarii*, |
| *Clostridium akagii*, |
| *Clostridium aldenense*, |
| *Clostridium aldrichii*, |
| *Clostridium algidicarni*, |
| *Clostridium algidixylanolyticum*, |
| *Clostridium algifaecis*, |
| *Clostridium algoriphilum*, |
| *Clostridium alkalicellulosi*, |
| *Clostridium aminophilum*, |

TABLE 3-continued

| EXAMPLE BACTERIA |
|---|
| *Clostridium aminovalericum*, |
| *Clostridium amygdalinum*, |
| *Clostridium amylolyticum*, |
| *Clostridium arbusti*, |
| *Clostridium arcticum*, |
| *Clostridium argentinense*, |
| *Clostridium asparagiforme*, |
| *Clostridium aurantibutyricum*, |
| *Clostridium autoethanogenum*, |
| *Clostridium baratii*, |
| *Clostridium barkeri*, |
| *Clostridium bartlettii*, |
| *Clostridium beijerinckii*, |
| *Clostridium bifermentans*, |
| *Clostridium bolteae*, |
| *Clostridium bornimense*, |
| *Clostridium botulinum*, |
| *Clostridium bowmanii*, |
| *Clostridium bryantii*, |
| *Clostridium butyricum*, |
| *Clostridium cadaveris*, |
| *Clostridium caenicola*, |
| *Clostridium caminithermale*, |
| *Clostridium carboxidivorans*, |
| *Clostridium carnis*, |
| *Clostridium cavendishii*, |
| *Clostridium celatum*, |
| *Clostridium celerecrescens*, |
| *Clostridium cellobioparum*, |
| *Clostridium cellulofermentans*, |
| *Clostridium cellulolyticum*, |
| *Clostridium cellulosi*, |
| *Clostridium cellulovorans*, |
| *Clostridium chartatabidum*, |
| *Clostridium chauvoei*, |
| *Clostridium chromiireducens*, |
| *Clostridium citroniae*, |
| *Clostridium clariflavum*, |
| *Clostridium clostridioforme*, |
| *Clostridium coccoides*, |
| *Clostridium cochlearium*, |
| *Clostridium colletant*, |
| *Clostridium colicanis*, |
| *Clostridium colinum*, |
| *Clostridium collagenovorans*, |
| *Clostridium cylindrosporum*, |
| *Clostridium difficile*, |
| *Clostridium diolis*, |
| *Clostridium disporicum*, |
| *Clostridium drakei*, |
| *Clostridium durum*, |
| *Clostridium estertheticum*, |
| *Clostridium estertheticum estertheticum*, |
| *Clostridium estertheticum laramiense*, |
| *Clostridium fallax*, |
| *Clostridium felsineum*, |
| *Clostridium fervidum*, |
| *Clostridium fimetarium*, |
| *Clostridium formicaceticum*, |
| *Clostridium frigidicarnis*, |
| *Clostridium frigoris*, |
| *Clostridium ganghwense*, |
| *Clostridium gasigenes*, |
| *Clostridium ghonii*, |
| *Clostridium glycolicum*, |
| *Clostridium glycyrrhizinilyticum*, |
| *Clostridium grantii*, |
| *Clostridium haemolyticum*, |
| *Clostridium halophilum*, |
| *Clostridium hastiforme*, |
| *Clostridium hathewayi*, |
| *Clostridium herbivorans*, |
| *Clostridium hiranonis*, |
| *Clostridium histolyticum*, |
| *Clostridium homopropionicum*, |
| *Clostridium huakuii*, |
| *Clostridium hungatei*, |
| *Clostridium hydrogeniformans*, |

TABLE 3-continued

| EXAMPLE BACTERIA |
| --- |
| *Clostridium hydroxybenzoicum*, |
| *Clostridium hylemonae*, |
| *Clostridium jejuense*, |
| *Clostridium indolis*, |
| *Clostridium innocuum*, |
| *Clostridium intestinale*, |
| *Clostridium irregulare*, |
| *Clostridium isatidis*, |
| *Clostridium josui*, |
| *Clostridium kluyveri*, |
| *Clostridium lactatifermentans*, |
| *Clostridium lacusfryxellense*, |
| *Clostridium laramiense*, |
| *Clostridium lavalense*, |
| *Clostridium lentocellum*, |
| *Clostridium lentoputrescens*, |
| *Clostridium leptum*, |
| *Clostridium limosum*, |
| *Clostridium litorale*, |
| *Clostridium lituseburense*, |
| *Clostridium ljungdahlii*, |
| *Clostridium lortetii*, |
| *Clostridium lundense*, |
| *Clostridium magnum*, |
| *Clostridium malenominatum*, |
| *Clostridium mangenotii*, |
| *Clostridium mayombei*, |
| *Clostridium methoxybenzovorans*, |
| *Clostridium methylpentosum*, |
| *Clostridium neopropionicum*, |
| *Clostridium nexile*, |
| *Clostridium nitrophenolicum*, |
| *Clostridium novyi*, |
| *Clostridium oceanicum*, |
| *Clostridium orbiscindens*, |
| *Clostridium oroticum*, |
| *Clostridium oxalicum*, |
| *Clostridium papyrosolvens*, |
| *Clostridium paradoxum*, |
| *Clostridium paraperfringens* (Alias: *C. welchii*), |
| *Clostridium paraputrificum*, |
| *Clostridium pascui*, |
| *Clostridium pasteurianum*, |
| *Clostridium peptidivorans*, |
| *Clostridium perenne*, |
| *Clostridium perfringens*, |
| *Clostridium pfennigii*, |
| *Clostridium phytofermentans*, |
| *Clostridium piliforme*, |
| *Clostridium polysaccharolyticum*, |
| *Clostridium populeti*, |
| *Clostridium propionicum*, |
| *Clostridium proteoclasticum*, |
| *Clostridium proteolyticum*, |
| *Clostridium psychrophilum*, |
| *Clostridium puniceum*, |
| *Clostridium purinilyticum*, |
| *Clostridium putrefaciens*, |
| *Clostridium putrificum*, |
| *Clostridium quercicolum*, |
| *Clostridium quinii*, |
| *Clostridium ramosum*, |
| *Clostridium rectum*, |
| *Clostridium roseum*, |
| *Clostridium saccharobutylicum*, |
| *Clostridium saccharogumia*, |
| *Clostridium saccharolyticum*, |
| *Clostridium saccharoperbutylacetonicum* |
| *Clostridium sardiniense*, |
| *Clostridium sartagoforme*, |
| *Clostridium scatologenes*, |
| *Clostridium schirmacherense*, |
| *Clostridium scindens*, |
| *Clostridium septicum*, |
| *Clostridium sordellii*, |
| *Clostridium sphenoides*, |
| *Clostridium spiroforme*, |

TABLE 3-continued

| EXAMPLE BACTERIA |
| --- |
| *Clostridium sporogenes*, |
| *Clostridium sporosphaeroides*, |
| *Clostridium stercorarium*, |
| *Clostridium stercorarium leptospartum*, |
| *Clostridium stercorarium stercorarium*, |
| *Clostridium stercorarium thermolacticum*, |
| *Clostridium sticklandii*, |
| *Clostridium straminisolvens*, |
| *Clostridium subterminale*, |
| *Clostridium sufflavum*, |
| *Clostridium sulfidigenes*, |
| *Clostridium symbiosum*, |
| *Clostridium tagluense*, |
| *Clostridium tepidiprofundi*, |
| *Clostridium termitidis*, |
| *Clostridium tertium*, |
| *Clostridium tetani*, |
| *Clostridium tetanomorphum*, |
| *Clostridium thermaceticum*, |
| *Clostridium thermautotrophicum*, |
| *Clostridium thermoalcaliphilum*, |
| *Clostridium thermobutyricum*, |
| *Clostridium thermocellum*, |
| *Clostridium thermocopriae*, |
| *Clostridium thermohydrosulfuricum*, |
| *Clostridium thermolacticum*, |
| *Clostridium thermopalmarium*, |
| *Clostridium thermopapyrolyticum*, |
| *Clostridium thermosaccharolyticum*, |
| *Clostridium thermosuccinogenes*, |
| *Clostridium thermosulfurigenes*, |
| *Clostridium thiosulfatireducens*, |
| *Clostridium tyrobutyricum*, |
| *Clostridium uliginosum*, |
| *Clostridium ultunense*, |
| *Clostridium villosum*, |
| *Clostridium vincentii*, |
| *Clostridium viride*, |
| *Clostridium xylanolyticum*, |
| *Clostridium xylanovorans* |
| Dactylosporangium |
| *Dactylosporangium aurantiacum* |
| *Dactylosporangium fulvum* |
| *Dactylosporangium matsuzakiense* |
| *Dactylosporangium roseum* |
| *Dactylosporangium thailandense* |
| *Dactylosporangium vinaceum* |
| Deinococcus |
| *Deinococcus aerius* |
| *Deinococcus apachensis* |
| *Deinococcus aquaticus* |
| *Deinococcus aquatilis* |
| *Deinococcus caeni* |
| *Deinococcus radiodurans* |
| *Deinococcus radiophilus* |
| Delftia |
| *Delftia acidovorans* |
| Desulfovibrio |
| *Desulfovibrio desulfuricans* |
| Diplococcus |
| *Diplococcus pneumoniae* |
| Echinicola |
| *Echinicola pacifica* |
| *Echinicola vietnamensis* |
| Enterobacter |
| *E. aerogenes* |
| *E. amnigenus* |
| *E. agglomerans* |
| *E. arachidis* |
| *E. asburiae* |
| *E. cancerogenous* |
| *E. cloacae* |
| *E. cowanii* |
| *E. dissolvens* |
| *E. gergoviae* |
| *E. helveticus* |
| *E. hormaechei* |
| *E. intermedius* |

TABLE 3-continued

| EXAMPLE BACTERIA |
| --- |
| *Enterobacter kobei* |
| *E. ludwigii* |
| *E. mori* |
| *E. nimipressuralis* |
| *E. oryzae* |
| *E. pulveris* |
| *E. pyrinus* |
| *E. radicincitans* |
| *E. taylorae* |
| *E. turicensis* |
| *E. sakazakii* |
| *Enterobacter soli* |
| Enterococcus |
| *Enterococcus durans* |
| *Enterococcus faecalis* |
| *Enterococcus faecium* |
| Erwinia |
| *Erwinia hapontici* |
| Escherichia |
| *Escherichia coli* |
| Faecalibacterium |
| *Faecalibacterium prausnitzii* |
| Fangia |
| *Fangia hongkongensis* |
| Fastidiosipila |
| *Fastidiosipila sanguinis* |
| Fusobacterium |
| *Fusobacterium nucleatum* |
| Flavobacterium |
| *Flavobacterium antarcticum* |
| *Flavobacterium aquatile* |
| *Flavobacterium aquidurense* |
| *Flavobacterium balustinum* |
| *Flavobacterium croceum* |
| *Flavobacterium cucumis* |
| *Flavobacterium daejeonense* |
| *Flavobacterium defluvii* |
| *Flavobacterium degerlachei* |
| *Flavobacterium denitrificans* |
| *Flavobacterium filum* |
| *Flavobacterium flevense* |
| *Flavobacterium frigidarium* |
| *Flavobacterium mizutail* |
| *Flavobacterium okeanokoites* |
| Gaetbulibacter |
| *Gaetbulibacter saemankumensis* |
| Gallibacterium |
| *Gallibacterium anatis* |
| Gallicola |
| *Gallicola barnesae* |
| Garciella |
| *Garciella nitratireducens* |
| Geobacillus |
| *Geobacillus thermoglucosidasius* |
| *Geobacillus stearothermophilus* |
| Geobacter |
| *Geobacter bemidjiensis* |
| *Geobacter bremensis* |
| *Geobacter chapellei* |
| *Geobacter grbiciae* |
| *Geobacter hydrogenophilus* |
| *Geobacter lovleyi* |
| *Geobacter metallireducens* |
| *Geobacter pelophilus* |
| *Geobacter pickeringii* |
| *Geobacter sulfurreducens* |
| Geodermatophilus |
| *Geodermatophilus obscurus* |
| Gluconacetobacter |
| *Gluconacetobacter xylinus* |
| Gordonia |
| *Gordonia rubripertincta* |
| Haemophilus |
| *Haemophilus aegyptius* |
| *Haemophilus aphrophilus* |
| *Haemophilus felis* |
| *Haemophilus gallinarum* |
| *Haemophilus haemolyticus* |

TABLE 3-continued

| EXAMPLE BACTERIA |
| --- |
| *Haemophilus influenzae* |
| *Haemophilus paracuniculus* |
| *Haemophilus parahaemolyticus* |
| *Haemophilus parainfluenzae* |
| *Haemophilus paraphrohaemolyticus* |
| *Haemophilus parasuis* |
| *Haemophilus pittmaniae* |
| Hafnia |
| *Hafnia alvei* |
| Hahella |
| *Hahella ganghwensis* |
| Halalkalibacillus |
| *Halalkalibacillus halophilus* |
| Helicobacter |
| *Helicobacter pylori* |
| Ideonella |
| *Ideonella azotifigens* |
| Idiomarina |
| *Idiomarina abyssalis* |
| *Idiomarina baltica* |
| *Idiomarina fontislapidosi* |
| *Idiomarina loihiensis* |
| *Idiomarina ramblicola* |
| *Idiomarina seosinensis* |
| *Idiomarina zobellii* |
| Ignatzschineria |
| *Ignatzschineria larvae* |
| Ignavigranum |
| *Ignavigranum ruoffiae* |
| Ilumatobacter |
| *Ilumatobacter fluminis* |
| Ilyobacter |
| *Ilyobacter delafieldii* |
| *Ilyobacter insuetus* |
| *Ilyobacter polytropus* |
| *Ilyobacter tartaricus* |
| Janibacter |
| *Janibacter anophelis* |
| *Janibacter corallicola* |
| *Janibacter limosus* |
| *Janibacter melonis* |
| *Janibacter terrae* |
| Jannaschia |
| *Jannaschia cystaugens* |
| *Jannaschia helgolandensis* |
| *Jannaschia pohangensis* |
| *Jannaschia rubra* |
| Janthinobacterium |
| *Janthinobacterium agaricidamnosum* |
| *Janthinobacterium lividum* |
| Jejuia |
| *Jejuia pallidilutea* |
| Jeotgalibacillus |
| *Jeotgalibacillus alimentarius* |
| Jeotgalicoccus |
| *Jeotgalicoccus halotolerans* |
| Kaistia |
| *Kaistia adipata* |
| *Kaistia soli* |
| Kangiella |
| *Kangiella aquimarina* |
| *Kangiella koreensis* |
| Kerstersia |
| *Kerstersia gyiorum* |
| Kiloniella |
| *Kiloniella laminariae* |
| Klebsiella |
| *K. granulomatis* |
| *K. oxytoca* |
| *K. pneumoniae* |
| *K. terrigena* |
| *K. variicola* |
| Kluyvera |
| *Kluyvera ascorbata* |
| Kocuria |
| *Kocuria roasea* |
| *Kocuria varians* |
| Kurthia |

TABLE 3-continued

| EXAMPLE BACTERIA |
|---|
| *Kurthia zopfii* |
| Labedella |
| *Labedella gwakjiensis* |
| Labrenzia |
| *Labrenzia aggregata* |
| *Labrenzia alba* |
| *Labrenzia alexandrii* |
| *Labrenzia marina* |
| Labrys |
| *Labrys methylaminiphilus* |
| *Labrys miyagiensis* |
| *Labrys monachus* |
| *Labrys okinawensis* |
| *Labrys portucalensis* |
| Laceyella |
| *Laceyella putida* |
| Lechevalieria |
| *Lechevalieria aerocolonigenes* |
| Listeria |
| *L. aquatica* |
| *L. booriae* |
| *L. cornellensis* |
| *L. fleischmannii* |
| *L. floridensis* |
| *L. grandensis* |
| *L. grayi* |
| *L. innocua* |
| *Listeria ivanovii* |
| *L. marthii* |
| *L. monocytogenes* |
| *L. newyorkensis* |
| *L. riparia* |
| *L. rocourtiae* |
| *L. seeligeri* |
| *L. weihenstephanensis* |
| *L. welshimeri* |
| Listonella |
| *Listonella anguillarum* |
| Macrococcus |
| *Macrococcus bovicus* |
| Marinobacter |
| *Marinobacter algicola* |
| *Marinobacter bryozoorum* |
| *Marinobacter flavimaris* |
| Meiothermus |
| *Melothermus ruber* |
| Methylophilus |
| *Methylophilus methylotrophus* |
| Microbacterium |
| *Microbacterium ammoniaphilum* |
| *Microbacterium arborescens* |
| *Microbacterium liquefaciens* |
| *Microbacterium oxydans* |
| Micrococcus |
| *Micrococcus luteus* |
| *Micrococcus lylae* |
| Moraxella |
| *Moraxella bovis* |
| *Moraxella nonliquefaciens* |
| *Moraxella osloensis* |
| Nakamurella |
| *Nakamurella mulipartita* |
| Nannocystis |
| *Nannocystis pusilla* |
| Natranaerobius |
| *Natranaerobius thermophilus* |
| *Natranaerobius trueperi* |
| Naxibacter |
| *Naxibacter alkalitolerans* |
| Neisseria |
| *Neisseria cinerea* |
| *Neisseria denitrificans* |
| *Neisseria gonorrhoeae* |
| *Neisseria lactamica* |
| *Neisseria mucosa* |
| *Neisseria sicca* |
| *Neisseria subflava* |
| Neptunomonas |

TABLE 3-continued

| EXAMPLE BACTERIA |
|---|
| *Neptunomonas japonica* |
| Nesterenkonia |
| *Nesterenkonia holobia* |
| Nocardia |
| *Nocardia argentinensis* |
| *Nocardia corallina* |
| *Nocardia otitidiscaviarum* |
| Lactobacillus |
| *L. acetotolerans* |
| *L. acidifarinae* |
| *L. acidipiscis* |
| *L. acidophilus* |
| *Lactobacillus agilis* |
| *L. algidus* |
| *L. alimentarius* |
| *L. amylolyticus* |
| *L. amylophilus* |
| *L. amylotrophicus* |
| *L. amylovorus* |
| *L. animalis* |
| *L. antri* |
| *L. apodemi* |
| *L. aviarius* |
| *L. bifermentans* |
| *L. brevis* |
| *L. buchneri* |
| *L. camelliae* |
| *L. casei* |
| *L. kitasatonis* |
| *L. kunkeei* |
| *L. leichmannii* |
| *L. lindneri* |
| *L. malefermentans* |
| *L. catenaformis* |
| *L. ceti* |
| *L. coleohominis* |
| *L. collinoides* |
| *L. composti* |
| *L. concavus* |
| *L. coryniformis* |
| *L. crispatus* |
| *L. crustorum* |
| *L. curvatus* |
| *L. delbrueckii* subsp. *Bulgaricus* |
| *L. delbrueckii* subsp. *Delbrueckii* |
| *L. delbrueckii* subsp. *Lactis* |
| *L. dextrinicus* |
| *L. diolivorans* |
| *L. equi* |
| *L. equigenerosi* |
| *L. farraginis* |
| *L. farciminis* |
| *L. fermentum* |
| *L. fornicalis* |
| *L. fructivorans* |
| *L. frumenti* |
| *L. mali* |
| *L. manihotivorans* |
| *L. mindensis* |
| *L. mucosae* |
| *L. murinus* |
| *L. nagelii* |
| *L. namurensis* |
| *L. nantensis* |
| *L. oligofermentans* |
| *L. oris* |
| *L. panis* |
| *L. pantheris* |
| *L. parabrevis* |
| *L. parabuchneri* |
| *L. paracasei* |
| *L. paracollinoides* |
| *L. parafarraginis* |
| *L. homohiochii* |
| *L. iners* |
| *L. ingluviei* |
| *L. intestinalis* |
| *L. fuchuensis* |

TABLE 3-continued

| EXAMPLE BACTERIA |
|---|
| *L. gallinarum* |
| *L. gasseri* |
| *L. parakefiri* |
| *L. paralimentarius* |
| *L. paraplantarum* |
| *L. pentosus* |
| *L. perolens* |
| *L. plantarum* |
| *L. pontis* |
| *L. protectus* |
| *L. psittaci* |
| *L. rennini* |
| *L. reuteri* |
| *L. rhamnosus* |
| *L. rimae* |
| *L. rogosae* |
| *L. rossiae* |
| *L. ruminis* |
| *L. saerimneri* |
| *L. jensenii* |
| *L. johnsonii* |
| *L. kalixensis* |
| *L. kefiranofaciens* |
| *L. kefiri* |
| *L. aviarius* |
| *L. helveticus* |
| *L. hilgardii* |
| *L. sakei* |
| *L. salivarius* |
| *L. sanfranciscensis* |
| *L. satsumensis* |
| *L. secaliphilus* |
| *L. sharpeae* |
| *L. siliginis* |
| *L. spicheri* |
| *L. suebicus* |
| *L. thailandensis* |
| *L. ultunensis* |
| *L. vaccinostercus* |
| *L. vaginalis* |
| *L. versmoldensis* |
| *L. vini* |
| *L. vitulinus* |
| *L. zeae* |
| *L. zymae* |
| *L. gastricus* |
| *L. ghanensis* |
| *L. graminis* |
| *L. hammesii* |
| *L. hamsteri* |
| *L. harbinensis* |
| *L. hayakitensis* |
| Legionella |
| *Legionella adelaidensis* |
| *Legionella anisa* |
| *Legionella beliardensis* |
| *Legionella birminghamensis* |
| *Legionella bozemanae* |
| *Legionella brunensis* |
| *Legionella busanensis* |
| *Legionella cardiaca* |
| *Legionella cherrii* |
| *Legionella cincinnatiensis* |
| *Legionella clemsonensis* |
| *Legionella donaldsonii* |
| *Legionella drancourtii* |
| *Legionella dresdenensis* |
| *Legionella drozanskii* |
| *Legionella dumoffii* |
| *Legionella erythra* |
| *Legionella fairfieldensis* |
| *Legionella fallonii* |
| *Legionella feeleii* |
| *Legionella geestiana* |
| *Legionella genomospecies* |
| *Legionella gormanii* |
| *Legionella gratiana* |
| *Legionella gresilensis* |

TABLE 3-continued

| EXAMPLE BACTERIA |
|---|
| *Legionella hackeliae* |
| *Legionella impletisoli* |
| *Legionella israelensis* |
| *Legionella jamestowniensis Candidatus* |
| *Legionella jeonii* |
| *Legionella jordanis* |
| *Legionella lansingensis* |
| *Legionella londiniensis* |
| *Legionella longbeachae* |
| *Legionella lytica* |
| *Legionella maceachernii* |
| *Legionella massiliensis* |
| *Legionella micdadei* |
| *Legionella monrovica* |
| *Legionella moravica* |
| *Legionella nagasakiensis* |
| *Legionella nautarum* |
| *Legionella norrlandica* |
| *Legionella oakridgensis* |
| *Legionella parisiensis* |
| *Legionella pittsburghensis* |
| *Legionella pneumophila* |
| *Legionella quateirensis* |
| *Legionella quinlivanii* |
| *Legionella rowbothamii* |
| *Legionella rubrilucens* |
| *Legionella sainthelensi* |
| *Legionella santicrucis* |
| *Legionella shakespearei* |
| *Legionella spiritensis* |
| *Legionella steelei* |
| *Legionella steigerwaltii* |
| *Legionella taurinensis* |
| *Legionella tucsonensis* |
| *Legionella tunisiensis* |
| *Legionella wadsworthii* |
| *Legionella waltersii* |
| *Legionella worsleiensis* |
| *Legionella yabuuchiae* |
| Oceanibulbus |
| *Oceanibulbus indolifex* |
| Oceanicaulis |
| *Oceanicaulis alexandrii* |
| Oceanicola |
| *Oceanicola batsensis* |
| *Oceanicola granulosus* |
| *Oceanicola nanhaiensis* |
| Oceanimonas |
| *Oceanimonas baumannii* |
| Oceaniserpentilla |
| *Oceaniserpentilla haliotis* |
| Oceanisphaera |
| *Oceanisphaera donghaensis* |
| *Oceanisphaera litoralis* |
| Oceanithermus |
| *Oceanithermus desulfurans* |
| *Oceanithermus profundus* |
| Oceanobacillus |
| *Oceanobacillus caeni* |
| Oceanospirillum |
| *Oceanospirillum linum* |
| Paenibacillus |
| *Paenibacillus thiaminolyticus* |
| Pantoea |
| *Pantoea agglomerans* |
| Paracoccus |
| *Paracoccus alcaliphilus* |
| Paucimonas |
| *Paucimonas lemoignei* |
| Pectobacterium |
| *Pectobacterium aroidearum* |
| *Pectobacterium atrosepticum* |
| *Pectobacterium betavasculorum* |
| *Pectobacterium cacticida* |
| *Pectobacterium carnegieana* |
| *Pectobacterium carotovorum* |
| *Pectobacterium chrysanthemi* |
| *Pectobacterium cypripedii* |

TABLE 3-continued

| EXAMPLE BACTERIA |
|---|
| *Pectobacterium rhapontici* |
| *Pectobacterium wasabiae* |
| Planococcus |
| *Planococcus citreus* |
| Planomicrobium |
| *Planomicrobium okeanokoites* |
| Plesiomonas |
| *Plesiomonas shigelloides* |
| Proteus |
| *Proteus vulgaris* |
| Prevotella |
| *Prevotella albensis* |
| *Prevotella amnii* |
| *Prevotella bergensis* |
| *Prevotella bivia* |
| *Prevotella brevis* |
| *Prevotella bryantii* |
| *Prevotella buccae* |
| *Prevotella buccalis* |
| *Prevotella copri* |
| *Prevotella dentalis* |
| *Prevotella denticola* |
| *Prevotella disiens* |
| *Prevotella histicola* |
| *Prevotella intermedia* |
| *Prevotella maculosa* |
| *Prevotella marshii* |
| *Prevotella melaninogenica* |
| *Prevotella micans* |
| *Prevotella multiformis* |
| *Prevotella nigrescens* |
| *Prevotella oralis* |
| *Prevotella oris* |
| *Prevotella oulorum* |
| *Prevotella pallens* |
| *Prevotella salivae* |
| *Prevotella stercorea* |
| *Prevotella tannerae* |
| *Prevotella timonensis* |
| *Prevotella veroralis* |
| Providencia |
| *Providencia stuartii* |
| Pseudomonas |
| *Pseudomonas aeruginosa* |
| *Pseudomonas alcaligenes* |
| *Pseudomonas anguillispetica* |
| *Pseudomonas fluorescens* |
| *Pseudoalteromonas haloplanktis* |
| *Pseudomonas mendocina* |
| *Pseudomonas pseudoalcaligenes* |
| *Pseudomonas putida* |
| *Pseudomonas tutzeri* |
| *Pseudomonas syringae* |
| Psychrobacter |
| *Psychrobacter faecalis* |
| *Psychrobacter phenylpyruvicus* |
| Quadrisphaera |
| *Quadrisphaera granulorum* |
| Quatrionicoccus |
| *Quatrionicoccus australiensis* |
| Quinella |
| *Quinella ovalis* |
| Ralstonia |
| *Ralstonia eutropha* |
| *Ralstonia insidiosa* |
| *Ralstonia mannitolilytica* |
| *Ralstonia pickettil* |
| *Ralstonia pseudosolanacearum* |
| *Ralstonia syzygii* |
| *Ralstonia solanacearum* |
| Ramlibacter |
| *Ramlibacter henchirensis* |
| *Ramlibacter tataouinensis* |
| Raoultella |
| *Raoultella ornithinolytica* |
| *Raoultella planticola* |
| *Raoultella terrigena* |
| Rathayibacter |

TABLE 3-continued

| EXAMPLE BACTERIA |
|---|
| *Rathayibacter caricis* |
| *Rathayibacter festucae* |
| *Rathayibacter iranicus* |
| *Rathayibacter rathayi* |
| *Rathayibacter toxicus* |
| *Rathayibacter tritici* |
| Rhodobacter |
| *Rhodobacter sphaeroides* |
| Ruegeria |
| *Ruegeria gelatinovorans* |
| Saccharococcus |
| *Saccharococcus thermophilus* |
| Saccharomonospora |
| *Saccharomonospora azurea* |
| *Saccharomonospora cyanea* |
| *Saccharomonospora viridis* |
| Saccharophagus |
| *Saccharophagus degradans* |
| Saccharopolyspora |
| *Saccharopolyspora erythraea* |
| *Saccharopolyspora gregorii* |
| *Saccharopolyspora hirsuta* |
| *Saccharopolyspora hordei* |
| *Saccharopolyspora rectivirgula* |
| *Saccharopolyspora spinosa* |
| *Saccharopolyspora taberi* |
| Saccharothrix |
| *Saccharothrix australiensis* |
| *Saccharothrix coeruleofusca* |
| *Saccharothrix espanaensis* |
| *Saccharothrix longispora* |
| *Saccharothrix mutabilis* |
| *Saccharothrix syringae* |
| *Saccharothrix tangerinus* |
| *Saccharothrix texasensis* |
| Sagittula |
| *Sagittula stellata* |
| Salegentibacter |
| *Salegentibacter salegens* |
| Salimicrobium |
| *Salimicrobium album* |
| Salinibacter |
| *Salinibacter ruber* |
| Salinicoccus |
| *Salinicoccus alkaliphilus* |
| *Salinicoccus hispanicus* |
| *Salinicoccus roseus* |
| Salinispora |
| *Salinispora arenicola* |
| *Salinispora tropica* |
| Salinivibrio |
| *Salinivibrio costicola* |
| Salmonella |
| *Salmonella bongori* |
| *Salmonella enterica* |
| *Salmonella subterranea* |
| *Salmonella typhi* |
| Sanguibacter |
| *Sanguibacter keddieii* |
| *Sanguibacter suarezii* |
| Saprospira |
| *Saprospira grandis* |
| Sarcina |
| *Sarcina maxima* |
| *Sarcina ventriculi* |
| Sebaldella |
| *Sebaldella termitidis* |
| Serratia |
| *Serratia fonticola* |
| *Serratia marcescens* |
| Sphaerotilus |
| *Sphaerotilus natans* |
| Sphingobacterium |
| *Sphingobacterium multivorum* |
| Stenotrophomonas |
| *Stenotrophomonas maltophilia* |
| Streptomyces |
| *Streptomyces achromogenes* |

TABLE 3-continued

| EXAMPLE BACTERIA |
| --- |
| *Streptomyces cesalbus* |
| *Streptomyces cescaepitosus* |
| *Streptomyces cesdiastaticus* |
| *Streptomyces cesexfoliatus* |
| *Streptomyces fimbriatus* |
| *Streptomyces fradiae* |
| *Streptomyces fulvissimus* |
| *Streptomyces griseoruber* |
| *Streptomyces griseus* |
| *Streptomyces lavendulae* |
| *Streptomyces phaeochromogenes* |
| *Streptomyces thermodiastaticus* |
| *Streptomyces tubercidicus* |
| Tatlockia |
| *Tatlockia maceachernii* |
| *Tatlockia micdadei* |
| Tenacibaculum |
| *Tenacibaculum amylolyticum* |
| *Tenacibaculum discolor* |
| *Tenacibaculum gallaicum* |
| *Tenacibaculum lutimaris* |
| *Tenacibaculum mesophilum* |
| *Tenacibaculum skagerrakense* |
| Tepidanaerobacter |
| *Tepidanaerobacter syntrophicus* |
| Tepidibacter |
| *Tepidibacter formicigenes* |
| *Tepidibacter thalassicus* |
| Thermus |
| *Thermus aquaticus* |
| *Thermus filiformis* |
| *Thermus thermophilus* |
| Staphylococcus |
| *S. arlettae* |
| *S. agnetis* |
| *S. aureus* |
| *S. auricularis* |
| *S. capitis* |
| *S. caprae* |
| *S. carnosus* |
| *S. caseolyticus* |
| *S. chromogenes* |
| *S. cohnii* |
| *S. condimenti* |
| *S. delphini* |
| *S. devriesei* |
| *S. epidermidis* |
| *S. equorum* |
| *S. felis* |
| *S. fleurettii* |
| *S. gallinarum* |
| *S. haemolyticus* |
| *S. hominis* |
| *S. hyicus* |
| *S. intermedius* |
| *S. kloosii* |
| *S. leei* |
| *S. lentus* |
| *S. lugdunensis* |
| *S. lutrae* |
| *S. lyticans* |
| *S. massiliensis* |
| *S. microti* |
| *S. muscae* |
| *S. nepalensis* |
| *S. pasteuri* |
| *S. petrasii* |
| *S. pettenkoferi* |
| *S. piscifermentans* |
| *S. pseudintermedius* |
| *S. pseudolugdunensis* |
| *S. pulvereri* |
| *S. rostri* |
| *S. saccharolyticus* |
| *S. saprophyticus* |
| *S. schleiferi* |
| *S. sciuri* |
| *S. simiae* |

TABLE 3-continued

| EXAMPLE BACTERIA |
| --- |
| *S. simulans* |
| *S. stepanovicii* |
| *S. succinus* |
| *S. vitulinus* |
| *S. warneri* |
| *S. xylosus* |
| Streptococcus |
| *Streptococcus agalactiae* |
| *Streptococcus anginosus* |
| *Streptococcus bovis* |
| *Streptococcus canis* |
| *Streptococcus constellatus* |
| *Streptococcus downei* |
| *Streptococcus dysgalactiae* |
| *Streptococcus equines* |
| *Streptococcus faecalis* |
| *Streptococcus ferus* |
| *Streptococcus infantarius* |
| *Streptococcus iniae* |
| *Streptococcus intermedius* |
| *Streptococcus lactarius* |
| *Streptococcus milleri* |
| *Streptococcus mitis* |
| *Streptococcus mutans* |
| *Streptococcus oralis* |
| *Streptococcus tigurinus* |
| *Streptococcus orisratti* |
| *Streptococcus parasanguinis* |
| *Streptococcus peroris* |
| *Streptococcus pneumoniae* |
| *Streptococcus pseudopneumoniae* |
| *Streptococcus pyogenes* |
| *Streptococcus ratti* |
| *Streptococcus salivariu* |
| *Streptococcus thermophilus* |
| *Streptococcus sanguinis* |
| *Streptococcus sobrinus* |
| *Streptococcus suis* |
| *Streptococcus uberis* |
| *Streptococcus vestibularis* |
| *Streptococcus viridans* |
| *Streptococcus zooepidemicus* |
| Uliginosibacterium |
| *Uliginosibacterium gangwonense* |
| Ulvibacter |
| *Ulvibacter litoralis* |
| Umezawaca |
| *Umezawaea angerina* |
| Undibacterium |
| *Undibacterium pigrum* |
| Ureaplasma |
| *Ureaplasma urealyticum* |
| Ureibacillus |
| *Ureibacillus composti* |
| *Ureibacillus suwonensis* |
| *Ureibacillus terrenus* |
| *Ureibacillus thermophilus* |
| *Ureibacillus thermosphaericus* |
| Vagococcus |
| *Vagococcus carniphilus* |
| *Vagococcus elongatus* |
| *Vagococcus fessus* |
| *Vagococcus fluvialis* |
| *Vagococcus lutrae* |
| *Vagococcus salmoninarum* |
| Variovorax |
| *Variovorax boronicumulans* |
| *Variovorax dokdonensis* |
| *Variovorax paradoxus* |
| *Variovorax soli* |
| Veillonella |
| *Veillonella atypica* |
| *Veillonella caviae* |
| *Veillonella criceti* |
| *Veillonella dispar* |
| *Veillonella montpellierensis* |
| *Veillonella parvula* |
| *Veillonella ratti* |

TABLE 3-continued

| EXAMPLE BACTERIA |
|---|
| *Veillonella rodentium* |
| Venenivibrio |
| *Venenivibrio stagnispumantis* |
| Verminephrobacter |
| *Verminephrobacter eiseniae* |
| Verrucomicrobium |
| *Verrucomicrobium spinosum* |
| Vibrio |
| *Vibrio aerogenes* |
| *Vibrio aestuarianus* |
| *Vibrio albensis* |
| *Vibrio alginolyticus* |
| *Vibrio campbellii* |
| *Vibrio cholerae* |
| *Vibrio cincinnatiensis* |
| *Vibrio coralliilyticus* |
| *Vibrio cyclitrophicus* |
| *Vibrio diazotrophicus* |
| *Vibrio fluvialis* |
| *Vibrio furnissii* |
| *Vibrio gazogenes* |
| *Vibrio halioticoli* |
| *Vibrio harveyi* |
| *Vibrio ichthyoenteri* |
| *Vibrio mediterranei* |
| *Vibrio metschnikovii* |
| *Vibrio mytili* |
| *Vibrio natriegens* |
| *Vibrio navarrensis* |
| *Vibrio nereis* |
| *Vibrio nigripulchritudo* |
| *Vibrio ordalii* |
| *Vibrio orientalis* |
| *Vibrio parahaemolyticus* |
| *Vibrio pectenicida* |
| *Vibrio penaeicida* |
| *Vibrio proteolyticus* |
| *Vibrio shilonii* |
| *Vibrio splendidus* |
| *Vibrio tubiashii* |
| *Vibrio vulnificus* |
| Virgibacillus |
| *Virgibacillus halodenitrificans* |
| *Virgibacillus pantothenticus* |
| Weissella |
| *Weissella cibaria* |
| *Weissella confusa* |
| *Weissella halotolerans* |
| *Weissella hellenica* |
| *Weissella kandleri* |
| *Weissella koreensis* |
| *Weissella minor* |
| *Weissella paramesenteroides* |
| *Weissella soli* |
| *Weissella thailandensis* |
| *Weissella viridescens* |
| Williamsia |
| *Williamsia marianensis* |
| *Williamsia maris* |
| *Williamsia serinedens* |
| Winogradskyella |
| *Winogradskyella thalassocola* |
| Wolbachia |
| *Wolbachia persica* |
| Wolinella |
| *Wolinella succinogenes* |
| Zobellia |
| *Zobellia galactanivorans* |
| *Zobellia uliginosa* |
| Zoogloea |
| *Zoogloea ramigera* |
| *Zoogloea resiniphila* |
| Xanthobacter |
| *Xanthobacter agilis* |
| *Xanthobacter aminoxidans* |
| *Xanthobacter autotrophicus* |
| *Xanthobacter flavus* |
| *Xanthobacter tagetidis* |

TABLE 3-continued

| EXAMPLE BACTERIA |
|---|
| *Xanthobacter viscosus* |
| Xanthomonas |
| *Xanthomonas albilineans* |
| *Xanthomonas alfalfae* |
| *Xanthomonas arboricola* |
| *Xanthomonas axonopodis* |
| *Xanthomonas campestris* |
| *Xanthomonas citri* |
| *Xanthomonas codiaei* |
| *Xanthomonas cucurbitae* |
| *Xanthomonas euvesicatoria* |
| *Xanthomonas fragariae* |
| *Xanthomonas fuscans* |
| *Xanthomonas gardneri* |
| *Xanthomonas hortorum* |
| *Xanthomonas hyacinthi* |
| *Xanthomonas perforans* |
| *Xanthomonas phaseoli* |
| *Xanthomonas pisi* |
| *Xanthomonas populi* |
| *Xanthomonas theicola* |
| *Xanthomonas translucens* |
| *Xanthomonas vesicatoria* |
| Xylella |
| *Xylella fastidiosa* |
| Xylophilus |
| *Xylophilus ampelinus* |
| Xenophilus |
| *Xenophilus azovorans* |
| *Xenorhabdus* |
| *Xenorhabdus beddingii* |
| *Xenorhabdus bovienii* |
| *Xenorhabdus cabanillasii* |
| *Xenorhabdus doucetiae* |
| *Xenorhabdus griffiniae* |
| *Xenorhabdus hominickii* |
| *Xenorhabdus koppenhoeferi* |
| *Xenorhabdus nematophila* |
| *Xenorhabdus poinarii* |
| Xylanibacter |
| *Xylanibacter oryzae* |
| Yangia |
| *Yangia pacifica* |
| Yaniella |
| *Yaniella flava* |
| *Yaniella halotolerans* |
| Yeosuana |
| *Yeosuana aromativorans* |
| Yersinia |
| *Yersinia aldovae* |
| *Yersinia bercovieri* |
| *Yersinia enterocolitica* |
| *Yersinia entomophaga* |
| *Yersinia frederiksenii* |
| *Yersinia intermedia* |
| *Yersinia kristensenii* |
| *Yersinia mollaretii* |
| *Yersinia philomiragia* |
| *Yersinia pestis* |
| *Yersinia pseudotuberculosis* |
| *Yersinia rohdei* |
| *Yersinia ruckeri* |
| Yokenella |
| *Yokenella regensburgei* |
| Yonghaparkla |
| *Yonghaparkia alkaliphila* |
| Zavarzinia |
| *Zavarzinia compransoris* |
| Zooshikella |
| *Zooshikella ganghwensis* |
| Zunongwangia |
| *Zunongwangia profunda* |
| Zymobacter |
| *Zymobacter palmae* |
| Zymomonas |
| *Zymomonas mobilis* |
| Zymophilus |
| *Zymophilus paucivorans* |

TABLE 3-continued

| EXAMPLE BACTERIA |
| --- |
| *Zymophilus raffinosivorans* |
| Zobellella |
| *Zobellella denitrificans* |
| *Zobellella taiwanensis* |
| Zeaxanthinibacter |
| *Zeaxanthinibacter enoshimensis* |
| Zhihengliuella |
| *Zhihengliuella halotolerans* |
| Xylanibacterium |
| *Xylanibacterium ulmi* |

TABLE 4

SEQUENCES
Nucleotide sequences are written in 5' to 3' direction; amino acid sequences are written in N- to C-terminal direction,

| SEQ ID NO: | Description | Sequence |
| --- | --- | --- |
| 1 | Cas-S1.1 amino acid sequence | LNHPVESVYSALTSILLPYMGEPVPVQRNCSCCGRAPSEFDGVGFELVNAYRERVVHCRPCQTFFVSAPELMGVENPKKPTTG<br>QKFGMWSGVGAVINVEDNSSVLLAPQGVVNKLPEHFFDHVEVITATSGQHLEYLFNTELKFPLIYIQNFGVKTYELVRSLRVSL<br>SADAIYTCADQLLTRQNEVLYMLDLTKAKELHQEIKNYSKKEIDIFIRTVTLLAYSRITPEAASNEFKKNNLIPLLLLLPTDPH<br>QRLSILHLLKKV |
| 2 | Cas-S2.1 amino acid sequence | MIYYDNAFRLRIRHTSVYQIHQHLDFFMQERKGEKLPYSFKIFPGTGDDSLLLVRTATALELPGEKKRELILSEGHEIKFITSM<br>AIFHKGTKSEGRGRRQFAPSEEASYQLALTKLAKAGFKPGQIVVSGPKFVHIVKGNAGRGFTLPVFTVQGTAIISNQQEAEVGI<br>VYGVGPKRVFGCGFMHLAGQ |
| 3 | Cas-S3.1 amino acid sequence | MNTSAVFESAGLSLRKVQQDYIEAAAGALTQDHKVALISAETGVGKTLGYLVPALLILLKNPEAKFVIATNSHALMHQIFRSDR<br>PLLEQIAEQCGIKVTFSRLMGKANYVSLEKVRGLLLMDEFTDLDTVKVLEKLANWSKPLVEFEEEYGELPAQITPEMVTYSIWD<br>DIQDIDDIRLNALSANFIVTTHAMVMVDCMCNHRILGDKENMYLIIDEADIFVDMLEVWKQRRFNLRELTSAFNEHIPRNGVHV<br>IDQLMNDVTSIAGDLHFCSTPAAVALFDNSFNALSKVGREIKNEAARKAFFDCIYSWEMLGLSGGQKGVGVSNKRREPALIAV<br>NPFIGMNVGRYCTQWRSALLTSATLSITSTPETGMEWLCKALGLTSDTISIRKIFSPDVYGSMKLTIAGADFPKVFNDPKEQIF<br>SGQWLKAVVEQLSCIQGPALVLTASHYETRMIANQLGEVSQPVYIQKAGQALSEIIKQYQEIPGILISAGASVGVSPRGENGEQ<br>IFQDLIITRIPFLPPDRMKAESLYGYLKERGYSRTFEAVNRNIYLDNLRKVIRKAKQSIGRGIRSENDTVRIIILDPRFPEPTD<br>LSSKHRSLEHIIPVRFRRAYRSCEILSPAYCEEDIQC |
| 4 | Cas-S4.1 amino acid sequence | VLNFKPYRVIMSSLTPVVISGIAPSLDGILYEALSQAIPSNEPGVVLARLKEILLFNDELGVFHASSLRFGITPEQGIGATTSV<br>RCDYLSPEKLSTAMFSPRIHRGVFTRVLLTGGPTKRRMTTRPAYSAPYLTFDFVGSSEAVEILLNHAHVGVGYDFFSAANGEFN<br>NVTILPLDIDTSISNEGMALRPVPVNSGLNGIKGVSPLIPPYFVGEKLNIVHPAPVRTQLISSLLRG |
| 5 | Cas-S5.1 amino acid sequence | MRTLNFNGKISTLEPLTVTVKNAVSTSGHRLPRNGGFNAAPYFPGTSIRGTLRHAAHKVIVDRVGLNADGKSSFDLAEHFMLA<br>QGVDINGEAETFAPGEINAGAELRSKNPLISLFGRWGLSGKVGIGNAIPDGDNQWGMFGGGARSIMFQRDESLMEFLETDQV<br>DRLERLLEEQAEASVDISQIKTEQDALKKAMKSADKDTKAELQIKVRELDEKIQARKDQKQESRESIRRPIDPYEAFITGAELS<br>HRMSIKNATDEEAGLFISALIRFAAEPRFGGHANHNCGLVEAHWTVTTWKPGELVPVTLGEIVITPNGVEITGDELFAMVKAFN<br>ENQSFDFTAR |
| 6 | Repeat sequence | GTATTCCCCCCGTGTGCGGGGGTTATCGG |
| 7 | Cas-S1.1 DNA sequence | TTGAATCATCCTGTAGAGTCAGTATATAGCGCTCTGACGAGTATTTTATTGCCCTATATGGGTGAGCCTGTGCCTGTGCAA<br>CGAAATTGCTCATGCTGCGGCAGAGCGCCCTCAGAGTTCGACGGGGTAGGCTTCGAGCTGGTCAACGCCTACAGGGAAC<br>GTGTTGTGCATTGCCGTCCTTGCCAGACATTTTTTGTTTCTGCTCCAGAACTGATGGGCGTGGAGAACCCCAAAAAACCAA<br>CAACCGGCCAGAAATTTGGCATGTGGTCTGGTGTTGGGGCTGTTATTAACGTTGAAGACAATTCTTCGGTTCTTTTAGCC<br>CCTCAGGGAGTGGTCAATAAACTACCTGAGCATTTTTTCGATCACGTAGAAGTCATCACGGCCACCAGCGGTCAGCACCTG<br>GAATACCTGTTTAACACCGAACTTAAATTCCCGCTGATTTATATTCAAAACTTCGGCGTGAAAACCTACGAGCTTGTTCGC<br>TCACTGGGGGTCAGTCTGAGTGCCGACGCAATTTATACCTGTGCCGATCAACTACTGACCCGGCAGAACGAAGTCCTTTAC<br>ATGCTGGATTTAACAAAGGCTAAAGAACTCCATCAGGAAATAAAAAACTACTCCAAAAAAGAGATAGACATCTTTATCAGA<br>ACAGTAACCCTGCTGGCCTATTCGCGGATAACTCCTGAAGCTGCCTCGAATGAGTTTAAGAAAAACAACCTCATTCCGTTA<br>CTGCTGCTTCTGCCGACTGATC |
| 8 | Cas-S2.1 DNA sequence | ATGATTTACTACGATAATGCGTTTCGGTTGCGTATCCGTCACACAAGTGTTTACCAGATCCACCAGCACCTGGATTTTTTC<br>ATGCAGGAACGTAAGGGAGAGAAGCTGCCGTACTCTTTTAAAATTTTTCCCGGTACCGGGGATGATTCGTTACTCCTGGT<br>CCGCACAGCCACAGCTCTGGAGTTGCCAGGGGAGAAAAAAAGAGAGCTTATTCTCTCTGAGGGCCATGAAATCAAGTTCA<br>TTACGTCAATGGCCATCTTTCATAAAGGAACAAAGTCAGAAGGCCGTGGCCGACGCCAGTTTGCTCCATCCGAAGAGGCT<br>AGTTATCAGTTGGCCCTCACCAAATTAGCGAAGGCTGGTTTTAAACCCGGTCAAATCGTCGTCAGTGGCCCGAAATTCGTC<br>CATATCGTCAAAGGAAATGCTGGACGCGGTTTTACGCTACCCGTATTCACGGTACAGGGTACCGCCATAATCAGCAATCAA<br>CAGGAAGCTGAAGTTGGAATCGTTTATGGCGTAGGCCCTAAACGCGTATTTGGTTGCGGTTTCATGCATCTGGCGGGGCA<br>GTAG |
| 9 | Cas-S3.1 DNA sequence | ATGAATACATCAGCGGTATTTGAGTCTGCCGGATTGTCGTTACGTAAGGTCCAACAGGATTATATCGAGGCTGCAGCTGG<br>TGCGCTGACTCAGGATCATAAAGTTGCACTGATTAGTGCTGAAACAGGTGTAGGAAAAACGCTGGGCTATCTGGTACCGG<br>CGCTTCTGATTCTGCTGAAAAACCCAGAGGCAAAATTTGTGATAGCCACGAATTCTCATGCCCTGATGCACCAGATATTCA<br>GAAGCGATCGTCCTCTCCTTGAACAGATAGCTGAACAATGCGGCATAAAAGTTACTTTTTCCCGGCTTATGGGGAAAGCAA<br>ATTACGTATCCCTGGAGAAAGTACGTGGACTGTTACTCATGGACGAATTTACCGATCTGGATACGGTTAAGGTCCTTGAAA<br>AACTCGCTAACTGGTCAAAACCTCTGGTTGAGTTTGAAGAAGAGTATGGTGAACTGCCAGCGCAGATCACGCCAGAGATG<br>GTCACCTACTCCATCTGGGATGATATACAGGACATTGATGATATTCGCCTGAATGCTCTCAGTGCTAACTTTATAGTTACG<br>ACCCATGCGATGGTAATGGTCGACTGTATGTGTAATCACCGCATCCTCGGTGACAAAGAAAATATGTACCTCATTATTGAT |

TABLE 4-continued

| SEQUENCES Nucleotide sequences are written in 5' to 3' direction; amino acid sequences are written in N- to C-terminal direction, | | |
|---|---|---|
| SEQ ID NO: | Description | Sequence |
| | | GAGGCAGACATTTTTGTAGATATGCTTGAGGTCTGGAAACAGCGGCGCTTCAACCTCAGAGAGTTGACCAGTGCGTTCAA<br>TGAACATATTCCACGTAATGGCGTGCATGTCATCGACCAGTTAATGAACGACGTGACTTCGATAGCGGGCGATCTGCATTT<br>TTGTAGTACGCCTGCAGCGGTTGCCTTGTTTGACAATAGCTTTAACGCCTTATCAAAGGTAGGGGGGGAAATAAAAAATG<br>AAGCGGCCCGGAAAGCTTTCTTTGACTGTATCTACAGCTGGGAAATGCTCGGATTGTCCGGGGGGCAAAAGGGTGTAGG<br>CGTTTCCAATAAACGTCGTGAACCAGCCCTGATCGCTGTAAACCCGTTTATCGGGATGAATGTGGGCAGATACTGCACTCA<br>ATGGCGTAGTGCGTTACTGACGTCGGCTACGCTCTCAATTACCAGTACCCCAGAGACCGGAATGGAGTGGTTATGTAAAG<br>CTCTGGGGTTAACCAGCGATACGATTTCAATCAGGAAAATATTCTCCCCAGACGTCTATGGCTCAATGAAGCTGACCATCG<br>CCGGTGCTGATTTTCCAAAGGTGTTCAATGACCCGAAAGAACAGATATTTTCAGGTCAATGGTTAAAGGCAGTAGTTGAAC<br>AATTGTCCTGTATTCAGGGGCCAGCTCTGGTATTAACTGCCAGCCATTATGAAACCAGGATGATTGCCAATCAGCTGGGT<br>GAGGTCTCGCAACCAGTTTATATTCAGAAAGCAGGTCAGGCCCTGTCCGAAATTATTAAACAGTATCAGGAGATACCAGG<br>GATTCTTATTTCTGCCGGTGCTTCTGTTGGTGTGAGCCCACGAGGCGAGAATGGGGAACAGATTTTCCAGGATTTAATCA<br>TTACCCGGATACCTTTCTTACCTCCGGACAGAATGAAGGCTGAAAGCCTTTATGGGTATCTGAAGGAACGAGGCTATAGT<br>CGTACCTTTGAGGCAGTTAACCGTAACATCTACCTGGATAATTTGCGGAAAGTTATTCGTAAAGCAAAGCAGTCTATAGGG<br>CGGGGGATTCGTAGTGAAAATGATACCGTCAGGATAATTATCCTCGATCCGCGTTTCCCGGAACCTACTGACCTTTCGTCT<br>AAACATCGGTCGCTTGAACACATTATTCCCGTTCGATTTCGTCGTGCATATCGTTCGTGTGAAATTTTATCTCCGGCGTAT<br>TGTGAAGAGGATATCCAGTG |
| 10 | Cas-S4.1 DNA sequence | GTGTTAAATTTTAAACCGTATCGGGTCATCATGTCTTCTCTGACACCGGTGGTCATCAGTGGGATAGCCCCATCGCTGGAC<br>GGCATTCTGTATGAAGCACTGTCTCAGGCGATACCCAGTAACGAGCCAGGAGTCGTATTGGCTCGTCTTAAGGAAATACT<br>TCTATTCAACGATGAACTGGGTGTTTTCCATGCTTCATCTCTACGTTTTGGCATAACGCCCGAACAGGGGATTGGGGCGA<br>CAACAAGCGTACGTTGCGATTATCTCAGTCCCGAAAAACTGAGCACTGCAATGTTCTCTCCTCGTATCCACAGGGGGGTGT<br>TTACGCGTGTCCTCCTGACCGGGGGCCCCACGAAGAGAAGGATGACAACCCGTCCAGCTTATTCTGCACCCTATTTAACG<br>TTTGATTTTGTCGGCTCTTCTGAGGCTGTAGAAATACTGCTTAACCATGCCCATGTTGGCGTTGGTTATGACTTTTTCTCT<br>GCAGCTAATGGAGAGTTTAACAATGTGACAATTCTTCCTCTCGATATCGACACGAGTATATCCAACGAGGGTATGGCATTG<br>CGTCCGGTACCTGTTAATTCGGGTCTGAATGGTATCAAAGGAGTATCACCACTTATTCCTCCCTATTTCGTTGGTGAAAAG<br>CTAAACATTGTCCACCCAGCACCAGTTCGTACTCAATTGATTTCTTCTTTATTGCGAGGCTAA |
| 11 | Cas-S5.1 DNA sequence | ATGAGAACTTTAAACTTCAACGGTAAAATTTCGACTCTGGAACCACTGACTGTAACAGTAAAAAATGCGGTCTCAACTTCC<br>GGCCATCGCTTGCCTCGTAACGGTGGATTCAATGCAGCCCCGTACTTTCCAGGTACCAGCATTCGGGGAACTCTTCGTCA<br>TGCTGCGCATAAGGTCATTGTCGATCGTGTGGGCCTTAATGCAGACGGAAAATCATCCTTCGACCTGGCAGAACATTTCA<br>TGCTGGCCCAGGGGGTGGATATCAATGGTGAAGCCGAAACCTTCGCGCCAGGTGAAATCAATGCTGGTGCTGAACTACGT<br>AGCAAAAACCCGTTAATCAGCTTGTTTGGTCGTTGGGGATTAAGCGGCAAAGTTGGTATAGGGAATGCTATCCCGGATGG<br>TGATAACCAGTGGGGGATGTTTGGTGGTGGTGCCCGCTCAATTATGTTTCAGCGTGACGAAAGTCTGATGGAGTTTCTTG<br>AGACAGACCAGGTTGATCGTCTTGAACGCCTGCTCGAGGAACAGGCTGAGGCAAGTGTGGATATCTCTCAGATCAAAACA<br>GAGCAAGATGCACTCAAAAAGGCGATGAAGTCGGCTGATAAAGACACCAAAGCTGAGCTTCAAATCAAAGTACGGGAGCT<br>CGATGAAAAAATTCAGGCCCGCAAAGATCAGAAGCAGGAATCTCGCGAGTCAATTCGCCGCCCGATTGACCCGTATGAAG<br>CGTTTATCACCGGCGCAGAACTCAGCCATCGCATGAGTATTAAAAATGCGACTGATGAGGAAGCAGGGCTTTTCATTTCT<br>GCATTAATCCGCTTTGCAGCCGAACCACGTTTTGGGGGTCATGCGAATCATAACTGCGGTCTGGTGGAGGCTCACTGGAC<br>AGTTACGACCTGGAAGCCGGGTGAACTGGTACCAGTTACACTTGGAGAAATCGTCATCACACCGAATGGTGTTGAGATTA<br>CCGGGGACGAGTTGTTTGCTATGGTAAAGGCATTCAATGAAAATCAATCTTTTGATTTCACTGCCCGCTAA |
| 12 | DNA sequence encoding Cas-S1.1, 2.1, 3.1, 4.1 and 5.1 | TTGAATCATCCTGTAGAGTCAGTATATAGCGCTCTGACGAGTATTTTATTGCCCTATATGGGTGAGCCTGTGCCTGTGCAA<br>CGAAATTGCTCATGCTGCGGCAGAGCGCCCTCAGAGTTCGACGGGGTAGGCTTCGAGCTGGTCAACGCCTACAGGGAAC<br>GTGTTGTGCATTGCCGTCCTTGCCAGACATTTTTTGTTTCTGCTCCAGAACTGATGGGCGTGGAGAACCCCAAAAAACCAA<br>CAACCGGCCAGAAATTTGGCATGTGGTCTGGTGTTGGGGCTGTTATTAACGTTGAAGACAATTCTTCGGTTCTTTTAGCC<br>CCTCAGGGAGTGGTCAATAAACTACCTGAGCATTTTTTCGATCACGTAGAAGTCATCACGGCCACCAGCGGTCAGCACCTG<br>GAATACCTGTTTAACACCGAACTTAAATTCCCCGCTGATTTATATTCAAAACTTCGGCGTGAAAACCTACGAGCTTGTTCGC<br>TCACTGCGGGTCAGTCTGAGTGCCGACGCAATTTATACCTGTGCCGATCAACTACTGACCCGGCAGAACGAAGTCCTTTAC<br>ATGCTGGATTTAACAAAGGCTAAAGAACTCCATCAGGAAATAAAAAACTACTCCAAAAAAGAGATAGACATCTTTATCAGA<br>ACAGTAACCCTGCTGGCCTATTCGCGGATAACTCCTGAAGCTGCCTCGAATGAGTTTAAGAAAAACAACCTCATTCCGTTA<br>CTGCTGCTTCTGCCGACTGATCCCCATCAACGCCTGAGCATTTTGCACCTCTTGAAAAAGGTATAACCATGATTTACTACG<br>ATAATGCGTTTCGGTTGCGTATCCGTCACACAAGTGTTTACCAGATCCACCAGCACCTGGATTTTTTCATGCAGGAACGTA<br>AGGGAGAGAAGCTGCCGTACTCTTTTAAAATTTTTCCCGGTACCGGGGATGATTCGTTACTCCTGGTCCGCACAGCCACA<br>GCTCTGGAGTTGCCAGGGGAGAAAAAAAGAGAGCTTATTCTCTCTGAGGGCCATGAAATCAAGTTCATTACGTCAATGGC<br>CATCTTTCATAAAGGAACAAAGTCAGAAGGCCGTGGCCGACGCCAGTTTGCTCCATCCGAAGAGGCTAGTTATCAGTTGG<br>CCCTCACCAAATTAGCGAAGGCTGGTTTTAAACCCGGTCAAATCGTCGTCAGTGGCCCGAAATTCGTCCATATCGTCAAAG<br>GAAATGCTGGACGCGGTTTTACGCTACCCGTATTCACGGTACAGGGTACCGCCATAATCAGCAATCAACAGGAAGCTGAA<br>GTTGGAATCGTTTATGGCGTAGGCCCTAAACGCGTATTTGGTTGCGGTTTCATGCATCTGGGGGGGCAGTAGTCATGAAT<br>ACATCAGCGGTATTTGAGTCTGCCGGATTGTCGTTACGTAAGGTCCAACAGGATTATATCGAGGCTGCAGCTGGTGCGCT<br>GACTCAGGATCATAAAGTTGCACTGATTAGTGCTGAAACAGGTGTAGGAAAAACGCTGGGCTATCTGGTACCGGCGCTTC<br>TGATTCTGCTGAAAAACCCAGAGGCAAAATTTGTGATAGCCACGAATTCTCATGCCCTGATGCACCAGATATTCAGAAGCG<br>ATCGTCCTCTCCTTGAACAGATAGCTGAACAATGCGGCATAAAAGTTACTTTTTCCCGGCTTATGGGGAAAGCAAATTACG<br>TATCCCTGGAGAAAGTACGTGGACTGTTACTCATGGACGAATTTACCGATCTGGATACGGTTAAGGTCCTTGAAAAACTCG<br>CTAACTGGTCAAAACCTCTGGTTGAGTTTGAAGAAGAGTATGGTGAACTGCCAGCGCAGATCACGCCAGAGATGGTCACC<br>TACTCCATCTGGGATGATATACAGGACATTGATGATATTCGCCTGAATGCTCTCAGTGCTAACTTTATAGTTACGACCCAT<br>GCGATGGTAATGGTCGACTGTATGTGTAATCACCGCATCCTCGGTGACAAAGAAAATATGTACCTCATTATTGATGAGGCA<br>GACATTTTTGTAGATATGCTTGAGGTCTGGAAACAGCGGCGCTTCAACCTCAGAGAGTTGACCAGTGCGTTCAATGAACA<br>TATTCCACGTAATGGCGTGCATGTCATCGACCAGTTAATGAACGACGTGACTTCGATAGGGGGCGATCTGCATTTTTGTA<br>GTACGCCTGCAGCGGTTGCCTTGTTTGACAATAGCTTTAACGCCTTATCAAAGGTAGGGGGGGAAATAAAAAATGAAGCG<br>GCCCGGAAAGCTTTCTTTGACTGTATCTACAGCTGGGAAATGCTCGGATTGTCCGGGGGGCAAAAGGGTGTAGGCGTTTC<br>CAATAAACGTCGTGAACCAGCCCTGATCGCTGTAAACCCGTTTATCGGGATGAATGTGGGCAGATACTGCACTCAATGGC<br>GTAGTGCGTTACTGACGTCGGCTACGCTCTCAATTACCAGTACCCCAGAGACCGGAATGGAGTGGTTATGTAAAGCTCTG |

TABLE 4-continued

| SEQ ID NO: | Description | Sequence |
|---|---|---|
| | | GGGTTAACCAGCGATACGATTTCAATCAGGAAAATATTCTCCCCAGACGTCTATGGCTCAATGAAGCTGACCATCGCCGGT GCTGATTTTCCAAAGGTGTTCAATGACCCGAAAGAACAGATATTTTCAGGTCAATGGTTAAAGGCAGTAGTTGAACAATTG TCCTGTATTCAGGGGCCAGCTCTGGTATTAACTGCCAGCCATTATGAAACCAGGATGATTGCCAATCAGCTGGGTGAGGT CTCGCAACCAGTTTATATTCAGAAAGCAGGTCAGGCCCTGTCCGAAATTATTAAACAGTATCAGGAGATACCAGGGATTCT TATTTCTGCCGGTGCTTCTGTTGGTGTGAGCCCACGAGGCGAGAATGGGGAACAGATTTTCCAGGATTTAATCATTACCC GGATACCTTTCTTACCTCCGGACAGAATGAAGGCTGAAAGCCTTTATGGGTATCTGAAGGAACGAGGCTATAGTCGTACC TTTGAGGCAGTTAACCGTAACATCTACCTGGATAATTTGCGGAAAGTTATTCGTAAAGCAAAGCAGTCTATAGGGGGGGG GATTCGTAGTGAAAATGATACCGTCAGGATAATTATCCTCGATCCGCGTTTCCCGGAACCTACTGACCTTTCGTCTAAACA TCGGTCGCTTGAACACATTATTCCCGTTCGATTTCGTCGTGCATATCGTTCGTGTGAAATTTTATCTCCGGCGTATTGTGA AGAGGATATCCAGTGTTAAATTTTAAACCGTATCGGGTCATCATGTCTTCTCTGACACCGGTGGTCATCAGTGGGATAGCC CCATCGCTGGACGGCATTCTGTATGAAGCACTGTCTCAGGCGATACCCAGTAACGAGCCAGGAGTCGTATTGGCTCGTCT TAAGGAAATACTTCTATTCAACGATGAACTGGGTGTTTTCCATGCTTCATCTCTACGTTTTGGCATAACGCCCGAACAGGG GATTGGGGCGACAACAAGCGTACGTTGCGATTATCTCAGTCCCGAAAAACTGAGCACTGCAATGTTCTCTCCTCGTATCCA CAGGGGGGTGTTTACGCGTGTCCTCCTGACCGGGGGCCCCACGAAGAGAAGGATGACAACCCGTCCAGCTTATTCTGCAC CCTATTTAACGTTTGATTTTGTCGGCTCTTCTGAGGCTGTAGAAATACTGCTTAACCATGCCCATGTTGGCGTTGGTTATG ACTTTTTCTCTGCAGCTAATGGAGAGTTTAACAATGTGACAATTCTTCCTCTCGATATCGACACGAGTATATCCAACGAGG GTATGGCATTGCGTCCGGTACCTGTTAATTCGGGTCTGAATGGTATCAAAGGAGTATCACCACTTATTCCTCCCTATTTCG TTGGTGAAAAGCTAAACATTGTCCACCCAGCACCAGTTCGTACTCAATTGATTTCTTCTTTATTGCGAGGCTAATTTCATG AGAACTTTAAACTTCAACGGTAAAATTTCGACTCTGGAACCACTGACTGTAACAGTAAAAAATGCGGTCTCAACTTCCGGC CATCGCTTGCCTCGTAACGGTGGATTCAATGCAGCCCCGTACTTTCCAGGTACCAGCATTCGGGGAACTCTTCGTCATGCT GCGCATAAGGTCATTGTCGATCGTGTGGGCCTTAATGCAGACGGAAAATCATCCTTCGACCTGGCAGAACATTTCATGCT GGCCCAGGGGGTGGATATCAATGGTGAAGCCGAAACCTTCGCGCCAGGTGAAATCAATGCTGGTGCTGAACTACGTAGCA AAAACCCGTTAATCAGCTTGTTTGGTCGTTGGGGATTAAGCGGCAAAGTTGGTATAGGGAATGCTATCCCGGATGGTGAT AACCAGTGGGGGATGTTTGGTGGTGGTGCCCGCTCAATTATGTTTCAGCGTGACGAAAGTCTGATGGAGTTTCTTGAGAC AGACCAGGTTGATCGTCTTGAACGCCTGCTCGAGGAACAGGCTGAGGCAAGTGTGGATATCTCTCAGATCAAAACAGAGC AAGATGCACTCAAAAAGGCGATGAAGTCGGCTGATAAAGACACCAAAGCTGAGCTTCAAATCAAAGTACGGGAGCTCGAT GAAAAAATTCAGGCCCGCAAAGATCAGAAGCAGGAATCTCGCGAGTCAATTCGCCGCCCGATTGACCCGTATGAAGCGTT TATCACCGGCGCAGAACTCAGCCATCGCATGAGTATTAAAAATGCGACTGATGAGGAAGCAGGGCTTTTCATTTCTGCATT AATCCGCTTTGCAGCCGAACCACGTTTTGGCGGTCATGCGAATCATAACTGCGGTCTGGTGGAGGCTCACTGGACAGTTA CGACCTGGAAGCCGGGTGAACTGGTACCAGTTACACTTGGAGAAATCGTCATCACACCGAATGGTGTTGAGATTACCGGG GACGAGTTGTTTGCTATGGTAAAGGCATTCAATGAAAATCAATCTTTTGATTTCACTGCCCGCTAACTCCAAAAGCTGGTG GATTTTAGTGGCGCTATTTAATATTTTATAATCAACCGGTTATTTTTAGAGTATTCCCCCCGTGTGCGGGGGTTATCGGTG GGGCGTTGTTGAATAAATAGATATTATGCTGGGGGCCTACCAAAACGTCGGTCTTTCCCAACGCAAAATCAGTAGGTTAA GGTTAAAGTCGGGAGCTACTCACAATAGTGACAAGCATCTTTGACTAAAGCAGGCGCGCCAAAACAGCATGATTCCCTATT ATTCAACAAAGCCTATCGGTGGTGCTCTCAACCGTCACCCGCTGGCTGGAAGTATTCCCCCCGTGTGCGGGGGTTATCGG TCGTGTTGTCCACGGTTACCCGCTGGCTGGAAGTATTCCCCCCGCATGCGGGGGTTATCGGTTACCAATGGGGAAAAATC TTCATTTGTAAATGTATTCCCCCCGCATGCGGGGGTTATCGGAACATCAGTGGAAATCCACTGCGGCGTATTCtCCCCGCA TGCGGGGGTTATCGGCGAAAACGGCAACCTTCATAAAAACGTCTTTTGTATTCCCCCCGTGTGCGGGGGTTATCGGCCGA GATTGAGTAAAGCAAAGTAACGGCGGTGGTATTCCCCCCGCATGCGGGGGTTATCGGCAGGTTATACTGGCAAAACGTCG ATG |
| 13 | PAM | AAG |
| 14 | pBolA promoter | aacctaaatatttgttgttaagctgcaatggaaacggtaaaagcggctagtatttaaaggGatggatgacatctcagcgtt gtcg |
| 15 | P70a promoter | CCTGATGCGTGAACGTGACGGACGTAACCACCGCGACATGTGTGTGCTGTTCCGCTGGGCATGCTGAGCTAACACCGTGC GTGTTGACAATTTTACCTCTGGCGGTGATAATGGTTGCAGCTAGCAATAATTTTGTTTAACTTTAAGAAGGAGATATACC |
| 16 | XTEN linker (nucleotide) | agcggcagcgagactcccgggacctcagagtccgccacacccgaaagt |
| 17 | XTEN linker (amino acid) | SGSETPGTSESATPES |
| 18 | PmCDA1 cytidine deaminase (nucleotide) | ATGACCGACGCTGAGTACGTGAGAATCCATGAGAAGTTGGACATCTACACGTTTAAGAAACAGTTTTTCAACAACAAAAAA TCCGTGTCGCATAGATGCTACGTTCTCTTTGAATTAAAACGACGGGGTGAACGTAGAGCGTGTTTTTGGGGCTATGCTGT GAATAAACCACAGAGCGGGACAGAACGTGGCATTCACGCCGAAATCTTTAGCATTAGAAAAGTCGAAGAATACCTGCGCG ACAACCCCGGACAATTCACGATAAATTGGTACTCATCCTGGAGTCCTTGTGCAGATTGCGCTGAAAAGATCTTAGAATGGT ATAACCAGGAGCTGCGGGGGAACGGCCACACTTTGAAAATCTGGGCTTGCAAACTCTATTACGAGAAAAATGCGAGGAAT CAAATTGGGCTGTGGAATCTCAGAGATAACGGGGTTGGGTTGAATGTAATGGTAAGTGAACACTACCAATGTTGCAGGAA AATATTCATCCAATCGTCGCACAATCAATTGAATGAGAATAGATGGCTTGAGAAGACTTTGAAGCGAGCTGAAAAACGACG GAGCGAGTTGTCCATTATGATTCAGGTAAAAATACTCCACACCACTAAGAGTCCTGCTGTT |
| 19 | PmCDA1 cytidine deaminase (amino acid) | MTDAEYVRIHEKLDIYTFKKQFFNNKKSVSHRCYVLFELKRRGERRACFWGYAVNKPQSGTERGIHAEIFSIRKVEEYLRDN PGQFTINWYSSWSPCADCAEKILEWYNQELRGNGHTLKIWACKLYYEKNARNQIGLWNLRDNGVGLNVMVSEHYQCCRKIFI QSSHNQLNENRWLEKTLKRAEKRRSELSIMIQVKILHTTKSPAV |

TABLE 4-continued

SEQUENCES
Nucleotide sequences are written in 5' to 3' direction; amino acid sequences are written in N- to C-terminal direction,

| SEQ ID NO: | Description | Sequence |
|---|---|---|
| 20 | Uracil DNA glycosylase inhibitor (UGI) protein (nucleotide) | ATGACCAACCTTTCCGACATCATAGAGAAGGAAACAGGCAAACAGTTGGTCATCCAAGAGTCGATACTCATGCTTCCTGAA GAAGTTGAGGAGGTCATTGGGAATAAGCCGGAAAGTGACATTCTCGTACACACTGCGTATGATGAGAGCACCGATGAGAA CGTGATGCTGCTCACGTCAGATGCCCCAGAGTACAAACCCTGGGCTCTGGTGATTCAGGACTCTAATGGAGAGAACAAGA TCAAGATGCTATAA |
| 21 | Uracil DNA glycosylase inhibitor (UGI) protein (amino acid) | MTNLSDIIEKETGKQLVIQESILMLPEEVEEVIGNKPESDILVHTAYDESTDENVMLLTSDAPEYKPWALVIQDSNGENKIK ML |
| 22 | Linker (nucleotide) | TCTGGTGGATCTGGAGGTTCTGGTGGATCT |
| 23 | Linker (amino acid) | SGGSGGSGGS |
| 24 | pBAD promoter (nucleotide) | gaccaaagccatgacaaaaacgcgtaacaaaagtgtctataatcacggcagaaaagtccacattgattatttgcacggcgt cacactttgctatgccatagcatttttatccataagattagcggatcctacctgacgctttttatcgcaactctctactgt ttctccatacccgtttttttgggaattcgagctctaaggaggttataaaaa |
| 25 | Non-target Protospacer sequence | GGAGACGTCATGTCAAGCTCATAGGCGTCTCG |
| 26 | U1kF protospacer sequence | ACATACGCTTCTTGCTGAGTACGTGAGTTCAC |
| 27 | U2kF protospacer sequence | CAGATTGCTGGTCAGGAGCATATTGATCCGCT |
| 28 | S1F protospacer sequence | AAGGAGATATACCATGGAGCTTTTCACTGGCG |
| 29 | S2F protospacer sequence | TTCAGCGTGTCCGGCGAGGGCGAGGGCGATGC |
| 30 | S3F protospacer sequence | CTGCCCGTGCCCTGGCCCACCCTCGTGACCAC |
| 31 | S4F protospacer sequence | GAGAAGCGCGATCACATGGTCCTGCTGGAGTT |
| 32 | S5F protospacer sequence | TACCAGATGGCATTGCGCCATCTGGCAGAGTG |
| 33 | S6F protospacer sequence | AAAGTCAGGTTGCGCAGGCAGGGTAATCGGGG |
| 34 | U1kR protospacer sequence | TCACGTACTCAGCAAGAAGCGTATGTGTTTGC |
| 35 | U2KR protospacer sequence | ACCTCTGTCAGCTCGCTGACATTCCCCGCCAG |
| 36 | S1R protospacer sequence | TTAAACAAAATTATTGCTAGCTGCAACCATTA |

TABLE 4-continued

| SEQUENCES Nucleotide sequences are written in 5' to 3' direction; amino acid sequences are written in N- to C-terminal direction, | | |
|---|---|---|
| SEQ ID NO: | Description | Sequence |
| 37 | S2R protospacer sequence | CTCCATGGTATATCTCCTTCTTAAAGTTAAAC |
| 38 | S3R protospacer sequence | CACTGCACGCCGTAGGTCAGGGTGGTCACGAG |
| 39 | S4R protospacer sequence | TCCAGCAGGACCATGTGATCGCGCTTCTCGTT |
| 40 | S5R protospacer sequence | CACTCTGCCAGATGGCGCAATGCCATCTGGTA |
| 41 | S6R protospacer sequence | CTGACTTTGTTGTCGGCCCGGGGGGCACTCAA |
| 42 | I-TevI cleavage site sequence | CAACG |
| 43 | I-TevI DNA spacer sequence | CTCAGTAGATGTTTTCTTGGGTCTACCGTTA |
| 44 | I-TevI sequence (nucleo-tide) | ATGAAAAGCGGAATTTATCAGATTAAAAATACTTTAAACAATAAAGTATATGTAGGAAGTGCTAAAGATTTTGAAAAGAGA TGGAAGAGGCATTTTAAAGATTTAGAAAAAGGATGCCATTCTTCTATAAAACTTCAGAGGTCTTTTAACAAACATGGTAAT GTGTTTGAATGTTCTATTTTGGAAGAAATTCCATATGAGAAAGATTTGATTATTGAACGAGAAAATTTTTGGATTAAAGAG CTTAATTCTAAAATTAATGGATACAATATTGCTGATGCAACGTTTGGTGATACATGTTCTACGCATCCATTAAAAGAAGAA ATTATTAAGAAACGTTCTGAAACTGTTAAAGCTAAGATGCTTAAACTTGGACCTGATGGTCGGAAAGCTCTTTACAGTAAA CCCGGAAGTAAAAACGGGCGTTGGAATCCAGAAACCCATAAGTTTTGTAAGTGCGGTGTTCGCATACAAACTTCTGCTTAT ACTTGTAGTAAATGCAGAAATCGTTCAGGTGAAAATAATTCATTCTTTAATCATAAGCATTCAGACATAACTAAATCTAAA ATATCAGAAAAGATGAAAGGTAAAAAGCCTAGTAATATTAAAAAGATTTCA |
| 45 | I-TevI sequence (amino acid) | MKSGIYQIKNTLNNKVYVGSAKDFEKRWKRHFKDLEKGCHSSIKLQRSFNKHGNVFECSILEEIPYEKDLIIERENFWIKE LNSKINGYNIADATFGDTCSTHPLKEEIIKKRSETVKAKMLKLGPDGRKALYSKPGSKNGRWNPETHKFCKCGVRIQTSAY TCSKCRNRSGENNSFFNHKHSDITKSKISEKMKGKKPSNIKKIS |
| 46 | 31 nt long I-TevI DNA spacer in TevCasS target plasmid (p2497) | CTCAGTAGATGTTTTCTTGGGTCTACCGTTA |
| 47 | 29 nt long I-TevI DNA spacer in TevCasS target plasmid (p2498) | CTCAGTAGATGTTTTCTTGGGTCTACCGT |

TABLE 4-continued

SEQUENCES
Nucleotide sequences are written in 5' to 3' direction; amino acid sequences are written in N- to C-terminal direction,

| SEQ ID NO: | Description | Sequence |
|---|---|---|
| 48 | 27 nt long I-TevI DNA spacer in TevCasS target plasmid (p2499) | CTCAGTAGATGTTTTCTTGGGTCTACC |
| 49 | 25 nt long I-TevI DNA spacer in TevCasS target plasmid (p2500) | CTCAGTAGATGTTTTCTTGGGTCTA |
| 50 | 23 nt long I-TevI DNA spacer in TevCasS target plasmid (p2501) | CTCAGTAGATGTTTTCTTGGGTC |
| 51 | 21 nt long I-TevI DNA spacer in TevCasS target plasmid (p2502) | CTCAGTAGATGTTTTCTTGGG |
| 52 | 19 nt long I-TevI DNA spacer in TevCasS target plasmid (p2503) | CTCAGTAGATGTTTTCTTG |
| 53 | 17 nt long I-TevI DNA spacer in TevCasS target plasmid (p2504) | CTCAGTAGATGTTTTCT |
| 54 | 15 nt long I-TevI DNA spacer in TevCasS target plasmid (p2505) | CTCAGTAGATGTTTT |

TABLE 4-continued

SEQUENCES
Nucleotide sequences are written in 5' to 3' direction; amino acid sequences are written in N- to C-terminal direction,

| SEQ ID NO: | Description | Sequence |
|---|---|---|
| 55 | 13 nt long I-TevI DNA spacer in TevCasS target plasmid (p2506) | CTCAGTAGATGTT |
| 56 | 11 nt long I-TevI DNA spacer in TevCasS target plasmid (p2507) | CTCAGTAGATG |
| 57 | 9 nt long I-TevI DNA spacer in TevCasS target plasmid (p2508) | CTCAGTAGA |
| 58 | 7 nt long I-TevI DNA spacer in TevCasS target plasmid (p2509) | CTCAGTA |
| 59 | 5 nt long I-TevI DNA spacer in TevCasS target plasmid (p2510) | CTCAG |
| 60 | 33 nt long I-TevI DNA spacer in TevCasS target plasmid (p2575) | CTCAGTAGATGTTTTCTTGGGTCTACCGTTACG |
| 61 | 35 nt long I-TevI DNA spacer in TevCasS target plasmid (p2576) | CTCAGTAGATGTTTTCTTGGGTCTACCGTTACGGA |

TABLE 4-continued

| SEQ ID NO: | Description | Sequence |
|---|---|---|
| | SEQUENCES Nucleotide sequences are written in 5' to 3' direction; amino acid sequences are written in N- to C-terminal direction, | |
| 62 | 37 nt long I-TevI DNA spacer in TevCasS target plasmid (p2577) | CTCAGTAGATGTTTTCTTGGGTCTACCGTTACGGATT |
| 63 | 39 nt long I-TevI DNA spacer in TevCasS target plasmid (p2578) | CTCAGTAGATGTTTTCTTGGGTCTACCGTTACGGATTAG |
| 64 | 28 nt long I-TevI DNA spacer in TevCasS target plasmid (p2655) | CTCAGTAGATGTTTTCTTGGGTCTACCG |
| 65 | 30 nt long I-TevI DNA spacer in TevCasS target plasmid (p2656) | CTCAGTAGATGTTTTCTTGGGTCTACCGTT |
| 66 | 32 nt long I-TevI DNA spacer in TevCasS target plasmid (p2657) | CTCAGTAGATGTTTTCTTGGGTCTACCGTTAC |
| 67 | 34 nt long I-TevI DNA spacer in TevCasS target plasmid (p2658) | CTCAGTAGATGTTTTCTTGGGTCTACCGTTACGG |
| 68 | 36 nt long I-TevI DNA spacer in TevCasS target plasmid (p2659) | CTCAGTAGATGTTTTCTTGGGTCTACCGTTACGGAT |

TABLE 4-continued

SEQUENCES
Nucleotide sequences are written in 5' to 3' direction; amino acid sequences are written in N- to C-terminal direction,

| SEQ ID NO: | Description | Sequence |
|---|---|---|
| 69 | 1st spacer in wild type Type-S CRISPR array (32 nt), also used as protospacer in Example 6 | TCGTGTTGTCCACGGTTACCCGCTGGCTGGAA |
| 70 | Repeat sequence | GTATTCCCCCCGCATGCGGGGGTTATCGG |

The invention claimed is:

1. A CRISPR-Cas system comprising:

(i) one or more vectors comprising nucleotide sequences encoding polypeptides of:

a) a polypeptide which comprises an amino acid sequence that is at least 90% identical to SEQ ID NO:2;

b) a polypeptide which comprises an amino acid sequence that is at least 90% identical to SEQ ID NO:4; and c) a polypeptide which comprises an amino acid sequence that is at least 90% identical to SEQ ID NO:5; and (ii) a crRNA or guide RNA, or a nucleotide sequence encoding the crRNA or guide RNA;

wherein the crRNA or guide RNA comprises a spacer that is cognate to a protospacer in a target sequence, wherein at least one of the nucleotide sequences is operably connected to a promoter that is (i) heterologous to the at least one nucleotide sequence;

(ii) not an *E. coli, Pseudomonas* or *Klebsiella* promoter;

(iii) a eukaryotic cell promoter;

(iv) an animal promoter;

(v) a plant promoter;

(vi) a fungus promoter;

(vii) an insect promoter; or (viii) a virus promoter.

2. The system of claim 1, wherein the system further comprises a polypeptide which comprises an amino acid sequence that is at least 90% identical to SEQ ID NO: 1, or a vector comprising a nucleotide sequence encoding the polypeptide.

3. The system of claim 2, wherein the system further comprises a polypeptide which comprises an amino acid sequence that is at least 90% identical to SEQ ID NO: 3, or a vector comprising a nucleotide sequence encoding the polypeptide.

4. The system of claim 1, wherein the system further comprises a polypeptide which comprises an amino acid sequence that is at least 90% identical to SEQ ID NO: 3, or a vector comprising a nucleotide sequence encoding the polypeptide.

5. The system of claim 1, wherein the protospacer is not found in *E. coli, Pseudomonas* and/or *Klebsiella*.

6. The system of claim 1, wherein the protospacer is a eukaryotic cell protospacer, an animal protospacer, a plant protospacer, an insect protospacer, a fungus cell protospacer, or a human protospacer.

7. The system of claim 1, wherein at least one of the nucleotide sequences is operably connected to a promoter that is heterologous to the at least one nucleotide sequence.

8. The system of claim 1, wherein the promoter is a constitutive promoter.

9. The system of claim 1, wherein the promoter is an inducible promoter.

10. The system of claim 1, wherein the one or more vectors comprise i) a nuclear localization sequence (NLS);

ii) a phage packaging sequence;

iii) a plasmid origin of replication;

iv) a plasmid origin of transfer;

v) a bacterial plasmid backbone;

vi) a eukaryotic plasmid backbone;

vii) a human virus structural protein gene;

viii) a virus rep and/or cap sequence;

ix) a selection marker or sequence encoding a selectable marker;

x) a eukaryotic promoter; or xi) a nucleotide sequence of a human, animal, plant or fungus gene.

11. The system of claim 1, wherein each of the one or more vectors is i) a plasmid vector;

ii) a transposon vector;

iii) a virus vector;

iv) a phagemid; or v) a nanoparticle.

12. The system of claim 1, wherein the protospacer is immediately adjacent to a Protospacer Adjacent Motif (PAM) sequence in the target sequence selected from the group consisting of 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3', 5'-TAG-3', 5'-ACC-3', 5'-AGG-3', 5'-ATT-3', 5'-GAC-3' and 5'-GTG-3'.

13. A CRISPR-Cas system comprising:

(i)

a) a polypeptide which comprises an amino acid sequence that is at least 90% identical to SEQ ID NO:2;

b) a polypeptide which comprises an amino acid sequence that is at least 90% identical to SEQ ID NO:4; and c) a polypeptide which comprises an amino acid sequence that is at least 90% identical to SEQ ID NO:5; or one or more vectors comprising nucleotide sequences encoding the polypeptides of a) to c); and (ii) a crRNA or guide RNA, or a nucleotide sequence encoding the crRNA or guide RNA;

wherein the crRNA or guide RNA comprises a spacer that is cognate to a protospacer in a target sequence, wherein the protospacer is not found in a bacterium which comprises endogenous nucleotide sequences that encode the polypeptides of (i) a) to c).

14. The system of claim 13, wherein the system further comprises a polypeptide which comprises an amino acid sequence that is at least 90% identical to SEQ ID NO: 1, or a vector comprising a nucleotide sequence encoding the polypeptide.

15. The system of claim 14, wherein the system further comprises a polypeptide which comprises an amino acid sequence that is at least 90% identical to SEQ ID NO:3, or a vector comprising a nucleotide sequence encoding the polypeptide.

16. The system of claim 13, wherein the system further comprises a polypeptide which comprises an amino acid sequence that is at least 90% identical to SEQ ID NO: 3, or a vector comprising a nucleotide sequence encoding the polypeptide.

17. The system of claim 13, wherein the protospacer is a eukaryotic cell protospacer, an animal protospacer, a plant protospacer, an insect protospacer, a fungus cell protospacer, or a human protospacer.

18. The system of claim 13, wherein the protospacer is immediately adjacent to a Protospacer Adjacent Motif (PAM) sequence in the target sequence selected from the group consisting of 5'-AAC-3', 5'-ATG-3', 5'-AAA-3', 5'-AAG-3', 5'-ACG-3', 5'-AAT-3', 5'-ACA-3', 5'-ACT-3', 5'-ATC-3', 5'-ATA-3', 5'-GAG-3', 5'-TAG-3', 5'-ACC-3', 5'-AGG-3', 5'-ATT-3', 5'-GAC-3' and 5'-GTG-3'.

19. A fusion protein comprising a polypeptide (Px), wherein the Px

I. comprises an amino acid sequence that is at least 90% identical to a sequence selected from the group consisting of SEQ ID NOs: 1-5; and II. is fused to a heterologous polypeptide (Py).

20. The fusion protein of claim 19, wherein Py is a nuclease or nickase.

21. A ribonucleoprotein complex comprising the fusion protein of claim 19 and a crRNA or guide RNA, wherein the crRNA or guide RNA comprises a spacer that is cognate to a protospacer in the target sequence.

22. A method of modifying a target sequence in a nucleic acid, the method comprising contacting the nucleic acid comprising the target sequence with a ribonucleoprotein complex comprising:

(a) a polypeptide which comprises an amino acid sequence that is at least 90% identical to SEQ ID NO:2; a polypeptide which comprises an amino acid sequence that is at least 90% identical to SEQ ID NO:4; and a polypeptide which comprises an amino acid sequence that is at least 90% identical to SEQ ID NO:5, and (b) a crRNA or guide RNA, wherein the crRNA or guide RNA comprises a spacer that is cognate to a first protospacer in the target sequence;

wherein the complex is guided to a target site comprising the target sequence to modify the target sequence or replication thereof.

23. A method of treating or preventing a disease or condition that is mediated by target cells in a subject comprising performing the method of claim 22, wherein said contacting comprises administering the polypeptides, or vectors comprising nucleotide sequences encoding the polypeptides, to the subject, and wherein the modification treats or prevents the disease or condition.

24. A method of modifying transcription of a region of a target DNA, comprising contacting the target DNA with the system of claim 13, whereby the system binds to the target DNA in the region defined by complementary binding of a spacer sequence of the crRNA to a protospacer in the target DNA, whereby the system up- or down-regulates transcription of the region of the target DNA or an adjacent gene.

25. A method of modifying a target dsDNA of a cell without introducing dsDNA breaks, comprising contacting the dsDNA with the system of claim 13, wherein the system targets a target dsDNA comprised by the cell, whereby the system binds to the dsDNA in the region defined by complementary binding of a spacer sequence of the crRNA to a protospacer in the target dsDNA, whereby the dsDNA is modified without introducing dsDNA breaks.

26. A method of inhibiting the growth or proliferation of a cell without introducing lethal dsDNA breaks, the method comprising introducing into the cell the system of claim 13, whereby the system binds to a target DNA in the region defined by complementary binding of a spacer sequence of the crRNA to the protospacer in the target DNA, whereby replication of the DNA is inhibited without introducing lethal dsDNA breaks in the DNA, thereby inhibiting the growth or proliferation of a cell.

27. A method of modifying a target sequence in a nucleic acid, the method comprising contacting the nucleic acid comprising the target sequence with a ribonucleoprotein complex comprising the fusion protein of claim 19 and a crRNA or guide RNA, wherein the crRNA or guide RNA comprises a spacer that is cognate to a first protospacer in the target sequence; and wherein the complex is guided to a target site comprising the target sequence to modify the target sequence or replication thereof.

28. A method of treating or preventing a disease or condition that is mediated by target cells in a subject comprising performing the method of claim 27, wherein said contacting comprises administering the fusion protein to the subject, and wherein the modification treats or prevents the disease or condition.

29. A method of modifying transcription of a region of a target DNA, comprising contacting the target DNA with the complex of claim 21, whereby the complex binds to the target DNA in the region defined by complementary binding of a spacer sequence of the crRNA to a protospacer in the target DNA, whereby the complex up- or down-regulates transcription of the region of the target DNA or an adjacent gene.

30. A method for cleaving a target double stranded DNA (dsDNA), comprising contacting the dsDNA with the complex of claim 21, wherein Py comprises a nuclease, whereby the nuclease cleaves the DNA in the region defined by complementary binding of a spacer sequence of the crRNA to a protospacer in the target dsDNA.

31. A method for cleaving a target single stranded DNA (ssDNA), comprising contacting said ssDNA with the complex of claim 21, wherein Py comprises a nickase, whereby the nickase cleaves a single strand of the ssDNA in the region defined by complementary binding of a spacer sequence of the crRNA to a protospacer in the target ssDNA.

* * * * *